US009051363B2

(12) United States Patent
Basi et al.

(10) Patent No.: US 9,051,363 B2
(45) Date of Patent: *Jun. 9, 2015

(54) HUMANIZED ANTIBODIES THAT RECOGNIZE BETA AMYLOID PEPTIDE

(75) Inventors: Guriq Basi, Palo Alto, CA (US); Jose William Saldanha, Enfield (GB); Dale B. Schenk, Burlingame, CA (US)

(73) Assignees: JANSSEN SCIENCES IRELAND UC (IE); WYETH LLC, Madison, NJ (US)

( * ) Notice: Subject to any disclaimer, the term of this patent is extended or adjusted under 35 U.S.C. 154(b) by 1128 days.

This patent is subject to a terminal disclaimer.

(21) Appl. No.: 11/842,042

(22) Filed: Aug. 20, 2007

(65) Prior Publication Data

US 2009/0069544 A1  Mar. 12, 2009

Related U.S. Application Data

(63) Continuation of application No. 11/516,724, filed on Sep. 5, 2006, now abandoned, which is a continuation of application No. 11/413,638, filed on Apr. 28, 2006, now abandoned, which is a continuation of application No. 10/388,389, filed on Mar. 12, 2003, now Pat. No. 7,179,892, which is a continuation-in-part of application No. 10/010,942, filed on Dec. 6, 2001, now Pat. No. 7,189,819, which is a continuation-in-part of application No. 10/232,030, filed on Aug. 30, 2002, now Pat. No. 7,582,733, which is a continuation-in-part of application No. 11/058,757, filed on Feb. 14, 2005, now abandoned, which is a continuation-in-part of application No. 09/724,940, filed on Nov. 28, 2000, now Pat. No. 6,905,686, which is a continuation of application No. 09/580,015, filed on May 26, 2000, now abandoned, which is a continuation-in-part of application No. 09/322,289, filed on May 28, 1999, now Pat. No. 7,964,192, which is a continuation-in-part of application No. 09/201,430, filed on Nov. 30, 1998, now Pat. No. 6,787,523, which is a continuation of application No. 10/703,713, filed on Nov. 7, 2003, now abandoned, which is a continuation of application No. 11/520,438, filed on Sep. 12, 2006, now Pat. No. 7,790,856, which is a continuation of application No. 11/396,417, filed on Mar. 30, 2006, now abandoned, which is a continuation of application No. 10/704,070, filed on Nov. 7, 2003, now abandoned.

(60) Provisional application No. 60/251,892, filed on Dec. 6, 2000, provisional application No. 60/080,970, filed on Apr. 7, 1998, provisional application No. 60/067,740, filed on Dec. 2, 1997, provisional application No. 61/251,895, filed on Dec. 6, 2000.

(51) Int. Cl.
| | |
|---|---|
| *A61K 39/395* | (2006.01) |
| *C07K 16/18* | (2006.01) |
| *A61K 9/48* | (2006.01) |
| *A61K 31/00* | (2006.01) |
| *A61K 31/739* | (2006.01) |
| *A61K 38/19* | (2006.01) |
| *A61K 47/48* | (2006.01) |
| *C07K 14/47* | (2006.01) |
| *A61K 9/00* | (2006.01) |
| *A61K 9/20* | (2006.01) |
| *A61K 9/70* | (2006.01) |
| *A61K 39/00* | (2006.01) |

(52) U.S. Cl.
CPC ............. *C07K 16/18* (2013.01); *A61K 39/3955* (2013.01); *A61K 9/0019* (2013.01); *A61K 9/2009* (2013.01); *A61K 9/2031* (2013.01); *A61K 9/2054* (2013.01); *A61K 9/4866* (2013.01); *A61K 9/7023* (2013.01); *A61K 31/00* (2013.01); *A61K 31/739* (2013.01); *A61K 38/193* (2013.01); *A61K 39/00* (2013.01); *A61K 39/0007* (2013.01); *A61K 47/4833* (2013.01); *A61K 2039/505* (2013.01); *A61K 2039/53* (2013.01); *A61K 2039/55505* (2013.01); *A61K 2039/55555* (2013.01); *A61K 2039/55566* (2013.01); *A61K 2039/55572* (2013.01); *A61K 2039/55577* (2013.01); *A61K 2039/6037* (2013.01); *A61K 2039/605* (2013.01); *C07K 14/4711* (2013.01); *C07K 2317/24* (2013.01); *C07K 2317/34* (2013.01); *C07K 2317/565* (2013.01); *C07K 2317/567* (2013.01); *C07K 2317/77* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| 4,666,829 A | 5/1987 | Glenner et al. |
|---|---|---|
| 4,713,366 A | 12/1987 | Stevens |

(Continued)

FOREIGN PATENT DOCUMENTS

| AU | 707083 | 7/1999 |
|---|---|---|
| EP | 285 159 A1 | 10/1988 |

(Continued)

OTHER PUBLICATIONS

Rudikoff et al (Proc Natl Acad Sci USA 1982 vol. 79 p. 1979-1983).*
MacCallum et al. J. Mol. Biol. (1996) 262, pp. 732-745.*
Pascalis et al. (The Journal of Immunology (2002) 169, pp. 3076-3084).*
Casset et al. (2003) BBRC 307, pp. 198-205.*
Vajdos et al. (J. Mol. Biol, 2002, vol. 320, pp. 415-428).*
Chen et al. (J. Mol. Bio., 1999, vol. 293, pp. 865-881).*
Wu et al. (J. Mol. Biol., 1999, vol. 294, pp. 151-162).*
Begley DJ, Pharmacol. Therapy, vol. 104(1), pp. 29-45, 2004, Abstract.*
Misra et al. (J. Pharmacy and Pharmaceutical Sciences, vol. 6(2), pp. 252-273, 2003, Abstract.*

(Continued)

*Primary Examiner* — Kimberly A Ballard
(74) *Attorney, Agent, or Firm* — Alston & Bird LLP

(57) ABSTRACT

The invention provides improved agents and methods for treatment of diseases associated with amyloid deposits of Aβ in the brain of a patient. Preferred agents include humanized antibodies.

6 Claims, 10 Drawing Sheets

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,879,213 A | 11/1989 | Fox et al. |
| 4,883,666 A | 11/1989 | Sabel et al. |
| 4,912,206 A | 3/1990 | Goldgaber et al. |
| 4,966,753 A | 10/1990 | McMichael |
| 5,004,697 A | 4/1991 | Pardridge |
| 5,057,540 A | 10/1991 | Kensil et al. |
| 5,096,706 A | 3/1992 | Flint |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,225,539 A | 7/1993 | Winter |
| 5,227,159 A | 7/1993 | Miller |
| 5,231,000 A | 7/1993 | Majocha et al. |
| 5,231,170 A | 7/1993 | Averback |
| 5,245,015 A | 9/1993 | Fung et al. |
| 5,258,498 A | 11/1993 | Huston et al. |
| 5,262,332 A | 11/1993 | Selkoe |
| 5,270,165 A | 12/1993 | Van Nostrand et al. |
| 5,278,049 A | 1/1994 | Baker et al. |
| 5,358,708 A | 10/1994 | Patel |
| 5,385,887 A | 1/1995 | Yim et al. |
| 5,387,742 A | 2/1995 | Cordell |
| 5,417,986 A | 5/1995 | Reid et al. |
| 5,434,170 A | 7/1995 | Andrulis, Jr. |
| 5,441,870 A | 8/1995 | Seubert et al. |
| 5,464,823 A | 11/1995 | Lehrer et al. |
| 5,470,951 A | 11/1995 | Roberts |
| 5,472,693 A | 12/1995 | Gourlie et al. |
| 5,514,548 A | 5/1996 | Krebber et al. |
| 5,530,101 A | 6/1996 | Queen et al. |
| 5,571,499 A | 11/1996 | Hafler et al. |
| 5,571,500 A | 11/1996 | Hafler et al. |
| 5,576,184 A | 11/1996 | Better et al. |
| 5,583,112 A | 12/1996 | Kensil et al. |
| 5,585,089 A | 12/1996 | Queen et al. |
| 5,585,100 A | 12/1996 | Mond et al. |
| 5,589,154 A | 12/1996 | Anderson |
| 5,593,846 A | 1/1997 | Schenk et al. |
| 5,601,827 A | 2/1997 | Collier et al. |
| 5,605,811 A | 2/1997 | Seubert et al. |
| 5,612,486 A | 3/1997 | McConlogue et al. |
| 5,618,920 A | 4/1997 | Robinson et al. |
| 5,620,844 A | 4/1997 | Neurath et al. |
| 5,622,701 A | 4/1997 | Berg |
| 5,624,821 A | 4/1997 | Winter et al. |
| 5,624,937 A | 4/1997 | Reel et al. |
| 5,641,473 A | 6/1997 | Hafler et al. |
| 5,641,474 A | 6/1997 | Hafler et al. |
| 5,645,820 A | 7/1997 | Hafler et al. |
| 5,648,260 A | 7/1997 | Winter et al. |
| 5,652,334 A | 7/1997 | Roberts |
| 5,677,425 A | 10/1997 | Bodmer et al. |
| 5,679,348 A | 10/1997 | Nesburn et al. |
| 5,688,651 A | 11/1997 | Solomon |
| 5,693,761 A | 12/1997 | Queen et al. |
| 5,693,762 A | 12/1997 | Queen et al. |
| 5,702,906 A | 12/1997 | Rosenthal |
| 5,721,130 A | 2/1998 | Seubert et al. |
| 5,723,130 A | 3/1998 | Hancock et al. |
| 5,731,284 A | 3/1998 | Williams |
| 5,733,547 A | 3/1998 | Weiner et al. |
| 5,733,548 A | 3/1998 | Restifo et al. |
| 5,736,142 A | 4/1998 | Sette et al. |
| 5,744,132 A | 4/1998 | Warne et al. |
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,766,846 A | 6/1998 | Schlossmacher et al. |
| 5,770,700 A | 6/1998 | Webb et al. |
| 5,773,007 A | 6/1998 | Penney et al. |
| 5,776,468 A | 7/1998 | Hauser et al. |
| 5,780,587 A | 7/1998 | Potter |
| 5,786,180 A | 7/1998 | Konig et al. |
| 5,798,102 A | 8/1998 | McMichael et al. |
| 5,817,626 A | 10/1998 | Findeis et al. |
| 5,824,322 A | 10/1998 | Balasubramanian |
| 5,837,268 A | 11/1998 | Potter et al. |
| 5,837,473 A | 11/1998 | Maggio et al. |
| 5,837,672 A | 11/1998 | Schenk et al. |
| 5,846,533 A | 12/1998 | Prusiner |
| 5,849,298 A | 12/1998 | Weiner et al. |
| 5,851,996 A | 12/1998 | Kline |
| 5,854,204 A | 12/1998 | Findeis et al. |
| 5,854,215 A | 12/1998 | Findeis et al. |
| 5,858,981 A | 1/1999 | Schreiber et al. |
| 5,859,205 A | 1/1999 | Adair et al. |
| 5,866,129 A | 2/1999 | Chang et al. |
| 5,869,046 A | 2/1999 | Presta et al. |
| 5,869,054 A | 2/1999 | Weiner et al. |
| 5,869,093 A | 2/1999 | Weiner et al. |
| 5,877,399 A | 3/1999 | Hsiao et al. |
| 5,891,991 A | 4/1999 | Wasco et al. |
| 5,895,654 A | 4/1999 | Hartford et al. |
| 5,910,427 A | 6/1999 | Mikayama |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,985,242 A | 11/1999 | Findeis et al. |
| 5,989,566 A | 11/1999 | Cobb et al. |
| 5,994,083 A | 11/1999 | Felici et al. |
| 6,015,662 A | 1/2000 | Hackett et al. |
| 6,022,859 A | 2/2000 | Kiessling et al. |
| 6,054,297 A | 4/2000 | Carter et al. |
| 6,057,098 A | 5/2000 | Buechler et al. |
| 6,057,367 A | 5/2000 | Stamler et al. |
| 6,096,318 A | 8/2000 | Stevens et al. |
| 6,114,133 A | 9/2000 | Seubert et al. |
| 6,121,022 A | 9/2000 | Presta et al. |
| 6,150,091 A | 11/2000 | Pandolfo et al. |
| 6,165,745 A | 12/2000 | Ward et al. |
| 6,175,057 B1 | 1/2001 | Mucke et al. |
| 6,180,370 B1 | 1/2001 | Queen et al. |
| 6,194,551 B1 | 2/2001 | Idusogie et al. |
| 6,210,671 B1 | 4/2001 | Co |
| 6,218,506 B1 | 4/2001 | Krafft et al. |
| 6,261,569 B1 | 7/2001 | Comis et al. |
| 6,262,335 B1 | 7/2001 | Hsiao et al. |
| 6,267,958 B1 | 7/2001 | Andya et al. |
| 6,270,757 B1 | 8/2001 | Warne |
| 6,277,375 B1 | 8/2001 | Ward |
| 6,284,221 B1 | 9/2001 | Schenk et al. |
| 6,284,533 B1 | 9/2001 | Thomas |
| 6,294,171 B2 | 9/2001 | McMichael |
| 6,303,567 B1 | 10/2001 | Findeis et al. |
| 6,331,440 B1 | 12/2001 | Nordstedt et al. |
| 6,339,068 B1 | 1/2002 | Krieg et al. |
| 6,372,716 B1 | 4/2002 | Bush et al. |
| 6,399,314 B1 | 6/2002 | Krishnamurthy |
| 6,407,213 B1 | 6/2002 | Carter et al. |
| 6,417,178 B1 | 7/2002 | Klunk et al. |
| 6,432,710 B1 | 8/2002 | Boss, Jr. et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,562,341 B2 | 5/2003 | Prusiner et al. |
| 6,582,945 B1 | 6/2003 | Raso |
| 6,610,493 B1 | 8/2003 | Citron et al. |
| 6,632,927 B2 | 10/2003 | Adair et al. |
| 6,639,055 B1 | 10/2003 | Carter et al. |
| 6,710,226 B1 | 3/2004 | Schenk |
| 6,713,450 B2 | 3/2004 | Frangione et al. |
| 6,727,349 B1 | 4/2004 | LaRosa et al. |
| 6,743,427 B1 | 6/2004 | Schenk |
| 6,750,324 B1 | 6/2004 | Schenk et al. |
| 6,761,888 B1 | 7/2004 | Schenk |
| 6,787,129 B1 | 9/2004 | Schenk |
| 6,787,138 B1 | 9/2004 | Schenk |
| 6,787,139 B1 | 9/2004 | Schenk |
| 6,787,140 B1 | 9/2004 | Schenk |

(56) References Cited

U.S. PATENT DOCUMENTS

| | | |
|---|---|---|
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,808,712 B2 | 10/2004 | Schenk |
| 6,818,218 B2 | 11/2004 | Schenk |
| 6,824,780 B1 | 11/2004 | Devaux et al. |
| 6,866,849 B2 | 3/2005 | Schenk |
| 6,866,850 B2 | 3/2005 | Schenk |
| 6,875,434 B1 | 4/2005 | Schenk |
| 6,890,535 B1 | 5/2005 | Schenk |
| 6,905,686 B1 | 6/2005 | Schenk |
| 6,913,745 B1 * | 7/2005 | Schenk .................... 424/130.1 |
| 6,923,964 B1 | 8/2005 | Schenk |
| 6,933,368 B2 | 8/2005 | Co et al. |
| 6,936,698 B2 | 8/2005 | Taylor |
| 6,946,135 B2 | 9/2005 | Schenk |
| 6,962,707 B2 | 11/2005 | Schenk |
| 6,962,984 B2 | 11/2005 | Ishiwata et al. |
| 6,972,127 B2 | 12/2005 | Schenk |
| 6,982,084 B2 | 1/2006 | Schenk |
| 7,014,855 B2 | 3/2006 | Schenk |
| 7,112,661 B1 | 9/2006 | Miller |
| 7,147,851 B1 | 12/2006 | Ponath et al. |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 7,582,733 B2 | 9/2009 | Basi et al. |
| 7,625,560 B2 | 12/2009 | Basi et al. |
| 7,790,856 B2 | 9/2010 | Schenk |
| 7,871,615 B2 | 1/2011 | Basi et al. |
| 7,893,214 B2 | 2/2011 | Schenk |
| 7,906,626 B2 | 3/2011 | Raso |
| 7,928,203 B2 | 4/2011 | Schenk et al. |
| 2001/0018053 A1 | 8/2001 | McMichael |
| 2001/0021769 A1 | 9/2001 | Prusiner |
| 2002/0009445 A1 | 1/2002 | Du et al. |
| 2002/0058267 A1 | 5/2002 | Ozenberger et al. |
| 2002/0077288 A1 | 6/2002 | Frangione |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0009104 A1 | 1/2003 | Hyman et al. |
| 2003/0039645 A1 | 2/2003 | Adair et al. |
| 2003/0054484 A1 | 3/2003 | Fong et al. |
| 2003/0068316 A1 | 4/2003 | Klein et al. |
| 2003/0068325 A1 | 4/2003 | Wang |
| 2003/0073655 A1 | 4/2003 | Chain |
| 2003/0092145 A1 | 5/2003 | Jira et al. |
| 2003/0135035 A1 | 7/2003 | Shannon |
| 2003/0147882 A1 | 8/2003 | Solomon et al. |
| 2003/0165496 A1 | 9/2003 | Basi et al. |
| 2003/0166557 A1 | 9/2003 | Minna et al. |
| 2003/0166558 A1 | 9/2003 | Frangione et al. |
| 2003/0202972 A1 | 10/2003 | Andya et al. |
| 2003/0207828 A1 | 11/2003 | Ishiwata et al. |
| 2004/0043418 A1 | 3/2004 | Holtzman et al. |
| 2004/0081657 A1 | 4/2004 | Schenk |
| 2004/0082762 A1 | 4/2004 | Basi et al. |
| 2004/0087777 A1 | 5/2004 | Basi et al. |
| 2004/0171815 A1 | 9/2004 | Schenk et al. |
| 2004/0171816 A1 | 9/2004 | Schenk et al. |
| 2004/0197324 A1 | 10/2004 | Liu et al. |
| 2004/0213800 A1 | 10/2004 | Seubert et al. |
| 2004/0219146 A1 | 11/2004 | Schenk |
| 2004/0241164 A1 | 12/2004 | Bales et al. |
| 2004/0247590 A1 | 12/2004 | Schenk et al. |
| 2004/0247591 A1 | 12/2004 | Schenk et al. |
| 2004/0247612 A1 | 12/2004 | Wang |
| 2004/0265301 A1 | 12/2004 | Schenk et al. |
| 2004/0265308 A1 | 12/2004 | Schenk |
| 2004/0265919 A1 | 12/2004 | Vanderstichele et al. |
| 2005/0009150 A1 | 1/2005 | Basi et al. |
| 2005/0013815 A1 | 1/2005 | Schenk |
| 2005/0019328 A1 | 1/2005 | Schenk |
| 2005/0019330 A1 | 1/2005 | Schenk |
| 2005/0048049 A1 | 3/2005 | Schenk |
| 2005/0059591 A1 | 3/2005 | Schenk et al. |
| 2005/0059802 A1 | 3/2005 | Schenk et al. |
| 2005/0090648 A1 | 4/2005 | Tsurushita et al. |
| 2005/0118651 A1 | 6/2005 | Basi et al. |
| 2005/0123534 A1 | 6/2005 | Adair et al. |
| 2005/0123544 A1 | 6/2005 | Schenk et al. |
| 2005/0136054 A1 | 6/2005 | Adair et al. |
| 2005/0142132 A1 | 6/2005 | Schenk et al. |
| 2005/0147613 A1 | 7/2005 | Raso |
| 2005/0152878 A1 | 7/2005 | Solomon et al. |
| 2005/0158304 A1 | 7/2005 | Schenk et al. |
| 2005/0163788 A1 | 7/2005 | Schenk |
| 2005/0169925 A1 | 8/2005 | Bardroff et al. |
| 2005/0191292 A1 | 9/2005 | Schenk |
| 2005/0191314 A1 | 9/2005 | Schenk |
| 2005/0196399 A1 | 9/2005 | Schenk et al. |
| 2005/0214222 A1 | 9/2005 | McKinnon et al. |
| 2005/0249725 A1 | 11/2005 | Schenk et al. |
| 2005/0249727 A1 | 11/2005 | Schenk |
| 2005/0255122 A1 | 11/2005 | Schenk |
| 2006/0029611 A1 | 2/2006 | Schenk |
| 2006/0034858 A1 | 2/2006 | Schenk |
| 2006/0057701 A1 | 3/2006 | Rosenthal et al. |
| 2006/0099206 A1 | 5/2006 | Sinacore |
| 2006/0121038 A9 | 6/2006 | Schenk et al. |
| 2006/0153772 A1 | 7/2006 | Jacobsen |
| 2006/0160161 A1 | 7/2006 | Pavlikova et al. |
| 2006/0165682 A1 | 7/2006 | Basi et al. |
| 2006/0182321 A1 | 8/2006 | Hu et al. |
| 2006/0188512 A1 | 8/2006 | Yednock et al. |
| 2006/0193850 A1 | 8/2006 | Warne et al. |
| 2006/0198851 A1 | 9/2006 | Basi et al. |
| 2006/0210557 A1 | 9/2006 | Luisi et al. |
| 2006/0210964 A1 | 9/2006 | Hyslop et al. |
| 2006/0234912 A1 | 10/2006 | Wang et al. |
| 2006/0240486 A1 | 10/2006 | Johnson-Wood et al. |
| 2006/0257396 A1 | 11/2006 | Jacobsen |
| 2006/0280743 A1 | 12/2006 | Basi et al. |
| 2007/0021454 A1 | 1/2007 | Coburn et al. |
| 2007/0072307 A1 | 3/2007 | Godavarti et al. |
| 2007/0082367 A1 | 4/2007 | Godavarti et al. |
| 2007/0134762 A1 | 6/2007 | Arumugham et al. |
| 2007/0154480 A1 | 7/2007 | Schenk et al. |
| 2007/0161088 A1 | 7/2007 | Arumugham et al. |
| 2007/0196375 A1 | 8/2007 | Tobinick |
| 2007/0238154 A1 | 10/2007 | Basi et al. |
| 2008/0031954 A1 | 2/2008 | Paris et al. |
| 2008/0050367 A1 | 2/2008 | Basi et al. |
| 2008/0096818 A1 | 4/2008 | Schenk |
| 2008/0145373 A1 | 6/2008 | Arumugham et al. |
| 2008/0219931 A1 | 9/2008 | Klunk et al. |
| 2009/0069544 A1 | 3/2009 | Basi et al. |
| 2009/0142270 A1 | 6/2009 | Schroeter et al. |
| 2009/0155256 A1 | 6/2009 | Black et al. |
| 2009/0297511 A1 | 12/2009 | Schenk |
| 2010/0221187 A1 | 9/2010 | Lieberburg et al. |
| 2010/0266505 A1 | 10/2010 | Black |
| 2011/0142824 A1 | 6/2011 | Burbidge et al. |
| 2011/0229413 A1 | 9/2011 | Lieberburg et al. |
| 2012/0070379 A1 | 3/2012 | Black et al. |
| 2013/0058869 A1 | 3/2013 | Schenk et al. |

FOREIGN PATENT DOCUMENTS

| | | |
|---|---|---|
| EP | 0 391 714 A2 | 10/1990 |
| EP | 451 700 A1 | 10/1991 |
| EP | 506 785 B1 | 10/1992 |
| EP | 276 723 B1 | 12/1993 |

(56) References Cited

FOREIGN PATENT DOCUMENTS

| | | |
|---|---|---|
| EP | 613007 A2 | 2/1994 |
| EP | 616 814 A1 | 3/1994 |
| EP | 597 101 A1 | 5/1994 |
| EP | 0 613 007 A2 | 8/1994 |
| EP | 613 007 A2 | 8/1994 |
| EP | 620 276 A1 | 10/1994 |
| EP | 626 390 A1 | 11/1994 |
| EP | 666 080 A1 | 8/1995 |
| EP | 359 783 B1 | 11/1995 |
| EP | 683 234 A1 | 11/1995 |
| EP | 440 619 B1 | 1/1996 |
| EP | 758 248 B1 | 2/1997 |
| EP | 758 901 B1 | 2/1997 |
| EP | 526 511 B1 | 5/1997 |
| EP | 782 859 A1 | 7/1997 |
| EP | 783 104 A1 | 7/1997 |
| EP | 594 607 B1 | 8/1997 |
| EP | 752 886 B1 | 1/1998 |
| EP | 845 270 A1 | 6/1998 |
| EP | 1 690 547 A1 | 8/1998 |
| EP | 863 211 A1 | 9/1998 |
| EP | 868 918 A2 | 10/1998 |
| EP | 652 962 B1 | 12/1998 |
| EP | 911 036 A2 | 4/1999 |
| EP | 561 087 B1 | 8/1999 |
| EP | 639 081 B1 | 11/1999 |
| EP | 506 785 B1 | 3/2000 |
| EP | 1 172 378 A1 | 1/2002 |
| EP | 1 481 992 A2 | 12/2004 |
| EP | 1 481 992 A3 | 12/2004 |
| EP | 921 189 B1 | 1/2005 |
| EP | 1 033 998 B1 | 10/2005 |
| EP | 1 185 298 B1 | 6/2009 |
| EP | 1 690 547 B1 | 7/2009 |
| EP | 1 321 166 B1 | 1/2011 |
| EP | 1524994 B1 | 4/2011 |
| EP | 1160256 B2 | 11/2011 |
| EP | 1994937 B1 | 11/2011 |
| EP | 1842859 B1 | 1/2013 |
| EP | 1950991 B1 | 3/2013 |
| GB | 2 220 211 A | 1/1990 |
| GB | 2 335 192 A | 9/1999 |
| JP | 62-267297 A | 11/1987 |
| JP | 07-132033 A | 5/1995 |
| JP | 7-165799 A | 6/1995 |
| JP | 9208485 A | 6/1997 |
| JP | 09/208485 | 8/1997 |
| JP | 9215492 | 8/1997 |
| JP | 9119929 A | 5/1999 |
| WO | WO 87/02671 A | 5/1987 |
| WO | WO 87/06838 A1 | 11/1987 |
| WO | WO 88/07089 A1 | 9/1988 |
| WO | WO 88/10120 A1 | 12/1988 |
| WO | WO 89/01343 A1 | 2/1989 |
| WO | WO 89/03687 A1 | 5/1989 |
| WO | WO 89/06242 A1 | 7/1989 |
| WO | WO 89/06689 A1 | 7/1989 |
| WO | WO 90/05142 A1 | 5/1990 |
| WO | WO 90/07861 A1 | 7/1990 |
| WO | WO 90/12870 A1 | 11/1990 |
| WO | WO 90/12871 A1 | 11/1990 |
| WO | WO 90/14837 A1 | 12/1990 |
| WO | WO 90/14840 A1 | 12/1990 |
| WO | WO 91/08760 A1 | 6/1991 |
| WO | WO 91/09967 A1 | 7/1991 |
| WO | WO 91/10741 A1 | 7/1991 |
| WO | WO 91/12816 A1 | 9/1991 |
| WO | WO 91/16819 A1 | 11/1991 |
| WO | WO 91/16928 A1 | 11/1991 |
| WO | WO 91/17271 A1 | 11/1991 |
| WO | WO 91/19795 A1 | 12/1991 |
| WO | WO 91/19810 A1 | 12/1991 |
| WO | WO 92/01047 A1 | 1/1992 |
| WO | WO 92/01059 A1 | 1/1992 |
| WO | WO 92/05793 A1 | 4/1992 |
| WO | WO 92/06187 A1 | 4/1992 |
| WO | WO 92/06708 A1 | 4/1992 |
| WO | WO 92/07944 A1 | 5/1992 |
| WO | WO 92/13069 A1 | 8/1992 |
| WO | WO 92/15330 A1 | 9/1992 |
| WO | WO 92/19267 A1 | 11/1992 |
| WO | WO 92/22653 A1 | 12/1992 |
| WO | WO 93/02189 A1 | 2/1993 |
| WO | WO 93/04194 A1 | 3/1993 |
| WO | WO 93/12227 A1 | 6/1993 |
| WO | WO 93/14200 A1 | 7/1993 |
| WO | WO 93/15760 A1 | 8/1993 |
| WO | WO 93/16724 A1 | 9/1993 |
| WO | WO 93/21950 A1 | 11/1993 |
| WO | WO 94/00153 A1 | 1/1994 |
| WO | WO 94/01772 A1 | 1/1994 |
| WO | WO 94/03208 A1 | 2/1994 |
| WO | WO 94/03615 A1 | 2/1994 |
| WO | WO 94/05311 A1 | 3/1994 |
| WO | WO 94/09364 A1 | 4/1994 |
| WO | WO 94/09823 A1 | 5/1994 |
| WO | WO 94/10569 A1 | 5/1994 |
| WO | WO 94/16731 A1 | 8/1994 |
| WO | WO 94/17197 A1 | 8/1994 |
| WO | WO 94/21288 A1 | 9/1994 |
| WO | WO 94/28412 A1 | 12/1994 |
| WO | WO 94/29459 A1 | 12/1994 |
| WO | WO 95/04151 A2 | 2/1995 |
| WO | WO 95/05393 A2 | 2/1995 |
| WO | WO 95/05849 A1 | 3/1995 |
| WO | WO 95/05853 A1 | 3/1995 |
| WO | WO 95/06407 A1 | 3/1995 |
| WO | WO 95/07301 A1 | 3/1995 |
| WO | WO 95/07707 A1 | 3/1995 |
| WO | WO 95/08999 A1 | 4/1995 |
| WO | WO 95/11008 A2 | 4/1995 |
| WO | WO 95/11311 A1 | 4/1995 |
| WO | WO 95/11994 A1 | 5/1995 |
| WO | WO 95/12815 A1 | 5/1995 |
| WO | WO 95/17085 A1 | 6/1995 |
| WO | WO 95/23166 A1 | 8/1995 |
| WO | WO 95/23860 A2 | 9/1995 |
| WO | WO 95/31996 A1 | 11/1995 |
| WO | WO 96/01126 A1 | 1/1996 |
| WO | WO 96/03144 A1 | 2/1996 |
| WO | WO 96/08565 A2 | 3/1996 |
| WO | WO 96/14061 A1 | 5/1996 |
| WO | WO 96/15799 A1 | 5/1996 |
| WO | WO 96/18900 A1 | 6/1996 |
| WO | WO 96/22373 A1 | 7/1996 |
| WO | WO 96/25435 A1 | 8/1996 |
| WO | WO 96/28471 A1 | 9/1996 |
| WO | WO 96/29421 A1 | 9/1996 |
| WO | WO 96/33739 A1 | 10/1996 |
| WO | WO 96/37621 A2 | 11/1996 |
| WO | WO 96/39176 A1 | 12/1996 |
| WO | WO 96/39834 A1 | 12/1996 |
| WO | WO 96/40895 A1 | 12/1996 |
| WO | WO 97/03192 A3 | 1/1997 |
| WO | WO 97/05164 A1 | 2/1997 |
| WO | WO 97/08320 A1 | 3/1997 |
| WO | WO 97/10505 A1 | 3/1997 |
| WO | WO 97/13855 A1 | 4/1997 |
| WO | WO 97/17613 A1 | 5/1997 |
| WO | WO 97/18855 A1 | 5/1997 |
| WO | WO 97/21728 A1 | 6/1997 |
| WO | WO 97/36913 A1 | 7/1997 |
| WO | WO 97/28816 A1 | 8/1997 |
| WO | WO 97/32017 A1 | 9/1997 |
| WO | WO 97/36601 A1 | 10/1997 |
| WO | WO 97/37031 A1 | 10/1997 |
| WO | WO 97/40147 A1 | 10/1997 |
| WO | WO 98/02462 A1 | 1/1998 |
| WO | WO 98/04720 A1 | 2/1998 |
| WO | WO 98/05350 A1 | 2/1998 |
| WO | WO 98/07850 A2 | 2/1998 |
| WO | WO 98/08098 A2 | 2/1998 |
| WO | WO 98/08868 A1 | 3/1998 |
| WO | WO 98/22120 A1 | 5/1998 |

(56) References Cited

FOREIGN PATENT DOCUMENTS

| WO | WO 98/33815 A1 | 8/1998 |
|---|---|---|
| WO | WO 98/39303 A1 | 9/1998 |
| WO | WO 98/44955 A1 | 10/1998 |
| WO | WO 98/46642 A1 | 10/1998 |
| WO | WO 98/56418 A1 | 12/1998 |
| WO | WO 99/00150 A2 | 1/1999 |
| WO | WO 99/06066 A2 | 2/1999 |
| WO | WO 99/06587 A2 | 2/1999 |
| WO | WO 99/10008 A1 | 3/1999 |
| WO | WO 99/27911 A1 | 6/1999 |
| WO | WO 99/27944 A1 | 6/1999 |
| WO | WO 99/27949 A1 | 6/1999 |
| WO | WO 99/06545 A2 | 11/1999 |
| WO | WO 99/58564 A1 | 11/1999 |
| WO | WO 99/60021 A2 | 11/1999 |
| WO | WO 99/60024 A1 | 11/1999 |
| WO | WO 00/20027 A2 | 4/2000 |
| WO | WO 00/23082 A1 | 4/2000 |
| WO | WO 00/26238 A2 | 5/2000 |
| WO | WO 00/43039 A1 | 7/2000 |
| WO | WO 00/43049 A1 | 7/2000 |
| WO | WO 00/68263 A1 | 11/2000 |
| WO | WO 00/72870 A1 | 12/2000 |
| WO | WO 00/72876 A2 | 12/2000 |
| WO | WO 00/72876 A3 | 12/2000 |
| WO | WO 00/72880 A2 | 12/2000 |
| WO | WO 00/72880 A3 | 12/2000 |
| WO | WO 00/77178 A1 | 12/2000 |
| WO | WO 01/05355 A2 | 1/2001 |
| WO | WO 01/10900 A2 | 2/2001 |
| WO | WO 01/18169 A3 | 3/2001 |
| WO | WO 01/39796 A2 | 6/2001 |
| WO | WO 01/42306 A2 | 6/2001 |
| WO | WO 01/62284 A2 | 8/2001 |
| WO | WO 01/62801 A2 | 8/2001 |
| WO | WO 01/77167 A2 | 10/2001 |
| WO | WO 01/78777 A2 | 10/2001 |
| WO | WO 01/90182 A2 | 11/2001 |
| WO | WO 02/03911 A2 | 1/2002 |
| WO | WO 02/21141 A2 | 3/2002 |
| WO | WO 02/34777 A1 | 5/2002 |
| WO | WO 02/34878 A2 | 5/2002 |
| WO | WO 02/46237 A2 | 6/2002 |
| WO | WO 02/46237 A3 | 6/2002 |
| WO | WO 02/060481 A1 | 8/2002 |
| WO | WO 02/088306 A2 | 11/2002 |
| WO | WO 02/088307 A2 | 11/2002 |
| WO | WO 02/096457 A2 | 12/2002 |
| WO | WO 02/096937 A2 | 12/2002 |
| WO | WO 03/009817 A2 | 2/2003 |
| WO | WO 03/015691 A2 | 2/2003 |
| WO | WO 03/016466 A2 | 2/2003 |
| WO | WO 03/016467 A2 | 2/2003 |
| WO | WO 03/016467 A3 | 2/2003 |
| WO | WO 03/020212 A2 | 3/2003 |
| WO | WO 03/039485 A2 | 5/2003 |
| WO | WO 03/051374 A2 | 6/2003 |
| WO | WO 03/072036 A2 | 9/2003 |
| WO | WO 03/072036 A3 | 9/2003 |
| WO | WO 03/074081 A1 | 9/2003 |
| WO | WO 03/077858 A2 | 9/2003 |
| WO | WO 03/077858 A3 | 9/2003 |
| WO | WO 03/104437 A2 | 12/2003 |
| WO | WO 03/105894 A1 | 12/2003 |
| WO | WO 2004/013172 A2 | 2/2004 |
| WO | WO 2004/013172 A3 | 2/2004 |
| WO | WO 2004/016282 A1 | 2/2004 |
| WO | WO 2004/029629 A1 | 4/2004 |
| WO | WO 2004/031400 A2 | 4/2004 |
| WO | WO 2004/044204 A2 | 5/2004 |
| WO | WO 2004/044204 A3 | 5/2004 |
| WO | WO 2004/055164 A2 | 7/2004 |
| WO | WO 2004/069182 A2 | 8/2004 |
| WO | WO 2004/069182 A3 | 8/2004 |
| WO | WO 2004/071408 A2 | 8/2004 |
| WO | WO 2004/080419 A2 | 9/2004 |
| WO | WO 2004/080419 A3 | 9/2004 |
| WO | WO 2004/108895 A2 | 12/2004 |
| WO | WO 2004/108895 A3 | 12/2004 |
| WO | WO 2005/014041 A2 | 2/2005 |
| WO | WO 2005/026211 A2 | 3/2005 |
| WO | WO 2005/026211 A3 | 3/2005 |
| WO | WO 2005/035753 A | 4/2005 |
| WO | WO 2005/058940 A2 | 6/2005 |
| WO | WO 2005/058941 A2 | 6/2005 |
| WO | WO 2005/090315 A1 | 9/2005 |
| WO | WO 2006/042158 A | 4/2006 |
| WO | WO 2006/066049 A2 | 6/2006 |
| WO | WO 2006/066171 A1 | 6/2006 |
| WO | WO 2006/081587 A2 | 8/2006 |
| WO | WO 2006/081587 A3 | 8/2006 |
| WO | WO 2006/083689 A2 | 8/2006 |
| WO | WO 2006/121656 A2 | 11/2006 |
| WO | WO 2008/011348 A2 | 1/2008 |
| WO | WO 2008/114801 A1 | 9/2008 |
| WO | WO 2008/131298 A2 | 10/2008 |
| WO | WO 2008/131298 A3 | 10/2008 |
| WO | WO 2008/131298 A3 | 12/2008 |
| WO | WO 2009/017467 A1 | 2/2009 |
| WO | WO 2009/052439 A2 | 4/2009 |
| WO | WO 2010/033861 A1 | 3/2010 |
| WO | WO 2010/044803 A1 | 4/2010 |
| WO | WO 2011/106732 A1 | 9/2011 |
| WO | WO 2011/133919 A1 | 10/2011 |

OTHER PUBLICATIONS

Chao CP et al. (2006) Cerebral amyloid angiopathy: CT and MR imaging findings. Radiographics, 26(5):1517-1531.*
U.S. Appl. No. 11/303,478, Office Action mailed Oct. 16, 2008.
U.S. Appl. No. 11/516,724, Office Action mailed Jan. 27, 2009.
U.S. Appl. No. 09/322,289, Examiner Interview Summary mailed Jan. 15, 2009.
U.S. Appl. No. 09/723,765, Examiner Interview Summary mailed Jan. 16, 2009.
U.S. Appl. No. 09/723,765, Examiner Interview Summary mailed Oct. 8, 2008.
U.S. Appl. No. 10/429,216, Examiner Interview Summary mailed Mar. 6, 2006.
U.S. Appl. No. 10/544,093, Office Action mailed Feb. 9, 2009.
U.S. Appl. No. 10/923,471, Examiner Interview Summary mailed Oct. 20, 2008.
U.S. Appl. No. 11/304,986, Office Action mailed Dec. 31, 2008.
U.S. Appl. No. 11/305,899 Office Action mailed Dec. 10, 2008.
U.S. Appl. No. 11/342,353, Office Action mailed Nov. 14, 2008.
U.S. Appl. No. 11/842,023, Office Action mailed Nov. 13, 2008.
U.S. Appl. No. 09/322,289, Office Action mailed Nov. 4, 2008.
U.S. Appl. No. 10/858,855 Office Action mailed Dec. 12, 2008.
U.S. Appl. No. 11/244,678, Office Action mailed Sep. 23, 2008.
U.S. Appl. No. 11/245,916, Office Action mailed Oct. 31, 2008.
U.S. Appl. No. 10/429,216, Office Action mailed Oct. 16, 2008.
U.S. Appl. No. 09/723,765, Office Action mailed Dec. 5, 2008.
U.S. Appl. No. 09/724,288, Office Action mailed Dec. 22, 2008.
U.S. Appl. No. 10/429,216, Office Action mailed Mar. 6, 2009.
U.S. Appl. No. 10/777,792, Office Action mailed Nov. 18, 2008.
U.S. Appl. No. 10/923,469. Office Action mailed Dec. 29, 2008.
U.S. Appl. No. 12/106,206, filed Apr. 18, 2008, Schroeter.
U.S. Appl. No. 12/037,045, filed Feb. 25, 2008, Seubert.
U.S. Appl. No. 60/999,423, filed Oct. 17, 2007, Black.
U.S. Appl. No. 11/894,789, filed Aug. 20, 2007, Basi.
U.S. Appl. No. 11/894,754, filed Aug. 20, 2007.
U.S. Appl. No. 11/894,714, filed Aug. 20, 2007, Basi.
U.S. Appl. No. 11/894,665, filed Aug. 20, 2007, Schenk.
U.S. Appl. No. 11/893,123, filed Aug. 20, 2007.
U.S. Appl. No. 11/893,110, filed Aug. 20, 2007.
U.S. Appl. No. 11/893,103, filed Aug. 20, 2007.
U.S. Appl. No. 11/893,094, filed Aug. 20, 2007.
U.S. Appl. No. 11/842,120, filed Aug. 20, 2007, Schenk.
U.S. Appl. No. 11/842,116, filed Aug. 20, 2007, Schenk.
U.S. Appl. No. 11/842,113, filed Aug. 20, 2007, Schenk.

(56) References Cited

OTHER PUBLICATIONS

U.S. Appl. No. 11/842,101, filed Aug. 20, 2007, Schenk.
U.S. Appl. No. 11/842,056, filed Aug. 20, 2007, Basi.
U.S. Appl. No. 11/842,042, filed Aug. 20, 2007, Basi.
U.S. Appl. No. 11/842,023, filed Aug. 20, 2007, Basi.
U.S. Appl. No. 11/841,993, filed Aug. 20, 2007, Arumugham.
U.S. Appl. No. 11/841,950, filed Aug. 20, 2007, Arumugham.
U.S. Appl. No. 11/841,919, filed Aug. 20, 2007, Arumugham.
U.S. Appl. No. 11/841,897, filed Aug. 20, 2007, Arumugham.
U.S. Appl. No. 11/841,882, filed Aug. 20, 2007, Arumugham.
U.S. Appl. No. 11/841,857, filed Aug. 20, 2007, Warne et al.
U.S. Appl. No. 11/841,849, filed Aug. 20, 2007, Arumugham.
U.S. Appl. No. 11/841,794, filed Aug. 20, 2007, Warne et al.
U.S. Appl. No. 11/841,832, filed Aug. 20, 2007, Warne et al.
U.S. Appl. No. 60/793,014, filed Apr. 18, 2006.
U.S. Appl. No. 11/396,417, filed Mar. 30, 2006, Schenk.
U.S. Appl. No. 11/396,391, filed Mar. 30, 2006, Schenk.
U.S. Appl. No. 11/358,951, filed Feb. 22, 2006, Solomon et al.
U.S. Appl. No. 60/736,119, filed Nov. 10, 2005, Jacobson.
U.S. Appl. No. 60/736,045, filed Nov. 10, 2005, Johnson-Wood.
U.S. Appl. No. 60/735,687, filed Nov. 10, 2005, Jacobson.
U.S. Appl. No. 11/245,524, filed Oct. 7, 2005, Schenk.
U.S. Appl. No. 11/245,916, filed Oct. 7, 2005, Schenk.
U.S. Appl. No. 60/691,821, filed Jun. 17, 2005, Godavarti.
U.S. Appl. No. 09/980,568, filed Mar. 12, 2005, Hirtzer.
U.S. Appl. No. 60/648,639, filed Jan. 28, 2005, Luisi et al.
U.S. Appl. No. 60/648,631, filed Jan. 28, 2005, Luisi et al.
U.S. Appl. No. 60/637,253, filed Dec. 16, 2004, Jacobson.
U.S. Appl. No. 60/637,138, filed Dec. 16, 2004, Jacobson.
U.S. Appl. No. 60/636,842, filed Dec. 15, 2004, Jacobson.
U.S. Appl. No. 60/636,810, filed Dec. 15, 2004, Jacobson.
U.S. Appl. No. 60/636,776, filed Dec. 15, 2004, Basi.
U.S. Appl. No. 60/636,687, filed Dec. 15, 2004, Johnson-Wood.
U.S. Appl. No. 60/636,684, filed Dec. 15, 2004, Basi.
U.S. Appl. No. 60/622,525, filed Oct. 26, 2004, Pavliakova.
U.S. Appl. No. 60/616,474, filed Oct. 5, 2004, Sinacore.
U.S. Appl. No. 60/530,481, filed Dec. 17, 2003, Arumugham.
U.S. Appl. No. 60/474,654, filed May 30, 2003, Basi.
U.S. Appl. No. 60/444,150, filed Feb. 1, 2003, Yednock.
U.S. Appl. No. 09/979,701, filed Mar. 13, 2002, Schenk.
U.S. Appl. No. 60/363,751, filed Mar. 12, 2002, Basi.
U.S. Appl. No. 60/254,465, filed Dec. 8, 2000, Holtzman et al.
U.S. Appl. No. 60/254,498, filed Dec. 8, 2000, Holtzman et al.
U.S. Appl. No. 60/251,892, filed Dec. 6, 2000, Basi et al.
U.S. Appl. No. 09/724,842, filed Nov. 28, 2000, Chalifour et al.
U.S. Appl. No. 09/724,929, filed Nov. 28, 2000, Weiner.
U.S. Appl. No. 09/724,921, filed Nov. 28, 2000, Weiner.
U.S. Appl. No. 09/724,575, filed Nov. 28, 2000, Schenk.
U.S. Appl. No. 09/724,291, filed Nov. 28, 2000, Schenk.
U.S. Appl. No. 09/724,288, filed Nov. 28, 2000, Schenk.
U.S. Appl. No. 09/724,273, filed Nov. 28, 2000, Schenk.
U.S. Appl. No. 09/723,765, filed Nov. 28, 2000, Schenk.
U.S. Appl. No. 09/723,544, filed Nov. 28, 2000, Schenk.
U.S. Appl. No. 09/724,495, filed Nov. 27, 2000, Schenk.
U.S. Appl. No. 09/724,319, filed Nov. 27, 2000, Schenk.
U.S. Appl. No. 09/723,766, filed Nov. 27, 2000, Hirtzer.
U.S. Appl. No. 09/723,760, filed Nov. 27, 2000, Schenk.
U.S. Appl. No. 09/723,725, filed Nov. 27, 2000, Hirtzer.
U.S. Appl. No. 09/723,713, filed Nov. 27, 2000, Schenk.
U.S. Appl. No. 09/585,656.
U.S. Appl. No. 09/580,019, filed May 26, 2000, Schenk.
U.S. Appl. No. 09/580,015, filed May 26, 2000, Schenk.
U.S. Appl. No. 09/579,690, filed May 26, 2000, Brayden.
U.S. Appl. No. 60/186,295, filed Mar. 1, 2000, Rasmussen et al.
U.S. Appl. No. 60/184,601, filed Feb. 24, 2000, Holtzman et al.
U.S. Appl. No. 09/497,553, filed Feb. 3, 2000, Schenk.
U.S. Appl. No. 60/169,687, filed Dec. 8, 1999, Chain.
U.S. Appl. No. 60/168,594, filed Nov. 29, 1999, Chalifour et al.
U.S. Appl. No. 09/441,140, filed Nov. 16, 1999, Solomon et al.
U.S. Appl. No. 60/139,408, filed Jun. 16, 1999, Raso.
U.S. Appl. No. 60/137,047, filed Jun. 1, 1999, Hirtzer.
U.S. Appl. No. 60/137,010, filed Jun. 1, 1999, Schenk.
U.S. Appl. No. 60/136,655, filed May 28, 1999, Brayden.
U.S. Appl. No. 09/322,289, filed May 28, 1999, Schenk.
U.S. Appl. No. 60/080,970, filed Jan. 11, 1999, Schenk.
U.S. Appl. No. 09/204,838, filed Dec. 3, 1998, Weiner.
U.S. Appl. No. 60/079,697, filed Mar. 27, 1998, Weiner et al.
U.S. Appl. No. 60/067,740, filed Dec. 2, 1997, Schenk.
U.S. Appl. No. 60/067,219, filed Dec. 3, 1997, Weiner et al.
U.S. Appl. No. 60/925,228.
Aguzzi et al., "Prion research: the next frontiers," *Nature*, 389:795-798 (1997).
Aisen, P., "Inflammation and Alzheimer's Disease: Mechanisms and Therapeutic Strategies," *Gerontology*, 43:143-149 (1997).
Akiyama et al., "Occurrence of the Diffuse Amyloid β-Protein (Aβ) Deposits With Numerous Aβ-Containing Glial Cells in the Cerebral Cortex of Patients With Alzheimer's Disease," *Glia*, 25:324-331 (1999).
Akiyama et al., "Inflammation and Alzheimer's disease," *Neurobiology of Aging*, 21:383-421 (2000).
Akiyama et al., "The amino-terminally truncated forms of amyloid β-protein in brain macrophages in the ischemic lesions of Alzheimer's disease patients," *Neuroscience Letters*, 219:115-118 (1996).
Alberts et al., eds. *Molecular Biology of the Cell, Third Edition*, chapter 23, pp. 1208-1209 (1994).
Alberts et al., eds. *Molecular Biology of the Cell, Third Edition*, chapter 23, pp. 1216-1218 (1994).
Alberts et al., *Molecular Biology of the Cell, 2nd Edition*, pp. 266-267, Garland Publishing Inc., New York (1989).
Amit et al., "Three-Dimensional Structure of an Antigen-Antibody Complex at 2.8 Å Resolution," *Science*, 233:747-753 (1986).
Andersen et al., "Do nonsteroidal anti-inflammatory drugs decrease the risk for Alzheimer's disease?", *Neurology*, 45:1441-1445 (1995).
Anderson, J. P., "Exact cleavage site of Alzheimer amyloid precursor in neuronal PC-12 cells," *Neuroscience Letters*, 128(1):126-128 (1991).
Anderson, M. W., "Amending the amyloid hypothesis," *The Scientist*, 18(20):28-29.
Andrew et al., *Current Protocols in Immunology*, 2.7.1-2.9.8, John Wiley & Sons, Inc. (1997).
Ankarcrona et al., "Biomarkers for apoptosis in Alzheimer's disease," *Int. J. Geriatric Psychiatry*, 20:101-105 (2005).
Ard et al., "Scavenging of Alzheimer's Amyloid β-Protein by Microglia in Culture," *J. Neuroscience Research*, 43:190-202 (1996).
Arendiash et al., "Behavioral assessment of Alzheimer's transgenic mice following long-term Aβ vaccination: Task specificity and correlations between Aβ deposition and spatial memory," *DNA and Cell Biology*, 20(11):737-744 (2001).
Askelof et al., "Protective immunogenicity of two synthetic peptides selected from the amino acid sequence of *Bordetella pertussis* toxin subunit S1," *PNAS*, 87:1347-1351 (1990).
Associated Press, "Immune cells may promote Alzheimer's, a study finds," *The Boston Globe* (Apr. 13, 1995).
Auld et al., "Alzheimer's disease and the basal forebrain cholinergic system: relations to β-amyloid peptides, cognition, and treatment strategies," *Progress in Neurobiol.*, 68:209-245 (2002).
Bacskai et al., "Imaging of amyloid-β deposits in brains of living mice permits direct observation of clearance of plaques with immunotherapy," *Nature Medicine*, 7(3):369-372 (2001).
Bacskai et al., "Non-Fc-mediated mechanisms are involved in clearance of amyloid-β in vivo by immunotherapy," *J. Neurosci.*, 22(18):7873-7878 (2002).
Balbach et al., "Amyloid fibril formation by $A\beta_{16-22}$, a seven-residue fragment of the Alzheimer's β-amyloid peptide, and structural characterization by solid state NMR," *Biochemistry*, 39:13748-13759 (2000).
Bales et al., "Administration of an Anti-Aβ Fab Fragment to $APP^{V717F}$ Transgenic Mice Reduces Neuritic Plaque," Abstract P4-396, presented at Poster Session P4: Therapeutics and Therapeutic Strategies—Therapeutic Strategies, Amyloid-Based, *Neurogiology of Aging*, 25:S587 (2004).

(56) References Cited

OTHER PUBLICATIONS

Bales et al., "Cholinergic dysfunction in a mouse model of Alzheimer disease is reversed by an anti-Aβ antibody," *J. Clin. Invest.*, 116(3):825-832 (2006).
Bard et al., "Peripherally administered antibodies against amyloid β-peptide enter the central nervous system and reduce pathology in a mouse model of Alzheimer disease," *Nature Medicine*, 6(8):916-919 (2000).
Bard et al., "Epitope and isotype specificities of antibodies to β-amyloid peptide for protection against Alzheimer's disease-like neuropathology," *PNAS*, 100(4):2023-2028 (2003).
Barrow et al., "Solution Conformations and aggregational Properties of Synthetic Amyloid Beta-Peptides of Alzheimer's Disease. Analysis of Circular Dichroism Spectra," *J. Mol. Biol.*, 225(4):1075-1093 (1992).
Bauer et al., "Interleukin-6 and α-2-macroglobulin indicate an acute-phase state in Alzheimer's disease cortices," *FEBS Letters*, 285(1):111-114 (1991).
Beasley, "Alzheimer's traced to proteins caused by aging," Reuters, Apr. 20, 2001 7:56 PM ET.
Bellotti et al., "Application of Monoclonal Anti-idiotypes in the Study of AL Amyloidosi: Therapeutic Implications," *Renal Failure*, 15(3):365-371 (1993).
Bending, "Humanization of Rodent Monoclonal Antibodies by CDR Grafting," *A Companion to Methods in Enzymology*, 8:83-93 (1995).
Benjamini et al., from *Immunology A Short Course*, Second Edition, Chapter 4, Antibody Structure, pp. 49-65, 1991, published by Wiley-Liss, Inc., New York, New York.
Benjamini et al., from *Immunology A Short Course*, Second Edition, pp. 136-138, 143, 73-74, 372-373, and 400-401, 1991, published by Wiley-Liss, Inc., New York, New York.
Benkirane, et al, "Antigenicity and Immunogenicity of Modified Synthetic Peptides Containing D-Amino Acid Residues," *J. Biol. Chem.*, 268(23):26279-26285 (1993).
Ben-Yedidia et al., "Design of peptide and polypeptide vaccines," *Current Opinion in Biotechnology*, 8:442-448 (1997).
Bercovici et al., "Chronic Intravenous Injections of Antigen Induce and Maintain Tolerance in T Cell Receptor-Transgenic Mice," *Eur. J. Immunol.*, 29:345-354 (1999).
Bickel et al., "Site Protected, Cationized Monoclonal Antibody Against Beta Amyloid as a Potential Diagnostic Imaging Technique for Alzheimer's Diseases," *Soc. for Neuroscience Abstracts*, 18:764 (1992).
Bickel et al., "Development and in Vitro Characterization of a Cationized Monoclonal Antibody against βA4 Protein: A Potential Probe for Alzheimer's Disease," *Bioconjugate Chem.*, 5:119-125 (1994).
Blasberg et al., "Regional Localization of Glioma-assoicated Antigen Defined by Monoclonal Antibody 81C6 in Vivo: Kinetics and Implications for Diagnosis and Therapy," *Cancer Research*, 47:4432-4443 (1987).
Blass, "Immunologic Treatment of Alzheimer's Disease," *New England J. Medicine*, 341(22):1694 (1999).
Bodmer et al., "Transforming Growth Factor-Beta Bound to Soluble Derivatives of the Beta Amyloid Precursor Protein of Alzheimer's Disease," *Biochem. Biophys. Res. Comm.*, 171(2):890-897 (1990).
Borchelt et al., "Accelerated Amyloid Deposition in the Brains of Transgenic Mice Coexpressing Mutant Presenilin 1 and Amyloid Precursor Proteins," *Neuron*, 19:939-945 (1997).
Borenstein, S., "New Alzheimer's vaccine to be tested on people soon, Early experiments on mice halted condition; considered safe for humans," *Free Press*, Jul. 23, 2001.
Boris-Lawrie et al., "Recent advances in retrovirus vector technology," *Cur. Opin. Genetic Develop.*, 3:102-109 (1993).
Bork et al., "Go hunting in sequence databases but watch out for the traps," *Trends in Genetics*, 12(10):425-427 (1996).
Bork, P., "Powers and Pitfalls in Sequence Analysis: The 70% Hurdle," *Genome Research*, 10:398-400 (2000).

Brazil et al., "Effects of Incorporation of Immunoglobulin G and Complement Component C1q on Uptake and Degradation of Alzheimer's Disease Amyloid Fibrils by Microglia," *J. Biol. Chem.*, 275(22):16941-16947 (2000).
Brenner, S. E., "Errors in genome annotation," *Trends in Genetics*, 15(4):132-133 (1999).
Brice et al., "Absence of the amyloid precursor protein gene mutation (APP717 : Val->lle) in 85 cases of early onset Alzheimer's disease," *J. Neurology, Neurosurg. Psychiatry*, 56:112-115 (1993).
Britt et al., "Formulation of an immunogenic human cytomegalovirus vaccine: responses in mice," *J. Infect. Dis.*, 171:18-25 Abstract (1995).
Broadwell et al., "Serum proteins bypass the blood-brain fluid barriers for extracellular entry to the central nervous system," *Exp. Neurol.*, 120(2):245-263 (1993).
Brookmeyer et al., "Projections of Alzheimer's Disease in the United States and the Public Health Impact of Delaying Disease Onset," *Am. J. Public Health*, 88:1337-1342 (1998).
Burdick et al., "Assembly and aggregartion properties of synthetic Alzheimer's A4/β amyloid peptide antigens," *J. Biol. Chem.*, 267:546-555 (1992).
Bussiere et al., "Morphological Characterization of Thioflavin-S-Positive Amyloid Plaques in Transgenic Alzheimer Mice and Effect of Passive Aβ Immunotherapy on Their Clearance," *Am. J. Pathology*, 165(3):987-995 (2004).
Cameron, "Recent Advances in Transgenic Technology," *Molecular Biotechnology*, 7:253-265 (1997).
Caputo et al., "Therapeutic approaches targeted at the amyloid proteins in Alzheimer's disease," *Clin. Neuropharm.*, 15:414A-414B (1992).
Casadesus et al., "The Estrogen Myth: Potential Use of Gonadotropin-Releasing Hormone Agonists for the Treatment of Alzheimer's Disease," *Drugs R D*, 7(3):187-193 (2006).
Casey, S.O., "Posterior Reversible Encephalopathy Syndrome: Utility of Fluid-attenuated Inversion Recovery MR Imaging in the Detection of Cortical and Subcortical Lesions," *Amer J Neuroradiol*, 21:1199-1206 (2000).
Castillo et al., "Amylin / Islet Amyloid Polypeptide: Biochemistry, Physiology, Patho-Physiology," *Diabete & Metabolisme* (Paris), 21:3-25 (1995).
Cassell et al., "Demography and Epidemiology of Age-Associated Neuronal Impairment," chapter 4, pp. 31-50 from *Funcitional Neurobiology of Aging*, Hof et al., eds., Academic Press (2001).
Casset et al., "A Peptide Mimetic of an Anti-CD4 Monoclonal Antibody by Rational Design," *Biochemical and Biophysical Research Commiunications*, 307:198-205 (2003).
Center for Biologics Evaluation and Research, U.S. Food and Drug Administration, Thimerosal in Vaccines (Mercury in Plasma-Derived Products), web site contents found at : http://www.fda.gov/cber/vaccine/thimerosal.htm, last updated May 16, 2002.
Chakrabarti et al., "Vaccinia Virus Expression Vector: Coexpression of B-Galactosidas Provides Visual Screening of Recombinant Virus Plaques," *Molecular and Cellular Biology*, 5(12):3403-3409 (1985).
Chang et al., "Adjuvant activity of incomplete Freund's adjuvant," *Advanced Drug Delivery Reviews*, 32:173-186 (1998).
Chao et al., "Transforming Growth Factor-β Protects human Neurons Against β-Amyloid-Induced Injury," *Soc. Neurosci. Abstracts*, 19:513-7 (1993).
Chapman, "Model behavior," *Nature*, 408:915-916 (2000).
Check, "Battle of the Mind," *Nature*, 422:370-372 (2003).
Chemical Abstract database, Abstract of "Injection of Newborn Mice with Seven Chemical Adjuvants to Help Determine Their Safety in Use in Biologicals," Chemical Abstract database. (Publication date unknown.).
Chimicon International, "Mouse Anti-Amyloid Beta Protein Monoclonal Antibody," Catalog #MAB1561 (2003-2005).
Chen et al., "Neurodegenerative Alzheimer-like pathology in PDAPP 717V→F transgenic mice," *Progress in Brain Research*, 117:327-337 (1998).
Chen et al., "A learning deficit related to age and beta-amyloid plaques in a mouse model of Alzheimer's disease," *Nature*, 408(6815):975-979 (2000).

(56) References Cited

OTHER PUBLICATIONS

Chen et al., "An Antibody to β Amyloid Precursor Protein Inhibits Cell-substratum Adhesion in Many Mammalian Cell Types," *Neuroscience Letters*, 125:223-226 (1991).
Chishti et al., "Early-onset Amyloid Deposition and Cognitive Deficits in Transgenic Mice Expressing a Double Mutant Form of Amyloid Precursor Protein 695," *J. Biol.Chem.*, 276(24):21562-70 (2001).
Chothia et al., "Domain Association in Immunoglobulin Molecules," *J. Mol. Biol.*, 186:651-663 (1985).
Chromy et al., "Self-assembly of Aβ(1-42) into globular neurotoxins," *Biochemistry*, 42(44):12749-12760 (2003).
Chung et al., "Uptake, Degradation, and Release of Fibrillar and Soluble Forms of Alzheimer's Amyloid β-Peptide by Microglial Cells," *J. Biol. Chem.*, 274(45):32301-32308 (1999).
Cirrito et al., "Amyloid β and Alzheimer disease therapeutics: the devil may be in the details," *J. Clin. Invest.*, 112:321-323 (2000).
Citron et al., "Evidence that the 42- and 40-amino acid forms of amyloid-β protein are generated from the β-amyloid precursor protein by different protease activities," *PNAS*, 93(23):13170-13175 (1996).
Citron, M., "Alzheimer's disease: treatments in discovery and development," *Nat. Neurosci.*, 5:1055-1057 (2002).
Clayton et al., "Synucleins in Synaptic Plasticity and Neurodegenerative Disorders," *J. Neurosci. Res.*, 58:120-129 (1999).
Co et al., "Chimeric and humanized antibodies with specificity for the CD33 antigen," *J. Immunol.*, 148:1149-1154 (1992).
Coico et al., *Immunology A Short Course, Fifth Edition*, pp. 18-24 (2003).
Colman, "Effects of Amino Acid Sequence Changes on Antibody-Antigen Interactions," *Research in Immunology*, 145:33-36 (1994).
Coloma et al., "Transport Across the Primate Blood-Brain Barrier of a Genetically Engineered Chimeric Monoclonal Antibody to the Human Insulin Receptor," *Pharm. Res.*, 17:266-274 (2000).
Colombian Patent Application No. 98071271, Technical Opinion of Jean Paul Vemot submitted on Jun. 22, 2005 as evidence with the brief amending the nullity action (with English translation) (drafted Nov. 2004).
Comery et al., "Passive Immunization Against β-Amyloid Leads to Acute Cognition Improvement," *Society for Neuroscience*, abstract, Washington DC, 11/12-16/05.
Conway et al., "Acceleration of oligomerization, not fibrillization, is a shared property of both α-synuclein mutations linked to early-onset Parkinson's disease: Implications for pathogenesis and therapy," *PNAS*, 97(2):571-576 (2000).
Cordell, B., "β-Amyloid formation as a potential therapeutic target for Alzheimer's disease," *Ann. Rev. Pharmacol. Toxicol.*, 34:69-89 (1994).
Corey-Bloom et al., "Clinical features distinguishing large cohorts with possible AD, probable AD, and mixed dementia," *J. Am. Geriatr. Soc.*, 41(1):31-37 Abstract (1993).
Costa et al., "Immunoassay for transthyretin variants associated with amyloid neuropathy," *Scand. J. Immunol.*, 38:177-182 (1993).
Cox et al., "Adjuvants—a classification and review of their modes of action," *Vaccine*, 15(3):248-256 (1997).
Cribbs et al, "All-D-Erantiomers of Beta-Amyloid Exhibit Similar Biological Properties to All-L-Beta-Amyloids," *J. Biol. Chem.*, 272:7431-7436 (1997).
Daly, et al., "Detection of the membrane-retained carboxy-terminal tail containing polypeptides of the amyloid precursor protein in tissue from Alzheimer's Disease brain," *Life Sci.*, 63:2121-2131 (1998).
Das et al., "Amyloid-β Immunization Effectively Reduces Amyloid Deposition in FcRγ Knock-Out-Mice," *J. Neuroscience*, 23(24):8532-8538 (2003).
Das et al., "Reduced effectiveness of Aβ-42 immunization in APP transgenic mice with significant amyloid deposition," *Neurobiology of Aging*, 22:721-727 (2001).
Davis, S. S., "Nasal Vaccines," *Advanced Drug Delivery Reviews*, 51:21-42 (2001).

De Felice et al., "β-Amyloid production, aggregation, and clearance as targets for therapy in Alzheimer's disease," *Cell Mol. Neurobiol.*, 22(5/6):545-563 (2002).
De La Cruz et al, "Immumogenicity [sic] and Epitope Mapping of Foreign Sequences via Genetically Engineered Filamentous Phage," *J Biol Chem*, 263(9):4318-4322 (1988).
De Lustig et al., "Peripheral Markers and Diagnostic Criteria in Alzheimer's Disease: Critical Evaluations," *Rev. in Neurosciences*, 5:213-225 (1994).
Demattos et al., "Peripheral anti-Aβ antibody alters CNS and plasma clearance and decreases Aβ burden in a mouse model of Alzheimer's disease," *PNAS*, 98(15):8850-8855 (2001).
Demattos et al., "Peripheral Anti Aβ Antibody Alters CNS and Plasma Aβ Clearance and Decreases Brain Aβ Burden in a Mouse Model of Alzheimer's Disease," published online before print Jul. 3, 2001 at 10.1073/pnas.151261398; *PNAS*, 98(15):8850-8855 (2001).
Demattos et al., "Plaque-associated disruption of CSF and plasma amyloid-β (Aβ) equilibrium in a mouse model of Alzheimer's disease," *J. Neurochem.*, 81:229-236 (2002).
Demattos et al., "Brain to plasma amyloid-β efflux: a measure of brain amyoid burden in a mouse model of Alzheimer's disease," *Science*, 295(5563):2264-2267 (2002).
Dewitt et al., "Astrocytes regulate microglial phagocytosis of senile plaque cores of Alzheimer's disease," *Experimental Neurology*, 149:329-340 (1998).
Dialog/Derwent, Abstract of WPI Acc No. 1997-054436/199706: Stable vaccine compsns.—comprise a macrocyclic lactone, a milbemycin, an avermectin, an antigen, a dispersing agent, an adjuvant, a water sol. organic solvent and saline or water, Derwent File 351: Derwent WPI database (1997).
Dickey et al., "Duration and specificity of humoral immune responses in mice vaccinated with the Alzheimer's disease-associated β-amyloid 1-42 peptide," *DNA and Cell Biology*, 20(11):723-729 (2001).
Dickson et al., "Neuroimmunology of Alzheimer's disease: a conference report," *Neurobiology of Aging*, 13(6):793-798 (1992), abstract only.
Dictionary.com definition of "prophylactic", pp. 1-3 downloaded from internet Oct. 12, 2005.
Di Martino et al., "Production and Characterization of Antibodies to Mouse Scrapie-Amyloid Protein Elicited by Non-carrier Linked Synthetic Peptide Immunogens," *J. Molecular Recognition*, 4(2-3):85-91 (1991).
Diomede et al., "Activation effects of a prion protein fragment [PrP-(106-126)] on human leucocytes," *Biochem. J.*, 320:563-570 (1996).
Disis et al., "Granulocyte-macrophage colony-stimulating factor: An effective adjuvant for protein and peptide-based vaccines," *Blood*, 88(1):202-210 (1996).
Dodart, "Immunotherapy for Alzheimer's disease: will vaccination work?," *Trends in Molecular Medicine*, 9(3):85-87 (2003).
Dodart et al., "Immunization reverses memory deficits without reducing brain Aβ burden in Alzheimer's disease model," *Nat. Neurosci.*, 5(5):452-457 (2002).
Dodel et al., "Immunotherapy for Alzheimer's disease," *Lancet Neurol.*, 2(4):215-220.
Doerks et al., "Protein annotation: detective work for function prediction," *Trends in Genetics*, 14(6):248-250 (1998).
Dovey et al., "Functional gamma-secretase inhibitors reduce beta-amyloid peptide levels in brain," *J. Neurochem.*, 76(1):173-181 (2001).
Drew et al., "Vaccination by cholera toxin conjugated to a herpes simplex virus type 2 glycoprotein D peptide," *Journal of General Virology*, 73:2357-2366 (1992).
Du et al., "Reduced levels of amyloid beta-peptide antibody in Alzheimer disease," *Neurology*, 57(5):801-5 (2001).
Du et al., "$\alpha_2$-Macroglobulin as a β-Amyloid Peptide-Binding Plasma Protein," *J. Neurochemistry*, 69(1):299-305 (1997).
Duff et al., "Mouse model made," *Nature*, 373:476-477 (1995).
Duff et al., "Increased amyloid-β42(43) in brains of mice expressing mutant presenilin 1," *Nature*, 383(6602):710-713 (1996).
Dumery et al., "β-Amyloid protein aggregation: its implication in the physiopathology of Alzheimer's disease," *Pathol. Biol.*, 49:72-85 (2001).

(56) References Cited

OTHER PUBLICATIONS

Eck et al., *Goodman and Gilman's The pharmacological basis of therapeutics*, Chapter 5, pp. 77-101 (1996).
Ecuador Patent Application No. SP 98/2764, English translation of Expert Report submitted Apr. 19, 2007 in support of the Appeal filed on Jul. 29, 2005.
El-Agnaf et al., "The influence of the central region containing residues 19-25 on the aggregation properties and secondary structure of Alzheimer's beta-amyloid peptide," *Eur. J. Biochem.*, 256(3):560-569 (1998).
Elan, "Elan and AHP Provide an Update on the Phase 2A Clinical Trial of AN-1792," Press Release. (Jan. 18, 2002).
Elan, "Elan and Wyeth Provide Update on Status of Alzheimer's Collaboration," Press Release (Mar. 1, 2002).
Elizan et al., "Antineurofilament antibodies in a postencephalitic and idiopathic Parkinson's disease," *J. Neurol. Sciences*, 59:341-347 (1983).
Eriksen et al., "NSAIDs and enantiomers of flurbiprofen target γ-secretase and lower Aβ42 in vivo," *J. Clin. Invest.*, 112(3):440-449 (2003).
Esiri, "Is an effective immune intervention for Alzheimer's disease in prospect?", *Trends in Pharm, Sci.*, 22:2-3 (2001).
Esler et al., "Point substitution in the central hydrophobic cluster of a human β-amyloid congener disrupts peptide folding and abolishes plaque competence," *Biochemistry*, 35:13914-13921 (1996).
European Search Report of May 22, 2006 for European Application 06075704.4-2107.
European Search Report of May 22, 2006 for European Application 06075479.3-2107.
European Search Report of Jan. 16, 2007 for European Application 04776252.1-2405.
European Examination Report of Mar. 9, 2007 for European Application 01995364.5-1222.
European Examination Report of Sep. 26, 2007 for European Application 04720353.4-1222.
European Examination Report of Oct. 8, 2007 for European Application 01995364.5-1222.
Felsenstein et al., "Processing of the β-amyloid precursor protein carrying the familial, Dutch-type, and a novel recombinant C-terminal mutation," *Neuroscience Letters*, 152:185-189 (1993).
Felsenstein et al., "Transgenic Rat and In-Vitro Studies of B-Amyloid Precursor Protein Processing;" *Alzheimer's and Parkinson's Diseases*, Hanin et al. Ed., pp. 401-409, Plenum Press, New York, (1995).
Finch et al., "Evolutionary Perspectives on Amyloid and Inflammatory Features of Alzheimer Disease," *Neurobiology of Aging*, 17(5):809-815 (1996).
Findeis et al, "Modified peptide inhibitors of amyloid B-peptide polymerization," *Biochemistry*, 38:6791-6800 (1999).
Findeis, M. A., "Approaches to discovery and characterization of inhibitors of amyloid β-peptide polymerization," *Biochem. Biophys. Acta*, 1502(1):76-84 (2000).
Fisher et al., "Expression of the amyloid precursor protein gene in mouse oocytes and embryos," *PNAS*, 88:1779-1782 (1991).
Flanders et al., "Altered expression of transforming growth factor-β in Alzheimer's disease," *Neurology*, 45:1561-1569 (1995).
Flood et al., "An amyloid β-Protein fragment, A β [12-28J, equipotently impairs post-training memory processing when injected into different limbic system structures," *Brain Res*, 663(2):271-276 (1994).
Flood, et al, "Topography of a binding site for small amnestic peptides deduced from structure-activity studies: Relation to amnestic effect of amyloid B protein," *PNAS*, 91:380-384 (1994).
Fonseca et al., "The Presence of Isoaspartic Acid in β-Amyloid Plaques Indicates Plaque Age," *Experimental Neurology*, 157(2):277-288 (1999).
Foote et al., "Antibody Framework Residues Affecting the Conformation of the Hypervariable Loops," *J. Mol. Biol.*, 224:487-499 (1992).

Fox et al., "Presymptomatic cognitive deficits in individuals at risk of familial Alzheimer's disease," *Brain*, 121:1631-1639 (1998).
Frautschy et al., "Effects of injected Alzheimer β-amyloid cores in rat brain," *PNAS*, 88:8362-8366 (1991).
Frazer et al., "Immunoglobulins: Structure and Function," chapter 3, pp. 37-74 from *Fundamental Immunology, fourth edition*, W.E. Paul, eds., Lippincott-Raven publishers, Philadelphia (1999).
Frenkel et al., "Generation of auto-antibodies towards Alzheimer's disease vaccination," *Vaccine*, 19:2615-2619 (2001).
Frenkel et al., "High affinity binding of monoclonal antibodies to the sequential epitope EFRH of β-amyloid peptide is essential for modulation of fibrillar aggregation," *J. of Neuroimmunology*, 95:136-142 (1999).
Frenkel et al., "Immunization against Alzheimer's β-amyloid plaques via EFRH phage administration," *PNAS*, 97:11455-11459 (2000).
Frenkel et al., "N-terminal EFRH sequence of Alzheimer's β-amyloid peptide represents the epitope of its anti-aggregating antibodies," *J. of Neuroimmunology*, 88:85-90 (1998).
Frenkel, et al., "Modulation of Alzheimer's β-amyloid neurotoxicity by site-directed single chain antibody," *J. of Neuroimmunoloqy*, 106:23-31 (2000).
Frenkel et al., "Reduction of β-amyloid plaques in brain of transgenic mouse model of Alzheimer's disease by EFRH-phage immunization," *Vaccine*, 21(11-12):1060-1065 (2003).
Frenkel et al., "Towards Alzheimer's β-amyloid vaccination," *Biologicals*, 29(3-4):243-247 (2001).
Friedland et al., "Development of an anti-Aβ monoclonal antibody for in vivo imaging of amyloid angiopathy in Alzheimer's disease," *Mol. Neurology*, 9:107-113 (1994).
Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York (1997).
Fukutani et al., "Cerebeller pathology in sporadic and familial Alzheimer's disease including APP 717 (Val->lle) mutation cases: A morphometric investigation," *J. Neurologic Sci.*, 149:177-184 (1997).
Furlan et al., "Vaccination with amyloid-β peptide induces autoimmune encephalomyelitis in C57/BL6 mice," *Brain*, 126:285-291 (2003).
Games et al., "Alzheimer-type neuropathology in transgenic mice overexpressing V717F β-amyloid precursor protein," *Nature*, 373(6514):523-527 (1995).
Games et al., "Prevention and Reduction of AD-type Pathology in PDAPP Mice Immunized with Aβ$_{1-42}$," *Annals of the New York Academy of Science*, 920:274-284 (2000).
Gandy et al., "Amyloidogenesis in Alzheimer's disease: some possible therapeutic opportunities," *TiPS*, 13:108-113 (1992).
Gardella et al., "Intact Alzheimer amyloid precursor protein (APP) is present in platelet membranes and is encoded by platelet mRNA," *Biochem. Biophys. Res. Comm.*, 173:1292-1298 (1990).
Gaskin et al., "Human antibodies reactive with beta-amyloid protein in Alzheimer's disease," *J. Exp. Med.*, 177:1181-1186 (1993).
Geddes, "N-terminus truncated β-amyloid peptides and C-terminus truncated secreted forms of amyloid precursor protein: distinct roles in the pathogenesis of Alzheimer's disease," *Neurobiology of Aging*, 20:75-79 (1999).
Gelinas et al., "Immunotherapy for Alzheimer's disease," *PNAS*, 101(suppl. 2):14657-14662 (2004).
Genbank Accession No. AAB48800, "Anti-DNA immunoglobulin light chain IgG [*Mus musculus*]," Sep. 14, 2001.
Genbank Accession No. CAA46659, "IgE antibody light chain(VJ)," Jun. 15, 1993.
Genbank Accession No. X65775.1, "*M. musculus* DNA for IgE antibody light chain (VJ)," Jun. 15, 1993.
Genbank Accession No. AAD26773, "Immunoglobulin heavy chain VH3609-JH3 region [*Mus musculus*]," Apr. 22, 1999.
Geylis et al., "Immunotherapy of Alzheimer's disease 9AD): From murine models to anti-amyloid beta 9Ab) human monodonal antibodies," *Autoimmunity Rev.*, 5:33-39 (2000).

(56) References Cited

OTHER PUBLICATIONS

Ghiso et al., "Epitope map of two polyclonal antibodies that recognize amyloid lesions in patients with Alzheimer's disease," *Biochem. J.*, 282 (Pt 2):517-522 (1992).
Gibson et al., "Abnormalities in Alzheimer's Disease Fibroblasts Bearing the APP670/671 Mutation," *Neurobiology of Aging*, 18(6):573-580 (1997).
Gilman, S. et al., "Clinical Effects of Aβ Immunization (AN1792) in Patients with AD in an Interrupted Trial," *Neurology*, 64:1553-1562 (2005).
Giulian et al., "Specific domains of β-amyloid from Alzheimer plaque elicit neuron killing in human microglia," *J Neurosci.*, 16 (19):6021-6037 (1996).
Giulian, et al., "The HHQK Domain of b-Amyloid Provides a Structural Basis for the Immunopathology of Alzheimer's Disease," *J. Biol. Chem..*, 273:29719-29726 (1998).
Glenn et al., "Skin immunization made possible by cholera toxin," *Nature*, 391:851 (1998).
Glenner et al., "Alzheimer's Disease and Downs Syndrome: Sharing of a Unique Cerebrovascular Amyloid Fibril Protein," *Biochem. Biophys. Res. Comm.*, 122(3): 1131-1135 (1984).
Glenner et al., "Alzheimer's Disease: Initial Report of the Purification and Characterization of a Novel Cerebrovascular Amyloid Protein," *Biochem. Biophys. Res. Comm.*, 120(3): 885-890 (1994).
Goate et al., "Segregation of a missense mutation in the amyloid precursor protein gene with familial Alzheimer's disease," *Nature*, 349:704-706 (1991).
Goldfarb et al., "The Transmissible Spongiform Encephalopathies," *Ann. Rev. Med.*, 46:57-65 (1995).
Goldsby et al., "Vaccines," Chapter 18 from *Immunology, 4th Edition*, W.H. Freeman and Company, New York, pp. 449-465 (2000).
Goldsteins et al., "Exposure of cryptic epitopes on transthyretin only in amypoid and in amyloidogenic mutants," *PNAS*, 96:3108-3113 (1999).
Gong et al., "Alzheimer's disease-affected brain: presence of oligomeric Aβ ligands (ADDLs) suggests a molecular basis for reversible memory loss," *PNAS*, 100(18)10417-10422 (2003).
Gonzales-Fernandez et al., "Low antigen dose favors selection of somatic mutants with hallmarks of antibody affinity maturation," *Immunology*, 93:149-153 (1998).
Gorevic et al., "Ten to fourteen residue peptides of Alzheimer's disease protein are sufficient for amyloid fibril formation and its characteristic X ray diffraction pattern" *Biochem. and Biophy. Res. Commun.*, 147(2):854-862 (1987).
Gortner, *Outlines of Biochemistry*, pp. 322-323, John Wiley & Sons, Inc., New York (1949).
Gozes et al., "Neuroprotective strategy for Alzheimer disease: Intranasal administration of a fatty neuropeptide," *PNAS*, 93:427-432 (1996).
Gravina et al., "Amyloid β Protein (Aβ) in Alzheimer's Disease," *J. Biol. Chem.*, 270(13):7013-7016 (1995).
Greenberg et al., "Alzheimer disease's double-edged vaccine," *Nat. Med.*, 9(4):389-390.
Gross et al., "Microvascular specializations promoting rapid interstitial solute dispersion in nucleus tractus solitarius," *Am J Physiol Regul Integr Comp Physiol*, 259:R1131-R1138 (1990).
Grubeck-Loebenstein, et al., "Immunization with β-amyloid: could T-cell activation have a harmful effect?", *TINS*, 23:114 (2000).
Gupta et al., "Adjuvants for human vaccines—current status, problems, and future prospects," *Vaccine*, 13(14):1263-1275 (1995).
Gupta et al., "Differences in the immunogenicity of native and formalized cross reacting material (CRM197) of diptheria toxin in mice and guinea pigs and their implications on the development and control of diphtheria vaccine based on CRMs," *Vaccine*, 15(12/13): 1341-1343 (1997).
Haass et al. "Amyloid beta-peptide is produced by cultured cells during normal metabolism," *Nature*, 359(6393):322-325 (1992).
Haass et al., "Protofibrils, the unifying toxic molecule of neurodegenerative disorders?," *Nature Neuroscience*, 4(9):859-860 (2001).

Haass, C., "New hope for Alzheimer disease vaccine," *Nat Med.*, 8(11):1195-1196 (2002).
Haga et al., "Synthetic Alzheimer amyloid β/A4 peptides enhance production of complement C3 component by cultured microglial cells," *Brain Research*, 601:88-94 (1993).
Hanan and Solomon, "Inhibitory effect of monoclonal antibodies on Alzheimer's β-amyloid peptide aggregation," *Int. J. Exp. Clin. Invest.*, 3:130-133 (1996).
Hanes et al., "New advances in microsphere-based single-dose vaccines," *Advanced Drug Delivery Reviews*, 28: 97-119 (1997).
Hara et al., "Development of a safe oral Aβ vaccine using recombinant adeno-associated virus vector for Alzheimer's disease," *J. Alzheimer's Disease*, 6:483-488 (2004).
Hardy, "Amyloid, the presenilins and Alzheimer's disease," *TINS*, 20(4): 154-159 (1997).
Hardy, John, "New Insights into the Genetics of Alzheimer's Disease," *Annals of Med.*, 28:255-258 (1996).
Harigaya, et al., "Modified amyloid β protein ending at 42 or 40 with different solubility accumulates in the brain of Alzheimer's disease," *Biochem. Biophys. Res. Comm.*, 211:1015-1022 (1995).
Harlow et al., eds., *Antibodies: A Laboratory Manual*, pp. 71-82 (1998).
Harlow et al., eds., *Antibodies: A Laboratory Manual*, p. 98 (1998).
Harrington et al., "Characterization of an epitope specific to the neuron-specific isoform of human enolase recognized by a monoclonal antibody raised against a synthetic peptide corresponding to the C-terminus of β / A4-protein," *Biochimica Biophysica Acta*, 1158:120-128 (1993).
Hazama, et al., "Intranasal Immunization Against Herpes Simplex Virus Infection by Using a Recombinant Glycoprotein D Fused With Immunomodulating Proteins, the B Subunit of *Escherichia coli* Heat-Labile Enterotoxin and Interleukin-2," *Immunology*, 78:643-649 (1993).
He et al., "Humanization and pharmacokinetics of a monoclonal antibody with specificity for both E- and P-selectin," *J. Immunol*, 160:1029-1035 (1998).
Helmuth, "Further Progress on a β-Amyloid Vaccine," *Science*, 289:375 (2000).
Herlyn et al., "Monoclonal antibodies in cell-mediated cytotoxicity against human melanoma and colorectal carcinoma*," *Eur. J. Immunol.*, 9:657-659 (1979).
Hilbich et al., "Aggregation and secondary structure of synthetic amylold βA4 peptides of Alzheimer's disease," *J. Mol. Biol.*, 218:149-163 (1991).
Hilbich et al., "Substitutions of hydrophobic amino acid reduce the amyloidogenicity of Alzheimer's disease βA4 peptides" *J. Mol. Biol.*, 228:460-473 (1992).
Hilbich et al., "Human and rodent sequence analogs of Alzheimer's amyloid βA4 share similar properties and can be solubilized in buffers of pH 7.4," *Eur. J. Biochem.*, 201:61-69 (1991).
Hirschfield et al., "Amylodiosis: new strategies for treatment," *Int. J. Biochem. & Cell Biol.*, 35:1608-1613 (2003).
Hock et al., "Antibodies against β-Amyloid Slow Cognitive Decline in Alzheimer's Disease," *Neuron*, 38:542-554 (2003).
Hock et al., "Generation of antibodies specific for β-amyloid by vaccination of patients with Alzheimer disease," *Nat. Med.*, 8(11):1270-1275 (2002).
Holtzman et al., "Aβ immunization and anti-Aβ antibodies: potential therapies for the prevention and treatment of Alzheimer's disease," *Advanced Drug Delivery Reviews*, 54:1603-1613 (2002).
Hsiao et al., "Correlative Memory Deficits, Aβ Elevation, and Amyloid Plaques in Transgenic Mice," *Science*, 274: 99-102 (1996).
Huberman et al., "Correlation of cytokine secretion by mononuclear cells of Alzheimer's patients and their disease stage," *J. Neuroimmunology*, 52:147-152 (1994).
Human Immunology & Cancer Program brochure, from The University of Tennessee Medical Center/ Graduate School of Medicine, Knoxville, Tennessee (publication date unknown).
Hyman et al., "Molecular Epidemiology of Alzheimer's Disease," *N. E. J. Medicine*, 333(19):1283-1284 (1995).
Ida et al., "Analysis of Heterogeneous βA4 Peptides in Juman Cerebrospinal Fluid and Blood by a Newly Developed Sensitive Western Blot Assay," *J. Biol. Chem.*, 271(37):22908-22914 (1996).

(56) References Cited

OTHER PUBLICATIONS

Idusogie et al., "Mapping of the C1q Binding Site on Rituxan, a Chimeric Antibody with a Human IgG1 Fc," *J. Immunology*, 164:4178-4184 (2000).
Ikeda, et al., "Immunogold labeling of cerebrovascular and neuritic plaque amyloid fibrils in Alzheimer's disease with an anti-β protein monoclonal antibody," *Lab. Invest.*, 57:446-449 (1987).
Irizarry et al., "Aβ Deposition is Associated with Neuropil Changes, but not with Overt Neuronal Loss in the Human Amyloid Precursor Protein V717F (PDAPP) Transgenic Mouse," *J. Neuroscience*, 17(18):7053-7059 (1997).
Irizarry et al., "Alzheimer disease therapeutics," *J. Neuropathol. Exp. Neurol.*, 60(10):923-928 (2001).
Itagaki et al., "Relationship of microglia and astrocytes to amyloid deposits of Alzheimer's disease," *J. Neuroimmunology*, 24:173-182 (1989).
Iwatsubo et al., "Visualization of Aβ42(43) and Aβ40 in Senile Plaques with End-Specific Aβ Monoclonals: Evidence That an Initially Deposited Species Is Aβ 42(43)," *Neuron*, 13:45-53 (1994).
Jahrling et al., "Opsonization of Alphaviruses in Hamsters," *J. Medical Virology*, 12:1-16 (1983).
Jakes et al., "Characterisation of an Antibody Relevant to the Neuropathology of Alzheimer Disease," *Alzheimer Disease and Associated Disorders*, 9(1):47-51 (1995).
Jansen et al., "Immunotoxins: Hybrid Molecules Combining High Specificity and Potent Cytotoxicity," *Immun. Rev.*, 62: 185-216 (1982).
Jansen et al., "Use of Highly Encapsulated *Streptococcus pneumoniae* Strains in a Flow-Cytometric Assay for Assessment of the Phagocytic Capacity of Serotype-Specifid Antibodies," *Clinical & Diagnostic Lab. Immunol.*, 5(5):703-710 (1998).
Janus et al., "A beta peptide immunization reduces behavioural impairment and plaques in a model of Alzheimer's disease," *Nature*, 408(6815):979-982 (2000).
Janus et al., "Transgenic mouse models of Alzheimer's Disease," *Physiol. Behav.*, 73(5):873-886 (2001).
Jen, et al., "Preparation and purification of antisera against different regions or isoforms of b-amyloid precursor protein," *Brain Research Protocols*, 2:23-30 (1997).
Joachim et al., "Antibodies to Non-beta Regions of the Beta-amyloid Precursor Protein Detect a Subset of Senile Plaques," *Am. J. of Pathology*, 138:373-384 (1991).
Jobling et al., "Analysis of structure and function of the B subunit of cholera toxin by the use of site-directed mutagenesis," *Molecular Microbiology*, 5(7):1755-1767 (1991).
Johnson-Wood et al., "Amyloid precursor protein processing and Aβ$_{42}$ deposition in a transgenic mouse model of Alzheimer disease," *PNAS*, 94:1550-1555 (1997).
Johnstone et al., Nuclear and Cytoplasmic Localization of the β-Amyloid Peptide (1-43) in Transfected 293 Cells, *Biochem. Biophys. Res. Comm.*, 220:710-718 (1996).
Jorbeck et al., "Artificial *Salmonella* Vaccines: *Salmonella typhimurium* O-antigen-Specific Oligosaccharide-Protein Conjugates Elicit Opsonizing Antibodies that Enhance Phagocytosis," *Infection and Immunity*, 32(2):497-502 (1981).
Jung et al., "Alzheimer's Beta-amyloid Precursor Protein is Expressed on the Surface of Immediately Ex Vivo Brain Cells: a Flow Cytometric Study," *J. Neurosci. Res.*, 46(3):336-348 (1996).
Kajkowski et al., "β-Amyloid Peptide-induced Apoptosis Regulated by a Novel Protein Containing a G Protein Activation Module," *J. Biol. Chem.*, 276(22):18748-18756 (2001).
Kalaria, R. N., "Serum amyloid P and related molecules associated with the acute-phase response in Alzheimer's disease," *Res. Immunology*, 143:637-641 (1992).
Kalback et al., "APP Transgenic Mice Tg2576 Accumulate Aβ Peptides That Are Distinct from the Chemically Modified and Insoluble Peptides Deposited in Alzheimer's Disease Senile Plaques," *Biochemistry*, 41:922-928 (2002).

Kascsak et al., "Mouse Polyclonal and Monoclonal Antibody to Scrapie-Associated Fibril Proteins," *J. Virology*, 61(12):3688-3693 (1987).
Katzav-Gozansky et al., "Effect of monoclonal antibodies in preventing carboxypeptidase A aggregation," *Biotechnol. Appl. Biochem.*, 23:227-230 (1996).
Kawabata et al., "Amyloid plaques, neurofibrillary tangles and neuronal loss in brains of transgenic mice overexpressing a C-terminal fragment of human amyloid precursor protein," *Nature*, 354:476-478 (1991).
Kayed et al., "Conformational Transitions of Islet Amyloid Polypeptide (IAPP) in Amyloid Formation In Vitro," *J. Mol. Biol.*, 287:781-796 (1999).
Kelly, J. W., "Alternative conformations of amyloidogenic proteins govern their behavior," *Current Opinion in Structural Biology*, 6:11-17 (1996).
Kettleborough et al., "Humanization of a mouse monoclonal antibody by CDR-grafting: the importance of framework residues on loop conformation," *Protein Engineering*, 4(7):773-783 (1991).
Khatoon et al., "Levels of normal and abnormally phosphorylated tau in different cellular and regional compartments of Alzheimer's disease and control brains," *FEBS Letters*, 351:80-84 (1994).
Kida, et al., "Early amyloid-β deposits show different immunoreactivity to the amino- and carboxy-terminal regions of b-peptide in Alzheimer's disease and Down's syndrome brain," *Neuroscience Letters*, 193:105-108 (1995).
Kimchi et al., "Analysis of cerebral amyloid angiopathy in a transgenic mouse model of Alzheimer disease using in vivo multiphoton microscopy," *J. Neuropath Exp. Neurol.*, 60(3):274-279 (2001).
Klein et al., "Targeting small Aβ oligomers: the solution to an Alzheimer's disease conundrum?," *Trends in Neurosciences*, 24(4):219-224 (2001).
Klyubin et al., "Anti-Aβ Antibodies Prevent Block of Long-Term Potentiation in the CA1 Area of Rat Hippocampus InVivo by naturally Produced Aβ Oligomers," *Neurobiology of Aging*, 25:S224-S225, abstract P2-004, pp. S224-S225 (2004).
Kofler et al., "Mechanism of Allergic Cross-Reactions—III. cDNA Cloning and Variable-Region Sequence Analysis of Two IgE Antibodies Specific for Trinitrophenyl," *Mol. Immunology*, 29(2):161-166 (1992).
Kofler et al., "Immunoglobulin $_k$ Light Chain Variable Region Gene Complex Organization and Immunoglobulin Genes Encoding Anti-DNA Autoantibodies in Lupus Mice," *J. Clin. Invest.*, 82:852-860 (1988).
Konig et al., "Development and Characterization of a Monoclonal Antibody 369.2B Specific for the Carboxyl-Terminus of the βA4 Peptide," *Annals of NY Acad. Sci.*, 777:344-355 (1996).
Kotilinek et al., "Reversible memory loss in a mouse transgenic model of Alzheimer's disease," *J. Neurosci.*, 22(15):6331-6335 (2002).
Koudinov et al., "The soluble form of Alzheimer's amyloid beta protein is complexed to high density lipoprotein 3 and very high density lipoprotein in normal human plasma," *Biochem. & Biophys. Res. Comm*, 205:1164-1171 (1994).
Kovács et al., "Mutations of the Prion Protein Gene Phenotypic Spectrum," *J. Neurol.*, 249:1567-1582 (2002).
Krishnan et al., "Correlation Between the Amino Acid Position of Arginine in VH-CDR3 and Specificity for Native DNA Among Autoimmune Antibodies[1,2]," *J. Immunol.*, 157(6):2430-2439 (1996).
Kuby, J., eds., p. 123 from *Immunology, Third Edition*, W.H. Freeman & co., (1997).
Kuby, J., eds., pp. 108-109, 131-132 from *Immunology, Third Edition*, W.H. Freeman & co., (1997).
Kuo et al., "High levels of circulating Abeta42 are sequestered by plasma proteins in Alzheimer's disease," *Biochem. Biophys. Res. Comm.*, 257(3):787-791 (1999).
Kuo et al., "Water-soluble Aβ (N-40, N-42) Oligomers in Normal and Alzheimer Disease Brains," *J. Biol. Chem.*, 271(8):4077-4081 (1996).

(56) References Cited

OTHER PUBLICATIONS

Kuo et al., "Comparative Analysis of Amyloid-β Chemical Structure and Amyloid Plaque Morphology of Transgenic Mouse and Alzheimer's Disease Brains," *J. Biol. Chem.*, 276(16):12991-12998 (2001).
Kurashima et al., "Production of Monoclonal Antibody against Amyloid Fibril Protein and its Immunohistochemical Application," *Appl. Pathol.*, 3(1-2):39-54 (1985).
LaDu et al., "Isoform-specific Binding of Apolipoprotein E to β-Amyloid," *J. Biol. Chem.*, 269(38):23403-23406 (1994).
Lambert et al., "Diffusible, nonfibrillar ligands derived from Aβ1-42 are potent central nervous system neurotoxins," *PNAS*, 95:6448-6453 (1998).
Lambert et al., "Vaccination with soluble Aβ oligomers generates toxicity-neutralizing antibodies," *J. Neurochem.*, 79:595-605 (2001).
Lampert-Etchells et al., "Regional Localization of Cells Containing Complement C1q and C4 mRNAs in the Frontal Cortex During Alzheimer's Disease," *Neurodegeneration*, 2:111-121 (1993).
Landolfi et al., "The Integrity of the Ball-and Socket Joint Between V and C Domains is Essential for Complete Activity of a Humanized Antibody," *J. Immunology*, 166(3):1748-1754 (2001).
Langer, "New Methods of Drug Delivery," *Science*, 249:1527-1532 (1990).
Lannfelt et al., "Alzheimer's disease: molecular genetics and transgenic animal models," *Behavioural Brain Res.*, 57:207-213 (1993).
Lansbury, Peter T., "Inhibition of amyloid formation: a strategy to delay the onset of Alzheimer's disease," *Curr. Ops. in Chemical Biology*, 1:260-267 (1997).
Lavie et al., "EFRH-Phage Immunization of Alzheimer's Disease Animal Model Improves Behavioral Performance in Morris Water Maze Trials," *J. Molecular Neuroscience*, 24:105-113 (2004).
Lee et al., "Aβ immunization: Moving Aβ peptide from brain to blood," *PNAS*, 98(16):8931-8932 (2001).
Lemere et al., "Mucosal Administration of Aβ Peptide Decreases Cerebral Amyloid Burden in Pd-App Transgenic Mice," *Society for Neuroscience Abstracts*, 25(part )I, Abstract 519.6, 29th Annual Meeting, (Oct. 23-28, 1999).
Lemere, et al., "Nasal Aβ treatment induces anti-Aβ antibody production and decreases cerebral amyloid burden in PD-APP mice," *Annals of the NY Acad. Sci.*, 920:328-331 (2000).
Lemere et al., "Intranasal immunotherapy for the treatment of Alzheimer's disease: *Escherichia coli* LT and LT(R192G) as mucosal adjuvants," *Neurobiology of Aging*, 23(6):991-1000 (2002).
Leverone et al., "Aβ1-15 is less immunogenic than Aβ1-40/42 for intranasal immunization of wild-type mice but may be effective for 'boosting'," *Vaccine*, 21:2197-2206 (2003).
Levitt, M., "Molecular dynamics of native protein," *J. Mol . Biol.*, 168:595-620 (1983).
Levey, A. I., "Immunization for Alzheimer's disease: A shot in the arm or a whiff?," *Ann. Neurology*, 48(4):553-555 (2000).
Li et al., "Thermal Stabilization of Carboxypeptidase A as a Function of PH and Ionic Milieu," *Biochem. Mol. Biol. Int.*, 43(3):601-611 (1997).
Licastro et al., "Is immunotherapy an effective treatment for Alzheimer's disease?," *Immunity & Aging*, 1:1-2 (2004).
Linke, "Monoclonal antibodies against amyloid fibril protein AA. Production, specificity, and use for immunohistochemical localization and classification of AA-type amyloidosis," *J. Histochemistry and Cytochemistry*, 32(3):322-328 (1982).
Liu et al., "Amyloid β peptide alters intracellular vesicle trafficking and cholesterol homeostasis," *Proc. Natl. Acad. Sci.*, 95:13266-13271 (1998).
Livingston et al., "The Hepatitis B Virus-Specific CTL Responses Induced in Humans by Lipopeptide Vaccination are Comparable to Those Elicited by Acute Viral Infection," *J. Immunol.*, 159:1383-1392 (1997).
Lo et al., "High level expression and secretion of Fc-X fusion proteins in mammalian cells," *Protein Engineering*, 11(6):495-500 (1998).
Lopez et al., "Serum auto-antibodies in Alzheimer's disease," *Acta. Neurol. Scand.*, 84:441-444 (1991).
Lue et al., "Soluble β-amyloid Peptide Concentration as a Predictor of Synaptic Change in Alzheimer's Disease," *Am. J. Pathol.*, 155:853-562 (1999).
MacCallum et al., Antibody-antigen Interactions: *Contact Analysis and Binding Site Topography*, 262:732-745 (1996).
Maggio et al., "Brain Amyloid—A Physicochemical Perspective," *Brain Pathology*, 6:147-162 (1996).
Majocha et al., "Development of a Monoclonal Antibody Specific for β/A4 Amyloid in Alzheimer's Disease Brain for Application to In Vitro Imaging of Amyloid Angiopathy," *The J. of Nuclear Med.*, 33:2184-2189 (1992).
Mak, et al., "Polyclonals to b-amyloid (1-42) identify most plaque and vascular deposits in Alzheimer cortex, but not striatum," *Brain Research*, 667:138-142 (1994).
Mamikonyan et al., "Anti-Aβ$_{1-11}$ Antibody Binds to Different β-Amyloid Species, Inhibits Fibril Formation, and Disaggregates Preformed Fibrils but Not the Most Toxic Oligomers," *J Biol Chem*, 282(31) 22376-22386 (2007).
Mandel et al., "Clinical trials in neurological disorders using AAV vectors: promises and challenges," *Curr. Opin. Mol. Ther.*, 6(5):482-490 (2004).
Mann, et al., "Amyloid β protein (Aβ) deposition in chromosome 14-linked Alzheimer's disease: Predominance of Aβ$_{42(43)}$," *Annals of Neurology*, 40:149-156 (1996).
Mann, et al., "The extent of amyloid deposition in brain in patients with Down's syndrome does not depend upon the apolipoprotein E genotype," *Neuroscience Letters*, 196:105-108 (1995).
Manning et al., "Genetic Immunization with Adeno-Associated Virus Vectors Expressing Herpes Simplex Virus Type 2 Glycoproteins B and D," *Journal of Virology*, 71(10):7960-7962 (1997).
Manoj et al., "Approaches to Enhance the Efficacy of DNA Vaccines," *Critical Rev. Clin. Lab. Sci.*, 41(1):1-39 (2004).
Marhaug et al., "Monoclonal hybridoma antibodies to human amyloid related protein SAA," *Clin. Exp. Immunol.*, 50(2):390-396 (1982).
Marotta et al., "Overexpression of amyloid precursor protein A4 (β-amyloid) immunoreactivity in genetically transformed cells: Implications for a cellular model of Alzheimer amyloidosis," *PNAS*, 86:337-341 (1989).
Marshall, E., "Gene Therapy's Growing Pains," *Science*, 269:1050-1055 (1995).
Masliah et al., "Amyloid Protien Precursor Stimulates Excitatory Amino Acid Transport," *The Journal of Biological Chemisrty*, 273(20):12548-12554 (1998).
Masliah et al., "β-Amyloid peptides enhance α-synuclein accumulation and neuronal deficits in a transgenic mouse model linking Alzheimer's disease and Parkinson's disease," *PNAS*, 98(21):12245-12250 (2001).
Masliah et al., "Comparison of Neurodegenerative Pathology in Transgenic Mice Overexpressing V717F β-Amyloid Precursor Protein and Alzheimer's Disease," *J. Neuroscience*, 16(18):5795-5811 (1996).
Masters et al., "Amyloid Plaque core protein in Alzheimer Disease and Down Syndrome," *PNAS*, 82:4245-4249 (1985).
Mattson, "Cellular actions of beta-amyloid precursor protein and its soluble and fibrillogenic derivatives," *Physiol Rev.*, 77(4):1081-132 (1997).
Mattson et al., "Good and bad amyloid antibodies," *Science*, 301(5641):1845-1849 (2003).
Maury et al., "Immunohistochemical Localization of Amyloid in Finnish Hereditary Amyloidosis with Antibodies to Gelsolin Peptides," *Laboratory Investigation*, 64(3):400-404 (1991).
McGee et al., "The encapsulation of a model protein in poly (D, L lactide-co-glycolide) microparticles of various sizes: an evaluation of process reproducibility," *J. Micro. Encap.*, 14(2):197-210 (1997).
McGeer, et al., "Immunohistochemical localization of beta-amyloid precursor protein sequences in Alzheimer and normal brain tissue by light and electron microscopy," *J. of Neuroscience Res.*, 31:428-442 (1992).

(56) References Cited

OTHER PUBLICATIONS

McLaurin et al., "Therapeutically effective antibodies against amyloid-β peptide target amyloid-β residues and 4-10 and inhibit cytotoxicity and fibrillogenesis," *Nat Med.*, 8(11):1263-1269 (2002).
McLean et al., "Soluble pool of Aβ amyloid as a determinant of severity of neurodegeneration in Alzheimer's disease," *Amer. Neurological Assoc*, 46:860-866 (1999).
McNeal et al., "Stimulation of local immunity and protection in mice by intramuscular immunization with triple- or double-layered rotavirus particles and QS-21," *Virology*, 243:158-166 (1998).
Meda et al., "Activation of microglial cells by β-amyloid protein and interferon-γ," *Nature*, 374:647-650 (1995).
Mena, et al., "Monitoring pathological assembly of tau and β-amyloid proteins in Alzheimer's disease," *Acta Neuropathol.*, 89:50-56 (1995).
Merluzzi, et al., "Humanized antibodies as potential drugs for therapeutic use," *Adv Clin Path.*, 4(2):77-85 (2000).
Merriam-Webster online medical dictionary, entry for "cure", accessed Sep. 5, 2006.
Miller et al., "Antigen-driven Bystander Suppression after Oral Administration of Antigens," *J. Exp. Med.*, 174:791-798 (1991).
Monsonego et al., "Immune hyporesponsiveness to amyloid β-peptide in amyloid precursor protein transgenic mice: Implications for the pathogenesis and treatment of Alzheimer's disease," *PNAS*, 98(18):10273-10278 (2001).
Monsonego et al., "Increased T cell reactivity to amyloid β protein in older humans and patients with Alzheimer's disease," *J. Clin. Invest.*, 112(3):415-422 (2003).
Monsonego et al., "Immunotherapeutic approaches to Alzheimer's disease," *Science*, 302(5646):834-838 (2003).
Morgan, et al., "A beta peptide vaccination prevents memory loss in an animal model of Alzheimer's disease," *Nature*, 408(6815):982-985 (2000).
Morgan et al., "The N-terminal end of the $C_H2$ domain of chimeric human IgG1 anti-HLA-DR is necessary for C1q, FcγRII and FcγRII binding," *Immunology*, 86:319-324 (1995).
Mori et al., "Mass Spectrometry of Purified Amyloid β Protein in Alzheimer's Disease," *J. Biol. Chem.*, 267(24):17082-17088 (1992).
Morris, et al., "The Consortium to Establish a registry for Alzheimer's Disease (CERAD)," *Neurology*, 39:1159-1165 (1989).
Munch et al., "Potentional neurotoxic inflammatory response to Aβ vaccination in humans," *J. Neural Transm.*, 109:1081-1087 (2002).
Munson eds., *Principals of Pharmacology: Basic Concepts & Clinical Applications*, pp. 47-48, Chapman & Hall, New York, New York (1995).
Murphy et al., "Development of a Monoclonal Antibody Specific for the COOH-Terminal of β-Amyloid 1-42 and its Immunohistochemical Reactivity in Alzheimer's Disease and Related Disorders," *Am. J. Pathology*, 144(5):1082-1088 (1994).
Mutschler et al., *Drug Actions: Basic Principles and Therapeutic Aspects* pp. 7, 11-12, Medpharm Scientific Publishers, Stuttgart, Germany (1995).
Nakamura et al., "Histopathological studies on senile plaques and cerebral amyloid angiopathy in aged cynomologus monkeys," *Exp. Anim.*, 43:711-718 (1995).
Nakamura, et al., "Carboxyl end-specific monoclonal antibodies to amyloid β protein (Aβ) subtypes (Aβ40 and Aβ42(43) differentiate Ab in senile plaques and amyloid angiopathy in brains of aged cynomolgus monkeys," *Neuroscience Letters*, 201:151-154 (1995).
Nakayama et al., "Histopathological studies of senile plaques and cerebral amyloidosis in cynomolgus monkeys," *J. of Med. Primatology*, 27:244-252 (1998).
Nalbantoglu, J., "Beta-amyloid protein in Alzheimer's disease," *Can. J. Neurol. Sci.*, 18(3 suppl.):424-427 (1991), abstract only.
Naslund et al., "Correlation between elevated levels of amyloid β peptide in the brain and cognitive decline," *J. Am. Med. Assoc.*, 283:1571 (2000).
Nathanson et al., "Bovine Spongiform Encephalopathy (BSE): Causes and Consequences of a Common Source Epidemic," *Am. J. Epidemiol.*, 145(11):959-969 (1997).

New York Times National, "Anti-Inflammatory Drugs May Impede Alzheimer's," (Feb. 20, 1994).
Newcombe et al., "Solubility characteristics of isolated amyloid fibrils," *Biochim. Biophys. Acta*, 104:480-486 (1965).
Ngo et al., "Computational Complexity, Protein Structure Prediction, and the Levinthal Paradox," pp. 492-495 from Chapter 14 of *The Protein Folding Problem and Tertiary Structure Prediction*, Merz et al., eds., Birkhauser Boston (1994).
Nicoll et al., "Neuropathology of human Alzheimer's disease after immunization with amyloid-β peptide: a case report," *Nature Medicine*, 9(4):448-452 (2003).
Niemann, "Transgenic farm animals get off the ground;" *Transgenic Research*, 7:73-75 (1998).
Novotny et al., "Structural invariants of antigen binding: Comparison of immunoglobulin $V_L$-$V_H$ and $V_L$-$V_L$ domain dimmers," *PNAS*, 82:4592-4596 (1985).
Okie, S., "Promising Vaccine Targets Ravager of Minds," *Washington Post*, p. A01, May 8, 2001.
Okura et al., "Nonviral Aβ DNA vaccine therapy against Alzheimer's disease: Long-term effect and safety," *PNAS*, 103(25):9619-9624 (2006).
Orkin et al., *Report and Recommendations of the Panel to Assess the NIH Investment in Research on Gene Therapy*, Dec. 7, 1995.
Orlandi et al., "Cloning immunoglobulin variable domains for expression by the polymerase chain reaction," *PNAS*, 86:3833-3837 (1989).
Paganetti et al., "Amyloid precursor protein truncated at any of the γ-secretase sites is not cleaved to β-amyloid," *J. Neurosci. Res.*, 46(3):283-293 (1996).
Palha et al., "Antibody recognition of amyloidogenic transthyretin variants in serum of patients with familial amyloidiotic polyneuropathy," *J. Mol. Med.*, 78:703-707 (2001).
Pallitto et al., "Recognition sequence design for peptidyl modulators of β-amyloid aggregation and toxicity," *Biochemistry*, 38(12):3570-3578 (1999).
Pan et al., "Antibodies to β-Amyloid Decrease the Blood-to-Brain Transfer of β-Amyloid Peptide," *Exp. Biol. Med.*, 227(8):609-615 (2002).
Panka et al., "Variable region framework differences result in decreased or increased affinity of variant anti-digoxin antibodies," *PNAS*, 85:3080-3084 (1998).
Pardridge et al., "Chimeric peptides as a vehicle for peptide pharmaceutical delivery through the blood-brain barrier," *Biochem. Biophys. Res. Comm.*, 146:307-313(1987).
Pardridge et al., "The Blood-Brain Barrier: Bottleneck in Brain Drug Development," *J. Am. Soc. Exp. Neurotherapeutics*, 2:3-14 (2005).
Paresce et al., "Microglial cells influence aggregates of the Alzheimer's disease amyloid beta-protein via a scavenger receptor," *Neuron*, 17:553-565 (Sep. 1996).
Parnetti et al., "Cognitive Enhancement Therapy for Alzheimer's Disease, The Way Forward," *Drugs*, 53(5):752-768 (1997).
Paul et al., "Transdermal immunization with large proteins by means of ultradeformable drug carriers," *Eur. J. Immunol.*, 25: 3521-3524 (1995).
Paul, W. E., eds., *Fundamental Immunology*, Third Edition, pp. 292-295, Raven Press, New York (1993).
PCT International Preliminary Examination Report of Feb. 9, 2004 for application PCT/US01/46587.
PCT Written Opinion of Dec. 14, 2004 for application PCT/US04/02856.
PCT International Preliminary Report on Patentability (Chapter I) of Sep. 16, 2005 with Written Opinion of May 9, 2005 for application PCT/US04/007503.
PCT International Preliminary Report on Patentability (Chapter II) of Dec. 21, 2006 for application PCT/US2006/002837.
PCT International Preliminary Report on Patentability (Chapter I) of Jul. 31, 2007 with Written Opinion for application PCT/US2006/004741.
PCT Written Opinion of Aug. 11, 2006 for application PCT/US2006/002837.
PCT Search Report of Aug. 11, 2006 for application PCT/US2006/002837.

(56) References Cited

OTHER PUBLICATIONS

PCT Search Report of Aug. 8, 2006 for appl;ication PCT/US2005/045515.
PCT International Preliminary Report on Patentability (Chapter II) of Apr. 27, 2006 for application PCT/US04/007503.
PCT Search Report of Apr. 6, 2006 and Written Opinion of Apr. 8, 2006 for application PCT/US04/44093.
PCT Search Report of Oct. 1, 2007 and Written Opinion of Oct. 1, 2007 for application PCT/US07/09499.
Peeters et al., "Comparison of four bifunctional reagents for coupling peptides to proteins and the effect of the three moieties on the immunogenicity of the conjugates," *J. Immunological Methods*, 120:133-143 (1989).
Perez et al., "The β-Amyloid Precursor Protein of Alzheimer's Disease Enhances Neuron Viability and Modulates Neuronal Polarity," *J. Neurosci.*, 17(24):9407-9414 (1997).
Persson et al., "IgG subclass-associated affinity differences of specific antibodies in humans," *J. Immunology*, 140(11):3875-3879 (1988), abstract only.
Perutz et al., "Amyloid fibers are water-filed nanotubes," *PNAS*, 99(8):5591-5595 (2002).
Peterson, et al., "Recombinant Antibodies: Alternative Strategies for Developing and Manipulating Murine-Derived Monoclonal Antibodies," *Laboratory Animal Science*, 46(1):8-14 (1996).
Pfeifer et al., "Cerebral hemorrhage after passive anti-Aβ immunotherapy," *Science*, 298(5597):1379 (2002).
Phelps et al., "Development and Characterization of Monoclonal Antibodies Specific for Amylin," *Hybridoma*, 15(5):379-386 (1996).
Philippe, et al. "Generation of a monoclonal antibody to the carboxy-terminal domain of tau by immunization with the amino-terminal domain of the amyloid precursor protein," *J. of Neuroscience Res.*, 46:709-719 (1996).
Piera et al., "Cytokines as adjuvants: effects on the immunogenicity of NeuAc alpha 2-GalNAc alpha-O-Ser/Thr (sialyl-Tn)," *Int. J. Cancer*, 55(1):148-152 (1993).
Pluckthun, A., "Mono- and Bivalent Antibody Fragments Produced in *Escherichia coli*: Engineering, Folding and Antigen Binding," *Immunological Reviews*, 130:151-188 (1992).
PNAS Information for Authors (revised Jan. 1997), Retrieved Apr. 21, 2008 from http://web.archive.org/web/19970610092808/www.pnas.org/iforc.shtml.
Poduslo et al., "Permeability of proteins at the blood-brain barrier in the normal adult mouse and double transgenic mouse model of Alzheimer's disease," *Neurobiol. Dis.*, 8(4):555-567 (2001).
Press Release, "Alzheimer's vaccine developer awarded Potamkin Prize," American Academy of Neurology, May 7, 2001.
Prieels et al., "Synergistic adjuvants for vaccines," *Chemical Abstracts*, 120(8):652, col. 1, abstract 86406t (1994).
Probert et al., "Spontaneous inflammatory demyelinating disease in transgenic mice showing central nervous system-specific expression of tunmor necrosis factor α," *PNAS*, 92:11294-11298 (1995).
Prusiner et al., "Ablation of the prion protein (PrP) gene in mice prevents scrapie and facilitates production of anti-PrP antibodies," *PNAS*, 90:10608-10612 (1993).
Qu et al., "A$β_{42}$ gene vaccination reduces brain amyloid plaque burden in transgenic mice," *J. Neurological Sciences*, 244:151-158 (2006).
Queen et al., "A humanized antibody that binds to the interleukin 2 receptor," *PNAS*, 86:10029-10033 (1989).
Quon et al., "Formation of β-Amyloid protein deposits in brains of transgenic mice," *Nature*, 352:239-241 (1991).
Racke et al., "Exacerbation of Cerebral Amyloid Angiopathy-Associated Microhemorrhage in Amyloid Precursor Protein Trasngenic Mice by Immunotherapy is Dependent on Antibody Recognition of Deposited Forms of amyloid β," *J. Neurosci.*, 25(3):629-636 (2005).
Ragusi et al., "Redistribution of Imipramine from Regions of the Brain Under the Influence of Circulating Specific Antibodies," *J. Neurochem.*, 70(5):2099-2105 (1998).
Rammensee, H.G., "Chemistry of peptides associated with MHC class I and class II molecules," *Current Opinion in Immunology*, 7:85-96 (1995).
Raso, "Immunotherapy of Alzheimer's Disease," *Immunotherapy Weekly*, Abstract (Apr. 2, 1998).
Raso, V.A., Grant application # 1 R43 AGI 5746-01 (non-redacted version), "Immunotherapy of Alzheimer's Disease" (publication date unknown).
Raso, V.A., Grant application # 1 R43 AGI 5746-01 (redacted version), "Immunotherapy of Alzheimer's Disease" (publication date unknown).
Research Corporation Technology News, "THP and SangStat Partner to Develop Humanized Polyclonal Antibody Drugs," Nov. 11, 2002.
"Researchers Develop Blood Test to Diagnose Alzheimer's—Type Changes in Mice," downloaded from www.businesswire.com on Dec. 15, 2004.
Rodriguez et al., "Enfermedad de Azlheimer. Situacion Actual y Estrategias Terapeuticas" (Alzheimer Disease: present situation and therapeutic strategies), *Rev Cubana Med* [online], 38(2):134-142 (1999).
Rogers et al., "Complement activation by β-amyloid in Alzheimer Disease," *PNAS*, 89:1-5 (1992).
Rosenberg, R. N., "The Potamkin Prize for Pick's, Alzheimer's Disease and Related Disorders," pp. 1-5.
Roses, A.D., "Apoplipoprotein E alleles as risk factors in Alzheimer's disease," *Annu. Rev. Med.*, 47:387-400 (1996).
Rossor et al., "Alzheimer's Disease Families with Amyloid Precursor Protein Mutations," *Annals of New York Academy of Sciences*, 695:198-202 (1993).
Rudikoff et al., "Single amino acid substitution altering antigen-binding specificity," *PNAS*, 79:1979-1983 (1982).
Rudinger, "Characteristics of the Amino Acids as Components of a Peptide Hormone Sequence," in *Peptide Hormones*, J.A. Parson, ed. University Park Press, Baltimore, pp. 1-7 (1976).
Saido et al., "Spatial Resolution of Fodrin Proteolysis in Postischemic Brain," *J. Biol. Chem.*, 268(33):25239-25243 (1993).
Saido et al., "Spatial Resolution of the Primary β-Amyloidogenic Process Induced in Postischemic Hippocampus," *J. Biol. Chem.*, 269(21):15253-15257 (1994).
Saito et al., "Vector-mediated delivery of $^{125}$I-labeled β-amyloid peptide Aβ$^{1-40}$ through the blood-brain barrier and binding to Alzheimer disease amyloid of the Aβ$^{1-40}$ vector complex," *PNAS*, 92:10227-10231 (1995).
Saitoh, N. et al., "Immunological analysis of Alzheimer's disease using anti-β-protein monoclonal antibodies," *Sapporo Med. J.*, 60:309-320 (1991).
Saldanha et al., "A single backmutation in the human kIV framework of a previously unsuccessfully humanized antibody restores the binding activity and increases the secretion in cos cells," *Molecular Immunology*, 36:709-719 (1999).
Sasaki et al., "Human choroid plexus is an uniquely involved area of the brain in amyloidosis: a histochemical, immunohistochemical and ultrastructural study," *Brain Res.*, 755:193-201 (1997).
Schenk et al., "Immunization with amyloid-β attenuates Alzheimer-disease-like pathology in the PDAPP mouse," *Nature*, 400:173-177 (1999).
Schenk et al., "Therapeutic Approaches Related to Amyloid-β Peptide and Alzheimer's Disease," *J. Med. Chem.*, 38(21):4141-4154 (1995).
Schenk et al., "β-peptide immunization," *Arch. Neurol.*, 57:934-936 (2000).
Schenk et al., "Immunotherapy with beta-amyloid for Alzheimer's disease: a new frontier," *DNA Cell Biol.*, 20(11):679-81 (2001).
Schenk, D., "Amyloid-β immunotherapy for Alzheimer's disease: the end of the beginning," *Nature Reviews*, 3:824-828 (2002).
Schenk et al., "Current progress in beta-amyloid immunotherapy," *Curr. Opin. Immunology*, 16(5):599-606 (2004).
Schmid, R. E., "Study suggest Alzheimer vaccine fix," from www.msnbc.com/news, pp. 1-5 (2002).
Schmitt et al., "Interactions of the alzheimer β amyloid fragment$_{(25-35)}$ with peripheral blood dendritic cells," *Mechanisms of Ageing and Development*, 94:223-232 (1997).

(56) References Cited

OTHER PUBLICATIONS

Schwarzman et al., "Transthyretin sequesters amyloid β protein and prevents amyloid formation," *PNAS*, 91:8368-8372 (1994).
Seidl et al., "Predominant $V_H$ genes expressed in innate antibodies are associated with distinctive antigen-binding sites," *PNAS*, 96:2262-2267 (1999).
Sela et al, "Different roles of D-amino acids in immune phenomena," *FASEB J*, 11(6):449-456 (1999).
Selkoe, "Alzheimer's Disease: A Central Role for Amyloid," *J. Neuropathol. Exp. Neurol.*, 53(5): 438-447 (1994).
Selkoe, "Physiological production of the β-amyloid protein and the mechanism of Alzheimer's disease," *Trends in Neurosciences*, 16(10): 403-409 (1993).
Selkoe, "The cell biology of beta-amyloid precursor protein and presenilin in Alzheimer's disease," *Trends Cell Biol.*, 8(11):447-53 (1998).
Selkoe, D.J., "Imaging Alzheimer's Amyloid," *Nat. Biotech.*, 18:823-824 (2000).
Selkoe, Dennis J., "Alzheimer's Disease: Genotypes, Phenotype, and Treatments," *Science*, 275:630-631 (1997).
Selkoe, Dennis J., "Amyloid Protein and Alzheimer's Disease . . . ," *Scientific American*, pp. 68-78 (1991).
Selkoe, Dennis J., "In the Beginning . . . ," *Nature*, 354:432-433 (1991).
Selkoe, Dennis J., "The Molecular pathology of Alzheimer's Disease," *Neuron*, 6:487-498 (1991).
Selkoe, D. J., "Alzheimer's disease is a synaptic failure," *Science*, 298(5594):789-791 (2002).
Sergeant et al., "Truncated beta-amyloid peptide species in pre-clinical Alzheimer's disease as new targets for the vaccination approach," *J. Neurochem.*, 85(6):1581-1591 (2003).
Seubert et al., "Isolation and quantification of soluble Alzheimer's β-peptide from biological fluids," *Nature*, 359: 325-327 (1992).
Seubert et al., "Antibody Capture of Soluble Aβ does not Reduce Cortical Aβ Amyloidosis in the PDAPP Mouse," *Neurodegenerative Diseases*, 5:65-71 (2008).
Shinkai et al., "Amyloid β-Proteins 1-40 and 1-42(43) in the Soluble Fraction of Extra- and Intracranial Blood Vessels," *Ann. Neurol.*, 38:421-428 (1995).
Shiosaka, S., "Attempts to make models for Alzheimer's disease," *Neuroscience Res.*, 13:237-255 (1992).
Sigmund, "Viewpoint: Are Studies in Genetically Altered Mice Out of Control," *Arterioscler Thromb Vasc Biol.*, 20:1425-1429 (2000).
Signet Laboratories, Inc., Product data sheet for mouse monoclonal clone 6E10, revised Jul. 13, 2005.
Sigurdsson et al., "A safer vaccine for Alzheimer's disease?," *Neurobiology of Aging*, 23:1001-1008 (2002).
Sigurdsson et al., "Anti-prion antibodies for prophylaxis following prion exposure in mice," *Neurosciences Letters*, 336:185-187 (2003).
Sigurdsson et al., "Immunization Delays the Onset of Prion Disease in Mice," *American Journal of Pathology*, 161:13-17 (2002).
Sigurdsson, et al., "In vivo reversal of amyloid-beta lesions in rat brain," *J Neuropathol Exp Neurol.*, 59(1):11-17 (2000).
Sigurdsson et al., "Immunization with a Nontoxic/Nonfibrillar Amyloid-β Homologous Peptide Reduces Alzheimer's Disease-Associated Pathology in Trasngenic Mice," *Am. J. Pathology*, 159(2):439-447 (2001).
Simmons, L., "Secondary structure of amyloid β peptide correlates with neurotoxic activity in vitro," *Molecular Pharmacology*, 45:373-379 (1994).
Singh, K. S., "Neuroautoimmunity: Pathogenic Implications for Alzheimer's Disease," *Gerontology*, 43:79-94 (1997).
Singh, V. K., "Studies of neuroimmune markers in Alzheimer's disease," *Mol. Neurobiology*, 9(1-3):73-81 (1994), abstract only.
Sinha, et al., "Recent advances in the understanding of the processing of APP to beta amyloid peptide," *Ann N Y Acad Sci.*, 920:206-8 (2000).
Sipe, "Amyloidosis," *Annu. Rev. Biochem.*, 61:947-975 (1992).

Skolnick and Fetrow, "From genes to protein structure and function: novel applications of computational approaches in the genomic era," *Trends in Biotech*, 18(1):34-39 (2000).
Small et al., "Alzheimer's disease and Abeta toxicity: from top to bottom," *Nat Rev Neurosci.*, 2(8):595-598 (2001).
Small et al., "Cerebral metabolic and cognitive decline in persons at genetic risk for Alzheimer's disease," *PNAS*, 97(11):6037-6042 (2000).
Small, "The Role of the Amyloid Protien Precursors (APP) in Alzheimer's Disease: Does the Normal Function of APP Explain the Topography of Neurodegeneration?," *Neurochemical Research*, 23(5):795-806 (1997).
Smith et al., "The challenges of genome sequence annotation or 'The devil is in the details,'" *Nature Biotechnology*, 15:1222-1223 (1997).
Smits et al., "Prion Protein and Scrapie Susceptibility," *Vet. Quart.*, 19(3):101-105 (1997).
Solomon and et al., "Modulation of the Catalytic Pathway of Carboxypeptidase A by Conjugation with Polyvinyl Alcohols," *Adv. Mol. Cell Biology*, 15A:33-45 (1996).
Solomon et al., "Activity of monoclonal antibodies in prevention of in vitro aggregation of their antigens," *Immunotechnology*, 2(4):305 (1996).
Solomon et al., "Disaggregation of Alzheimer β-amyloid by site-directed mAb," *PNAS*, 94:4109-4112 (1997).
Solomon et al., "Monoclonal antibodies inhibit in vitro fibrillar aggregation of the Alzheimer β-amyloid peptide," *PNAS*, 93:452-455 (1996).
Solomon et al., "The Amino Terminus of the β-Amyloid Peptide Contains an Essential Epitope for Maintaining Its Solubility," from *Progress in Alzheimer's and Parkinson's Diseases*, edited by Fisher et al., Plenum Press, New York, pp. 205-211 (1995).
Solomon, A., "Pro-Rx (Protein Therapeutics)," University of Tennessee Medical Center (publication date unknown).
Solomon, B., "New Approach Towards Fast Induction of Anti β-Amyloid Peptide Immune Response," Department of Molecular Microbiology & Biotechnology, Tel-Aviv University, Ramat Aviv, Tel-Aviv, Israel (publication date unknown).
Solomon, B., "Immunological approaches as therapy for Alzheimer's disease," *Expert Opin. Biol. Ther.*, 2(8):907-917 (2002).
Solomon, B., "Generation and brain delivery of anti-aggregating antibodies against β-amyloid plaques using phage display technology," *J. Neural Transm. Suppl.*, 62:321-325 (2002).
Solomon, B., "Immunotherapeutic strategies for prevention and treatment of Alzheimer's disease," *DNA and Cell Biology*, 20(11):697-703 (2001).
Solomon et al., "Fast induction of anti-β-amyloid peptide immune response," *Research and Practice in Alzheimer's Disease*, 6:260-264 (2002).
Soto et al., "Beta sheet breaker peptides inhibit fibrillogenesis in a rat brain model of amyloidosis: implications for Alzheimer's therapy," *Nature Medicine.*, 4(7):822-826 (1998).
Soto et al., "The α-helical to β-strand transition in the amino-terminal fragment of the amyloid β-peptide modulates amyloid formation," *J. Biol. Chem*, 270(7):3063-3067 (1995).
Soto et al., "The conformation of Alzheimer's beta peptide determines the rate of amyloid formation and its resistance to proteolysis," *Biochem. J.*, 314:701-707 (1996).
Souder et al., "Overview of Alzheimer's disease," *Nurs. Clin. N. Am.*, 39:545-559 (2004).
Southwick et al., "Assessment of Amyloid β protein in Cerebrospinal fluid as an Aid in the Diagnosis of Alzheimer's Disease," *J. Neurochemistry*, 66:259-265 (1996).
Spellerberg et al., "DNA Vaccines Against Lymphoma," *Journal of Immunology*, 159:1885-1892 (1997).
Spooner et al., "The generation and characterization of potentially therapeutic Aβ antibodies in mice: differences according to strain and immunization protocol," *Vaccine*, 21:290-297 (2002).
St. George-Hyslop et al., "Antibody clears senile plaques," *Nature*, 40:116-117 (1999).

(56) References Cited

OTHER PUBLICATIONS

Stein et al., "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380-7388 (2002).
Stern et al., "Antibodies to the β-amyloid peptide cross-react with conformational epitopes in human fibrinogen subunits from peripheral blood," *FEBS Letters*, 264(1):43-47 (1990).
Stoute et al., "A Preliminary Evaluation of a Recombinant Circumsporozoite Protein Vaccine Against *Plasmodium falciparum* Malaria", *N. Engl. J. Med.*, 336(2):86-91 (1997).
Strbak et al., "Passive Immunization and Hypothalamic Peptide Secretion", *Neuroendocrinology*, 58:210-217 (1993).
Sturchler-Pierrat et al., "Two amyloid precursor protein transgenic mouse models with Alzheimer disease-like pathology," *PNAS*, 94: 13287-13292 (1997).
Su et al., "Intravascular infusions of soluble β-amyloid compromise the blood-brain barrier, activate CNS Glial cells and induce peripheral hemorrhage," *Brain Research*, 818:105-107 (1999).
Suo et al., "Soluble Alzhelmers β-amyloid constricts the cerebral vasculature in vivo" *Neuroscience Letters*, 257:77-80 (1998).
Supplementary Partial European Search Report of Apr. 10, 2007 for European Application 04720353.4-1222.
Szendrei, et al., "The effects of aspartic acid-bond isomerization on in vitro properties of the amyloid β-peptide as modeled with N-terminal decapeptide fragments," *Int. J. Peptide Protein Res.*, 47:289-296 (1996).
Tabaton et al., "Soluble amyloid β-protein is a marker of Alzheimer amyloid in brain but not in cerebrospinal fluid," *Biochem. and Biophys. Res. Comm.*, 200(3):1598-1603 (1994).
Tal et al., "Complete Freund's Adjuvant Immunization Prolongs Survival in Experimental Prion Disease in Mice," *Journal of Neuroscience Research*, 71:286-290 (2003).
Tan et al., "Amyloidosis," *Histopathology*, 25:403-414 (1994).
Tanaka et al., "NC-1900, an active fragment analog of arginine vasopressin, improves learning and memory deficits induced by beta-amyloid protein in rats," *European J. Pharmacology*, 352:135-142 (1998).
Tang et al., "Genetic immunization is a siple method for eliciting an immune response," *Nature*, 356:152-154 (1992).
Teller et al., "Presence of soluble amyloid β-peptide precedes amyloid plaque formation in Down's syndrome" *Nature Medicine*, 2(1):93-95 (1996).
Tennent et al., "Serum amyloid P component prevents proteolysis of the amyloid fibrils of Alzheimer's disease and systemic amyloidosis," *PNAS*, 92:4299-4303 (1995).
Thorsett, E.D. et al., "Therapeutic approaches to Alzheimer's disease," *Curr. Op. in Chem. Biology*, 4:377-382 (2000).
Tjernberg et al., "A molecular model for Alzheimer amyloid β-peptide fibril formation," *J. Biol. Chem.*, 274(18):12619-12625 (1999).
Tjernberg et al., "Arrest of β-amyloid fibril formation by a pentapeptide ligand," *J. Biol. Chem.*, 271:8545-8548 (1996).
Tjernberg, et al, "Controlling amyloid beta-peptide fibril formation with protease-stable ligands," *J. Biol Chem.*, 272(19):12601-12605 (1997).
Town et al., "Characterization of murine immunoglobulin G antibodies against human amyloid-$\beta_{1-42}$" *Neurosci. Lett*, 307:101-104 (2001).
Travis, J., "A Vaccine for Alzheimer's Disease?®," *Science News Online*, 156(2) pp. 1-3 downloaded from internet (1999).
Travis, J., "Saving the Mind Faces High Hurdles," *Science*, 309:731-734 (2005).
Trieb et al., "Is Alzheimer beta amyloid precursor protein (APP) an autoantigen? Peptides corresponding to parts of the APP sequence stimulate T lymphocytes in normals, but not in patients with Alzheimer's disease," *Immunobiology*, 191(2-3):114-115 Abstract C.37, (1994).

Trieb et al., "APP Peptides Stimulate Lymphocyte Proliferation in Normals, But Not in Patients With Alzheimer's Disease," *Neurobiology of Aging*, 17(4):541-547 (1996).
Tsuzuki et al., "Amyloid β protein in rat soleus in choroquine-induced myopthy using end-specific antibodies for Aβ40 and Aβ42: immunohistochemical evidence for amyloid β protein," *Neuroscience Letters*, 2002:77-80 (1995).
Ulvestad et al., "Fc Receptors for IgG on Cultured Human Microglia Mediate Cytotoxicity and Phagocytosis of Antibody-coated Targets," *Journal of Neuropathology and Experimental Neurology*, 53(1):27-36 (1994).
UniProtKB/Swiss-Prot entry P18525, pp. 1-3 downloaded from http://www.expasy.org/cgi-bin/niceprot.pl/printable?ac=P18525 on Feb. 8, 1997, "HV54_Mouse" (Nov. 1, 1990).
Urmoneit et al., "Cerebrovascular Smooth Muscle CElls Internalize Alzheimer Amyloid Beta Protein via a Lipoprotein Pathway: Implications for Cerebral Amyloid Angiopathy," *Laboratory Investigation*, 77(2):157-166 (1997).
Valleix et al., "Hereditary renal amyloidosis caused by a new variant lysozyme W64R in a French family," *Kidney International*, 61:907-912 (2002).
Van Den Dobbelsteen et al., "Characteristics of Immune Responses to Native and Protein Conjugated Pneumococcal Polysaccharide Type 14," *Scand. J. Immunol.*, 41:273-280 (1995).
Van Gool et al., "Concentrations of amyloid-β protein in cerebrospinal fluid increase with age in patients free from neurodegenerative disease," *Neuroscience Letters*, 172:122-124 (1994).
Van Leuven, F., "Single and multiple transgenic mice as models for Alzheimer's disease," *Progress in Neurobiology*, 61:305-312 (2000).
Van Regenmortel et al, "D-peptides as immunogens and diagnostic reagents," *Curr. Opin. Biotechnol.*, 9(4):377-382 (1998).
Vanderstichele et al., "Standardization of Measurement of B-amyloid(1-42) in Cerebrospinal Fluid and Plasma:," *Int. J. Exp. Clin. Invest.*, 7(4):245-258 (2000).
Vehmas et al., "Beta-Amyloid peptide vaccination results in marked changes in serum and brain Abeta levels in APPswe/PS1 DeltaE9 mice, as detected by SELDI-TOF-based ProteinChip® technology," *DNA Cell Biol.*, (11):713-721 (2001).
Velazquez et al., "Aspartate residue 7 in amyloid β-protein is critical for classical complement pathway activation: Implications for Alzheimer's disease pathogenesis," *Nature Medicine*, 3(1):77-79 (1997).
Verbeek et al., "Accumulation of Intercellular Adhesion Molecule-1 in Senile Plaques in Brain Tissue of patients with Alzheimer's Disease," *Amer. Journ. Pathology*, 144(1):104-116 (1994).
Verma et al., "Gene therapy—promises, problems and prospects," *Nature*, 389:239-242 (1997).
*Vershigora A. E. Obshchaya Immynologiya*, pp. 35, 229-231 and 152-153 (1990).
Vickers, J. C., "A Vaccine Against Alzheimer's Disease," *Drugs Aging*, 19(7):487-494 (2002).
Vidanovic et al., "Effects of nonionic surfactants on the physical stability of immunoglobulin G in aqueous solution during mechanical agitation," *Die Pharmazie*, 58(6):399-404 (2003).
Walker et al., "Labeling of Cerebral Amyloid In Vivo with a Monoclonal Antibody," *J. Neuropath. Exp. Neurology*, 53(4):377-383 (1994).
Walsh et al., "Naturally secreted oligomers of amyloid β protein potently inhibit hippocampal long-term potentiation in vivo," *Nature*, 416(6880):535-539 (2002).
Wang et al., "The levels of soluble versus insoluble brain Aβ distinguish Alzheimer's disease from normal and pathologic aging," *Experimental Neurology*, 158:328-337 (1999).
Wang et al., "Soluble oligomers of β amyloid (1-42) inhibit long-term potentiation but not long-term depression in rate dentate gyrus," *Brain Research*, 924:133-140 (2002).
Wang, W., "Instability, stabilization, and formulation of liquid protein pharmaceuticals," *Int. J. Pharmaceutics*, 185(2):129-188 (1999).
Washington University in St. Louis School of Medicine, "Study gives Clues to Working of Anti-Alzheimer Antibody," downloaded from www.medicine.wustl.edu/~wumpa/news on Dec. 15, 2004.
*Webster's New World Dictionary*, p. 1387, therapeutic (1988).

(56) References Cited

OTHER PUBLICATIONS

*Webster's New World Dictionary of American English*, Third College Edition, p. 1078 (1988).
Weiner et al., "Nasal administration of amyloid-β peptide decreases cerebral amyloid burden in a mouse model of Alzheimer's disease," *Annals of Neurology*, 48:567-579 (2000).
Weiner et al., "Oral Tolerance: Immunologic Mechanisms and Treatment of Animal and Human Organ-Specific Autoimmune Diseases by Oral Administration of Autoantigens," *Annu. Rev. Immunol.*, 12:809-837 (1994).
Weiner, H. L., "Oral tolerance: immune mechanisms and treatment of autoimmune diseases," *Immunology Today*, 18:335-343 (1997).
Weinreb et al., "NACP, A Protein Implicated in Alzheimer's Disease and Learning, is Natively Unfolded," *Biochemistry*, 35(43):13709-13715 (1996).
Weissmann et al., "Bovine spongiform encephalopathy and early onset variant Creutzfeldt-Jakob disease," *Curr. Opin. Neurobiol.*, 7:695-700 (1997).
Weldon et al., "Neurotoxicity of Aβ Peptide: Confocal Imaging of Cellular Changes Induced by—Amyloid in Rat CNS In Vivo," *Society for Neuroscicence Abstracts*, 22(Part 1) (1996).
Wells, J. A., "Additivity of Mutational Effects in Proteins," *Biochemistry*, 29(37):8509-8517 (1990).
Wen, G.Y., "Alzheimer's Disease and Risk Factors," *J. Food Drug Analysis*, 6(2):465-476 (1998).
Wengenack et al., "Targeting Alzheimer amyloid plaques in vivo," *Nature Biotech.*, 18:868-872 (2000).
White et al., "Immunotherapy as a therapeutic treatment for neurodegenerative disorders," *J. Neurochem.*, 87(4):801-808 (2003).
Wikipedia definition of "epitope" printed from internet on Apr. 26, 2006.
Wikipedia definition of "antigen" printed from internet on Apr. 26, 2006.
Wikipedia definition of "route of administration including parenteral" printed from Internet on Apr. 26, 2006.
Winblad et al., "Hints of a therapeutic Vaccine for Alzheimer's?" *Neuron*, 38:517-519 (2003).
Winter et al., "Humanized antibodies" *Immunology Today*, 14(6):243-246 (1996).
Wisconsin Alumni Research Foundation, "Injection of Newborn Mice with Seven Chemical Adjuvants to Help Determine Their Safety in Use in Biologicals", U.S. Govt. Res. Develop. Rep., 70(24), 56 (1969).
Wisniewski et al., "Alzheimer's disease and soluble A beta," *Neurobiol. Aging*, 15(2):143-52 (1994).
Wisniewski et al., "Therapeutics in Alzheimer's and Prion Diseases," *Biochemical Society Transactions*, 30(4):574-587 (2002).
Whitcomb et al., "Characterization of saturable binding sites for circulating pancreatic polypeptide in rat brain," *Am J Pysiol Gastrointest Liver Physiol*, 259:G687-G691 (1990).
Wong et al., "Neuritic Plaques and Cerebrovascular Amyloid in Alzheimer Disease are Antigenically Related," *PNAS*, 82:8729-8732 (1985).
Wood et al., "Amyloid precursor protein processing and Aβ42 deposition in a transgenic mouse model of Alzheimer disease," *PNAS*, 94:1550-1555 (1997).
Wood et al., "Prolines and amyloidogenicily in fragments of the Alzheimer's peptide β/A4" *Biochemistry*, 34:724-730 (1995).
Wu et al., "Expression of immunogenic epitopes of hepatitis B surface antigen with hybrid flagellin proteins by a vaccine strain of *Salmonella*," *PNAS*, 86:4726-4730 (1989).
Wu, et al., "Drug targeting of a peptide radiopharmaceutical through the primate blood-brain barrier in vivo with a monoclonal antibody to the human insulin receptor," *J. Clin. Invest.*, 100:1804-1812 (1997).
Wu et al., "An Analysis of the Sequences of the Variable Regions of Bence Jones Proteins and Myeloma Light Chains and their Implications for Antibody Complementarity*," *J. Exp. Med.*, 132:211-250 (1970).
Wyeth, Annual Review 2005: Creating Value . . . Advancing Health (Feb. 27, 2006).
Xiang et al., "Manipulation of the immune response to a plasmid-encoded viral antigen by coinoculation with plasmids expressing cytokines," *Immunity*, 2(2):129-135 Abstract (1995).
Xu et al., "Increased incidence of anti-β-amyloid autoantibodies secreted by Epstein-Barr virus transformed B cell lines from patients with Alzheimer's disease," *Mechanisms of Ageing and Development*, 94:213-222 (1997).
Yamada et al., "Generation and Characterization of Rat Monoclonal Antibodies Against Human Serum Amyloid A," *Scand. J. Immunol.*, 46(2):175-179 (1997).
Yamaguchi et al., Diffuse plaques associated with astroglial amyloid β protein, possibly showing a disappearing stage of senile plaques, *Acta Neuropathol.*, 95:217-222 (1998).
Yang et al., "Effects of Racemization on the Aggregational Properties of the Amyloid β-Peptide in Alzheimer's Disease," abstract # 255 from American Chemical Society 214th National Meeting (1997).
Yankner et al., "Neurotrophic and Neurotoxic effects of Amyloid β Protein: Reversal by Tachykinin Neuropeptides," *Science*, 250:279-282 (1990).
Younkin, "Amyloid β vaccination: reduced plaques and improved cognition," *Nature Medicine*, 7:18-19 (2001).
Zameer et al., "Single Chain Fv Antibodies against 25-35 Peptide Fragment of Amyloid-β: Potential Therapeutic for Alzheimer's Disease," Abstract P4-420, p. S593, presented at Poster Session P4:Therapeutics and Therapeutic Strategies—Therapeutic Strateies, Amyloid-Based, also *Neurobiology of Aging*, 25(Suppl. 2): p. S593 (Jul. 2004).
Zhang et al., "Specialized Applications, Purification of Recombinant Proteins and Study of Protein Interaction by Epitope Tagging," *Current Protocols in Mol. Biol.*, Supp 41, pp. 10.15.1 through 10.15.9 (1998).
Zhang et al., "A novel recombinant adeno-associated virus vaccine reduces behavioral impairment and β-amyloid plaques in a mouse model of Alzheimer's disease," *Neurobiology of Disease*, 14:365-379 (2003).
Zlokovic et al., "Clearance of amyloid β-peptide from brain: transport or metabolism?" *Nature Medicine*, 6(7):718-719 (2000).
Zlokovic et al., "Glycoprotein 330/megalin: probable role in receptor-mediated transport of apolipoprotein J alone and in a complex with Alzheimer disease amyloid beta at the blood-brain and blood-cerebrospinal fluid barriers," *PNAS*, 93(9):4229-4334 (1996) abstract only.
U.S. Appl. No. 09/201,430, Office Action mailed Dec. 21, 1999.
U.S. Appl. No. 09/201,430, Office Action mailed May 10, 2000.
U.S. Appl. No. 09/204,838, Office Action mailed Mar. 17, 2000.
U.S. Appl. No. 09/322,289, Office Action mailed Sep. 29, 2000.
U.S. Appl. No. 09/497,553, Office Action mailed Oct. 3, 2003.
U.S. Appl. No. 09/580,015, Office Action mailed Feb. 11, 2002.
U.S. Appl. No. 09/580,018, Office Action mailed Mar. 12, 2002.
U.S. Appl. No. 09/580,019, Office Action mailed Mar. 12, 2002.
U.S. Appl. No. 09/723,544, Office Action mailed Sep. 23, 2002.
U.S. Appl. No. 09/723,760, Office Action mailed Mar. 12, 2002.
U.S. Appl. No. 09/723,765, Office Action mailed Mar. 12, 2002.
U.S. Appl. No. 09/723,766, Office Action mailed Mar. 5, 2002.
U.S. Appl. No. 09/723,766, Office Action mailed Jun. 11, 2002.
U.S. Appl. No. 09/724,273, Office Action mailed Jul. 2, 2002.
U.S. Appl. No. 09/724,273, Office Action mailed Nov. 8, 2005.
U.S. Appl. No. 09/724,288, Office Action mailed Mar. 12, 2002.
U.S. Appl. No. 09/724,288, Office Action mailed May 3, 2004.
U.S. Appl. No. 09/724,319, Office Action mailed Jul. 21, 2003.
U.S. Appl. No. 09/724,495, Office Action mailed Sep. 24, 2002.
U.S. Appl. No. 09/724,495, Office Action mailed Mar. 13, 2003.
U.S. Appl. No. 09/724,551, Office Action mailed Jul. 2, 2002.
U.S. Appl. No. 09/724,552, Office Action mailed May 6, 2002.
U.S. Appl. No. 09/724,567, Office Action mailed Mar. 27, 2002.
U.S. Appl. No. 09/724,575, Office Action mailed Mar. 27, 2002.
U.S. Appl. No. 09/724,921, Office Action mailed Apr. 30, 2002.
U.S. Appl. No. 09/724,929, Office Action mailed Mar. 22, 2002.
U.S. Appl. No. 09/724,940, Office Action mailed Mar. 13, 2003.
U.S. Appl. No. 09/724,953, Office Action mailed Mar. 26, 2002.
U.S. Appl. No. 09/724,961, Office Action mailed Mar. 12, 2002.
U.S. Appl. No. 09/979,701, Office Action mailed Feb. 15, 2005.
U.S. Appl. No. 09/979,701, Office Action mailed Sep. 15, 2005.

(56) References Cited

OTHER PUBLICATIONS

U.S. Appl. No. 09/979,952, Office Action mailed Aug. 7, 2003.
U.S. Appl. No. 09/980,568, Office Action mailed May 29, 2003.
U.S. Appl. No. 10/010,942, Office Action mailed Sep. 24, 2003.
U.S. Appl. No. 10/232,030, Office Action mailed Dec. 2, 2004.
U.S. Appl. No. 10/388,214, Office Action mailed May 31, 2005.
U.S. Appl. No. 10/388,389, Office Action mailed Nov. 22, 2005.
U.S. Appl. No. 10/429,216, Office Action mailed Dec. 28, 2005.
U.S. Appl. No. 10/544,093, Office Action, mailed Jun. 16, 2008.
U.S. Appl. No. 10/625,854, Office Action mailed Nov. 10, 2005.
U.S. Appl. No. 10/703,713, Office Action mailed Nov. 5, 2004.
U.S. Appl. No. 10/704,070, Office Action mailed Nov. 5, 2004.
U.S. Appl. No. 10/771,174, Office Action mailed Sep. 14, 2006.
U.S. Appl. No. 10/777,792, Office Action mailed Mar. 2, 2006.
U.S. Appl. No. 10/788,666, Office Action mailed Jan. 12, 2005.
U.S. Appl. No. 10/789,273, Office Action mailed Sep. 22, 2006.
U.S. Appl. No. 10/822,968, Office Action mailed Mar. 22, 2006.
U.S. Appl. No. 10/823,463, Office Action mailed Feb. 4, 2005.
U.S. Appl. No. 10/828,548, Office Action mailed Feb. 4, 2005.
U.S. Appl. No. 10/828,548, Office Action mailed Sep. 29, 2005.
U.S. Appl. No. 10/858,855, Office Action mailed Jun. 22, 2006.
U.S. Appl. No. 10/923,267, Office Action mailed Jul. 21, 2006.
U.S. Appl. No. 10/923,469, Office Action mailed Mar. 29, 2007.
U.S. Appl. No. 10/923,474, Office Action mailed Feb. 15, 2005.
U.S. Appl. No. 10/928,926, Office Action mailed Jan. 12, 2007.
U.S. Appl. No. 10/934,819, Office Action mailed Oct. 14, 2005.
U.S. Appl. No. 11/058,757, Office Action mailed May 3, 2005.
U.S. Appl. No. 11/058,757, Office Action mailed Aug. 24, 2005.
U.S. Appl. No. 11/244,678, Office Action mailed Apr. 18, 2007.
U.S. Appl. No. 11/245,524, Office Action mailed May 15, 2007.
U.S. Appl. No. 11/245,916, Office Action mailed Jan. 13, 2006.
U.S. Appl. No. 11/260,047, Office Action mailed Oct. 26, 2006.
U.S. Appl. No. 11/303,478, Office Action mailed Apr. 1, 2008.
U.S. Appl. No. 11/304,072, Office Action mailed Dec. 20, 2006.
U.S. Appl. No. 11/304,986, Office Action mailed Jan. 2, 2008.
U.S. Appl. No. 11/305,889, Office Action mailed Jul. 25, 2008.
U.S. Appl. No. 11/305,889, Office Action mailed May 4, 2007.
U.S. Appl. No. 11/305,899, Office Action mailed Apr. 4, 2008.
U.S. Appl. No. 11/342,353, Office Action mailed Mar. 26, 2008.
U.S. Appl. No. 11/342,353, Office Action mailed Jul. 9, 2008.
U.S. Appl. No. 11/454,772, Office Action mailed Feb. 27, 2007.
U.S. Appl. No. 09/201,430, Office Action mailed Jan. 17, 2001.
U.S. Appl. No. 09/201,430, Examiner Interview Summary mailed May 30, 2001.
U.S. Appl. No. 09/204,838, Office Action mailed Dec. 21, 2000.
U.S. Appl. No. 09/322,289, Office Action mailed Jun. 19, 2001.
U.S. Appl. No. 09/322,289, Examiner Interview Summary mailed Jun. 27, 2006.
U.S. Appl. No. 09/497,553, Office Action mailed Nov. 29, 2005.
U.S. Appl. No. 09/580,018, Office Action mailed May 20, 2003.
U.S. Appl. No. 09/723,384, Office Action mailed Oct. 9, 2002.
U.S. Appl. No. 09/723,384, Examiner Interview Summary mailed Mar. 28, 2003.
U.S. Appl. No. 09/723,544, Office Action mailed Aug. 11, 2003.
U.S. Appl. No. 09/723,713, Office Action mailed Mar. 26, 2002.
U.S. Appl. No. 09/723,760, Office Action mailed Dec. 19, 2002.
U.S. Appl. No. 09/723,762, Office Action mailed Oct. 2, 2001.
U.S. Appl. No. 09/723,765, Office Action mailed Dec. 3, 2002.
U.S. Appl. No. 09/723,765, Examiner Interview Summary mailed Mar. 18, 2003.
U.S. Appl. No. 09/723,765, Examiner Interview Summary mailed Jan. 25, 2006.
U.S. Appl. No. 09/723,766, Office Action mailed Nov. 1, 2002.
U.S. Appl. No. 09/724,102, Office Action mailed Oct. 3, 2001.
U.S. Appl. No. 09/724,273, Office Action mailed Apr. 21, 2003.
U.S. Appl. No. 09/724,288, Office Action mailed Dec. 11, 2002.
U.S. Appl. No. 9/724,319, Office Action mailed Apr. 26, 2004.
U.S. Appl. No. 09/724,319, Examiner Interview Summary mailed Jul. 19, 2004.
U.S. Appl. No. 09/724,319, Examiner Interview Summary mailed Apr. 9, 2008.
U.S. Appl. No. 09/724,477, Office Action mailed Oct. 2, 2001.
U.S. Appl. No. 09/724,489, Office Action mailed Oct. 2, 2002.
U.S. Appl. No. 09/724,495, Office Action mailed Jan. 16, 2004.
U.S. Appl. No. 09/724,551, Office Action mailed Jun. 3, 2003.
U.S. Appl. No. 09/724,552, Office Action mailed Jun. 3, 2003.
U.S. Appl. No. 09/724,552, Examiner Interview Summary mailed Dec. 3, 2003.
U.S. Appl. No. 09/724,567, Office Action mailed Nov. 15, 2002.
U.S. Appl. No. 09/724,575, Office Action mailed Nov. 21, 2002.
U.S. Appl. No. 09/724,575, Examiner Interview Summary mailed May 6, 2005.
U.S. Appl. No. 09/724,921, Office Action mailed Jan. 28, 2003.
U.S. Appl. No. 09/724,929, Office Action mailed Jul. 22, 2003.
U.S. Appl. No. 09/724,940, Office Action mailed Dec. 24, 2003.
U.S. Appl. No. 09/724,953, Office Action mailed Nov. 27, 2002.
U.S. Appl. No. 09/724,961 Office Action mailed May 16, 2003.
U.S. Appl. No. 09/724,961, Examiner Interview Summary mailed Dec. 3, 2003.
U.S. Appl. No. 09/979,701, Office Action mailed Jan. 10, 2006.
U.S. Appl. No. 09/979,952, Office Action mailed Dec. 30, 2003.
U.S. Appl. No. 09/980,568, Office Action mailed Feb. 23, 2004.
U.S. Appl. No. 10/010,942, Office Action mailed May 26, 2004.
U.S. Appl. No. 10/010,942, Examiner Interview Summary mailed Nov. 18, 2004.
U.S. Appl. No. 10/010,942, Examiner Interview Summary mailed Jan. 19, 2005.
U.S. Appl. No. 10/010,942, Examiner Interview Summary mailed Feb. 22, 2006.
U.S. Appl. No. 10/010,942, Examiner Interview Summary mailed May 10, 2006.
U.S. Appl. No. 10/010,942, Examiner Interview Summary mailed May 11, 2006.
U.S. Appl. No. 10/010,942, Examiner Interview Summary mailed May 11, 2006.
U.S. Appl. No. 10/232,030, Office Action mailed Oct. 14, 2005.
U.S. Appl. No. 10/232,030, Examiner Interview Summary mailed Feb. 17, 2006.
U.S. Appl. No. 10/388,214, Office Action mailed Jan. 31, 2006.
U.S. Appl. No. 10/388,214, Examiner Interview Summary mailed Oct. 2, 2006.
U.S. Appl. No. 10/388,214, Examiner Interview Summary mailed Nov. 6, 2006.
U.S. Appl. No. 10/388,389, Examiner Interview Summary mailed May 22, 2006.
U.S. Appl. No. 10/388,389, Examiner Interview Summary mailed May 31, 2006.
U.S. Appl. No. 10/429,216, Office Action mailed Apr. 11, 2006.
U.S. Appl. No. 10/625,854, Office Action mailed Feb. 7, 2006.
U.S. Appl. No. 10/625,854, Examiner Interview Summary mailed Jun. 26, 2007.
U.S. Appl. No. 10/703,713, Office Action mailed Sep. 27, 2005.
U.S. Appl. No. 10/703,713, Examiner Interview Summary mailed Feb. 21, 2006.
U.S. Appl. No. 10/703,713, Examiner Interview Summary mailed Mar. 2, 2006.
U.S. Appl. No. 10/704,070, Office Action mailed Sep. 26, 2005.
U.S. Appl. No. 10/771,174, Office Action mailed Nov. 27, 2006.
U.S. Appl. No. 10/777,792, Office Action mailed Aug. 7, 2006.
U.S. Appl. No. 10/788,666, Office Action mailed Dec. 15, 2005.
U.S. Appl. No. 10/823,463, Office Action mailed Sep. 30, 2005.
U.S. Appl. No. 10/828,548, Office Action mailed Feb. 13, 2006.
U.S. Appl. No. 10/858,855, Office Action mailed Mar. 7, 2007.
U.S. Appl. No. 10/890,000, Office Action mailed Apr. 13, 2005.
U.S. Appl. No. 10/890,024, Office Action mailed Nov. 2, 2005.
U.S. Appl. No. 10/890,070, Office Action mailed Apr. 8, 2005.
U.S. Appl. No. 10/890,071, Office Action mailed Dec. 18, 2006.
U.S. Appl. No. 10/889,999, Office Action mailed Jan. 5, 2005.
U.S. Appl. No. 10/923,469, Examiner Interview Summary mailed Apr. 9, 2008.
U.S. Appl. No. 10/923,469, Office Action mailed Jul. 3, 2007.
U.S. Appl. No. 10/923,471, Office Action mailed Jan. 5, 2005.

(56) References Cited

OTHER PUBLICATIONS

U.S. Appl. No. 10/923,474 Office Action mailed Nov. 17, 2005.
U.S. Appl. No. 10/923,605, Office Action mailed Apr. 12, 2007.
U.S. Appl. No. 10/934,818, Office Action mailed Mar. 26, 2007.
U.S. Appl. No. 10/934,819, Office Action mailed Jan. 24, 2006.
U.S. Appl. No. 11/058,757, Office Action mailed Oct. 20, 2005.
U.S. Appl. No. 11/108,102, Office Action mailed Jan. 11, 2006.
U.S. Appl. No. 11/244,678, Office Action mailed Jul. 13, 2007.
U.S. Appl. No. 11/245,524, Office Action mailed Sep. 27, 2007.
U.S. Appl. No. 11/245,916, Office Action mailed May 19, 2006.
U.S. Appl. No. 11/260,047, Office Action mailed May 15, 2007.
U.S. Appl. No. 11/260,047, Examiner Interview Summary mailed May 15, 2007.
U.S. Appl. No. 11/274,493, Office Action mailed Apr. 23, 2007.
U.S. Appl. No. 11/305,889, Office Action mailed Aug. 14, 2007.
U.S. Appl. No. 11/45,772, Examiner Interview Summary mailed Apr. 13, 2007.
U.S. Appl. No. 11/454,772, Office Action mailed Jun. 27, 2007.
U.S. Appl. No. 09/201,430, Office Action mailed Oct. 1, 2002.
U.S. Appl. No. 09/204,838, Office Action mailed Apr. 18, 2003.
U.S. Appl. No. 09/322,289, Office Action mailed Feb. 24, 2005.
U.S. Appl. No. 09/322,289, Office Action mailed Nov. 17, 2006.
U.S. Appl. No. 09/322,289, Office Action mailed Feb. 7, 2008.
U.S. Appl. No. 09/723,713, Office Action mailed Oct. 24, 2003.
U.S. Appl. No. 09/723,713, Office Action mailed Apr. 19, 2005.
U.S. Appl. No. 09/723,725, Office Action mailed Dec. 9, 2002.
U.S. Appl. No. 09/723,760, Office Action mailed May 4, 2005.
U.S. Appl. No. 09/723,765, Office Action mailed May 22, 2008.
U.S. Appl. No. 09/723,765, Office Action mailed Aug. 10, 2004.
U.S. Appl. No. 09/724,273, Office Action mailed Jun. 22, 2004.
U.S. Appl. No. 09/724,273, Office Action mailed Jun. 8, 2006.
U.S. Appl. No. 09/724,273, Office Action mailed Dec. 22, 2006.
U.S. Appl. No. 09/724,288, Office Action mailed Dec. 14, 2004.
U.S. Appl. No. 09/724,288, Office Action mailed Jun. 21, 2006.
U.S. Appl. No. 09/724,288, Office Action mailed Apr. 23, 2007.
U.S. Appl. No. 09/724,288, Office Action mailed Oct. 3, 2007.
U.S. Appl. No. 09/724,288, Office Action mailed Mar. 18, 2008.
U.S. Appl. No. 09/724,319, Office Action mailed Aug. 15, 2005.
U.S. Appl. No. 09/724,319, Office Action mailed May 16, 2007.
U.S. Appl. No. 09/724,319, Office Action mailed Jan. 11, 2008.
U.S. Appl. No. 09/724,575, Office Action mailed May 6, 2005.
U.S. Appl. No. 09/724,575, Office Action mailed Oct. 17, 2005.
U.S. Appl. No. 09/724,575, Office Action mailed Mar. 31, 2006.
U.S. Appl. No. 09/980,568, Office Action mailed Nov. 2, 2004.
U.S. Appl. No. 10/010,942, Office Action mailed Jan. 19, 2005.
U.S. Appl. No. 10/010,942, Office Action mailed Oct. 3, 2005.
U.S. Appl. No. 10/232,030, Office Action mailed Jun. 15, 2007.
U.S. Appl. No. 10/429,216, Office Action mailed Jan. 28, 2008.
U.S. Appl. No. 10/625,854, Office Action mailed May 15, 2007.
U.S. Appl. No. 10/703,713, Office Action mailed Jun. 2, 2006.
U.S. Appl. No. 10/777,792, Office Action mailed Apr. 3, 2008.
U.S. Appl. No. 10/828,548, Office Action mailed Sep. 11, 2007.
U.S. Appl. No. 10/889,999, Office Action mailed Aug. 15, 2005.
U.S. Appl. No. 10/890,000, Office Action mailed Sep. 19, 2005.
U.S. Appl. No. 10/890,000, Office Action mailed Mar. 10, 2006.
U.S. Appl. No. 10/890,070, Office Action mailed Sep. 29, 2005.
U.S. Appl. No. 10/923,469, Office Action mailed Mar. 24, 2008.
U.S. Appl. No. 10/923,471, Office Action mailed Aug. 24, 2005.
U.S. Appl. No. 10/923,471, Office Action mailed May 15, 2006.
U.S. Appl. No. 10/923,471, Office Action mailed Jul. 31, 2007.
U.S. Appl. No. 10/923,474 Office Action mailed Jun. 26, 2007.
U.S. Appl. No. 11/245,524, Office Action mailed Jun. 4, 2008.
U.S. Appl. No. 11/245,916, Office Action mailed Jan. 28, 2008.
U.S. Appl. No. 11/342,353, Office Action mailed Jul. 22, 2008.
U.S. Appl. No. 11/244,678, Office Action mailed Mar. 24, 2008.
U.S. Appl. No. 10/232,030, Advisory Action mailed Oct. 30, 2006.
U.S. Appl. No. 10/232,030, Office Action mailed Apr. 1, 2008.
U.S. Appl. No. 10/704,070, Office Action mailed Jun. 6, 2006.
U.S. Appl. No. 10/771,174, Office Action mailed Aug. 23, 2007.
U.S. Appl. No. 10/858,855, Office Action mailed Nov. 23, 2007.
U.S. Appl. No. 10/858,855, Advisory Action mailed Apr. 7, 2008.
U.S. Appl. No. 10/388,214, Office Action mailed Jul. 28, 2006.
U.S. Appl. No. 11/305,889, Office Action mailed May 23, 2008.
U.S. Appl. No. 11/454,772, Office Action mailed Dec. 21, 2007.
U.S. Appl. No. 09/201,430, Office Action mailed Nov. 26, 2001.
U.S. Appl. No. 09/201,430, Advisory Action mailed Jun. 18, 2002.
U.S. Appl. No. 09/322,289, Office Action mailed Oct. 16, 2005.
U.S. Appl. No. 09/322,289, Office Action mailed Nov. 29, 2005.
U.S. Appl. No. 09/322,289, Office Action mailed Jul. 17, 2007.
U.S. Appl. No. 09/723,713, Office Action mailed Feb. 12, 2002.
U.S. Appl. No. 09/723,713, Office Action mailed Jun. 3, 2004.
U.S. Appl. No. 09/723,713, Office Action mailed Jan. 11, 2006.
U.S. Appl. No. 09/723,713, Advisory Action mailed Dec. 20, 2004.
U.S. Appl. No. 09/723,760, Office Action mailed Feb. 23, 2004.
U.S. Appl. No. 09/723,760, Office Action mailed Dec. 29, 2005.
U.S. Appl. No. 09/723,760, Advisory Action mailed Dec. 16, 2004.
U.S. Appl. No. 09/724,319 Office Action mailed May 2, 2006.
U.S. Appl. No. 09/724,495, Office Action mailed Sep. 26, 2005.
U.S. Appl. No. 09/724,495, Advisory Action mailed May 16, 2004.
U.S. Appl. No. 10/828,548, Office Action mailed Oct. 24, 2006.
U.S. Appl. No. 10/828,548, Office Action mailed Jun. 4, 2008.
U.S. Appl. No. 10/828,548, Advisory Action mailed Jun. 8, 2007.
U.S. Appl. No. 10/923,471, Office Action mailed Dec. 29, 2006.
U.S. Appl. No. 10/923,471, Office Action mailed Apr. 24, 2008.
U.S. Appl. No. 10/923,474 Office Action mailed Aug. 4, 2006.
U.S. Appl. No. 10/923,474, Advisory Action mailed Feb. 22, 2007.
U.S. Appl. No. 11/058,757, Office Action mailed Aug. 11, 2006.
U.S. Appl. No. 11/058,757, Advisory Action mailed Mar. 5, 2007.
U.S. Appl. No. 09/724,273, Office Action mailed Oct. 16, 2003.
U.S. Appl. No. 09/724,273, Advisory Action mailed Mar. 18, 2004.
U.S. Appl. No. 09/724,273, Office Action mailed Dec. 28, 2004.
U.S. Appl. No. 09/724,273, Advisory Action mailed Jun. 16, 2005.
U.S. Appl. No. 09/724,273, Office Action mailed Aug. 22, 2007.
U.S. Appl. No. 09/724,288, Office Action mailed Sep. 9, 2003.
U.S. Appl. No. 09/724,288, Advisory Action mailed Jan. 6, 2004.
U.S. Appl. No. 09/724,288, Office Action mailed Jul. 12, 2005.
U.S. Appl. No. 09/724,288, Advisory Action mailed Mar. 3, 2006.
U.S. Appl. No. 10/777,792, Office Action mailed May 8, 2007.
U.S. Appl. No. 10/890,024, Office Action mailed Jun. 1, 2006.
U.S. Appl. No. 10/889,999, Office Action mailed Mar. 14, 2006.
U.S. Appl. No. 10/890,000, Office Action mailed Nov. 24, 2006.
U.S. Appl. No. 10/890,000, Advisory Action mailed Jan. 14, 2008.
U.S. Appl. No. 09/723,765, Office Action mailed Oct. 7, 2003.
U.S. Appl. No. 09/723,765, Advisory Action mailed Feb. 9, 2004.
U.S. Appl. No. 09/723,765, Office Action mailed May 4, 2005.
U.S. Appl. No. 09/204,838, Office Action mailed Sep. 27, 2001.
U.S. Appl. No. 09/724,567, Office Action mailed Jul. 23, 2003.
U.S. Appl. No. 09/724,575, Office Action mailed Jul. 25, 2003.
U.S. Appl. No. 09/724,575, Advisory Action mailed Feb. 12, 2004.
U.S. Appl. No. 09/724,575, Office Action mailed Oct. 12, 2006.
U.S. Appl. No. 09/724,953, Office Action mailed Jul. 25, 2003.
U.S. Appl. No. 11/274,493, Office Action mailed Nov. 2, 2007.
U.S. Appl. No. 10/625,854, Office Action mailed Aug. 23, 2006.
U.S. Appl. No. 10/625,854, Office Action mailed Nov. 7, 2007.
U.S. Appl. No. 10/625,854, Advisory Action mailed Jan. 8, 2008.
U.S. Appl. No. 11/108,102, Office Action mailed Sep. 6, 2006.
U.S. Appl. No. 11/245,916, Office Action mailed Jan. 12, 2007.
U.S. Appl. No. 11/245,916, Advisory Action mailed May 15, 2007.
U.S. Appl. No. 11/245,916, Advisory Action mailed Oct. 18, 2007.
U.S. Appl. No. 10/429,216, Office Action mailed Jan. 3, 2007.
U.S. Appl. No. 10/890,070, Office Action mailed Jun. 1, 2006.
U.S. Appl. No. 09/201,430, Notice of Allowance mailed Mar. 26, 2003.
U.S. Appl. No. 09/201,430, Notice of Allowance mailed Sep. 23, 2003.
U.S. Appl. No. 09/724,477, Notice of Allowance mailed Apr. 30, 2003.
U.S. Appl. No. 09/724,477, Notice of Allowance mailed Sep. 23, 2003.
U.S. Appl. No. 09/723,927, Notice of Allowance mailed Sep. 23, 2003.
U.S. Appl. No. 09/723,762, Notice of Allowance mailed May 1, 2003.

(56) References Cited

OTHER PUBLICATIONS

U.S. Appl. No. 09/724,102, Notice of Allowance mailed Aug. 22, 2003.
U.S. Appl. No. 09/724,489, Notice of Allowance mailed Mar. 25, 2003.
U.S. Appl. No. 09/724,489, Notice of Allowance mailed Sep. 22, 2003.
U.S. Appl. No. 10/232,030, Notice of Allowance mailed Sep. 4, 2008.
U.S. Appl. No. 10/816,022, Notice of Allowance mailed Jul. 1, 2004.
U.S. Appl. No. 10/816,529, Notice of Allowance mailed Jul. 1, 2004.
U.S. Appl. No. 10/815,391, Notice of Allowance mailed Jul. 1, 2004.
U.S. Appl. No. 10/815,353, Notice of Allowance mailed Jul. 1, 2004.
U.S. Appl. No. 10/816,380, Notice of Allowance mailed Dec. 22, 2004.
U.S. Appl. No. 10/815,404, Notice of Allowance mailed Oct. 15, 2004.
U.S. Appl. No. 10/884,892, Notice of Allowance mailed Mar. 28, 2005.
U.S. Appl. No. 09/723,384, Notice of Allowance mailed Mar. 31, 2003.
U.S. Appl. No. 09/724,940, Notice of Allowance mailed Oct. 4, 2004.
U.S. Appl. No. 09/724,961, Notice of Allowance mailed Dec. 3, 2003.
U.S. Appl. No. 09/580,018, Notice of Allowance mailed Dec. 3, 2003.
U.S. Appl. No. 09/724,552, Notice of Allowance mailed Dec. 3, 2003.
U.S. Appl. No. 09/724,551, Notice of Allowance mailed Dec. 4, 2003.
U.S. Appl. No. 09/724,567, Notice of Allowance mailed Mar. 3, 2004.
U.S. Appl. No. 09/724,953, Notice of Allowance mailed Mar. 11, 2004.
U.S. Appl. No. 09/979,952, Notice of Allowance mailed Nov. 12, 2004.
U.S. Appl. No. 10/934,609, Notice of Allowance mailed Dec. 22, 2004.
U.S. Appl. No. 10/934,609, Notice of Allowance mailed Aug. 17, 2005.
U.S. Appl. No. 10/933,559, Notice of Allowance mailed Sep. 7, 2005.
U.S. Appl. No. 10/933,559, Notice of Allowance mailed Aug. 17, 2005.
U.S. Appl. No. 10/933,559, Notice of Allowance mailed Dec. 22, 2004.
U.S. Appl. No. 10/010,942, Notice of Allowance mailed May 11, 2006.
U.S. Appl. No. 10/388,389, Notice of Allowance mailed May 31, 2006.
U.S. Appl. No. 10/388,214, Notice of Allowance mailed Mar. 1, 2007.
U.S. Appl. No. 09/724,288, Notice of Allowance mailed Mar. 23, 2009.
U.S. Appl. No. 11/304,986, Notice of Allowance mailed Jul. 10, 2009.
U.S. Appl. No. 11/707,639, Notice of Allowance mailed Aug. 20, 2009.
U.S. Appl. No. 11/303,478, Office Action mailed Mar. 18, 2009.
U.S. Appl. No. 11/520,438, Office Action mailed Aug. 6, 2009.
U.S. Appl. No. 11/842,042, Office Action mailed Jun. 24, 2009.
U.S. Appl. No. 11/842,056, Office Action mailed May 6, 2009.
U.S. Appl. No. 11/842,085, Office Action mailed Sep. 30, 2009.
U.S. Appl. No. 12/181,238, Office Action mailed May 28, 2009.
U.S. Appl. No. 60/530,480, filed Dec. 17, 2003, Arumugham.
Allen et al, "Reversible posterior leukoencephalopathy syndrome after bevacizumab/FOLFIRI Regimen for Metastatic Colon Caner," *Arch. Neurol.*, 63(10): 1475-1478 (2006), abstract only.
American Type Culture Collection (ATCC) Search Results for "1KTR, 1ETZ, 1JRH", http://www.atcc.org/, pp. 1-3, Feb. 22, 2007.
Armour et al., "Recombinant human IgG molecules lacking Fcγ receptor I binding and monocyte triggering activates," *J. Immunol*, 29:2613-2624 (1999).
Avis, "Perenteral Preparations," *Remington's Pharmaceutical Sciences*, 17:1518-1519 (1985).
Biewenga et al., "Cleavage of Protein A-binding IgA1 with IgA1 Protease From *Streptococcus* Sanguls," *Immunol Commun.*, 12(5):491-500 (1983), abstract only.
Borras-Cuesta et al., "Engineering of Immunogenic Peptides by Co-Linear Synthesis of Determinants Recognized by B and T Cells," *Eur. J. Immunol.*, 17:1213-1215 (1987).
Brinkman, "Splice Variants as Cancer Biomarkers," *Clinical Biochemistry*, 37(7):584-594 (2004).
Buttini et al., "β-Amyloid Immunotherapy Prevents Synaptic Degeneration in a Mouse Model of Alzheimer's Disease," *The Journal of Neuroscience*, 25(40):9096-9101 (2005).
Chen et al., "Selection and Analysis of an Optimized Anti-VEGF Antibody: Crystal Structure of an Affinity-matured Fab in Complex with Antigen," *J. Mol. Biol.*, 293:865-881 (1999).
Choi et al., "A Generic Intron Increases Gene Expression in Transgenic Mice," *Molecular and Cellular Biology*, 11(6):3070-3074 (1991).
Clark et al., *Chemical Immunology Antibody Engineering IgG Effector Mechanisms*, 65:88-110 (1997).
Corcoran et al., "Overexpression of hAPPswe Impairs Rewarded Alternation and Contextual Fear Conditioning in a Transgenic Mouse Model of Alzheimer's Disease," Learn Mem. 9(5):243-252:2000.
Database Geneseq, "Nucleotide Sequence of a Variable Heavy Chain of IgG4," EBI Accession No. GSN:ADZ51216 (2005).
Dialog/Derwent, Abstract of WPI Acc No. 1995-261292/199534: Novel monoclonal antibody against human high-affinity IgE receptor—and DNA fragment encoding the MAb, for the specific identification of human Fc-epsilon RI, Derwent WPI database (1995).
Ecuadorian Search Report of Jul. 2, 2009 for Ecuador Patent Application No. SP 03-4685.
Extended European Search Report of Dec. 18, 2008 for European Application 05812436.6-1212.
European Examination Report of Sep. 23, 2008 for European Application 04776252.1-2405.
European Examination Report as part of Dec. 8, 2008 communication for European Application 04720353.4.
European Examination Report of Nov. 20, 2008 for European Application 08011409.3.
Family and legal status of EP0613007, Inpadoc Search (2009).
Fragione et al., Familial cerebral amyloid angiopathy related to stroke and dementia. *Amyloid*, 8(Suppl 1):36-42 (2001), abstract only.
Genbank Accession No. AAA69734, Schroeder et al., "Immunoglobulin heavy chain [*Homo sapiens*], Anti-DNA immunoglobulin light chain IgG [*Mus musculus*]," Jul. 11, 1995.
Genbank Accession No. BAC01733, Akahori et al., "Immunoglobulin kappa light chain VLJ region [*Homo sapiens*]", Jul. 2, 2002.
Ghetie et al., "CD4 Peptide-Protein Conjugates, But Not Recombinant Human CD4, Bind to Recombinant gp120 From the Human Immunodeficiency Virus in the Presence of Serum From AIDS Patients.," *Proc. Natl. Acad. Sci.*, 88:5690-5693 (1991).
Golding et al., "Vaccine Strategies: Targeting Helper T Cell Responses," *Annals New York Academy of Sciences*, 31:126-137 (1995).
Harlow et al., eds., *Antibodies: A Laboratory Manual*, pp. 71-82 (1988).
Harlow et al., eds., *Antibodies: A Laboratory Manual*, p. 98 (1988).
Hezareh et al., "Effector Function Activities of a Panel of Mutants of a Broadly Neutralizing Antibody against Human Immunodeficiency Virus Type 1," *Journal of Virology*, 24(75):12161-12168 (2001).
Hillen-Maske et al., "Konichalcit", *Rompp Chemie Lexilkon*, 9th edition, p. 2322 (1990).
Hogarth, Fc Receptors Are Major Mediators of Antibody Based Inflammation in Autoimmunity, *Current Opinion in Immunology*, 14:798-802 (2002).

(56) References Cited

OTHER PUBLICATIONS

Holmes et al., "Long-term Effects of Aβ$_{42}$ Immunization in Alzheimer's Disease: Follow-up of a Randomised, Placebo-controlled Phase I Trial," *Lancet*, 372: 216-223 (2008).
Hopp et al., "Prediction of protein antigenic determinants from amino acid sequences," *Proc. Natl. Acad. Sci.*, 78:3824-3828 (1981).
Hussain et al., "Selective Increases in Antibody Isotopes and Immunoglobulin G Subclass Responses to Secreted Antigens in Tuberculosis Patients and Healthy Household Contacts of the Patients," *Clinical and Diagnostic Laboratory Immunology*, 2(6): 726-732 (1995).
Hyslop et al., "Will Anti-amyloid Therapies Work for Alzheimer's Disease?," *Lancet*, 372:180-182 (2008).
Janeway et al., *Immunobiology*, 3$^{rd}$ edition, pp. 8:18-8:19 (1997).
Mann et al., "Atypical Amyloid (ABeta) Deposition in the cerebellum in Alzheimer's Disease: An Immunohistochemical Study Using End-Specific ABeta Monoclonal Antibodies," *ACTA Neuropathologica*, 91:647-653 (1996).
Mann et al., "Predominant deposition of amyloid-beta 42(43) in plaques in cases of Alzheimer's disease and hereditary cerebral hemorrhage associated with mutations in the amyloid precursor protein gene," The *American Journal of Pathology APR*, 4(148): 1257-1266 (1996).
Mavragani et al., "A Case of Reversible Posterior Leucoencephalopathy Syndrome After Rityximab Infusion," *Rheumatology*, 43(11) 1450-1451 (2006).
Mitchell et al, "Prevention of Intracerebral Hemorrhage," *Current Drug Targets*, 8(7):832-838 (2007).
Mutschler et al., "*Arzneimittel-Wirkungen, Lehrbuch der Pharmakologie und Taxiklogie*," Wissenschftliche Verlagsgesellschaft mbH Stuttgart, 6$^{th}$ edition, pp. 651-656 (1991), (German Article).
Myers et. al., "Targeting Immune Effector Molecules to Human Tumor Cells Through Genetic Delivery of 5T4-Specific SCFV Fusion Proteins," *Cancer Gene Therapy*, 9(11):884-896 (2002).
Nashar et al., "Current progress in the development of the B subunits of cholera toxin and *Escherichia coli* heat-labile enterotoxin as carries for the oral delivery of herterologous antigens and epitopes," *Vaccine*, 11(2):235-40 (1993), abstract only.
Padlan et al., Structure of an Antibody-Antigen Complex: Crystal Structure of the HyHEL-10 Fab-lysozyme Complex, *Immunology*, 86:5938-5942 (1989).
Pangalos et al., "Disease Modifying Strategies for the Treatment of Alzheimer's Disease Targeted at Modulating Levels of β-amyloid Peptide," *Biochemical Society Transactions*, 33(4):553-558 (2005).
Pascalis et al., "Grafting of "Abbreviated" Complementarity-Determining Containing Specificity-Determining Residues Essential for Ligand Contact to Engineer a Less Immunogenic Humanized Monoclonal Antibody," *The Journal Immunology*, 169:3076-3084 (2002).
PCT Written Opinion of Dec. 22, 2008 for application PCT/US2008/80370.
PCT Search Report of Jan. 22, 2009 for application PCT/US2008/80370.
Prada et al., "Antibody-Mediated Clearance of Amyloid-β Peptide From Cerebral Amyloid Angiopathy Revealed by quantitative in Vivo Imaging," *Journal of Neuroscience*, 27(8):1973-1980 (2007).
Qu et al., "Aβ$_{42}$ gene Vaccine Prevents Aβ$_{42}$ deposition in brain of Double Transgenic Mice," *J. Neurological Sciences*, 260:204-213 (2007).
Putative CDR determination for SEQ Id Nos. 2 and 4 (pp. 1-2), Jun. 10, 2004.
Riechmann et al., "Reshaping Human Antibodies for Therapy," *Nature*, 332:323-327 (1988).
Robbins et al., "The Intronic Region of an Incompletely Spliced gp100 Gene Transcript Encodes an Epitope Recognized by Melanoma-Reactive Tumor-Infiltrating Lymphocytes," *Journal of Immunology*, 159(1):303-308 (1997).
Rolph et al., "Recombinant viruses as vaccines and immunological tools" *Immunity to Infection*, 9:517-521 (1997).

Saido et al., "Autolytic Transition of μ-Calpain Upon Activation as Resolved by Antibodies Distinguishing Between the Pre- and Post-Autolysis Forms," *J. Biochem.*, 111:81-86 (1992).
Schmidt et al., "Monoclonal Antibodies to a 100-kd protein reveal abundant A beta-negative plaques throughout gray matter of Alzheimer's disease brains," *The American Journal of Pathology*, 1(151):69-80 (1997).
Schroeder et al., "Preferential Utilization of Conserved Immunoglobulin Heavy Chain Variable Gene Segments During Human Fetal Life," *Immunology*, 87:6146-6150 (1990).
Seabrook et al., "Species-specific Immune response to Immunization with Human Versus rodent Abeta Peptide," *Neurobiology of Aging*, 25(9) 1141-1151 (2004).
Shepherd et al., "The design of the humanized antibody," *Monocolonal Antibodies: A Practical Approach*, 58-66 (2000).
Sidhu, "Page display in pharmaceutical biotechnology," *Current Opinion in Biotechnology*, 11:610-616 (2000).
Smith et al., "Phage Display," *Chemical Reviews, American Chemical Society*, 97(2):391-410 (1997).
Sood et al., "Synthetic Peptides: A Modern Approach to Vaccination," *Indian Journal of Experimental Biology*, 34:849-861 (1998).
Staunton et al., "Primary structures of ICAM-1 demonstrates interaction between members of the immunoglobulin and intergrin supergene families," *Cell* 52(6):925-33 (1988), abstract only.
Studnicka et al., "Human-engineered monocilnal antibodies retain full specific binding activity by preserving non-CDR complemenatary-modullating resudes," *Protien Eng.*, 7(6):805-814 (1994), Abstract only.
Tamaokaet al., "Antibodies to amyloid beta protein (A beta) crossreact with glyceraldehyde-3-phosphate dehyrogenase (GAPDH)," *Neurobiology of Aging*, 3(17):405-414 (1996).
Trang et al., "Pharmacokinetics of a Mouse/Human Chimeric Monoclonal Antibody (C-17-1A) in Metastatic Adencarcinoma Patients," *Pharmaceutical Research*, 7(6):587-592 (1990).
U.S. Appl. No. 09/316,387, Office Action mailed Sep. 10, 2007.
U.S. Appl. No. 09/316,387, Response to Jun. 20, 2005 Office Action filed Dec. 20, 2005.
U.S. Appl. No. 09/316,387, Declaration of Solomon, Hrncic, and Wall under 37 C.F.R. § 1.131 filed Mar. 6, 2006.
U.S. Appl. No. 09/316,387, Office Action mailed Jun. 20, 2005.
Vajdos et al., "Comprehensive Functional Maps of the Antigen-binging site of an Anti_ErbB2 Antibody Obtained with Shotgun Scanning Mutagenesis," *J. Mol. Biol.*, 320:415-428 (2002).
Ward et al., "Spontaneous Deletions in Ig Heavy Chain Genes Flaking Sequences Influence Splice Site Selection," *Nucleic Acids Research*, 19(23): 6475-6480 (1991).
Wikipedia entry for Antibody, retrieved Apr. 27, 2009 from http://en.wikipedia.org/wiki/Antibody.
Wilson et al., "Phage display: applications, innovations, and issues in phage and host biology," *Can. J. Microbiol*, 44:313-329 (1998).
Wu et al., "Humanization of a Murine Monoclonal Antibody by Simultaneous Optimization of Framework and CDR Residues," *J. Mol. Biol.*, 294:151-162 (1999).
Yanagisawa K et al., "Amyloid BETA-protein (Alpha-Beta) associated with lipid molecules: immunoreactivity distinct from that of soluble Alpha-Beta," *FEBS Letters*, 1(420): 43-46 (1997).
Yang et al., "Monoclonal Antibody to the C-terminus of Beta-Amyloid," *Neuroreport*, 16(5):2117-2120 (1994).
U.S. Appl. No. 11/520,438, Office Action mailed Apr. 2, 2009.
U.S. Appl. No. 11/707,639, Office Action mailed Apr. 3, 2009.
U.S. Appl. No. 11/842,085, Office Action mailed Apr. 14, 2009.
U.S. Appl. No. 11/842,113, Office Action mailed Dec. 17, 2009.
U.S. Appl. No. 11/842,120, Office Action mailed Apr. 14, 2009.
U.S. Appl. No. 12/328,740, Office Action mailed Oct. 9, 2009.
U.S. Appl. No. 10/858,855, Office Action mailed Dec. 15, 2009.
U.S. Appl. No. 10/923,471, Office Action mailed Mar. 20, 2009.
U.S. Appl. No. 11/245,524, Office Action mailed Apr. 17, 2009.
U.S. Appl. No. 11/842,023, Office Action mailed Aug. 14, 2009.
U.S. Appl. No. 09/322,289, Office Action mailed Jun. 4, 2009.
U.S. Appl. No. 09/724,319 Advisory Action mailed Oct. 28, 2009.
U.S. Appl. No. 09/724,319 Office Action mailed Apr. 8, 2009.
U.S. Appl. No. 10/923,469. Advisory Action mailed Apr. 16, 2009.
U.S. Appl. No. 11/245,524, Office Action mailed Nov. 20, 2009.

(56) References Cited

OTHER PUBLICATIONS

U.S. Appl. No. 11/245,916, Advisory Action mailed Jun. 10, 2009.
U.S. Appl. No. 09/322,289, Notice of Allowance mailed Nov. 15, 2010.
U.S. Appl. No. 10/858,855, Notice of Allowance mailed Jul. 12, 2010.
U.S. Appl. No. 11/842,023, Notice of Allowance mailed Oct. 6, 2010.
U.S. Appl. No. 12/181,238, Notice of Allowance mailed Mar. 5, 2010.
U.S. Appl. No. 12/181,238, Notice of Allowance mailed Mar. 11, 2011.
U.S. Appl. No. 09/724,319, Office Action mailed Dec. 21, 2010.
U.S. Appl. No. 09/724,495, Advisory Action mailed May 16, 2006.
U.S. Appl. No. 10/544,093, Office Action mailed Oct. 13, 2010.
U.S. Appl. No. 10/777,792, Advisory Action mailed Nov. 30, 2010.
U.S. Appl. No. 10/923,471, Office Action mailed Dec. 24, 2009.
U.S. Appl. No. 11/664,865, Office Action mailed Feb. 11, 2011.
U.S. Appl. No. 11/842,042, Office Action mailed Mar. 30, 2010.
U.S. Appl. No. 11/842,116, Office Action mailed Nov. 26, 2010.
U.S. Appl. No. 12/037,045, Office Action mailed Apr. 28, 2010.
U.S. Appl. No. 12/181,238, Examiner Interview Summary mailed Mar. 5, 2010.
U.S. Appl. No. 12/253,929, Office Action mailed Apr. 28, 2010.
U.S. Appl. No. 12/336,340, Office Action mailed Mar. 4, 2010.
U.S. Appl. No. 10/429,216, Office Action mailed May 24, 2011.
U.S. Appl. No. 12/037,045, Office Action mailed Nov. 4, 2011.
"AAB-001 in Patients with Mild to Moderate Alzheimer's Disease" ClinicalTrials.gov last updated Sep. 22, 2009 3 pages.
Abcam, "Anti-beta Amyloid antibody 6F/3D", *Nucleic Acids Res.* 38:D142-D148 (2010).
Agadjanyan et al., "Prototype Alzheimer's Disease Vaccine Using the Immunodominant B Cell Epitope From {beta}-Amyloid and Promiscuous T Cell Epitope Pan HLA DR-Binding Peptide," *J. Immunol.*, 174:1580-1586 (2005).
Aihara, et al., "Immunocytochemical Localization of Immunoglobulins in the Rat Brain: Relationship to the Blood-Brain Barrier", *J of Comparative Neurology* 342:481-496 (1994).
Alzheimer Research Forum, "Drugs in Clinical Trials" Oct. 18, 2010.
Applicants' submission in EP 07012421.9 dated Jun. 16, 2009.
Aquila Press Release, PR Newswire. May 6, 1997.
Assignment executed Dec. 8, 2000 in respect of U.S. Appl. No. 60/067,740.
Assignment executed Dec. 8, 2000 in respect of U.S. Appl. No. 60/080,970.
Auclair et al., "Effect of Active Immunization Against Oestriadiol in Developing Ram Lambs on Plasma Gonadotrophin and Testosterone Concentrations, Time of Onset of Puberty and Testicular Blood Flow," *Journal of Reproduction and Fertility*, 104:7-16 (1995).
Aylward et al., "Cerebellar Volume in Adults With Down Syndrome," *Arch Neurol.*, 4(2):209-212 (1997). Abstract only.
Bach et al., "Vaccination with AB-Displaying Virus-Like Particles Reduces Soluble and Insoluble Cerebral AB and Lowers Plaque Burden in APP Transgenic Mice," *J. Immunol.*, 2009, 182 7613-7624.
Bandlow et al., "Untersuchungen Zum Mechanismus Der Immunologischen Adjvanswirung des Vacciniavirus[1]," *Archiv für due gesamte Virusfoschung*, 38:192-204 (1972). German article.
Barelli et al., "Characterization of New Polyclonal Antibodies Specific for 40 and 42 Amino Acid-Long Amyloid β Peptides: Their Use to Examine the Cell Biology of Presenilins and the Immunohistochemistry of Sporadic Alzheimer's Disease and Cerebral Amyloid Angiopathy Cases," *Molecular Medicine*, 3(10):695-707 (1997).
Begley, "Delivery of Therapeutic Agents to the Central Nervouse System: The Problems and the Possibilities," *Pharmacol. Therapy*, 104(1): 29-45 (Oct. 2004).
Birmingham et al., "Set back to Alzheimer vaccine studies" *Nature Medicine* 8(3):199-200 (2002).
Black et al., "A Single Ascending Dose Study of Bainezumab, A Humanized Monoclonal Antibody to Aβ, In AD," *9th International Geneva/Springfield Symposium on Advances in Alzheimer Therapy*, 1 page (Apr. 20, 2006). Abstract only.
Boraschi et al., "Interleukin-1 and Interleukin-1 Fragments a Vaccine Adjuvants", Methods, 1999, 19, pp. 108-113.
Bruggermann, et al. "The Immunogenicity of Chimeric Antibodies" *J. Exp Med.*, 170(2):153-2157 (1989).
Burbach et al. "Vessel ultrastructure in APP23 transgenic mice after passive anti-Aβ immunotherapy and subsequent intracerebral hemorrhage" Neurobiology of Aging 28:202-212 (2007).
Chauhan et al. "Intracerebroventricular Passive Immunization With Anti-Aβ Antibody in Tg2576" J of Neuroscience 74:142-147 (2003).
Check, "Nerve Inflamtion Halts Trail for Alzheimer's Drugs," Nature, 415:462 (2002).
Claudio, "Ultrastructural features of the blood-brain barrier in biopsy tissue for Alzheimer's disease patients." *Acta Neuropathol.* 91:6-14 (1996).
Communication in EP 07012421.9 pursuant to Art. 94(3) EPC dated Nov. 5, 2010.
Constantino, Expert opinion Sep. 17, 2010.
Cribbs et al., "Adjuvant-dependant modulation of th1 and th2 responses to immunization with B-amyloid", International Immunology, 2003, vol. 15, No. 4, pp. 505-514.
Decision of Opposition Division in EP 1 160 256 dated Feb. 17, 2011.
Declaration of Dr. Mattias Staufenbiel Ph D. Jul. 15, 2011.
Declaration of Shyra J. Gardai dated Mar. 2, 2009.
Do et al., "Reprogramming Somatic Gene Activity by Fusion With Pluripotent Cells" *Stem Cell Reviews.*, 2:257-264 (2006).
Donnelly, "New Developments in Adjuvants," *Mechanism of Ageing and Development*, 93:171-177 (1997).
Druckexemplar in EP 1 160 256 dated Jan. 25, 2010.
Elan Reports First Quarter 2006 Financial Results. Business Wire (May 4, 2006) XP002620724.
Elan Reports First Quarter 2006 Financial Results. Business Wire (May 4, 2006) XP002620725.
European Search Report of Feb. 7, 2011 for European Application EP 08 74 6362.6.
Extract from EPO patent register of EP 1 160 256 retrieved on Sep. 7, 2011.
Extract from EPO patent register of EP 1 842 859 retrieved on Sep. 7, 2011.
Gambetti, et al., "Human brain amyloidosis," *Nephrology Dialysis Transplantation*, 13(Suppl. 7):33-40, (1998).
Gauthier et al., "Alzheimer's Disease: Current Knowledge, Management and Research," Can. Med. Assoc. J., 157:1047-1052 (Oct. 15, 1997).
Genbank Accession No. AAD00856.1, "Igm Heavy Chain Variable Region [*Homo sapiens*]," Jul. 31, 2001.
Genbank Accession No. AAB35009.1, Wang et al., "Antiidiotypic Ig 1F7 Light Chain Variable Region [Human, 1F7 Hybridoma Cells, Peptide Partial, 120aa]," Oct. 28, 1995.
GenBank, Accession No. AAA38630.1, "Immunoglobulin gamma-1 chain [*Mus musculus*]" May 5, 1994.
Ghersi-Egea et al., "Fate of Cerebrospinal Fluid-Borne Amyloid β-Peptide: Rapid Clearance into Blood and Appreciable Accunulation by Cerebral Arteries," *Journal of Neurochemistry.* vol. 67 No. 2:880-883 (1996).
Ghochikyan, "Rationale for Peptide and DNA Based Epitope Vaccine for Alzheimer's Disease Immunotherapy", CNS Neurol Disord Drug Targets, 2009: 8(2): 128 1-18.
Greenberg et al. "Amyloid Angiopathy-Related Vascular Congnitive Impairment" Stoke., 35:2616-2619 (2004).
Greisman et al., "A General Strategy for Selecting High-Affinity Zinc finger Proteins for Diverse DNA Target Sites" Science vol. 275:657-661 (1997).
Gustavsson et al., "Mechanisms of Transthyretin Amyloidogenesis Antigenic Mapping of Transthyretin Pruified from Plasma and Amyloid Fibrils and within in Situ Tissue Localizations" American Journal of Pathology 44(6):1301-1311 (1994).
Hamilton, "Molecular Engineering: Applications to the Clinical Laboratory," Clin. Chem. 39(9):1988-1997 (1993).
Hampel et al., "Measurement of Phosphorylated Tau epitopes in the Differential Diagnosis of Alzheimer Disease", Arch Gen Psychiatry (2004) 61(1):95-102.

(56) References Cited

OTHER PUBLICATIONS

Harlow et al., eds., *Antibodies: A Laboratory Manual*, pp. 139-195 (1988).
Hartwig, "Immune ageing and Alzheimer's disease," *NeuroReport*, 6:1274-1276 (1995).
Hellman et al., "Allergy Vaccines—A Review of Developments," *Clin. Immunother.*, 6(2): 130-142 (Aug. 1996).
Hermanson et al., "Amino Acids as Spacers," *Immobilized Affinity Ligand Techniques*, section 3.1.1.5:150-152 (1992).
Holm et al., "Functional Mapping and Single Chain Construction of the Anti-Cytokeratin 8 Monoclonal Antibody TS1," *Mol. Immunol.*, 44(6):1075-1084 (Feb. 2007).
Huang et al., "Amyloid β-Peptide Possesses a Transforming Growth Factor-β-Activity," *The Journal of Biological Chemistry*, 273(42):27640-27644 (Oct. 16, 1998).
Hudson et al., "Antibody as a Probe," *Practical Immunology*, Chapter 2, pp. 34-85 (1989).
Hyman, et al. "Kunitz Protease Inhibitor-Containing Amyloid β Protein Precursor Immunoreactivity in Alzheimer's Disease", *J. of Neuropathology*, 51(1):76-83 (1992).
Invitrogen Data Sheet, "Mouse anti-β-Amyloid Peptide", Catalog No. 13-0100Z (Rev Oct. 2008) DCC-08-1089.
Jagust et al., "Brain Imaging Evidence of preclinical Alzheimer's disease in normal aging" Ann Neurol, (2006) 59:67-681: abstract p. 676, table 1.
Janeway et al., *Immunobiology*, 3$^{rd}$ edition, pp. 2:7, 2:9, 2:12, 8:16-8:17, 12:43 (1997).
Janeway, et al., *Immunobiology: The Immune System in Health and Disease* 3rd Edition; cover pages and pp. 3.22-3.27 (1997).
Jarrett et al., "The Carboxy Terminus of the β Amyloid Protein is Critical for the Seeding of Amyloid Formation: Implications for the Pathogenesis of Alzheimer's Disease," *Biochemistry*, 32:4693-4697 (Nov. 5, 1993).
Jefferis, "Antibody therapeutic: isotype and glycoform selection", *Expert Opin. Biol. Ther*. 7(9):1401-1413 (2007).
Jennings, "Review of Selected Adjuvants Used in Antibody Production," *ILAR Journal*, 37(3) (1995).
Kallberg et al., "Prediction of Amyloid Fibril-Forming Proteins," *The Journal of Biological Chemistry*, 276(16):12945-12950 (Apr. 20, 2001).
Kardana et al., "Serum HCG β-Core Fragment is Masked by Associated Macromolecules," *Journal of Clinical Endocrinology and Metabolism*, 71(5):1393-1395, (1990).
Khan et al., "Immunopotentiation and Delivery Systems for Antigens for Single-Step Immunization: Recent Trends and Progress," *Pharmaceutical Research*, 11(1):2-11 (1994).
Kim et al., "In Vivo Engineering of a Cellular Immune Response by Coadministration of 1L-12 Expression Vector with a DNA Immunogen," *J. Immunol.*, 158:816-826 (1997).
Kinnecom et al., "Course of Cerebral Amyloid Angiopathy? Related Inflation," *Neurology*, 68(17):1411-1416 (2007).
Klafki et al., "Therapeutic approaches to Alzheimer's disease" *Brain* 129:2840-2825 (2006).
Kofke et al., "Remifentanil-Induced Cerebral Blood Flow Effects in Normal Humans: Dose and ApoE genotype," *Neurosurg Anesthes Neurosci.*, 105(1):167-175 (2007).
Koller et al., "Active Immunization of Mice with a Aβ-Hsp70 Vaccine," *Neurodegenerative Disases*, 1:20-28 (2004).
Kuby, *Immunology*, 2nd Ed., Freeman pp. 126 and 168-171 (1994).
Lemere, "Developing novel immunogens for a safe and effective Alzheimer's disease vaccine" Prog Brain Res. 2009; 175: 83 1-13.
Marx et al., "Immune recognition of the Alzheimer amyloid β protein" Poster presentation; Autoreactive T. cells P.5.18.03 Jun. 25, 1997.
Misra et al., "Drug Delivery to the Central Nervous System: A review," *J. Pharm Pharm Sci.*, 6(2):252-273 (May 2003). Abstract.
Moretto, et al., "Conformation-sensitive Antibodies against Alzheimer Amyloid-β by Immunization with a Thioredoxin-constrained B-cell Epitope Peptide", *J of Biological Chemistry*, 282(14):11436-11445 (2007).

Mount et al. "Alzheimer disease: progress or profit?" Market Analysis Nature Medicine 12(7) 780-784 (Jul. 2006).
Movsesyan et al., "Reducing AD-Lide Pathology in 3×Tg-AD Mouse Model by DNA epitope Vaccine—A Novel Immunotherapeutic Strategy", PloS ONE, 2008, vol. 3, issue 5, e2124 1-13.
Novartis, "Novartis MF59$^{TM}$—Adjuvanted Influenza Vaccine (Fluad®) Significantly Reduces Hospitalization in Elderly," Novartis Press Release, Oct. 19, 2007.
Patentee's Grounds of Appeal in EP Patent No. 1 033 996 dated Jul. 18, 2011.
PCT International Preliminary Report on Patentability (Chapter I) of Oct. 20, 2009 with Written Opinion of Oct. 3, 2008 for application PCT/US2008/060926.
PCT International Preliminary Report on Patentability (Chapter I) of Feb. 2, 2010 for application PCT/US07/09499.
PCT International Preliminary Report on Patentability (Chapter I) and Written Opinion Completed Dec. 22, 2008 for PCT/US2008/080370.
PCT Search Report of Mar. 25, 2009 for application PCT/US2008/80382.
PCT Search Report of Oct. 9, 2008 for application PCT/US2008/060926.
PCT Written Opinion of Mar. 8, 2009 for application PCT/US2008/80382.
PCT/US2011/026365 International Written Opinion and Search Report mailed Jul. 13, 2011.
PCT/US2011/033649 International Written Opinion and Search Report mailed Aug. 26, 2011.
Plant et al., "The Production of Amyloid β Peptide is a Critical Requirement for the Viability of Central Neurons," *The Journal of Neuroscience*, 23(13):5531-5535, (2003).
Poduslo et al., "Macromolecular permeability across the blood-nerve and blood-brain barriers." *Proc. Natl. Acad. Sci USA* . vol. 91 pp. 5705-5709 (1994).
Ramshaw et al., "DNA vaccines for the treatment of autoimmune disease," *Immunology and Cell Biology*, 75:409-413 (1997).
Ray. "Wyeth Study Finds Alzheimer's Drug Works in ApoE4 Non-Carriers". Poster 2008, [retrieved from the internet Jun. 16, 2011: <URL: elan2006.blogspot.com/2008/07/elan-wyeth-studfindalzheimerdrug.html>].
Robert et al., Engineered antibody intervention strategies for Alzheimer's disease and related dementias by targeting amyloid and toxic oligomers:, Protein Eng Des Sel. (2009) 22:(2):199-208.
Saido et al., "Amino-and-Carboxyl-Terminal Heterogeneity of β-Amyloid Peptides Deposited in Human Brain," Neuroscience Letters, 215:173-176 (Aug. 8, 1996).
Sheehan et al., "The Utilization of Individual $V_H$ Exons in the Primary Repertoire of Adult BALB/c Mice[1]," The Journal of Immunology, 151(10):5364-5375 (Nov. 15, 1993).
*Stedman's Medical Dictionary*, 27$^{th}$ Edition, "Vaccine," p. 1922, lines 1-3 (2000).
Stern, et al. "Monoclonal Antibodies to a Synthetic Peptide Homologous with the First 28 Amino Acids of Alzheimer's Disease β-Protein Recognize Amyloid and Diverse Glial and Neuronal Cell Types in the Central Nervous System" *Am J of Pathology*, 134(5):973-978 (1989).
Tahtinen et al., "Minimal Size of HIV-1 NEF Antigenic Epitopes Reconzied by Human Sera," Int. Conf. AIDS Jun. 16-21, 1991, Published Jun. 1991, abstract No. W.A. 1334.
Takahashi, et al. "Monoclonal antibody to β peptide, recognizing amyloid deposits, neuronal cells and lipofuscin pigments in systemic organs", *Acta Neuropathol*, 85:159-166 (1993).
Tam, "Synthetic peptide vaccine design: synthesis and properties of a high-density multiple antigenic peptide system", Proc. Natl. Acad. Sci., 1988, vol. 85, pp. 5409-5413.
Van Dam et al., "Symptomatic effect of donepezil, rivastigmine, galantamine and memantine on cognitive deficits in the APP23 model" *Psychopharmacology* 180:177-190 (2005).
Van Noort, Multiple sclerosis: an altered immune response or an altered stress response?, *J Mol Med* 74:285-296 (1996).
Vanengelen, et al "Immunoglobulin treatment in human and experimental epilepsy" *J of Neuro* (1994); 57 (supplement):72-75.
Vastag, "Monoclonals expand into neural disorders" Nature 24:6 p. 595-596 (Jun. 2006).

(56) References Cited

OTHER PUBLICATIONS

Viswanathan et al., "Cerebral Microhemorrhage", *Stroke.*, 37:550-555 (2006).
Wang et al, "Site-specific UBITh amyloid-β vaccine for immunotherapy of Alzheimer's disease" *Vaccine* 25 (2007) 3041-3052.
Wehner, Declaration May 21, 2007.
Welling et al., "Choice of Peptide and Peptide Length for the Generation of Antibodies Reactive With the Intact Protein," *FEBS Letters*, 182(1):81-84 (Mar. 1985).
Wiessler, et al "The Second-Generation Active Aβ Immunotherapy CAD106 Reduces Amyloid Accumulation in APP Transgenic Mice While Minimizing Potential Side Effects", *J. Neurosci.* 31(25):9323-9331 (2011).
Wikipedia entry for "Monoclonal antibody therapy" accessed on Sep. 22, 2011.
Wilcock, et al. "Deglycosylated anti-Amyloid-β Antibodies Eliminate Cognitive Deficits and Reduce Parenchymal Amyloid with Minimal Vascular Consequences in Aged Amyloid Precursor Protein Transgenic Mice" Neurobiology of Disease 26(20:5340-5346 (May 17, 2006).
Wu et al., "Saponin Adjuvant Enhancement of Antigen-Specific Immune Responses to an Experimental HIV-1 Vaccine" J of Immunology 149:1519-1525 (1992).
Zhao et al., "Macrophage-Mediated Degradation of β-Amyloid via an Apolipoprotein E Isoform-Dependent Mechanism", Neurobiology of disease (Mar. 18, 2009) 29(11):3603-3612.
Zlokovic et al., "Blood-Brain Barrier Transport of Circulating Alzheimer's Amyloid β." *Biochemical and Biophysical Research Communications.* vol. 197, No. 3, pp. 1034-1040 (1993).
Zotova et al., "Inflammation in Azheimer's disease: relevance to pathogenesis and therapy" Alzheimer's Research & Therapy 2:1 p. 2-9 (2010).
U.S. Appl. No. 10/923,469, Notice of Allowance mailed Jun. 1, 2011.
U.S. Appl. No. 11/893,123, Notice of Allowance mailed Nov. 2, 2011.
U.S. Appl. No. 12/297,636, Office Action mailed Jul. 20, 2011.
U.S. Appl. No. 12/297,636, Office Action mailed Oct. 28, 2011.
U.S. Appl. No. 12/608,869, Office Action mailed Jul. 5, 2011.
U.S. Appl. No. 13/123,898, Office Action mailed Nov. 15, 2011.
U.S. Appl. No. 12/608,869, Office Action mailed Oct. 25, 2011.
U.S. Appl. No. 12/977,013, Office Action mailed Jan. 6, 2012.
U.S. Appl. No. 10/429,216, Office Action mailed Mar. 12, 2010.
U.S. Appl. No. 10/429,216, Office Action mailed Sep. 15, 2010.
U.S. Appl. No. 10/544,093, Office Action mailed Jan. 22, 2010.
U.S. Appl. No. 11/245,524, Office Action mailed Dec. 10, 2010.
U.S. Appl. No. 11/245,916, Office Action mailed May 18, 2010.
U.S. Appl. No. 11/245,916, Office Action mailed Dec. 14, 2011.
U.S. Appl. No. 11/809,552, Office Action mailed Feb. 17, 2011.
U.S. Appl. No. 11/841,919, Office Action mailed Mar. 28, 2011.
U.S. Appl. No. 11/842,113, Office Action mailed Aug. 24, 2010.
U.S. Appl. No. 11/893,123, Office Action mailed May 11, 2011.
U.S. Appl. No. 12/106,206, Office Action mailed Jul. 9, 2010.
U.S. Appl. No. 11/842,116, Office Action mailed Mar. 31, 2010.
U.S. Appl. No. 12/106,206, Office Action mailed Feb. 5, 2010.
U.S. Appl. No. 12/253,929, Office Action mailed Jan. 25, 2010.
U.S. Appl. No. 09/723,765, BPAI Decision on Request for Re-hearing mailed Oct. 16, 2007.
U.S. Appl. No. 09/723,765, BPAI Order Returning Appeal to Examiner mailed Jun. 27, 2006.
U.S. Appl. No. 09/723,765, Examiner's Answer mailed Jan. 25, 2006.
U.S. Appl. No. 09/723,765, Reply Brief Noted mailed Jun. 16, 2006.
U.S. Appl. No. 10/777,792, BPAI Decision mailed Aug. 30, 2010.
U.S. Appl. No. 10/777,792, BPAI Decision on Request for Reconsideration mailed Nov. 30, 2010.
U.S. Appl. No. 10/777,792, Examiner's Answer mailed Oct. 27, 2009.
U.S. Appl. No. 10/777,792, Reply Brief Noted mailed Jan. 11, 2010.
U.S. Appl. No. 10/923,469, BPAI Decision mailed Feb. 22, 2011.
U.S. Appl. No. 10/923,469, Reply Brief Noted mailed Mar. 9, 2010.
U.S. Appl. No. 12/297,636, Office Action mailed Oct. 15, 2012,
U.S. Appl. No. 12/738,396, Office Action mailed Feb. 13, 2012.
U.S. Appl. No. 13/076,379, Office Action mailed Nov. 28, 2012.
U.S. Appl. No. 13/123,898, Office Action mailed Jul. 20, 2012.
U.S. Appl. No. 13/270,015, Office Action mailed Jun. 19, 2013.
U.S. Appl. No. 13/271,081, Office Action mailed Mar. 1, 2013.
U.S. Appl. No. 10/923,471, Office Action mailed Apr. 23, 2013.
U.S. Appl. No. 11/303,478, Office Action mailed Jan. 31, 2014.
U.S. Appl. No. 11/842,042, Office Action mailed May 22, 2014.
U.S. Appl. No. 12/738,396, Office Action mailed Sep. 21, 2012.
U.S. Appl. No. 12/977,013, Office Action mailed Jul. 1, 2013.
U.S. Appl. No. 13/123,898, Office Action mailed Apr. 17, 2013.
"Madrid: News from the Vaccine Front," Aug. 1, 2008 pp. 1-7.
The web page retrieved from >www.elan.com/company/about_us as archived by web.archive.org on Sep. 7, 2013 (downloaded from web.archive.org on Feb. 6, 2014).
Abott, et al., "Transporting therapeutics across the blood-brain barrier" *Molecular Medicine Today*, pp. 106-113, Mar. 1996.
Alzheimer's Forum report on Ponezumab, retrieved on Apr. 7, 2014 at www.alzforum.org/therapeutics/ponezumab<.
Andrews, et al., "Amino acid sequence of the variable regions of heavy chains from two idiotypically cross-reactive human IgM anti-gamma-globulins of the Wa group", *Biochemistry*, Sep. 29, 1981;20(20):5822-5830.
Andrews, et al., "Complete amino acid sequence of variable domains from two monoclonal human anti-gamma globulins of the Wa cross-idiotypic group: Suggestion that the J segments are involved in the structural correlate of the idiotype", *Proc. Natl. Acad. Sci. USA*, vol. 78, No. 6, pp. 3799-3803, Jun. 1981.
Annual Report of Johnson and Johnson p. 1-6 (2012).
Arai, et al., "Safety, Tolerability and Immunogenicity of an Immunotherapeutic Vaccine (Vanutide Cridificar (ACC-001)) and the QS-21Adjuvant in Japanese Individuals with Mild-to-Moderate Alzheimer's Disease: A Phase IIA, Multicenter, Randomized Adjuvant and Placebo Clinical Trial," *Alzheimer's and Dementia*, 9(4) supplemental p. P282 (2013).
Arriagada, et al., "Neurofibrillary tangles but not senile plaques parallel duration and severity of Alzheimer's disease", *Neurology*, 42:631-639 (1992).
Barbour, et al., Presentation of "Efficacy and Neuropathology of Passively Administered N-Terminal and Midregion Anti-Abeta Antibodies Alone and in Combination in the PDAPP Mouse" Elan Report pp. 1-99 May 2007.
Baxter Press Release, "Baxter Announces Topline Results of Phase III Study of Immunoglobulin for Alzheimer's Disease," retrieved at www.baxter.com/press_room/press_releases/2013/05_07_13_gat_study.html<.
Board of Appeal of the European Patent Office Appeal Decision in Case No. T219/01 on Dec. 15, 2004.
Capra, et al., "Structure of Antibodies with Shared Idiotypy: The Complete Sequence of the Heavy Chain Variable Regions of Two Immunoglobulin M Anti-Gamma Globulins", *Proc. Nat. Acad. Sci. USA*, vol. 71, No. 10, pp. 4032-4036, Oct. 1974.
Castillo, "Poor results halt production, studies on promising Alzheimer's drug bapineuzumab" *CBS Interactive Inc.*, Nov. 7, 2012 pp. 1/1.
Centers for Disease Control and Prevention, "Vaccine Safety" Retrieved from www.cdc.gov/vaccinesafety/concerns/adjuants.html (Oct. 18, 2012) p. 1-2.
Chalmers et al., "APOE epsilon 4 influences the pathological phenotype of Alzhemier's disease by favouring cerebrovascular over parechyma accumulation of A beta protein", Neuropathology and Applied Neurobiology, vol. 29, No. 3 pp. 231-238 (2003).
Chan, et al., "Therapeutic antibodies for autoimmunity and inflammation," *Nature Reviews Immunology*, 10:301-316 (2010).
Chao, et al., "Cerebral amyloid Angiopathy: CT and MR Imaging Findings[1]," *Radiographics*, 26(5):1517-1531 (2006).
Check, "Nerve inflammation halts trial for Alzheimer's drug", *Nature*, vol. 415:462 Jan. 2002.
Cleland, et al., "Emerging protein delivery methods," *Current Op Biotech*, 12(2):212-219 (2001).

(56) References Cited

OTHER PUBLICATIONS

Communication from European Patent Office that no opposition was filed in EP1842859 dated Nov. 13, 2013.
Consolidated list of documents of opposition proceedings against EP 1 994 937 (annexed to decision to revoke EP 1 994 937) dated Jul. 24, 2013.
Curriculum Vitae Professor Nancy Joan Abbott, Mar. 2013.
Deane, et al. "IgG-Assisted Age-Dependent Clearance of Alzheimer's Amyloid β Peptide by the Blood-Brain Barrier Neonatal Fc Receptor" *The Journal of Neuroscience*, Dec. 14, 2005 25(50):11495-11503.
Decision from European Patent Office to maintain the patent EP1160256 in amended form dated Oct. 13, 2011.
Declaration by Dr. Dale Schenk dated Nov. 21, 2011.
Declaration of Dr. Michael John Owen with CV and list of publications May 10, 2013.
Declaration of Georg Friedrich Melchers with CV and list of publications Apr. 6, 2013.
Declaration of Professor Nancy Joan Abbott, Apr. 8, 2013.
Dodel, et al., "Intravenous immunoglobulins containing antibodies against beta-amyloid for the treatment of Alzheimer's disease", *J. Neurol. Neurosurg. Psychiatry*, 75:1472-1474 (2004).
Dohi et al., "Reactivity of a Mouse/Human Chimeric Anti-GM2 Antibody KM966 with Brain Tumors" *Anticancer Research*, 14:2577-2582 (1994).
Doody, et al., "Phase 3 Trials of Solanezumab for Mild-to Moderate Alzheimer's Disease," *New England J Med*, 370;4, 311 321 (2014).
*Eli Lilly and Company vs Janssen Alzheimer Immunotherapy*, Approved Judgement, Case No. HC11C03400, Royal Courts of Justice, London, Jun. 25, 2013.
Eli Lilly, "Eli Lilly and Company Announces Top-Line Results on Solanezumab Phase 3 Clinical Trials in Patients with Alzheimer's Disease" Press Release, Aug. 24, 2012.
EP 1 994 937 Decision of Oral Proceedings from EPO Opposition Division dated Jul. 24, 2013.
EP 1160256 B2 Response to Notice of Opposition Jan. 19, 2009.
EP1160256 Druckexemplar in European Opposition Proceedings (2011).
European Extended Search Report of Dec. 6, 2011 for European Application 10183051.1.
European Extended Search Report of Mar. 1, 2012 for European Application 08839961.
European Extended Search Report of Mar. 15, 2012 for European Application 09075267.6.
European Search Report of Oct. 25, 2013 for European Application 08746362.6.
Extract from EPO patent register of EP1842859 Communication under Rule 71(3) Mar. 28, 2013.
Extract from EPO patent register of EP1842859 Decision to Grant Mar. 28, 2012.
Extract from the online Oxford Dictionary retrieved on Apr. 3, 2014 from >www.oxforddictionaries.com/definition/english/intact?a-intact<.
Farlow, et al., "Safety and biomarker effects of solanezumab in patients with Alzheimer's disease" *Alzheimer's & Dementia*, 8:261-271 (2012).
Geeraedts et al., "Superior Immunogenicity of Inactivated Whole Virus H5N1 Influenza Vaccine is Primarily Controlled by Toll-like Receptors Signalling", *PLoS Pathogens*, 2008, 4:1-8.
Gerald, et al., "Alzheimer's disease market: hope deferred", *Nature*, vol. 12:19-20 Jan. 2013.
Gluck et al, "Immunopotentiating Reconstituted Influenza Virus Virosome Vaccine Delivery System for Immunization against Hepatitis A", *J. Clin. Invest.*,(1992) vol. 90:2491-2495.
Gluck, "Immunopotentiating reconstituted influenza virosomes (IRIVs) and other adjuvants for improved presentation of small antigens", *Vaccine*, vol. 10, Issue 13 (1992) 915-919.
Greaves, et al., "Posterior reversible encephalopathy syndrome following antilymphocyte globulin treatment for severe aplastic anaemia" *British Journal of Hematology*, Aug. 2006: 13493):251.

Hagen, Declaration Oct. 31, 2011.
Hyslop et al., "Antibody Clears Senile Plaques" *Nature*, vol. 400, Jul. 8, 1999, p. 116-117.
Jacobsen, et al., "Reversal of CM Deficits: A) 2nd Generation of mAbs to central AB epitopes B) PSAPP (18 mo) by 12A11 hv. 1.0 & m266", *Wyeth Presentation* Apr. 27, 2004.
Janeway et al., Immunobiology, 3rd edition, pp. 8:32-8:36 (1997).
Janeway, et al., *Basic Concepts in Immunology*; pp. 1:21-1:13 and 8:1-8:2 (1997).
Janssen Alzheimer Immunotherapy Research & Development, LLC, "AAB-001 in Patients With Mild to Moderate Alzheimer's Disease", *Clinical Trials. Gov, NIH, 2005*, [retrieved on Jun. 19, 2012] Retrieved from the Internet: clinicaltrials.gov/ct2/show/NCT00112073?term=aab-001&rant=3>.
Johnson & Johnson, "Johnson & Johnson Announces Discontinuation of Phase 3 Development of Bapineuzumab Intravenous (IV) in Mild-to-Moderate Alzheimer's Disease", Press Release, Aug. 6, 2012.
Kambhampaty, "Roche's gantenerumab could face similar fate as failed drug bapineuzumab in Alzheimer's, experts say," Retrieved from the Internet sussexdrugdiscovery.wordpress.com/tag/bapineuzumab, (retrieved on Sep. 27, 2013) Jul. 5, 2013.
Karran, "Current status of vaccination therapies in Alzheimer's disease" *Journal of Neurochemistry*, 123:647-651 (2012).
Kerchner, et al., "Bapineuzumab", NIH Public Access, Expert Opin Biol Ther., 10(7) 1121-1130 Jul. 2010.
Kirschner, et al., "Synthetic peptide homologous to beta protein from Alzheimer disease forms amyloid-like fibrils in vitro", *Proc. Natl. Acad. Sci. USA*, 84:6953-6957 (1987).
Laino, "Cerebral Edema Common, but Found to Be Manageable, With Bapineuzumab", *Neurology Today*, Aug. 19, 2011.
Lee et al., "Aspects of Immunobiology and Immunotherapy and Uses of Monoclonal Antibodies and Biologic Immune Modifiers in Human Gliomas" *Neurologic Clinics*, vol. 3, No. 4, Nov. 1985, 901-917.
Lemere et al., "Amyloid-Beta Immunotherapy for the Prevention and Treatment of Alzheimer Disease: Lessons from Mice, Monkeys, and Humans", Rejuvenation Research 9(1):77-84 (2006).
Lu, "In Vitro Binding Analysis of LY2062430: Surface Plasmon Resonance and FACS Analysis" Report: bTDR185 Eli Lilly and Company Apr. 2012.
Marx et al., "The Possible Role of the Immune System in Alzheimer's Disease" *Exp Gerontology*, vol. 33, Nos. 7/8 pp. 871-881, 1998.
Miller et al., "Comparative efficacy of two immunocontraceptive vaccines" *Vaccine*, (1997) 15(17-18):1858-1862 (abstract only).
Muhs, et al., "Liposomel vaccines with conformation-specific amyloid peptide antigens define immune response and efficacy in AAP transgenic mice", *PNAS*, Jun. 5, 2007, vol. 104:23 pp. 9810-9815.
Oh, et al., "Reversible leukoencephalopathy associated with cerebral amyloid angiopathy", *Neurology*, 62 (Feb. 2004) 494-497.
Opposition by Biogen Idec, Inc. filed Sep. 29, 2011 against EP 1 994 937 B1.
Opposition by Eli Lilly filed Sep. 27, 2011 against EP 1 994 937 B1.
Opposition by F. Hoffman-La Roche AG filed Sep. 27, 2011 against EP 1 994 937 B1.
Orgogozo, et al., "Subacute meningoencephalitis in a subset of patients with AD after Aβ42 immunization" *Neurology*, 61:46-54 (2003).
PCT/US2011/026365 International Preliminary Report on Patenability mailed Mar. 5, 2012.
Pfizer Announces Co-Primary Clinical Endpoints Not Met in Second Phase 3 Bapineuzumab Study in Mild-to-Moderate Alzheimer's Disease Patients Who Do Not Carry The Apoe4 Genotype, Press Release, Aug. 6, 2012.
Pfizer Halts Development of AB Antibody, Alzheimer Research Forum, Nov. 2, 2011.
Pfizer Pipeline Report Aug. 11, 2011.
Pfizer Pipeline Report Aug. 9, 2013.
Pfizer, "Pfizer Announces Topline Results of First of Four Studies in Bapineuzumab Phase 3 Program", Press Release, Jul. 23, 2012.
Preliminary Opinion by European Opposition Division in EP 1 994 937 dated Nov. 12, 2012.

(56) References Cited

OTHER PUBLICATIONS

Raber, et al., "ApoE genotype accounts for the vast majority of AD risk and AD pathology" *Neurobiology of Aging*, 25:641-650 (2004).
Reilly, et al., "Oral Delivery of Antibodies," *Clin. Pharmacokinet*, 32(4):313-323 (1997).
Remes et al, "Hereditary dementia with intracerevbral hemorrhages and cerebral amyloid angiopathy". *Neurology* 63(2):234-240 (2004).
Rieber, et al., "The Effect of Freund's Adjuvants on Blood-Cerebrospinal Fluid Barrier Permeability" *Journal of the Neurological Sciences*, 63:55-61 (1984).
Rivero et al., "Suppression of experimental autoimmune encephalomyelitis (EAE) by intraperitoneal administration of soluble myelin antigens in Wistar rats" *J. Neuroimmunology*, (1997) 72, 3-10.
Roitt, Extracts from Roitt's Essential Immunology, Ninth Edition, (1997).
Salloway, et al., "Two Phase 3 Trials of Bapineuzumab in Mild-to-Moderate Alzheimer's Disease," *New England J Med*, 370;4, 322 333 (2014).
Servillo, et al., "Posterior reversible encphalopathy syndrome in intensive care medicine" *Intensive Care Med*, (2007) 33:230-236.
Seubert, et al., "Comparison of Immunization with AN1792 and AB1-7MAP and Passive Immunization of 3D6 and 266," *Elan Pharmaceuticals Final Report*, Study 150-006-98-040, Jul. 22, 2003.
Smith, et al., "Use of structural inaging to study the progression of Alzheimer's disease", *Brit. Med. Bull.*, 52(3):575-586, (1996).
Solomon, "Alzheimer's Disease and Immunotherapy", *Current Alzheimer Research*, 2004, 1, 149-163.
Solomon, "Beta-Amyloid-Based Immunotherapy as a Treatment of Alzheimer's Disease", *Drugs of Today*, 2007, 43(5):333-342.
Spack, "Antigen-specific therapies for the treatment of multiple sclerosis: a clinical trial update", *Exp. Opin. Invest. Drugs*, (1997) 6(11):1715-1727.
Sperling, et al., "Amyloid-related imaging abnormalities in amyloid-modifying therapeutic trials: Recommendations from the Alzheimer's Association Research Roundtable Workgroup" *Alzheimer's & Dementia*, 7 (2011) 397-385.
Sperling, et al., "Presentation and Transcript of Bapineuzumab Phase 3 trials in mild to moderate Alzheimer's disease dementia in apolipoprotein E ε4 carriers (Study 302) and non-carriers (Study 301)", *American Neurological Association*, Oct. 8, 2012.
Staykov, et al., "Posterior Reversible Encephalopathy Syndrome", *Journal of Intensive Care Medicine*, originally published online Jan. 21, 2011 at: jic.sagepub.com/content/27/1/11.
Submission, dated Apr. 10, 2013, filed by Opponent 2 (Eli Lilly) during Opposition proceedings against EP 1 994 937 B1.
Submission, dated Apr. 9, 2013, filed by Opponent 1 (F. Hoffman-La Roche AG) during Opposition proceedings against EP 1 994 937 B1.
Submission, dated Apr. 9, 2013, filed by Opponent 3 (Biogen Idec, Inc.) during Opposition proceedings against EP 1 994 937 B1.
Sussex Drug Discovery, "Bexarontene in Alzheimer's Disease: A case of lack of replication, lace of replication, lack of replication," Retrieved from the Internet sussexdrugdiscover.wordpress.com/tag/bapineuzumab, pp. 1-4 (retrieved on Sep. 27, 2013) Jun. 20, 2013.
Thompson, et al., "Laboratory investigation of cerebrospinal fluid proteins" *Ann Clin Biochem*, 27:425-435 (1990).
Triguero, et al., "Blood-brain barrier transport of cationized immunoglobulin G: Enhanced delivery compared to native protein" *Proc. Natl. Acad. Sci. USA*, vol. 86:4761-4765 Jun. 1989.
Triozzi et al., "Effects of a beta-human chorionic gonadotropin subunit immunogen administered in aqueous solution with a novel nonionic block copolymer adjuvant in patients with advanced cancer", *Clin. Cancer Res.*, (1997) 3(12 pt 1):2355-2362 (abstract only).
Trojano, et al., "Serum IgG to brain microvascular endothelial cells in multiple sclerosis" *Journal of the Neurological Sciences*, 143:107-113 (1996).
Tuomanen, et al., "Reversible opening of the blood-brain barrier by anti-bacterial antibodies" *Proc. Natl. Acad. Sci. USA*, vol. 90:7824-7828 (Aug. 1993).
Walls, et al., "Autoantibody responses in the cerebrospinal fluid of guinea pigs with chronic relapsing experimental allergic encephalomyelitis", *Acta Neruol. Scan.*, 78:422-428 (1988).
Weyer, et al., "A controlled study of 2 doses of idebenone in the treatment of Alzheimer's disease", *Neuropsychobiology*, 36(2):73-82, Abstract only (Jan. 1997).
Wick et al., "The Aging Immune System: Primary and Secondary Alterations of Immune Reactivity in the Elderly" *Exp. Geronology*, vol. 32, Nos. 4/5, pp. 401-413, 1997.
Wikipedia "Bapineuzumab", printed on Feb. 24, 2014.
Wilcock, et al. "Passive Amyloid Immunotherapy Clears Amyloid and Transiently Activates Microglia in a Transgenic Mouse Model of Amyloid Deposition" *The Journal of Neuroscience*, Jul. 7, 2004 24(27):6144-6151.
Wilcock, et al., "Number of AB Inoculations in APP+PSI Transgenic Mice Influences Antibody Titers, Microglial Activation, and Congophilic Plaque Levels" *DNA and Celll Biology*, vol. 20 No. 11: 731-736 (2001).
Wisniewski, et al., "Spectrum of morphological appearance of amyloid deposits in Alzheimer's disease," *Acta Neuropathol*, 78:337-347 (1989).
U.S. Appl. No. 10/923,471, Notice of Allowance mailed May 21, 2013.
U.S. Appl. No. 11/842,116, Notice of Allowance mailed Sep. 24, 2013.
U.S. Appl. No. 12/297,636, Notice of Allowance mailed May 28, 2013.
U.S. Appl. No. 13/123,898, Notice of Allowance mailed Jan. 17, 2014.
U.S. Appl. No. 10/544,093, Office Action mailed Mar. 13, 2014.
U.S. Appl. No. 12/608,869, Advisory Action mailed Mar. 13, 2013.
U.S. Appl. No. 12/608,869, Office Action mailed Aug. 23, 2012.
U.S. Appl. No. 12/738,396, Office Action mailed Apr. 16, 2013.
U.S. Appl. No. 12/977,013, Office Action mailed Sep. 14, 2012.
U.S. Appl. No. 13/270,015, Office Action mailed Nov. 14, 2013.

* cited by examiner

FIG. 2

Reshaping 3D6 VH

Aβ42 ELISA

Aβ42 ELISA
competition of 3D6-B

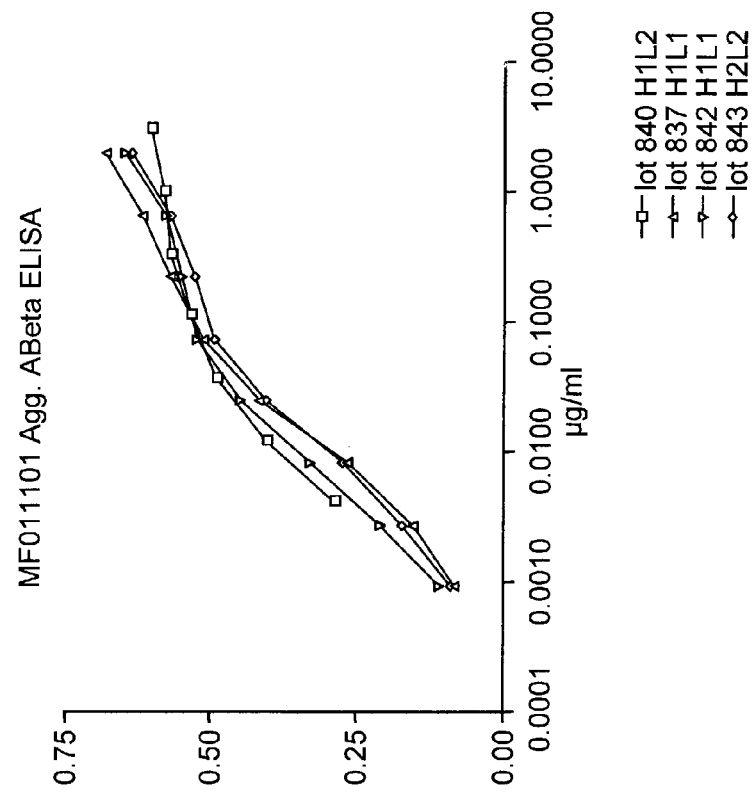
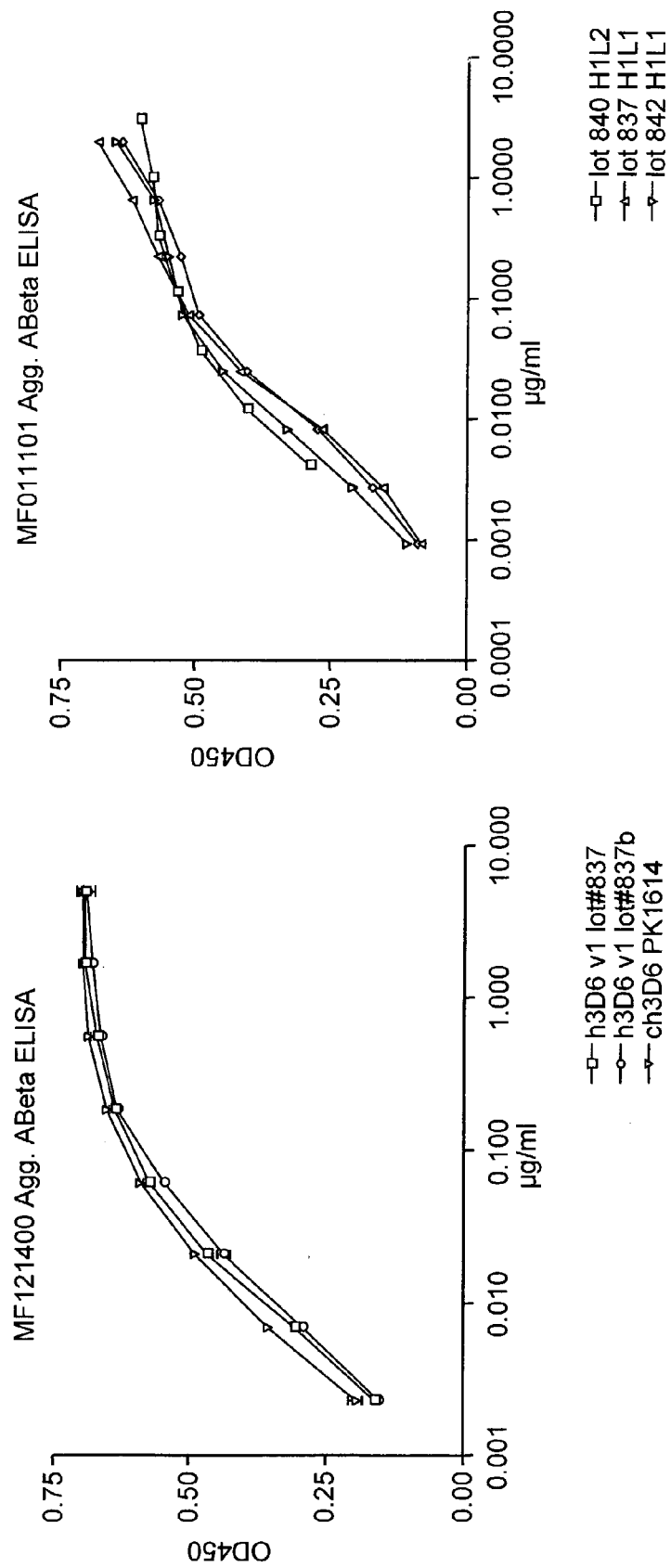
FIG. 5A
FIG. 5B

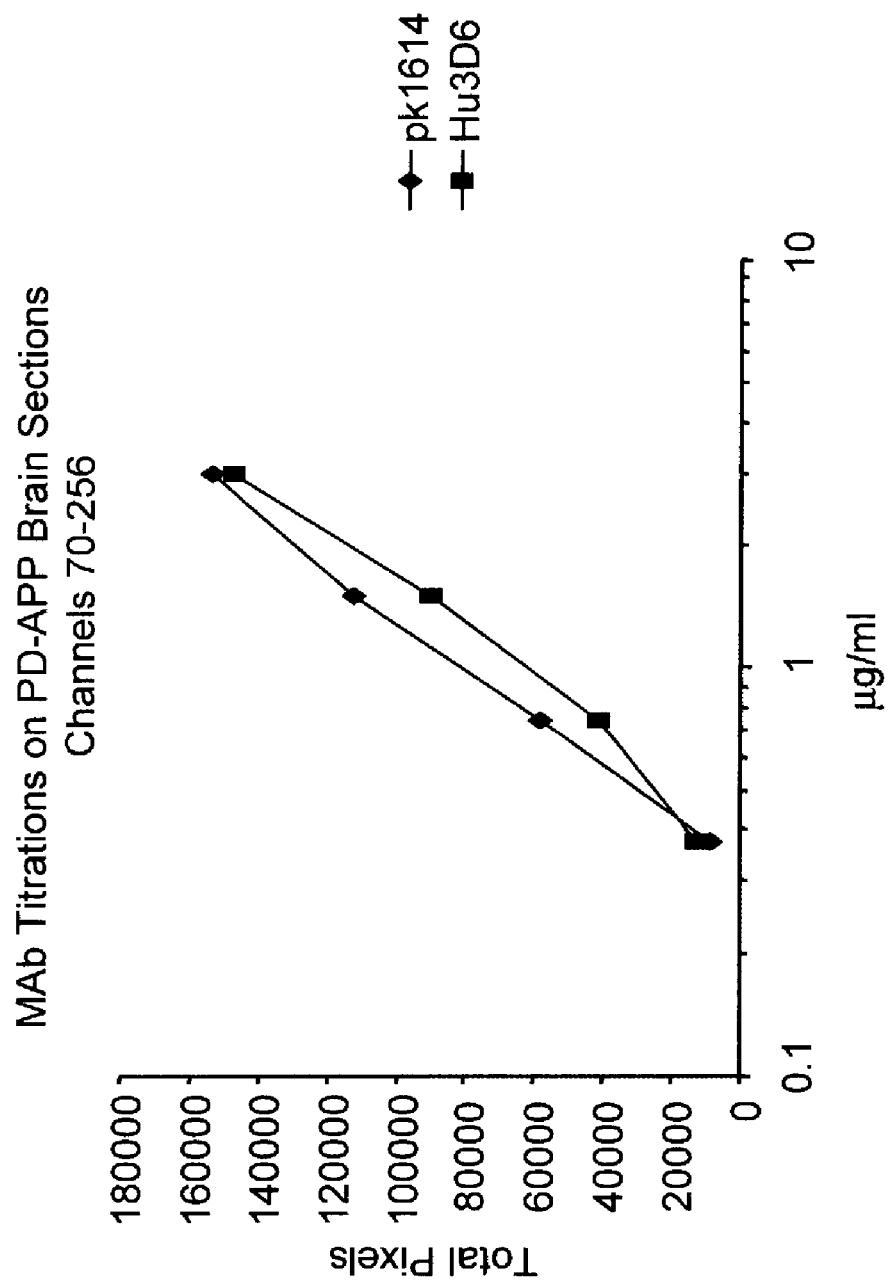

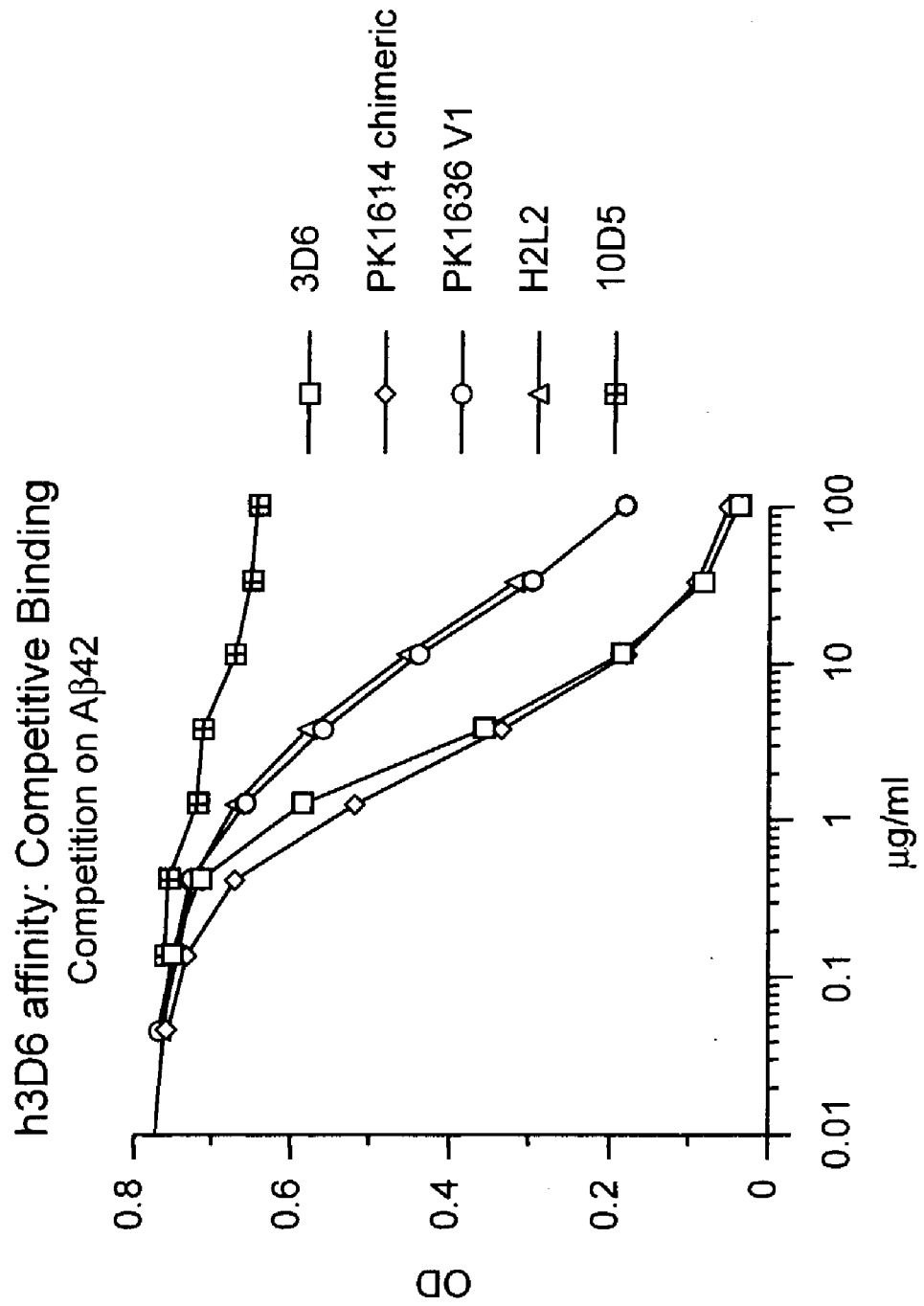

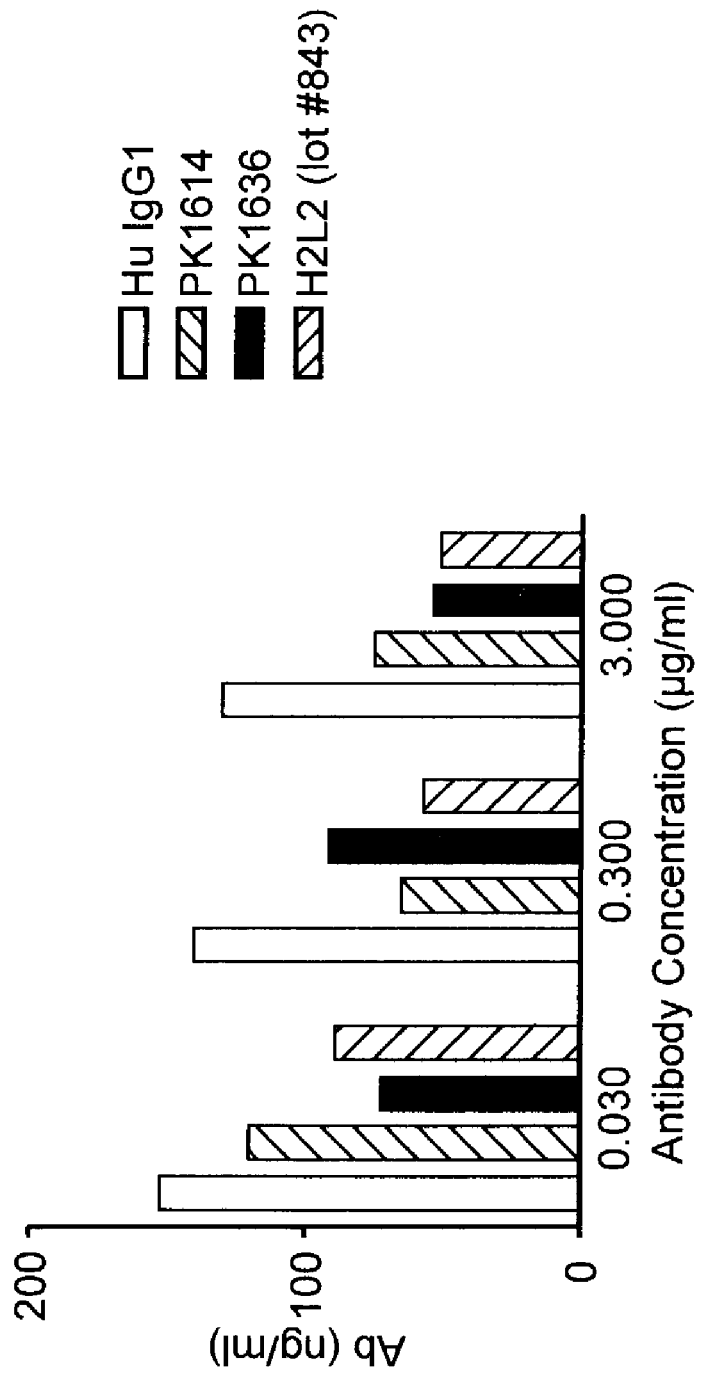

FIG. 9

```
10D5vl.pro  M K L P V R L L - V L M F W I P A S S S D V L M T Q T P L S   29
3D6vl.pro   M M S P A Q F L F L L V L W I R E T N G Y V V M T Q T P L T   30
                     10            20
10D5vl.pro  L P V S L G D Q A S I S C R S S Q S I V H S N G N T Y L E W   59
3D6vl.pro   L S V T I G Q P A S I S C K S S Q S L L D S D G K T Y L N W   60
            30            40            50
10D5vl.pro  Y L Q K P G Q S P K L L I Y K V S N R F S G V P D R F S G S   89
3D6vl.pro   L L Q R P G Q S P K R L I Y L V S K L D S G V P D R F T G S   90
            60            70            80
10D5vl.pro  G S G T D F T L K I K K V E A E D L G I Y Y C F Q G S H V P   119
3D6vl.pro   G S G T D F T L K I S R I E A E D L G L Y Y C W Q G T H F P   120
            90            100           110
10D5vl.pro  L T F G A G T K L E L E   131
3D6vl.pro   R T F G G G T K L E I K   132
            120           130
```

FIG. 10

```
              10                  20                  30
10D5vh.pro    M D - R L T S S F L L L I V P A Y V L S Q A T L K E S G P G    29
3D6vh.PRO     M N F G L S L I F L V L V L K G - V Q C E V K L V E S G G G    29

40                  50                  60
10D5vh.pro    I L Q S S Q T L S L T C S F S G F S L S T S G M G V S W I R    59
3D6vh.PRO     L V K P G A S L K L S C A A S G F T F S N Y G M - S W V R    57

70                  80                  90
10D5vh.pro    Q P S G K G L E W L A H I Y W D D D K R Y - N P S L K S R L    88
3D6vh.PRO     Q N S D K R L E W V A S I R S G G R T Y Y S D N V K G R F    87

100                 110                 120
10D5vh.pro    T I S K D T S R K Q V F L K I T S V D P A D T A T Y Y C V R    118
3D6vh.PRO     T I S R E N A K N T L Y L Q M S S L K S E D T A L Y Y C V R    117

130                 140
10D5vh.pro    R P I T P V L V D A M D Y W G Q G T S V T V S S                142
3D6vh.PRO     - - Y D H Y S G S S D Y W G Q G T T V T V S S                  138
```

HUMANIZED ANTIBODIES THAT RECOGNIZE BETA AMYLOID PEPTIDE

RELATED APPLICATIONS

This application is a continuation of U.S. application Ser. No. 11/516,724 filed Sep. 5, 2006, which is a continuation of U.S. application Ser. No. 11/413,638 filed Apr. 28, 2006, which is a continuation of U.S. application Ser. No. 10/388,389 filed Mar. 12, 2003, which is a continuation-in-part of U.S. application Ser. No. 10/010,942 filed Dec. 6, 2001, which is an application claiming benefit under 35 U.S.C. 119(e) of U.S. Application No. 60/251,892 filed Dec. 6, 2000. U.S. application Ser. No. 10/010,942 and 60/251,892 are both incorporated herein by reference. This application is a continuation of U.S. application Ser. No. 11/516,724 filed Sep. 5, 2006, which is a continuation-in-part of U.S. application Ser. No. 10/232,030 filed Aug. 30, 2002, which is a continuation of U.S. application Ser. No. 10/010,942 filed Dec. 6, 2001, which is an application claiming the benefit under 35 U.S.C. 119(e) of U.S. Application No. 60/251,892 filed Dec. 6, 2000. This application is a continuation of U.S. application Ser. No. 11/516,724 filed Sep. 5, 2006, which is a continuation-in-part of U.S. application Ser. No. 11/058,757 filed Feb. 14, 2005, which is a continuation of U.S. application Ser. No. 09/724,940 filed Nov. 28, 2000, which is a continuation of U.S. application Ser. No. 09/580,015 filed May 26, 2000, which is a continuation-in-part of U.S. application Ser. No. 09/322,289 filed May 28, 1999, which is a continuation-in-part of U.S. application Ser. No. 09/201,430 filed Nov. 30, 1998, which is an application claiming benefit under 35 U.S.C. 119(e) of U.S. Application No. 60/080,970 filed Apr. 7, 1998 and of U.S. Application No. 60/067,740 filed Dec. 2, 1997, respectively. This application is a continuation of U.S. application Ser. No. 11/516,724 filed Sep. 5, 2006, which is a continuation of U.S. application Ser. No. 10/703,713 filed Nov. 7, 2003. This application is a continuation of U.S. application Ser. No. 11/520,438 filed Sep. 12, 2006, which is a continuation-in-part of U.S. application Ser. No. 10/232,030 filed Aug. 30, 2002, which is a continuation of U.S. application Ser. No. 10/010,942 filed Dec. 6, 2001, which is an application claiming benefit under 35 U.S.C. 119(e) of U.S. Application No. 60/251,892 filed Dec. 6, 2000. This application is a continuation of U.S. application Ser. No. 11/520,438 filed Sep. 12, 2006 which is a continuation of U.S. Application Ser. No. 11/396,417 filed Mar. 30, 2006, which is a continuation of U.S. application Ser. No. 10/704,070 filed Nov. 7, 2003. This application is a continuation of U.S. application Ser. No. 11/520,438 filed Sep. 12, 2006, which is a continuation-in-part of U.S. application Ser. No. 11/058,757 filed Feb. 14, 2005, which is a continuation of U.S. application Ser. No. 09/724,940 filed Nov. 28, 2000, which is a continuation of U.S. application Ser. No. 09/580,015 filed May 6, 2000, which is a continuation-in-part of U.S. application Ser. No. 09/322,289 filed May 28, 1999, which is a continuation-in-part of U.S. application Ser. No. 09/201,430 filed Nov. 30, 1998, which is an application claiming benefit under 35 U.S.C. 119(e) of U.S. Application No. 60/080,970 filed Apr. 7, 1998 and of U.S. Application No. 60/067,740 filed Dec. 2, 1997, respectively.

BACKGROUND OF THE INVENTION

Alzheimer's disease (AD) is a progressive disease resulting in senile dementia. See generally Selkoe, TINS 16:403 (1993); Hardy et al., WO 92/13069; Selkoe, J. Neuropathol. Exp. Neurol. 53:438 (1994); Duff et al., Nature 373:476 (1995); Games et al., Nature 373:523 (1995). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 µm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed Aβ or β-amyloid peptide. Aβ peptide is a 4-kDa internal fragment of 39-43 amino acids of a larger transmembrane glycoprotein named protein termed amyloid precursor protein (APP). As a result of proteolytic processing of APP by different secretase enzymes, Aβ is primarily found in both a short form, 40 amino acids in length, and a long form, ranging from 42-43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of Alzheimer's disease. See, e.g., Goate et al., Nature 349:704) (1991) (valine$^{717}$ to isoleucine); Chartier Harlan et al. Nature 353:844 (1991)) (valine$^{717}$ to glycine); Murrell et al., Science 254:97 (1991) (valine$^{717}$ to phenylalanine); Mullan et al., Nature Genet. 1:345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PS1 and PS2, are thought indirectly to affect processing of APP to generate increased amounts of long form Aβ (see Hardy, TINS 20: 154 (1997)).

Mouse models have been used successfully to determine the significance of amyloid plaques in Alzheimer's (Games et al., supra, Johnson-Wood et al., Proc. Natl. Acad. Sci. USA 94:1550 (1997)). In particular, when PDAPP transgenic mice, (which express a mutant form of human APP and develop Alzheimer's disease at a young age), are injected with the long form of Aβ, they display both a decrease in the progression of Alzheimer's and an increase in antibody titers to the Aβ peptide (Schenk et al., Nature 400, 173 (1999)). The observations discussed above indicate that Aβ, particularly in its long form, is a causative element in Alzheimer's disease.

McMichael, EP 526,511, proposes administration of homeopathic dosages (less than or equal to 10$^{-2}$ mg/day) of Aβ to patients with preestablished AD. In a typical human with about 5 liters of plasma, even the upper limit of this dosage would be expected to generate a concentration of no more than 2 pg/ml. The normal concentration of Aβ in human plasma is typically in the range of 50-200 pg/ml (Seubert et al., Nature 359:325 (1992)). Because EP 526,511's proposed dosage would barely alter the level of endogenous circulating Aβ and because EP 526,511 does not recommend use of an adjuvant, as an immunostimulant, it seems implausible that any therapeutic benefit would result.

Accordingly, there exists the need for new therapies and reagents for the treatment of Alzheimer's disease, in particular, therapies and reagents capable of effecting a therapeutic benefit at physiologic (e.g., non-toxic) doses.

SUMMARY OF THE INVENTION

The present invention features new immunological reagents, in particular, therapeutic antibody reagents for the prevention and treatment of amyloidogenic disease (e.g., Alzheimer's disease). The invention is based, at least in part, on the identification and characterization of two monoclonal antibodies that specifically bind to Aβ peptide and are effective at reducing plaque burden and/or reducing the neuritic dystrophy associated with amyloidogenic disorders. Structural and functional analysis of these antibodies leads to the design of various humanized antibodies for prophylactic and/or therapeutic use. In particular, the invention features humanization of the variable regions of these antibodies and, accordingly provides for humanized immunoglobulin or antibody chains, intact humanized immunoglobulins or antibodies, and functional immunoglobulin or antibody fragments, in particular, antigen binding fragments, of the featured antibodies.

Polypeptides comprising the complementarity determining regions of the featured monoclonal antibodies are also disclosed, as are polynucleotide reagents, vectors and host suitable for encoding said polypeptides.

Methods of treatment of amyloidogenic diseases or disorders (e.g., Alzheimer's disease) are disclosed, as are pharmaceutical compositions and kits for use in such applications.

Also featured are methods of identifying residues within the featured monoclonal antibodies which are important for proper immunologic function and for identifying residues which are amenable to substitution in the design of humanized antibodies having improved binding affinities and/or reduced immunogenicity, when used as therapeutic reagents.

Also featured are antibodies (e.g., humanized antibodies) having altered effector functions, and therapeutic uses thereof.

BRIEF DESCRIPTION OF THE DRAWINGS

FIG. 2 depicts an alignment of the amino acid sequences of the heavy chain of mouse 3D6, humanized 3D6, Kabat ID 045919 and germline VH3-23 antibodies. Annotation is the same as for FIG. 1.

FIG. 3 graphically depicts the Aβ binding properties of 3D6, chimeric 3D6 and 10D5.

FIG. 5 graphically depicts the Aβ binding properties of chimeric 3D6 and humanized 3D6. FIG. 5A depicts ELISA results measuring the binding of humanized 3D6v1 and chimeric 3D6 to aggregated Aβ. FIG. 5B depicts ELISA results measuring the binding of humanized 3D6v1 and humanized 3D6v2 to aggregated Aβ.

FIG. 6 is a graph quantitating the binding of humanized 3D6 and chimeric 3D6 to Aβ plaques from brain sections of PDAPP mice.

FIG. 7 is a graph showing results of a competitive binding assay testing the ability of humanized 3D6 versions 1 and 2, chimeric 3D6, murine 3D6, and 10D5 to compete with murine 3D6 for binding to Aβ.

FIG. 8 graphically depicts of an ex vivo phagocytosis assay testing the ability of humanized 3D6v2, chimeric 3D6, and human IgG to mediate the uptake of Aβ by microglial cells.

FIG. 9 depicts an alignment of the 10D5 VL and 3D6 VL amino acid sequences. Bold indicates residues that match 10D5 exactly.

FIG. 10 depicts an alignment of the 10D5 VH and 3D6 VH amino acid sequences. Bold indicates residues that match 10D5 exactly.

DETAILED DESCRIPTION OF THE INVENTION

Figure 1:
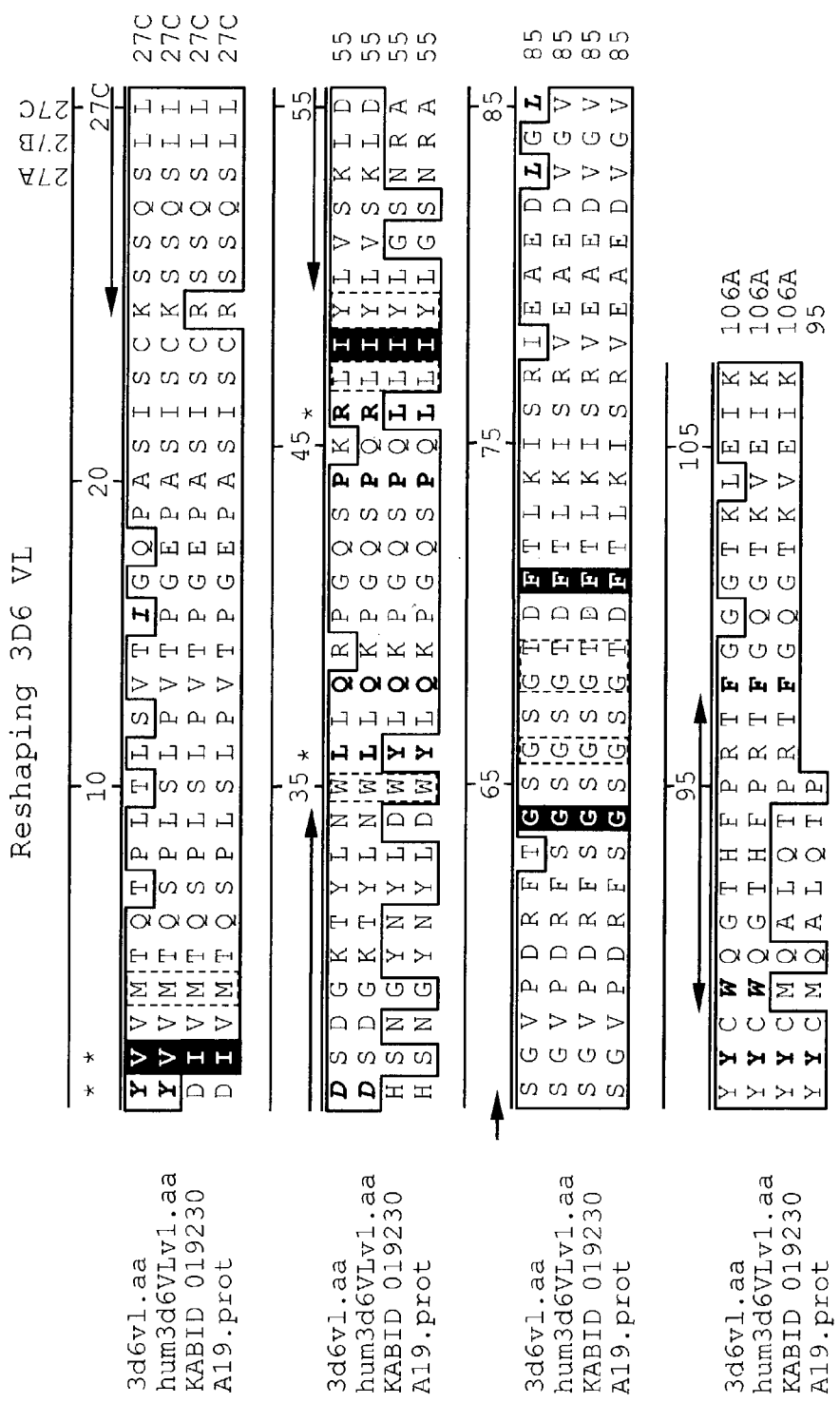
FIG. 1 depicts an alignment of the amino acid sequences of the light chain of mouse 3D6, humanized 3D6, Kabat ID 109230 and germline A19 antibodies. CDR regions are indicated by arrows. Bold italics indicate rare murine residues. Bold indicates packing (VH+VL) residues. Solid fill indicates canonical/CDR interacting residues. Asterisks indicate residues selected for backmutation in humanized 3D6, version 1.

The present invention features new immunological reagents and methods for preventing or treating Alzheimer's disease or other amyloidogenic diseases. The invention is based, at least in part, on the characterization of two monoclonal immunoglobulins, 3D6 and 10D5, effective at binding beta amyloid protein (Aβ) (e.g., binding soluble and/or aggregated Aβ), mediating phagocytosis (e.g., of aggregated Aβ), reducing plaque burden and/or reducing neuritic dystrophy (e.g., in patient). The invention is further based on the determination and structural characterization of the primary and secondary structure of the variable light and heavy chains of these immunoglobulins and the identification of residues important for activity and immunogenicity.

Immunoglobulins are featured which include a variable light and/or variable heavy chain of the preferred monoclonal immunoglobulins described herein. Preferred immunoglobulins, e.g., therapeutic immunoglobulins, are featured which include a humanized variable light and/or humanized variable heavy chain. Preferred variable light and/or variable heavy chains include a complementarity determining region (CDR) from the monoclonal immunoglobulin (e.g., donor immunoglobulin) and variable framework regions substantially from a human acceptor immunoglobulin. The phrase "substantially from a human acceptor immunoglobulin" means that the majority or key framework residues are from the human acceptor sequence, allowing however, for substitution of residues at certain positions with residues selected to improve activity of the humanized immunoglobulin (e.g., alter activity such that it more closely mimics the activity of the donor immunoglobulin) or selected to decrease the immunogenicity of the humanized immunoglobulin.

In one embodiment, the invention features a humanized immunoglobulin light or heavy chain that includes 3D6 variable region complementarity determining regions (CDRs) (i.e., includes one, two or three CDRs from the light chain variable region sequence set forth as SEQ ID NO:2 or includes one, two or three CDRs from the heavy chain variable region sequence set forth as SEQ ID NO:4), and includes a variable framework region substantially from a human acceptor immunoglobulin light or heavy chain sequence, provided that at least one residue of the framework residue is backmutated to a corresponding murine residue, wherein said backmutation does not substantially affect the ability of the chain to direct Aβ binding.

In another embodiment, the invention features a humanized immunoglobulin light or heavy chain that includes 3D6 variable region complementarity determining regions (CDRs) (e.g., includes one, two or three CDRs from the light chain variable region sequence set forth as SEQ ID NO:2 and/or includes one, two or three CDRs from the heavy chain variable region sequence set forth as SEQ ID NO:4), and includes a variable framework region substantially from a human acceptor immunoglobulin light or heavy chain sequence, provided that at least one framework residue is substituted with the corresponding amino acid residue from the mouse 3D6 light or heavy chain variable region sequence, where the framework residue is selected from the group consisting of (a) a residue that non-covalently binds antigen directly; (b) a residue adjacent to a CDR; (c) a CDR-interacting residue (e.g., identified by modeling the light or heavy chain on the solved structure of a homologous known immunoglobulin chain); and (d) a residue participating in the VL-VH interface.

In another embodiment, the invention features a humanized immunoglobulin light or heavy chain that includes 3D6 variable region CDRs and variable framework regions from a human acceptor immunoglobulin light or heavy chain sequence, provided that at least one framework residue is substituted with the corresponding amino acid residue from the mouse 3D6 light or heavy chain variable region sequence, where the framework residue is a residue capable of affecting light chain variable region conformation or function as identified by analysis of a three-dimensional model of the variable region, for example a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, an unusual residue, or a glycoslyation site residue on the surface of the structural model.

In another embodiment, the invention features a humanized immunoglobulin light chain that includes 3D6 variable region CDRs (e.g., from the 3D6 light chain variable region sequence set forth as SEQ ID NO:2), and includes a human acceptor immunoglobulin variable framework region, provided that at least one framework residue selected from the group consisting of L1, L2, L36 and L46 (Kabat numbering convention) is substituted with the corresponding amino acid residue from the mouse 3D6 light chain variable region sequence. In another embodiment, the invention features a humanized immunoglobulin heavy chain that includes 3D6 variable region CDRs (e.g., from the 3D6 heavy chain variable region sequence set forth as SEQ ID NO:4), and includes a human acceptor immunoglobulin variable framework region, provided that at least one framework residue selected from the group consisting of H49, H93 and H94 (Kabat numbering convention) is substituted with the corresponding amino acid residue from the mouse 3D6 heavy chain variable region sequence.

Preferred light chains include kappa II framework regions of the subtype kappa II (Kabat convention), for example, framework regions from the acceptor immunoglobulin Kabat ID 019230, Kabat ID 005131, Kabat ID 005058, Kabat ID 005057, Kabat ID 005059, Kabat ID U21040 and Kabat ID U41645. Preferred heavy chains include framework regions of the subtype III (Kabat convention), for example, framework regions from the acceptor immunoglobulin Kabat ID 045919, Kabat ID 000459, Kabat ID 000553, Kabat ID 000386 and Kabat ID M23691.

In one embodiment, the invention features a humanized immunoglobulin light or heavy chain that includes 10D5 variable region complementarity determining regions (CDRs) (i.e., includes one, two or three CDRs from the light chain variable region sequence set forth as SEQ ID NO:14 or includes one, two or three CDRs from the heavy chain variable region sequence set forth as SEQ ID NO:16), and includes a variable framework region substantially from a human acceptor immunoglobulin light or heavy chain sequence, provided that at least one residue of the framework residue is backmutated to a corresponding murine residue, wherein said backmutation does not substantially affect the ability of the chain to direct Aβ binding.

In another embodiment, the invention features a humanized immunoglobulin light or heavy chain that includes 10D5 variable region complementarity determining regions (CDRs) (e.g., includes one, two or three CDRs from the light chain variable region sequence set forth as SEQ ID NO:14 and/or includes one, two or three CDRs from the heavy chain variable region sequence set forth as SEQ ID NO:16), and includes a variable framework region substantially from a human acceptor immunoglobulin light or heavy chain sequence, provided that at least one framework residue is substituted with the corresponding amino acid residue from the mouse 3D6 light or heavy chain variable region sequence, where the framework residue is selected from the group consisting of (a) a residue that non-covalently binds antigen directly; (b) a residue adjacent to a CDR; (c) a CDR-interacting residue (e.g., identified by modeling the light or heavy chain on the solved structure of a homologous known immunoglobulin chain); and (d) a residue participating in the VL-VH interface.

In another embodiment, the invention features a humanized immunoglobulin light or heavy chain that includes 10D5 variable region CDRs and variable framework regions from a human acceptor immunoglobulin light or heavy chain sequence, provided that at least one framework residue is substituted with the corresponding amino acid residue from the mouse 10D5 light or heavy chain variable region sequence, where the framework residue is a residue capable of affecting light chain variable region conformation or function as identified by analysis of a three-dimensional model of the variable region, for example a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, an unusual residue, or a glycoslyation site residue on the surface of the structural model.

In another embodiment, the invention features, in addition to the substitutions described above, a substitution of at least one rare human framework residue. For example, a rare residue can be substituted with an amino acid residue which is common for human variable chain sequences at that position. Alternatively, a rare residue can be substituted with a corresponding amino acid residue from a homologous germline variable chain sequence (e.g., a rare light chain framework residue can be substituted with a corresponding germline residue from an A1, A17, A18, A2, or A19 germline immunoglobulin sequence or a rare heavy chain framework residue can be substituted with a corresponding germline residue from a VH3-48, VH3-23, VH3-7, VH3-21 or VH3-11 germline immunoglobulin sequence.

In another embodiment, the invention features a humanized immunoglobulin that includes a light chain and a heavy chain, as described above, or an antigen-binding fragment of said immunoglobulin. In an exemplary embodiment, the humanized immunoglobulin binds (e.g., specifically binds) to beta amyloid peptide (Aβ) with a binding affinity of at least $10^7$ M$^{-1}$, $10^8$ M$^{-1}$, or $10^9$ M$^{-1}$. In another embodiment, the immunoglobulin or antigen binding fragment includes a heavy chain having isotype γ1. In another embodiment, the immunoglobulin or antigen binding fragment binds (e.g., specifically binds) to both soluble beta amyloid peptide (Aβ) and aggregated Aβ. In another embodiment, the immunoglobulin or antigen binding fragment mediates phagocytosis (e.g., induces phagocytosis) of beta amyloid peptide (Aβ). In yet another embodiment, the immunoglobulin or antigen binding fragment crosses the blood-brain barrier in a subject. In yet another embodiment, the immunoglobulin or antigen binding fragment reduces both beta amyloid peptide (Aβ) burden and neuritic dystrophy in a subject.

In another embodiment, the invention features chimeric immunoglobulins that include 3D6 variable regions (e.g., the variable region sequences set forth as SEQ ID NO:2 or SEQ ID NO:4). As used herein, an antibody or immunoglobulin sequence comprising a VL and/or VH sequence as set forth in, for example, SEQ ID NO:2 or SEQ ID NO:4 can comprise either the full VL or VH sequence or can comprise the mature VL or VH sequence (i.e., mature peptide without the signal or leader peptide). In yet another embodiment, the invention features an immunoglobulin, or antigen-binding fragment thereof, including a variable heavy chain region as set forth in SEQ ID NO:8 and a variable light chain region as set forth in SEQ ID NO:5. In yet another embodiment, the invention features an immunoglobulin, or antigen-binding fragment thereof, including a variable heavy chain region as set forth in SEQ ID NO:12 and a variable light chain region as set forth in SEQ ID NO:11. In another embodiment, the invention features chimeric immunoglobulins that include 10D5 variable regions (e.g., the variable region sequences set forth as SEQ ID NO:14 or SEQ ID NO:16). In yet another embodiment, the immunoglobulin, or antigen-binding fragment thereof, further includes constant regions from IgG1.

The immunoglobulins described herein are particularly suited for use in therapeutic methods aimed at preventing or treating amyloidogenic diseases. In one embodiment, the invention features a method of preventing or treating an amyloidogenic disease (e.g., Alzheimer's disease) that involves administering to the patient an effective dosage of a humanized immunoglobulin as described herein. In another embodiment, the invention features pharmaceutical compositions that include a humanized immunoglobulin as described herein and a pharmaceutical carrier. Also featured are isolated nucleic acid molecules, vectors and host cells for producing the immunoglobulins or immunoglobulin fragments or chains described herein, as well as methods for producing said immunoglobulins, immunoglobulin fragments or immunoglobulin chains The present invention further features a method for identifying 3D6 or 10D5 residues amenable to substitution when producing a humanized 3D6 or 10D5 immunoglobulin, respectively. For example, a method for identifying variable framework region residues amenable to substitution involves modeling the three-dimensional structure of the 3D6 or 10D5 variable region on a solved homologous immunoglobulin structure and analyzing said model for residues capable of affecting 3D6 or 10D5 immunoglobulin variable region conformation or function, such that residues amenable to substitution are identified. The invention further features use of the variable region sequence set forth as SEQ ID NO:2 or SEQ ID NO:4, or any portion thereof, in producing a three-dimensional image of a 3D6 immunoglobulin, 3D6 immunoglobulin chain, or domain thereof. Also featured is the use of the variable region sequence set forth as SEQ ID NO:14 or SEQ ID NO:16, or any portion thereof, in producing a three-dimensional image of a 10D5 immunoglobulin, 10D5 immunoglobulin chain, or domain thereof.

The present invention further features immunoglobulins having altered effector function, such as the ability to bind effector molecules, for example, complement or a receptor on an effector cell. In particular, the immunoglobulin of the invention has an altered constant region, e.g., Fc region, wherein at least one amino acid residue in the Fc region has been replaced with a different residue or side chain. In one embodiment, the modified immunoglobulin is of the IgG class, comprises at least one amino acid residue replacement in the Fc region such that the immunoglobulin has an altered effector function, e.g., as compared with an unmodified immunoglobulin. In particular embodiments, the immunoglobulin of the invention has an altered effector function such that it is less immunogenic (e.g., does not provoke undesired effector cell activity, lysis, or complement binding), has improved amyloid clearance properties, and/or has a desirable half-life.

Prior to describing the invention, it may be helpful to an understanding thereof to set forth definitions of certain terms to be used hereinafter.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). "Variable" domains on the light chain are referred to interchangeably as "light chain variable regions", "light chain variable domains", "VL" regions or "VL" domains). "Variable" domains on the heavy chain are referred to interchangeably as "heavy chain constant regions", "heavy chain constant domains", "CH" regions or "CH" domains).

The term "region" refers to a part or portion of an antibody chain and includes constant or variable domains as defined herein, as well as more discrete parts or portions of said domains. For example, light chain variable domains or regions include "complementarity determining regions" or "CDRs" interspersed among "framework regions" or "FRs", as defined herein.

Immunoglobulins or antibodies can exist in monomeric or polymeric form. The term "antigen-binding fragment" refers to a polypeptide fragment of an immunoglobulin or antibody binds antigen or competes with intact antibody (i.e., with the intact antibody from which they were derived) for antigen binding (i.e., specific binding). The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

"Specific binding" of an antibody mean that the antibody exhibits appreciable affinity for antigen or a preferred epitope and, preferably, does not exhibit significant crossreactivity. "Appreciable" or preferred binding include binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant crossreactivity" is one that will not appreciably bind to an undesirable entity (e.g., an undesirable proteinaceous entity). For example, an antibody that specifically binds to Aβ will appreciably bind Aβ but will not significantly react with non-Aβ proteins or peptides (e.g., non-Aβ proteins or peptides included in plaques). An antibody specific for a preferred epitope will, for example, not significantly crossreact with remote epitopes on the same protein or peptide. Specific binding can be determined according to any art-recognized means for determining such binding. Preferably, specific binding is determined according to Scatchard analysis and/or competitive binding assays.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino acid sequence for comparison purposes, the region shares at least 80-90%, preferably 90-95%, more preferably 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "significant identity" means that two polypeptide sequences, when optimally aligned, such as by the programs GAP or BESTFIT using default gap weights, share at least 50-60% sequence identity, preferably 60-70% sequence identity, more preferably 70-80% sequence identity, more preferably at least 80-90% identity, even more preferably at least 90-95% identity, and even more preferably at least 95% sequence identity or more (e.g., 99% sequence identity or more). The term "substantial identity" means that two polypeptide sequences, when optimally aligned, such as by the programs GAP or BESTFIT using default gap weights, share at least 80-90% sequence identity, preferably 90-95% sequence identity, and more preferably at least 95% sequence identity or more (e.g., 99% sequence identity or more). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. The terms "sequence identity" and "sequence identity" are used interchangeably herein.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.*

48:443 (1970), by the search for similarity method of Pearson & Lipman, *Proc. Nat.'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Preferably, residue positions which are not identical differ by conservative amino acid substitutions. For purposes of classifying amino acids substitutions as conservative or non-conservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Nonconservative substitutions constitute exchanging a member of one of these classes for a member of another.

Preferably, humanized immunoglobulins or antibodies bind antigen with an affinity that is within a factor of three, four, or five of that of the corresponding non-human antibody. For example, if the nonhuman antibody has a binding affinity of $10^9$ $M^{-1}$, humanized antibodies will have a binding affinity of at least $3 \times 10^9$ $M^{-1}$, $4 \times 10^9$ $M^{-1}$ or $10^9$ $M^{-1}$. When describing the binding properties of an immunoglobulin or antibody chain, the chain can be described based on its ability to "direct antigen (e.g., Aβ) binding". A chain is said to "direct antigen binding" when it confers upon an intact immunoglobulin or antibody (or antigen binding fragment thereof) a specific binding property or binding affinity. A mutation (e.g., a back-mutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

An "antigen" is an entity (e.g., a protenaceous entity or peptide) to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

Exemplary epitopes or antigenic determinants can be found within the human amyloid precursor protein (APP), but are preferably found within the Aβ peptide of APP. Multiple isoforms of APP exist, for example $APP^{695}$ $APP^{751}$ and $APP^{770}$. Amino acids within APP are assigned numbers according to the sequence of the $APP^{770}$ isoform (see e.g., GenBank Accession No. $PO_{5067}$, also set forth as SEQ ID NO:38). Aβ (also referred to herein as beta amyloid peptide and A-beta) peptide is a ~4-kDa internal fragment of 39-43 amino acids of APP (Aβ39, Aβ40, Aβ41, Aβ42 and Aβ43). Aβ40, for example, consists of residues 672-711 of APP and Aβ42 consists of residues 673-713 of APP. As a result of proteolytic processing of APP by different secretase enzymes iv vivo or in situ, Aβ is found in both a "short form", 40 amino acids in length, and a "long form", ranging from 42-43 amino acids in length. Preferred epitopes or antigenic determinants, as described herein, are located within the N-terminus of the Aβ peptide and include residues within amino acids 1-10 of Aβ, preferably from residues 1-3, 1-4, 1-5, 1-6, 1-7 or 3-7 of Aβ42. Additional referred epitopes or antigenic determinants include residues 2-4, 5, 6, 7 or 8 of Aβ, residues 3-5, 6, 7, 8 or 9 of Aβ, or residues 4-7, 8, 9 or 10 of A42.

The term "amyloidogenic disease" includes any disease associated with (or caused by) the formation or deposition of insoluble amyloid fibrils. Exemplary amyloidogenic diseases include, but are not limited to systemic amyloidosis, Alzheimer's disease, mature onset diabetes, Parkinson's disease, Huntington's disease, fronto-temporal dementia, and the prion-related transmissible spongiform encephalopathies (kuru and Creutzfeldt-Jacob disease in humans and scrapie and BSE in sheep and cattle, respectively). Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ", e.g., in the brain of a subject or patient. The terms "β-amyloid protein", "β-amyloid peptide", "β-amyloid", "Aβ" and "Aβ peptide" are used interchangeably herein.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the patient's own immune system.

The term "patient" includes human and other mammalian subjects that receive either prophylactic or therapeutic treatment.

"Soluble" or "dissociated" Aβ refers to non-aggregating or disaggregated Aβ polypeptide. "Insoluble" Aβ refers to aggregating Aβ polypeptide, for example, Aβ held together by noncovalent bonds. Aβ (e.g., Aβ42) is believed to aggregate, at least in part, due to the presence of hydrophobic residues at the C-terminus of the peptide (part of the transmembrane domain of APP). One method to prepare soluble Aβ is to dissolve lyophilized peptide in neat DMSO with sonication. The resulting solution is centrifuged to remove any insoluble particulates.

The term "effector function" refers to an activity that resides in the Fc region of an antibody (e.g., an IgG antibody) and includes, for example, the ability of the antibody to bind effector molecules such as complement and/or Fc receptors, which can control several immune functions of the antibody such as effector cell activity, lysis, complement-mediated activity, antibody clearance, and antibody half-life.

The term "effector molecule" refers to a molecule that is capable of binding to the Fc region of an antibody (e.g., an IgG antibody) including, but not limited to, a complement protein or a Fc receptor.

The term "effector cell" refers to a cell capable of binding to the Fc portion of an antibody (e.g., an IgG antibody) typically via an Fc receptor expressed on the surface of the effector cell including, but not limited to, lymphocytes, e.g., antigen presenting cells and T cells.

The term "Fc region" refers to a C-terminal region of an IgG antibody, in particular, the C-terminal region of the heavy chain(s) of said IgG antibody. Although the boundaries of the Fc region of an IgG heavy chain can vary slightly, a Fc region is typically defined as spanning from about amino acid residue Cys226 to the carboxyl-terminus of an IGg heavy chain(s).

The term "Kabat numbering" unless otherwise stated, is defined as the numbering of the residues in, e.g., an IgG heavy chain antibody using the EU index as in Kabat et al. (Sequences of Proteins of Immunological Interest, 5th Ed. Public Health Service, National Institutes of Health, Bethesda, Md. (1991)), expressly incorporated herein by reference.

The term "Fc receptor" or "FcR" refers to a receptor that binds to the Fc region of an antibody. Typical Fc receptors which bind to an Fc region of an antibody (e.g., an IgG antibody) include, but are not limited to, receptors of the FcγRI, FcγRII, and FcγRIII subclasses, including allelic variants and alternatively spliced forms of these receptors. Fc receptors are reviewed in Ravetch and Kinet, Annu. Rev. Immunol 9:457-92 (1991); Capel et al., Immunomethods 4:25-34 (1994); and de Haas et al., J. Lab. Clin. Med. 126: 330-41 (1995).

I. Immunological and Therapeutic Reagents

Immunological and therapeutic reagents of the invention comprise or consist of immunogens or antibodies, or functional or antigen binding fragments thereof, as defined herein. The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda and are about 230 residues in length. Heavy chains are classified as gamma (γ), mu (μ), alpha (α), delta (δ), or epsilon (O), are about 450-600 residues in length, and define the antibody's isotype as IgG, IgM, IgA, IgD and IgE, respectively. Both heavy and light chains are folded into domains. The term "domain" refers to a globular region of a protein, for example, an immunoglobulin or antibody. Immunoglobulin or antibody domains include, for example, 3 or four peptide loops stabilized by β-pleated sheet and an interchain disulfide bond. Intact light chains have, for example, two domains ($V_L$ and $C_L$) and intact heavy chains have, for example, four or five domains ($V_H$, $C_H1$, $C_H2$, and $C_H3$).

Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y. (1989), Ch. 7, incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. Naturally-occurring chains or recombinantly produced chains can be expressed with a leader sequence which is removed during cellular processing to produce a mature chain. Mature chains can also be recombinantly produced having a non-naturally occurring leader sequence, for example, to enhance secretion or alter the processing of a particular chain of interest.

The CDRs of the two mature chains of each pair are aligned by the framework regions, enabling binding to a specific epitope. From N-terminal to C-terminal, both light and heavy chains comprise the domains FR1, CDR1, FR2, CDR2, FR3, CDR3 and FR4. "FR4" also is referred to in the art as the D/J region of the variable heavy chain and the J region of the variable light chain. The assignment of amino acids to each domain is in accordance with the definitions of Kabat, *Sequences of Proteins of Immunological Interest* (National Institutes of Health, Bethesda, Md., 1987 and 1991). An alternative structural definition has been proposed by Chothia et al., *J. Mol. Biol.* 196:901 (1987); *Nature* 342:878 (1989); and *J. Mol. Biol.* 186:651 (1989) (hereinafter collectively referred to as "Chothia et al." and incorporated by reference in their entirety for all purposes).

A. Aβ Antibodies

Therapeutic agents of the invention include antibodies that specifically bind to Aβ or other component of amyloid plaques. Such antibodies can be monoclonal or polyclonal. Some such antibodies bind specifically to the aggregated form of Aβ without binding to the soluble form. Some bind specifically to the soluble form without binding to the aggregated form. Some bind to both aggregated and soluble forms. Some such antibodies bind to a naturally occurring short form of Aβ (i.e., Aβ39, 40 or 41) without binding to a naturally occurring long form of Aβ (i.e., Aβ42 and Aβ43). Some antibodies bind to a long form of Aβ without binding to a short form. Some antibodies bind to Aβ without binding to full-length amyloid precursor protein. Antibodies used in therapeutic methods preferably have an intact constant region or at least sufficient of the constant region to interact with an Fc receptor. Human isotype IgG1 is preferred because of it having highest affinity of human isotypes for the FcRI receptor on phagocytic cells. Bispecific Fab fragments can also be used, in which one arm of the antibody has specificity for Aβ, and the other for an Fc receptor. Preferred antibodies bind to Aβ with a binding affinity greater than (or equal to) about $10^6$, $10^7$, $10^8$, $10^9$, or $10^{10}$ $M^{-1}$ (including affinities intermediate of these values).

Polyclonal sera typically contain mixed populations of antibodies binding to several epitopes along the length of Aβ. However, polyclonal sera can be specific to a particular segment of Aβ, such as Aβ1-10. Monoclonal antibodies bind to a specific epitope within Aβ that can be a conformational or nonconformational epitope. Prophylactic and therapeutic efficacy of antibodies can be tested using the transgenic animal model procedures described in the Examples. Preferred monoclonal antibodies bind to an epitope within residues 1-10 of Aβ (with the first N terminal residue of natural Aβ designated 1). Some preferred monoclonal antibodies bind to an epitope within amino acids 1-5, and some to an epitope within 5-10. Some preferred antibodies bind to epitopes within amino acids 1-3, 1-4, 1-5, 1-6, 1-7 or 3-7. Some preferred antibodies bind to an epitope starting at resides 1-3 and ending at residues 7-11 of Aβ. Less preferred antibodies include those binding to epitopes with residues 10-15, 15-20, 25-30, 10-20, 20, 30, or 10-25 of Aβ. It is recommended that such antibodies be screened for activity in the mouse models described in the Examples before use. For example, it has been found that certain antibodies to epitopes within residues 10-18, 16-24, 18-21 and 33-42 lack activity (e.g., lack the ability to reduce plaque burden and/or resolve the neuritic pathology associated with Alzheimer's disease). In some methods, multiple monoclonal antibodies having binding specificities to different epitopes are used. Such antibodies can be administered sequentially or simultaneously. Antibodies to amyloid components other than Aβ can also be used (e.g., administered or co-administered). For example, antibodies can be directed to the amyloid associated protein synuclein.

When an antibody is said to bind to an epitope within specified residues, such as Aβ 1-5 for example, what is meant is that the antibody specifically binds to a polypeptide containing the specified residues (i.e., Aβ1-5 in this an example). Such an antibody does not necessarily contact every residue within Aβ1-5. Nor does every single amino acid substitution or deletion with in Aβ1-5 necessarily significantly affect binding affinity. Epitope specificity of an antibody can be determined, for example, by forming a phage display library in which different members display different subsequences of Aβ. The phage display library is then selected for members specifically binding to an antibody under test. A family of sequences is isolated. Typically, such a family contains a common core sequence, and varying lengths of flanking sequences in different members. The shortest core sequence showing specific binding to the antibody defines the epitope bound by the antibody. Antibodies can also be tested for epitope specificity in a competition assay with an antibody whose epitope specificity has already been determined. For example, antibodies that compete with the 3D6 antibody for binding to Aβ bind to the same or similar epitope as 3D6, i.e., within residues Aβ1-5. Likewise antibodies that compete with the 10D5 antibody bind to the same or similar epitope, i.e., within residues Aβ 3-7. Screening antibodies for epitope specificity is a useful predictor of therapeutic efficacy. For example, an antibody determined to bind to an epitope within residues 1-7 of Aβ is likely to be effective in preventing and treating Alzheimer's disease according to the methodologies of the present invention.

Monoclonal or polyclonal antibodies that specifically bind to a preferred segment of Aβ without binding to other regions of Aβ have a number of advantages relative to monoclonal antibodies binding to other regions or polyclonal sera to intact Aβ. First, for equal mass dosages, dosages of antibodies that specifically bind to preferred segments contain a higher molar dosage of antibodies effective in clearing amyloid plaques. Second, antibodies specifically binding to preferred segments can induce a clearing response against amyloid deposits without inducing a clearing response against intact APP polypeptide, thereby reducing the potential side effects.

1. Production of Nonhuman Antibodies

The present invention features non-human antibodies, for example, antibodies having specificity for the preferred Aβ epitopes of the invention. Such antibodies can be used in formulating various therapeutic compositions of the invention or, preferably, provide complementarity determining regions for the production of humanized or chimeric antibodies (described in detail below). The production of non-human monoclonal antibodies, e.g., murine, guinea pig, primate, rabbit or rat, can be accomplished by, for example, immunizing the animal with Aβ. A longer polypeptide comprising Aβ or an immunogenic fragment of Aβ or anti-idiotypic antibodies to an antibody to Aβ can also be used. See Harlow & Lane, supra, incorporated by reference for all purposes). Such an immunogen can be obtained from a natural source, by peptide synthesis or by recombinant expression. Optionally, the immunogen can be administered fused or otherwise complexed with a carrier protein, as described below. Optionally, the immunogen can be administered with an adjuvant. The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages. Several types of adjuvant can be used as described below. Complete Freund's adjuvant followed by incomplete adjuvant is preferred for immunization of laboratory animals.

Rabbits or guinea pigs are typically used for making polyclonal antibodies. Exemplary preparation of polyclonal antibodies, e.g., for passive protection, can be performed as follows. 125 non-transgenic mice are immunized with 100 μg Aβ1-42, plus CFA/IFA adjuvant, and euthanized at 4-5 months. Blood is collected from immunized mice. IgG is separated from other blood components. Antibody specific for the immunogen may be partially purified by affinity chromatography. An average of about 0.5-1 mg of immunogen-specific antibody is obtained per mouse, giving a total of 60-120 mg.

Mice are typically used for making monoclonal antibodies. Monoclonals can be prepared against a fragment by injecting the fragment or longer form of Aβ into a mouse, preparing hybridomas and screening the hybridomas for an antibody that specifically binds to Aβ. Optionally, antibodies are screened for binding to a specific region or desired fragment of Aβ without binding to other nonoverlapping fragments of Aβ. The latter screening can be accomplished by determining binding of an antibody to a collection of deletion mutants of an Aβ peptide and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to Aβ. If the test and reference antibodies compete, then they bind to the same epitope or epitopes sufficiently proximal such that binding of one antibody interferes with binding of the other. The preferred isotype for such antibodies is mouse isotype IgG2a or equivalent isotype in other species. Mouse isotype IgG2a is the equivalent of human isotype IgG1.

2. Chimeric and Humanized Antibodies

The present invention also features chimeric and/or humanized antibodies (i.e., chimeric and/or humanized immunoglobulins) specific for beta amyloid peptide. Chimeric and/or humanized antibodies have the same or similar binding specificity and affinity as a mouse or other nonhuman antibody that provides the starting material for construction of a chimeric or humanized antibody.

A. Production of Chimeric Antibodies

The term "chimeric antibody" refers to an antibody whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. A typical chimeric antibody is thus a hybrid protein consisting of the V or antigen-binding domain from a mouse antibody and the C or effector domain from a human antibody.

B. Production of Humanized Antibodies

The term "humanized antibody" refers to an antibody comprising at least one chain comprising variable region framework residues substantially from a human antibody chain (referred to as the acceptor immunoglobulin or antibody) and at least one complementarity determining region substantially from a mouse-antibody, (referred to as the donor immunoglobulin or antibody). See, Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693,762, Selick et al., WO 90/07861, and Winter, U.S. Pat. No. 5,225,539 (incorporated by reference in their entirety for all purposes). The constant region(s), if present, are also substantially or entirely from a human immunoglobulin.

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., *Protein Engineering* 4:773 (1991); Kolbinger et al., *Protein Engineering* 6:971 (1993) and Carter et al., WO 92/22653.

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution is determined, in part, by computer modeling. Computer hardware and software are described herein for producing three-dimensional images of immunoglobulin molecules. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g., is within about 3-6 Å of a CDR region as determined by computer modeling), or
(4) participates in the VL-VH interface.

Residues which "noncovalently bind antigen directly" include amino acids in positions in framework regions which are have a good probability of directly interacting with amino acids on the antigen according to established chemical forces, for example, by hydrogen bonding, Van der Waals forces, hydrophobic interactions, and the like.

CDR and framework regions are as defined by Kabat et al. or Chothia et al., supra. When framework residues, as defined by Kabat et al., supra, constitute structural loop residues as defined by Chothia et al., supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233: 747 (1986), which is incorporated herein by reference) and selecting these amino acids from the donor may be desirable to keep all the antigen contacts that provide affinity in the original antibody.

Residues that "otherwise interact with a CDR region" include those that are determined by secondary structural analysis to be in a spatial orientation sufficient to effect a CDR region. In one embodiment, residues that "otherwise interact with a CDR region" are identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units (Å) of some atom in the CDRs and must contain an atom that could interact with the CDR atoms according to established chemical forces, such as those listed above.

In the case of atoms that may form a hydrogen bond, the 3 Å is measured between their nuclei, but for atoms that do not form a bond, the 3 Å is measured between their Van der Waals surfaces. Hence, in the latter case, the nuclei must be within about 6 Å (3 Å plus the sum of the Van der Waals radii) for the atoms to be considered capable of interacting. In many cases the nuclei will be from 4 or 5 to 6 Å apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids that are capable of interacting with amino acids in the CDRs, may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971), both of which are incorporated herein by reference). Framework amino acids may also occasionally interact with the CDRs indirectly, by affecting the conformation of another framework amino acid that in turn contacts the CDRs.

The amino acids at several positions in the framework are known to be capable of interacting with the CDRs in many antibodies (Chothia and Lesk, supra, Chothia et al., supra and Tramontano et al., J. Mol. Biol. 215:175 (1990), all of which are incorporated herein by reference). Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized immunoglobulin.

Residues which "participate in the VL-VH interface" or "packing residues" include those residues at the interface between VL and VH as defined, for example, by Novotny and Haber, Proc. Natl. Acad. Sci. USA, 82:4592-66 (1985) or Chothia et al, supra. Generally, unusual packing residues should be retained in the humanized antibody if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. Although not usually desirable, it is sometimes possible to make one or more conservative amino acid substitutions of CDR residues without appreciably affecting the binding affinity of the resulting humanized immunoglobulin. By conservative substitutions is intended combinations such as gly, ala; val, ile, leu; asp, glu; asn, gln; ser, thr; lys, arg; and phe, tyr.

Additional candidates for substitution are acceptor human framework amino acids that are unusual or "rare" for a human immunoglobulin at that position. These amino acids can be substituted with amino acids from the equivalent position of the mouse donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criterion help ensure that an atypical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the AbM and/or contact definitions. Notably, CDR1 in the variable heavy chain is defined as including residues 26-32.

Additional candidates for substitution are acceptor framework residues that correspond to a rare or unusual donor framework residue. Rare or unusual donor framework residues are those that are rare or unusual (as defined herein) for murine antibodies at that position. For murine antibodies, the subgroup can be determined according to Kabat and residue positions identified which differ from the consensus. These donor specific differences may point to somatic mutations in the murine sequence which enhance activity. Unusual residues that are predicted to affect binding are retained, whereas residues predicted to be unimportant for binding can be substituted.

Additional candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 85% sequence identity to a human variable framework region sequence or consensus of such sequences. In another embodiment, the variable framework region of the humanized immunoglobulin shares at least 90%, preferably 95%, more preferably 96%, 97%, 98% or 99% sequence identity to a human variable framework region sequence or consensus of such sequences. In general, however, such substitutions are undesirable.

The humanized antibodies preferably exhibit a specific binding affinity for antigen of at least $10^7$, $10^8$, $10^9$ or $10^{10}$ $M^{-1}$. Usually the upper limit of binding affinity of the humanized antibodies for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized antibody having no substitutions (e.g., an antibody having donor CDRs and acceptor FRs, but no FR substitutions). In such instances, the binding of the optimized antibody (with substitutions) is preferably at least two- to three-fold greater, or three- to four-fold greater, than that of the unsubstituted antibody. For making comparisons, activity of the various antibodies can be determined, for example, by BIACORE (i.e., surface plasmon resonance using unlabelled reagents) or competitive binding assays.

C. Production of Humanized 3D6 Antibodies

A preferred embodiment of the present invention features a humanized antibody to the N-terminus of Aβ, in particular, for use in the therapeutic and/or diagnostic methodologies described herein. A particularly preferred starting material for production of humanized antibodies is 3D6. 3D6 is specific for the N-terminus of Aβ and has been shown to mediate phagocytosis (e.g., induce phagocytosis) of amyloid plaque (see Examples I-V). The cloning and sequencing of cDNA encoding the 3D6 antibody heavy and light chain variable regions is described in Example VI.

Suitable human acceptor antibody sequences are identified by computer comparisons of the amino acid sequences of the mouse variable regions with the sequences of known human antibodies. The comparison is performed separately for heavy and light chains but the principles are similar for each. In particular, variable domains from human antibodies whose framework sequences exhibit a high degree of sequence identity with the murine VL and VH framework regions were identified by query of the Kabat Database using NCBI BLAST (publicly accessible through the National Institutes of Health NCBI internet server) with the respective murine framework sequences. In one embodiment, acceptor sequences sharing greater that 50% sequence identity with murine donor sequences are selected. Preferably, acceptor antibody sequences sharing 60%, 70%, 80%, 90% or more are selected.

A computer comparison of 3D6 revealed that the 3D6 light chain shows the greatest sequence identity to human light chains of subtype kappa II, and that the 3D6 heavy chain shows greatest sequence identity to human heavy chains of subtype III, as defined by Kabat et al., supra. Thus, light and heavy human framework regions are preferably derived from human antibodies of these subtypes, or from consensus sequences of such subtypes. The preferred light chain human variable regions showing greatest sequence identity to the corresponding region from 3D6 are from antibodies having Kabat ID Numbers 019230, 005131, 005058, 005057, 005059, U21040 and U41645, with 019230 being more preferred. The preferred heavy chain human variable regions showing greatest sequence identity to the corresponding region from 3D6 are from antibodies having Kabat ID Numbers 045919, 000459, 000553, 000386 and M23691, with 045919 being more preferred.

Residues are next selected for substitution, as follows. When an amino acid differs between a 3D6 variable framework region and an equivalent human variable framework region, the human framework amino acid should usually be substituted by the equivalent mouse amino acid if it is reasonably expected that the amino acid:

(1) noncovalently binds antigen directly,
(2) is adjacent to a CDR region, is part of a CDR region under the alternative definition proposed by Chothia et al., supra, or otherwise interacts with a CDR region (e.g., is within about 3 A of a CDR region) (e.g., amino acids at positions L2, H49 and H94 of 3D6), or
(3) participates in the VL-VH interface (e.g., amino acids at positions L36, L46 and H93 of 3D6).

Computer modeling of the 3D6 antibody heavy and light chain variable regions, and humanization of the 3D6 antibody is described in Example VII. Briefly, a three-dimensional model was generated based on the closest solved murine antibody structures for the heavy and light chains. For this purpose, an antibody designated 1CR9 (Protein Data Bank (PDB) ID: 1CR9, Kanyo et al., *J. Mol. Biol.* 293:855 (1999)) was chosen as a template for modeling the 3D6 light chain, and an antibody designated 1OPG (PDB ID: 1OPG, Kodandapani et al., *J. Biol. Chem.* 270:2268 (1995)) was chosen as the template for modeling the heavy chain. The model was further refined by a series of energy minimization steps to relieve unfavorable atomic contacts and optimize electrostatic and van der Walls interactions. The solved structure of 1 qkz (PDB ID: 1QKZ, Derrick et al., *J. Mol. Biol.* 293:81 (1999)) was chosen as a template for modeling CDR3 of the heavy chain as 3D6 and 1OPG did not exhibit significant sequence homology in this region when aligned for comparison purposes.

Three-dimensional structural information for the antibodies described herein is publicly available, for example, from the Research Collaboratory for Structural Bioinformatics' Protein Data Bank (PDB). The PDB is freely accessible via the World Wide Web internet and is described by Berman et al. (2000) *Nucleic Acids Research,* 28:235. Computer modeling allows for the identification of CDR-interacting residues. The computer model of the structure of 3D6 can in turn serve as a starting point for predicting the three-dimensional structure of an antibody containing the 3D6 complementarity determining regions substituted in human framework structures. Additional models can be constructed representing the structure as further amino acid substitutions are introduced.

In general, substitution of one, most or all of the amino acids fulfilling the above criteria is desirable. Accordingly, the humanized antibodies of the present invention will usually contain a substitution of a human light chain framework residue with a corresponding 3D6 residue in at least 1, 2 or 3, and more usually 4, of the following positions: L1, L2, L36 and L46. The humanized antibodies also usually contain a substitution of a human heavy chain framework residue with a corresponding 3D6 residue in at least 1, 2, and sometimes 3, of the following positions: H49, H93 and H94. Humanized antibodies can also contain a substitution of a heavy chain framework residue with a corresponding germline residue in at least 1, 2, and sometimes 3, of the following positions: H74, H77 and H89.

Occasionally, however, there is some ambiguity about whether a particular amino acid meets the above criteria, and alternative variant immunoglobulins are produced, one of which has that particular substitution, the other of which does not. In instances where substitution with a murine residue would introduce a residue that is rare in human immunoglobulins at a particular position, it may be desirable to test the antibody for activity with or without the particular substitution. If activity (e.g., binding affinity and/or binding specificity) is about the same with or without the substitution, the antibody without substitution may be preferred, as it would be expected to elicit less of a HAHA response, as described herein.

Other candidates for substitution are acceptor human framework amino acids that are unusual for a human immunoglobulin at that position. These amino acids can be substituted with amino acids from the equivalent position of more typical human immunoglobulins. Alternatively, amino acids from equivalent positions in the mouse 3D6 can be introduced into the human framework regions when such amino acids are typical of human immunoglobulin at the equivalent positions.

Figure 2:
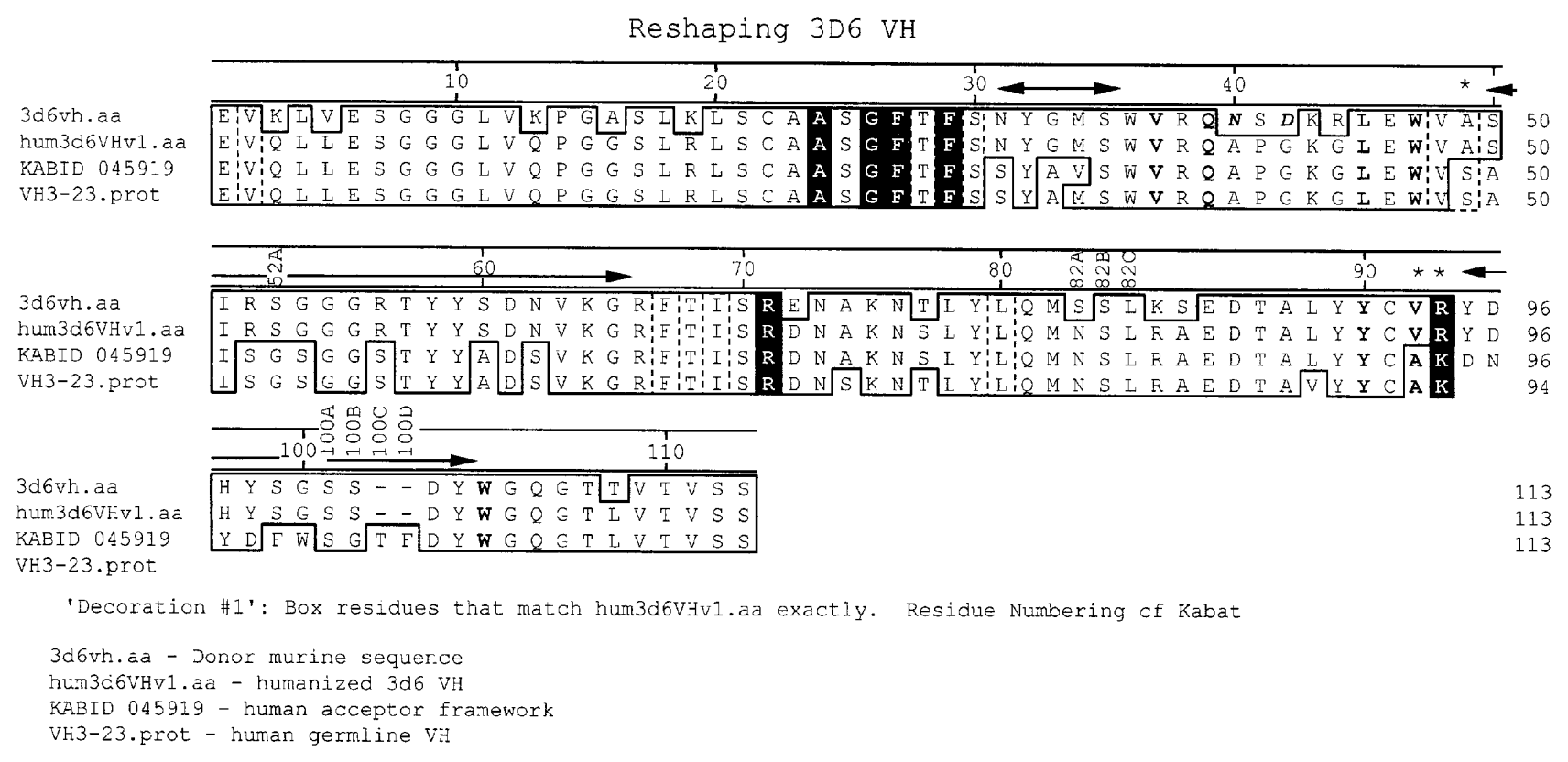

In additional embodiments, when the human light chain framework acceptor immunoglobulin is Kabat ID Number 019230, the light chain contains substitutions in at least 1, 2, 3, 4, 5, 6, 7, 8, 9, 10, 11, 12 or more usually 13, of the following positions: L7, L10, L12, L15, L17, L39, L45, L63, L78, L83, L85, L100 or L104. In additional embodiments when the human heavy chain framework acceptor immunoglobulin is Kabat ID Number 045919, the heavy chain contains substitutions in at least 1, 2, 3, 4, 5, 6, 7, 8, 9, 10, 11, 12, 13, 14, or more usually 15, of the following positions: H3, H5, H13, H16, H19, H40, H41, H42, H44, H72, H77, H82A, H83, H84, or H108. These positions are substituted with the amino acid from the equivalent position of a human immunoglobulin having a more typical amino acid residue. Examples of appropriate amino acids to substitute are shown in FIGS. 1 and 2.

Other candidates for substitution are non-germline residues occurring in a framework region. A computer comparison of 3D6 with known germline sequences revealed that heavy chains showing the greatest degree of sequence identity include germline variable region sequences VH3-48, VH3-23, VH3-7, VH3-21 and VH3-11, with VH3-23 being more preferred. Alignment of Kabat ID 045919 with VH3-23 reveals that residues H74, H77 and/or H89 may be selected for substitution with corresponding germline residues (e.g., residues H74, H77 and/or H89 when comparing Kabat ID 045919 and VH3-23). Likewise, germline sequences having the greatest degree of identity to the 3D6 light chain include A1, A17, A18, A2 and A19, with A19 being most preferred. Residues not matching between a selected light chain acceptor framework and one of these germline sequences could be selected for substitution with the corresponding germline residue.

Table 1 summarizes the sequence analysis of the 3D6 VH and VL regions. Additional mouse and human structures that can be used for computer modeling of the 3D6 antibody and additional human antibodies are set forth as well as germline sequences that can be used in selecting amino acid substitutions. Rare mouse residues are also set forth in Table 1. Rare mouse residues are identified by comparing the donor VL and/or VH sequences with the sequences of other members of the subgroup to which the donor VL and/or VH sequences belong (according to Kabat) and identifying the residue positions which differ from the consensus. These donor specific differences may point to somatic mutations which enhance activity. Unusual or rare residues close to the binding site may possibly contact the antigen, making it desirable to retain the mouse residue. However, if the unusual mouse residue is not important for binding, use of the corresponding acceptor residue is preferred as the mouse residue may create immunogenic neoepitopes in the humanized antibody. In the situation where an unusual residue in the donor sequence is actually a common residues in the corresponding acceptor sequence, the preferred residue is clearly the acceptor residue.

Health (NIH)). Homology searching of the NCBI "Ig Germline Genes" database is provided by IgG BLAST™.

In a preferred embodiment, a humanized antibody of the present invention contains (i) a light chain comprising a variable domain comprising murine 3D6 VL CDRs and a human acceptor framework, the framework having at least one, preferably two, three or four residues selected from the group consisting of L1, L2, L36, and L46 substituted with the corresponding 3D6 residue and (ii) a heavy chain comprising 3D6 VH CDRs and a human acceptor framework, the framework having at least one, preferably two or three residues selected from the group consisting of H49, H93 and H94 substituted with the corresponding 3D6 residue, and, optionally, at least one, preferably two or three residues selected from the group consisting of H74, H77 and H89 is substituted with a corresponding human germline residue.

In a more preferred embodiment, a humanized antibody of the present invention contains (i) a light chain comprising a

TABLE 1

Summary of 3D6 V-region sequence

| Chain | Heavy | Light |
|---|---|---|
| Mouse subgroup (Kabat seq ID#) | IIID (002688) | II (005840-005844, 005851-005853, 005857, 005863) |
| Mouse homologs (Kabat/Genbank) | 002727/163.1'CL<br>002711/H35-C6'CL<br>002733/8-1-12-5-3-1(A2-1)'CL<br>002715/ASWA2'CL<br>020669/#14'CL | 005840/1210.7<br>005843/42.4b.12.2'CL<br>005842/BXW-14'CL<br>005841/42.7B3.2'CL<br>005851/36-60CRI- |
| Rare amino acids (% frequency of occurrence in class) | N40 (0.233%)<br>D42 (0.699%) | Y1(.035%)<br>I15 (3.3%)<br>D27 (0.867%)-CDR1<br>I78 (0.677%)<br>L85 (0.625%)<br>W89 (0.815%)-CDR3<br>K106A (0.295%) |
| Human Subgroup | III (000488-000491, 000503, 000624) | II (005046) |
| Chothia canonical CDR groupings [pdb example] | H1: class 1 [2fbj]<br>H2: class 3 [1igc] | L1: class 4 [1rmf]<br>L2: class1 [1lmk]<br>L3: class 1 [1tet] |
| Closest solved mouse structures | PDB ID: 1OPG Kodandapani et al., supra; (72% 2 Å) | PDB ID: 1CR9; Kanyo et al., supra; (94%, 2 Å)<br>PDB ID: 1NLD; Davies et al., Acta Crystallogr. D. Biol. Crystallog. 53: 186 (1997); (98%, 2.8 Å) |
| Closest solved human structures | 1VH (68%, nmr)<br>443560 (65%, IgG, λ myeloma, 1.8 Å)<br>KOL/2FB4H (60%, myeloma, 3 Å) | 1LVE (57%, LEN)<br>1B6DA (54%, B-J dimer, 2.8 Å);<br>1VGEL (54%, autoAb) |
| Germline query (Hu) results (top 4) | VH3-48 (4512283/BAA75032.1)<br>VH3-23 (4512287/BAA75046.1)<br>VH3-7 (4512300/BAA75056.1)<br>VH3-21 (4512287/BAA75047.1)<br>VH3-11 (4152300/BAA75053.1) | A1 (x63402)<br>A17 (x63403)<br>A18 (X63396)<br>A2 (m31952)<br>A19 (x63397) |

*heavy chain and light chain from the same antibody (O-81, Hirabayashi et al. NAR 20: 2601).

Kabat ID sequences referenced herein are publicly available, for example, from the Northwestern University Biomedical Engineering Department's Kabat Database of Sequences of Proteins of Immunological Interest. Three-dimensional structural information for antibodies described herein is publicly available, for example, from the Research Collaboratory for Structural Bioinformatics' Protein Data Bank (PDB). The PDB is freely accessible via the World Wide Web internet and is described by Berman et al (2000) *Nucleic Acids Research*, p235-242. Germline gene sequences referenced herein are publicly available, for example, from the National Center for Biotechnology Information (NCBI) database of sequences in collections of Igh, Ig kappa and Ig lambda germline V genes (as a division of the National Library of Medicine (NLM) at the National Institutes of variable domain comprising murine 3D6 VL CDRs and a human acceptor framework, the framework having residue 1 substituted with a tyr (Y), residue 2 substituted with a val (V), residue 36 substituted with a leu (L) and/or residue 46 substituted with an arg (R), and (ii) a heavy chain comprising 3D6 VH CDRs and a human acceptor framework, the framework having residue 49 substituted with an ala (A), residue 93 substituted with a val (V) and/or residue 94 substituted with an arg (R), and, optionally, having residue 74 substituted with a ser (S), residue 77 substituted with a thr (T) and/or residue 89 substituted with a val (V).

In a particularly preferred embodiment, a humanized antibody of the present invention has structural features, as described herein, and further has at least one (preferably two, three, four or all) of the following activities: (1) binds aggregated Aβ1-42 (e.g., as determined by ELISA); (2) binds Aβ in plaques (e.g., staining of AD and/or PDAPP plaques); (3) binds Aβ with two- to three-fold higher binding affinity as compared to chimeric 3D6 (e.g., 3D6 having murine variable region sequences and human constant region sequences); (4) mediates phagocytosis of Aβ (e.g., in an ex vivo phagocytosis assay, as described herein); and (5) crosses the blood-brain barrier (e.g., demonstrates short-term brain localization, for example, in a PDAPP animal model, as described herein).

In another embodiment, a humanized antibody of the present invention has structural features, as described herein, binds Aβ in a manner or with an affinity sufficient to elicit at least one of the following in vivo effects: (1) reduce Aβ plaque burden; (2) prevent plaque formation; (3) reduce levels of soluble Aβ; (4) reduce the neuritic pathology associated with an amyloidogenic disorder; (5) lessens or ameliorate at least one physiological symptom associated with an amyloidogenic disorder; and/or (6) improves cognitive function.

In another embodiment, a humanized antibody of the present invention has structural features, as described herein, and specifically binds to an epitope comprising residues 1-5 or 3-7 of Aβ.

The activities described above can be determined utilizing any one of a variety of assays described herein or in the art (e.g., binding assays, phagocytosis assays, etc.). Activities can be assayed either in vivo (e.g., using labeled assay components and/or imaging techniques) or in vitro (e.g., using samples or specimens derived from a subject). Activities can be assayed either directly or indirectly. In certain preferred embodiments, neurological endpoints (e.g., amyloid burden, neuritic burden, etc) are assayed. Such endpoints can be assayed in living subjects (e.g., in animal models of Alzheimer's disease or in human subjects, for example, undergoing immunotherapy) using non-invasive detection methodologies. Alternatively, such endpoints can be assayed in subjects post mortem. Assaying such endpoints in animal models and/or in human subjects post mortem is useful in assessing the effectiveness of various agents (e.g., humanized antibodies) to be utilized in similar immunotherapeutic applications. In other preferred embodiments, behavioral or neurological parameters can be assessed as indicators of the above neuropathological activities or endpoints.

3. Human Antibodies

Human antibodies against Aβ are provided by a variety of techniques described below. Some human antibodies are selected by competitive binding experiments, or otherwise, to have the same epitope specificity as a particular mouse antibody, such as one of the mouse monoclonals described herein. Human antibodies can also be screened for a particular epitope specificity by using only a fragment of Aβ as the immunogen, and/or by screening antibodies against a collection of deletion mutants of Aβ. Human antibodies preferably have human IgG1 isotype specificity.

a. Trioma Methodology

The basic approach and an exemplary cell fusion partner, SPAZ-4, for use in this approach have been described by Oestberg et al., Hybridoma 2:361 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells; two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes or bone marrow of a human donor. If antibodies against a specific antigen or epitope are desired, it is preferable to use that antigen or epitope thereof for immunization. Immunization can be either in vivo or in vitro. For in vivo immunization, B cells are typically isolated from a human immunized with Aβ, a fragment thereof, larger polypeptide containing Aβ or fragment, or an anti-idiotypic antibody to an antibody to Aβ. In some methods, B cells are isolated from the same patient who is ultimately to be administered antibody therapy. For in vitro immunization, B-lymphocytes are typically exposed to antigen for a period of 7-14 days in a media such as RPMI-1640 (see Engleman, supra) supplemented with 10% human plasma.

The immunized B-lymphocytes are fused to a xenogeneic hybrid cell such as SPAZ-4 by well-known methods. For example, the cells are treated with 40-50% polyethylene glycol of MW 1000-4000, at about 37 degrees C., for about 5-10 min. Cells are separated from the fusion mixture and propagated in media selective for the desired hybrids (e.g., HAT or AH). Clones secreting antibodies having the required binding specificity are identified by assaying the trioma culture medium for the ability to bind to Aβ or a fragment thereof. Triomas producing human antibodies having the desired specificity are subcloned by the limiting dilution technique and grown in vitro in culture medium. The trioma cell lines obtained are then tested for the ability to bind Aβ or a fragment thereof.

Although triomas are genetically stable they do not produce antibodies at very high levels. Expression levels can be increased by cloning antibody genes from the trioma into one or more expression vectors, and transforming the vector into standard mammalian, bacterial or yeast cell lines.

b. Transgenic Non-Human Mammals

Human antibodies against Aβ can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545, 806, Nature 148:1547 (1994), *Nature Biotechnology* 14:826 (1996), Kucherlapati, WO 91/10741 (1991) (each of which is incorporated by reference in its entirety for all purposes). Transgenic mice are particularly suitable. Anti-Aβ antibodies are obtained by immunizing a transgenic nonhuman mammal, such as described by Lonberg or Kucherlapati, supra, with Aβ or a fragment thereof. Monoclonal antibodies are prepared by, e.g., fusing B-cells from such mammals to suitable myeloma cell lines using conventional Kohler-Milstein technology. Human polyclonal antibodies can also be provided in the form of serum from humans immunized with an immunogenic agent. Optionally, such polyclonal antibodies can be concentrated by affinity purification using Aβ or other amyloid peptide as an affinity reagent.

c. Phage Display Methods

A further approach for obtaining human anti-Aβ antibodies is to screen a DNA library from human B cells according to the general protocol outlined by Huse et al., Science 246: 1275-1281 (1989). As described for trioma methodology, such B cells can be obtained from a human immunized with Aβ, fragments, longer polypeptides containing Aβ or fragments or anti-idiotypic antibodies. Optionally, such B cells are obtained from a patient who is ultimately to receive antibody treatment. Antibodies binding to Aβ or a fragment thereof are selected. Sequences encoding such antibodies (or a binding fragments) are then cloned and amplified. The protocol described by Huse is rendered more efficient in combination with phage-display technology. See, e.g., Dower et al., WO 91/17271, McCafferty et al., WO 92/01047, Herzig et al., U.S. Pat. No. 5,877,218, Winter et al., U.S. Pat. No. 5,871,907, Winter et al., U.S. Pat. No. 5,858,657, Holliger et al., U.S. Pat. No. 5,837,242, Johnson et al., U.S. Pat. No. 5,733,743 and Hoogenboom et al., U.S. Pat. No. 5,565,332 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to an Aβ peptide or fragment thereof.

In a variation of the phage-display method, human antibodies having the binding specificity of a selected murine antibody can be produced. See Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for Aβ (e.g., at least 108 and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for Aβ are selected. These phage display the variable regions of completely human anti-Aβ antibodies. These antibodies usually have the same or similar epitope specificity as the murine starting material.

4. Production of Variable Regions

Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

5. Selection of Constant Regions

The variable segments of antibodies produced as described supra (e.g., the heavy and light chain variable regions of chimeric, humanized, or human antibodies) are typically linked to at least a portion of an immunoglobulin constant region (Fc), typically that of a human immunoglobulin. Human constant region DNA sequences can be isolated in accordance with well known procedures from a variety of human cells, but preferably immortalized B cells (see Kabat et al., supra, and Liu et al., WO87/02671) (each of which is incorporated by reference in its entirety for all purposes). Ordinarily, the antibody will contain both light chain and heavy chain constant regions. The heavy chain constant region usually includes CHI, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. The choice of constant region depends, in part, whether antibody-dependent complement and/or cellular mediated toxicity is desired. For example, isotopes IgG1 and IgG3 have complement activity and isotypes IgG2 and IgG4 do not. When it is desired that the antibody (e.g., humanized antibody) exhibit cytotoxic activity, the constant domain is usually a complement fixing constant domain and the class is typically IgG1. When such cytotoxic activity is not desirable, the constant domain may be of the IgG2 class. Choice of isotype can also affect passage of antibody into the brain. Human isotype IgG1 is preferred. Light chain constant regions can be lambda or kappa. The humanized antibody may comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

6. Expression of Recombinant Antibodies

Chimeric, humanized and human antibodies are typically produced by recombinant expression. Nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

E. coli is one prokaryotic host particularly useful for cloning the polynucleotides (e.g., DNA sequences) of the present invention. Other microbial hosts suitable for use include bacilli, such as Bacillus subtilus, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. Saccharomyces is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas. Preferably, the cells are nonhuman. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., J. Immunol. 148:1149 (1992).

Alternatively, antibody-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., Molecular Cloning: A Laboratory Manual (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

7. Antibody Fragments

Also contemplated within the scope of the instant invention are antibody fragments. In one embodiment, fragments of non-human, chimeric and/or human antibodies are provided. In another embodiment, fragments of humanized antibodies are provided. Typically, these fragments exhibit specific binding to antigen with an affinity of at least $10^7$, and more typically $10^8$ or $10^9$ $M^{-1}$. Humanized antibody fragments include separate heavy chains, light chains Fab, Fab' F(ab')$_2$, Fabc, and Fv. Fragments are produced by recombinant DNA techniques, or by enzymatic or chemical separation of intact immunoglobulins.

8. Testing Antibodies for Therapeutic Efficacy in Animal Models

Groups of 7-9 month old PDAPP mice each are injected with 0.5 mg in PBS of polyclonal anti-Aβ or specific anti-Aβ monoclonal antibodies. All antibody preparations are purified to have low endotoxin levels. Monoclonals can be prepared against a fragment by injecting the fragment or longer form of Aβ into a mouse, preparing hybridomas and screening the hybridomas for an antibody that specifically binds to a desired fragment of Aβ without binding to other nonoverlapping fragments of Aβ.

Mice are injected intraperitoneally as needed over a 4 month period to maintain a circulating antibody concentration measured by ELISA titer of greater than 1/1000 defined by ELISA to Aβ42 or other immunogen. Titers are monitored and mice are euthanized at the end of 6 months of injections. Histochemistry, Aβ levels and toxicology are performed post mortem. Ten mice are used per group.

9. Screening Antibodies for Clearing Activity

The invention also provides methods of screening an antibody for activity in clearing an amyloid deposit or any other antigen, or associated biological entity, for which clearing activity is desired. To screen for activity against an amyloid deposit, a tissue sample from a brain of a patient with Alzheimer's disease or an animal model having characteristic Alzheimer's pathology is contacted with phagocytic cells bearing an Fc receptor, such as microglial cells, and the antibody under test in a medium in vitro. The phagocytic cells can be a primary culture or a cell line, such as BV-2, C8-B4, or THP-1. In some methods, the components are combined on a microscope slide to facilitate microscopic monitoring. In some methods, multiple reactions are performed in parallel in the wells of a microtiter dish. In such a format, a separate miniature microscope slide can be mounted in the separate wells, or a nonmicroscopic detection format, such as ELISA detection of Aβ can be used. Preferably, a series of measurements is made of the amount of amyloid deposit in the in vitro reaction mixture, starting from a baseline value before the reaction has proceeded, and one or more test values during the reaction. The antigen can be detected by staining, for example, with a fluorescently labeled antibody to Aβ or other component of amyloid plaques. The antibody used for staining may or may not be the same as the antibody being tested for clearing activity. A reduction relative to baseline during the reaction of the amyloid deposits indicates that the antibody under test has clearing activity. Such antibodies are likely to be useful in preventing or treating Alzheimer's and other amyloidogenic diseases.

Analogous methods can be used to screen antibodies for activity in clearing other types of biological entities. The assay can be used to detect clearing activity against virtually any kind of biological entity. Typically, the biological entity has some role in human or animal disease. The biological entity can be provided as a tissue sample or in isolated form. If provided as a tissue sample, the tissue sample is preferably unfixed to allow ready access to components of the tissue sample and to avoid perturbing the conformation of the components incidental to fixing. Examples of tissue samples that can be tested in this assay include cancerous tissue, precancerous tissue, tissue containing benign growths such as warts or moles, tissue infected with pathogenic microorganisms, tissue infiltrated with inflammatory cells, tissue bearing pathological matrices between cells (e.g., fibrinous pericarditis), tissue bearing aberrant antigens, and scar tissue. Examples of isolated biological entities that can be used include Aβ, viral antigens or viruses, proteoglycans, antigens of other pathogenic microorganisms, tumor antigens, and adhesion molecules. Such antigens can be obtained from natural sources, recombinant expression or chemical synthesis, among other means. The tissue sample or isolated biological entity is contacted with phagocytic cells bearing Fc receptors, such as monocytes or microglial cells, and an antibody to be tested in a medium. The antibody can be directed to the biological entity under test or to an antigen associated with the entity. In the latter situation, the object is to test whether the biological entity is vicariously phagocytosed with the antigen. Usually, although not necessarily, the antibody and biological entity (sometimes with an associated antigen), are contacted with each other before adding the phagocytic cells. The concentration of the biological entity and/or the associated antigen remaining in the medium, if present, is then monitored. A reduction in the amount or concentration of antigen or the associated biological entity in the medium indicates the antibody has a clearing response against the antigen and/or associated biological entity in conjunction with the phagocytic cells (see, e.g., Example IV).

10. Chimeric/Humanized Antibodies Having Altered Effector Function

For the above-described antibodies of the invention comprising a constant region (Fc region), it may also be desirable to alter the effector function of the molecule. Generally, the effector function of an antibody resides in the constant or Fc region of the molecule which can mediate binding to various effector molecules, e.g., complement proteins or Fc receptors. The binding of complement to the Fc region is important, for example, in the opsonization and lysis of cell pathogens and the activation of inflammatory responses. The binding of antibody to Fc receptors, for example, on the surface of effector cells can trigger a number of important and diverse biological responses including, for example, engulfment and destruction of antibody-coated pathogens or particles, clearance of immune complexes, lysis of antibody-coated target cells by killer cells (i.e., antibody-dependent cell-mediated cytotoxicity, or ADCC), release of inflammatory mediators, placental transfer of antibodies, and control of immunoglobulin production.

Accordingly, depending on a particular therapeutic or diagnostic application, the above-mentioned immune functions, or only selected immune functions, may be desirable. By altering the Fc region of the antibody, various aspects of the effector function of the molecule, including enhancing or suppressing various reactions of the immune system, with beneficial effects in diagnosis and therapy, are achieved.

The antibodies of the invention can be produced which react only with certain types of Fc receptors, for example, the antibodies of the invention can be modified to bind to only certain Fc receptors, or if desired, lack Fc receptor binding entirely, by deletion or alteration of the Fc receptor binding site located in the Fc region of the antibody. Other desirable alterations of the Fc region of an antibody of the invention are cataloged below. Typically the Kabat numbering system is used to indicate which amino acid residue(s) of the Fc region (e.g., of an IgG antibody) are altered (e.g., by amino acid substitution) in order to achieve a desired change in effector function. The numbering system is also employed to compare antibodies across species such that a desired effector function observed in, for example, a mouse antibody, can then be systematically engineered into a human, humanized, or chimeric antibody of the invention.

For example, it has been observed that antibodies (e.g., IgG antibodies) can be grouped into those found to exhibit tight, intermediate, or weak binding to an Fc receptor (e.g., an Fc receptor on human monocytes (FcγRI)). By comparison of the amino-acid sequences in these different affinity groups, a monocyte-binding site in the hinge-link region (Leu234-Ser239) has been identified. Moreover, the human FcγRI receptor binds human IgG1 and mouse IgG2a as a monomer, but the binding of mouse IgG2b is 100-fold weaker. A comparison of the sequence of these proteins in the hinge-link region shows that the sequence 234 to 238, i.e., Leu-Leu-Gly-Gly-Pro in the strong binders becomes Leu-Glu-Gly-Gly-Pro in mouse gamma 2b, i.e., weak binders. Accordingly, a corresponding change in a human antibody hinge sequence can be made if reduced FcγI receptor binding is desired. It is understood that other alterations can be made to achieve the same or similar results. For example, the affinity of FcγRI binding can be altered by replacing the specified residue with a residue having an inappropriate functional group on its sidechain, or by introducing a charged functional group (e.g., Glu or Asp) or for example an aromatic non-polar residue (e.g., Phe, Tyr, or Trp).

These changes can be equally applied to the murine, human, and rat systems given the sequence homology between the different immunoglobulins. It has been shown that for human IgG3, which binds to the human FcγRI receptor, changing Leu 235 to Glu destroys the interaction of the mutant for the receptor. The binding site for this receptor can thus be switched on or switched off by making the appropriate mutation.

Mutations on adjacent or close sites in the hinge link region (e.g., replacing residues 234, 236 or 237 by Ala) indicate that alterations in residues 234, 235, 236, and 237 at least affect affinity for the FcγRI receptor. Accordingly, the antibodies of the invention can also have an altered Fc region with altered binding affinity for FcγRI as compared with the unmodified antibody. Such an antibody conveniently has a modification at amino acid residue 234, 235, 236, or 237.

Affinity for other Fc receptors can be altered by a similar approach, for controlling the immune response in different ways.

As a further example, the lytic properties of IgG antibodies following binding of the C1 component of complement can be altered.

The first component of the complement system, C1, comprises three proteins known as C1q, C1r and C1s which bind tightly together. It has been shown that C1q is responsible for binding of the three protein complex to an antibody.

Accordingly, the C1q binding activity of an antibody can be altered by providing an antibody with an altered CH 2 domain in which at least one of the amino acid residues 318, 320, and 322 of the heavy chain has been changed to a residue having a different side chain. The numbering of the residues in the heavy chain is that of the EU index (see Kabat et al., supra). Other suitable alterations for altering, e.g., reducing or abolishing specific C1q-binding to an antibody include changing any one of residues 318 (Glu), 320 (Lys) and 322 (Lys), to Ala.

Moreover, by making mutations at these residues, it has been shown that C1q binding is retained as long as residue 318 has a hydrogen-bonding side chain and residues 320 and 322 both have a positively charged side chain.

C1q binding activity can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish Clq binding. In addition, it is also be possible to use such polar non-ionic residues as Ser, Thr, Cys, and Met in place of residues 320 and 322, but not 318, in order to abolish Clq binding activity.

It is also noted that the side chains on ionic or non-ionic polar residues will be able to form hydrogen bonds in a similar manner to the bonds formed by the Glu residue. Therefore, replacement of the 318 (Glu) residue by a polar residue may modify but not abolish Clq binding activity.

It is also known that replacing residue 297 (Asn) with Ala results in removal of lytic activity while only slightly reducing (about three fold weaker) affinity for Clq. This alteration destroys the glycosylation site and the presence of carbohydrate that is required for complement activation. Any other substitution at this site will also destroy the glycosylation site.

The invention also provides an antibody having an altered effector function wherein the antibody has a modified hinge region. The modified hinge region may comprise a complete hinge region derived from an antibody of different antibody class or subclass from that of the CH1 domain. For example, the constant domain (CH1) of a class IgG antibody can be attached to a hinge region of a class IgG4 antibody. Alternatively, the new hinge region may comprise part of a natural hinge or a repeating unit in which each unit in the repeat is derived from a natural hinge region. In one example, the natural hinge region is altered by converting one or more cysteine residues into a neutral residue, such as alanine, or by converting suitably placed residues into cysteine residues. Such alterations are carried out using art recognized protein chemistry and, preferably, genetic engineering techniques, as described herein.

In one embodiment of the invention, the number of cysteine residues in the hinge region of the antibody is reduced, for example, to one cysteine residue. This modification has the advantage of facilitating the assembly of the antibody, for example, bispecific antibody molecules and antibody molecules wherein the Fc portion has been replaced by an effector or reporter molecule, since it is only necessary to form a single disulfide bond. This modification also provides a specific target for attaching the hinge region either to another hinge region or to an effector or reporter molecule, either directly or indirectly, for example, by chemical means.

Conversely, the number of cysteine residues in the hinge region of the antibody is increased, for example, at least one more than the number of normally occurring cysteine residues. Increasing the number of cysteine residues can be used to stabilize the interactions between adjacent hinges. Another advantage of this modification is that it facilitates the use of cysteine thiol groups for attaching effector or reporter molecules to the altered antibody, for example, a radiolabel.

Accordingly, the invention provides for an exchange of hinge regions between antibody classes, in particular, IgG classes, and/or an increase or decrease in the number of cysteine residues in the hinge region in order to achieve an altered effector function (see for example U.S. Pat. No. 5,677,425 which is expressly incorporated herein). A determination of altered antibody effector function is made using the assays described herein or other art recognized techniques.

Importantly, the resultant antibody can be subjected to one or more assays to evaluate any change in biological activity compared to the starting antibody. For example, the ability of the antibody with an altered Fc region to bind complement or Fc receptors can be assessed using the assays disclosed herein as well as any art recognized assay.

Production of the antibodies of the invention is carried out by any suitable technique including techniques described herein as well as techniques known to those skilled in the art. For example an appropriate protein sequence, e.g. forming part of or all of a relevant constant domain, e.g., Fc region, i.e., CH2, and/or CH3 domain(s), of an antibody, and include appropriately altered residue(s) can be synthesized and then chemically joined into the appropriate place in an antibody molecule.

Preferably, genetic engineering techniques are used for producing an altered antibody. Preferred techniques include, for example, preparing suitable primers for use in polymerase chain reaction (PCR) such that a DNA sequence which encodes at least part of an IgG heavy chain, e.g., an Fc or constant region (e.g., CH2, and/or CH3) is altered, at one or more residues. The segment can then be operably linked to the remaining portion of the antibody, e.g., the variable region of the antibody and required regulatory elements for expression in a cell.

The present invention also includes vectors used to transform the cell line, vectors used in producing the transforming vectors, cell lines transformed with the transforming vectors, cell lines transformed with preparative vectors, and methods for their production.

Preferably, the cell line which is transformed to produce the antibody with an altered Fc region (i.e., of altered effector function) is an immortalized mammalian cell line (e.g., CHO cell).

Although the cell line used to produce the antibody with an altered Fc region is preferably a mammalian cell line, any other suitable cell line, such as a bacterial cell line or a yeast cell line, may alternatively be used.

B. Nucleic Acid Encoding Immunologic and Therapeutic Agents

Immune responses against amyloid deposits can also be induced by administration of nucleic acids encoding antibodies and their component chains used for passive immunization. Such nucleic acids can be DNA or RNA. A nucleic acid segment encoding an immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see e.g., Lawrie and Tumin, *Cur. Opin. Genet. Develop.* 3:102-109 (1993)); adenoviral vectors (see, e.g., Bett et al., *J. Virol.* 67:5911 (1993)); adeno-associated virus vectors (see, e.g., Zhou et al., *J. Exp. Med.* 179:1867 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70:508 (1996)), Venezuelan equine encephalitis virus (see Johnston et al., U.S. Pat. No. 5,643,576) and rhabdoviruses, such as vesicular stomatitis virus (see Rose, WO 96/34625) and papillomaviruses (Ohe et al., *Human Gene Therapy* 6:325 (1995); Woo et al., WO 94/12629 and Xiao & Brandsma, *Nucleic Acids. Res.* 24, 2630-2622 (1996)).

DNA encoding an immunogen, or a vector containing the same, can be packaged into liposomes. Suitable lipids and related analogs are described by Eppstein et al., U.S. Pat. No. 5,208,036, Felgner et al., U.S. Pat. No. 5,264,618, Rose, U.S. Pat. No. 5,279,833, and Epand et al., U.S. Pat. No. 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., *J. Micro Encap.* (1996).

Gene therapy vectors or naked polypeptides (e.g., DNA) can be delivered in vivo by administration to an individual patient, typically by systemic administration (e.g., intravenous, intraperitoneal, nasal, gastric, intradermal, intramuscular, subdermal, or intracranial infusion) or topical application (see e.g., Anderson et al., U.S. Pat. No. 5,399,346). The term "naked polynucleotide" refers to a polynucleotide not complexed with colloidal materials. Naked polynucleotides are sometimes cloned in a plasmid vector. Such vectors can further include facilitating agents such as bupivacaine (Attardo et al., U.S. Pat. No. 5,593,970). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see Howell et al., WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

II. Prophylactic and Therapeutic Methods

The present invention is directed inter alia to treatment of Alzheimer's and other amyloidogenic diseases by administration of therapeutic immunological reagents (e.g., humanized immunoglobulins) to specific epitopes within Aβ to a patient under conditions that generate a beneficial therapeutic response in a patient (e.g., induction of phagocytosis of Aβ, reduction of plaque burden, inhibition of plaque formation, reduction of neuritic dystrophy, improving cognitive function, and/or reversing, treating or preventing cognitive decline) in the patient, for example, for the prevention or treatment of an amyloidogenic disease. The invention is also directed to use of the disclosed immunological reagents (e.g., humanized immunoglobulins) in the manufacture of a medicament for the treatment or prevention of an amyloidogenic disease.

The term "treatment" as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In one aspect, the invention provides methods of preventing or treating a disease associated with amyloid deposits of Aβ in the brain of a patient. Such diseases include Alzheimer's disease, Down's syndrome and cognitive impairment. The latter can occur with or without other characteristics of an amyloidogenic disease. Some methods of the invention entail administering an effective dosage of an antibody that specifically binds to a component of an amyloid deposit to the patient. Such methods are particularly useful for preventing or treating Alzheimer's disease in human patients. Exemplary methods entail administering an effective dosage of an antibody that binds to Aβ. Preferred methods entail administering an effective dosage of an antibody that specifically binds to an epitope within residues 1-10 of Aβ, for example, antibodies that specifically bind to an epitope within residues 1-3 of Aβ, antibodies that specifically bind to an epitope within residues 1-4 of Aβ, antibodies that specifically bind to an epitope within residues 1-5 of Aβ, antibodies that specifically bind to an epitope within residues 1-6 of Aβ, antibodies that specifically bind to an epitope within residues 1-7 of Aβ, or antibodies that specifically bind to an epitope within residues 3-7 of Aβ. In yet another aspect, the invention features administering antibodies that bind to an epitope comprising a free N-terminal residue of Aβ. In yet another aspect, the invention features administering antibodies that bind to an epitope within residues of 1-10 of Aβ wherein residue 1 and/or residue 7 of Aβ is aspartic acid. In yet another aspect, the invention features administering antibodies that specifically bind to Aβ peptide without binding to full-length amyloid precursor protein (APP). In yet another aspect, the isotype of the antibody is human IgG1.

In yet another aspect, the invention features administering antibodies that bind to an amyloid deposit in the patient and induce a clearing response against the amyloid deposit. For example, such a clearing response can be effected by Fc receptor mediated phagocytosis.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

The methods can be used on both asymptomatic patients and those currently showing symptoms of disease. The antibodies used in such methods can be human, humanized, chimeric or nonhuman antibodies, or fragments thereof (e.g., antigen binding fragments) and can be monoclonal or polyclonal, as described herein. In yet another aspect, the invention features administering antibodies prepared from a human immunized with Aβ peptide, which human can be the patient to be treated with antibody.

In another aspect, the invention features administering an antibody with a pharmaceutical carrier as a pharmaceutical composition. Alternatively, the antibody can be administered to a patient by administering a polynucleotide encoding at least one antibody chain. The polynucleotide is expressed to produce the antibody chain in the patient. Optionally, the polynucleotide encodes heavy and light chains of the antibody. The polynucleotide is expressed to produce the heavy and light chains in the patient. In exemplary embodiments, the patient is monitored for level of administered antibody in the blood of the patient.

The invention thus fulfills a longstanding need for therapeutic regimes for preventing or ameliorating the neuropathology and, in some patients, the cognitive impairment associated with Alzheimer's disease.

A. Patients Amenable to Treatment

Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are especially useful for individuals who have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

B. Treatment Regimes and Dosages

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

In some methods, administration of agent reduces or eliminates myocognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. The term "immune response" or "immunological response" includes the development of a humoral (antibody mediated) and/or a cellular (mediated by antigen-specific T cells or their secretion products) response directed against an antigen in a recipient subject. Such a response can be an active response, i.e., induced by administration of immunogen, or a passive response, i.e., induced by administration of immunoglobulin or antibody or primed T-cells.

An "immunogenic agent" or "immunogen" is capable of inducing an immunological response against itself on administration to a mammal, optionally in conjunction with an adjuvant. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages need to be titrated to optimize safety and efficacy.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg, preferably at least 1 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. Intervals can also be irregular as indicated by measuring blood levels of antibody to Aβ in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding antibodies range from about 10 ng to 1 g, 100 ng to 100 mg, 1 μg to 10 mg, or 30-300 μg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treatment of amyloidogenic disease. In the case of Alzheimer's and Down's syndrome, in which amyloid deposits occur in the brain, agents of the invention can also be administered in conjunction with other agents that increase passage of the agents of the invention across the blood-brain barrier.

C. Pharmaceutical Compositions

Agents of the invention are often administered as pharmaceutical compositions comprising an active therapeutic agent, i.e., and a variety of other pharmaceutically acceptable components. See Remington's Pharmaceutical Science (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation, which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)). The agents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25:3521 (1995); Cevc et al., *Biochem. Biophys. Acta* 1368:201-15 (1998)).

III. Monitoring the Course of Treatment

The invention provides methods of monitoring treatment in a patient suffering from or susceptible to Alzheimer's, i.e., for monitoring a course of treatment being administered to a patient. The methods can be used to monitor both therapeutic treatment on symptomatic patients and prophylactic treatment on asymptomatic patients. In particular, the methods are useful for monitoring passive immunization (e.g., measuring level of administered antibody).

Some methods entail determining a baseline value, for example, of an antibody level or profile in a patient, before administering a dosage of agent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the agent has achieved a desired response). If the value for immune response does not change significantly, or decreases, a negative treatment outcome is indicated.

In other methods, a control value (i.e., a mean and standard deviation) of level or profile is determined for a control population. Typically the individuals in the control population have not received prior treatment. Measured values of the level or profile in a patient after administering a therapeutic agent are then compared with the control value. A significant increase relative to the control value (e.g., greater than one standard deviation from the mean) signals a positive or sufficient treatment outcome. A lack of significant increase or a decrease signals a negative or insufficient treatment outcome. Administration of agent is generally continued while the level is increasing relative to the control value. As before, attainment of a plateau relative to control values is an indicator that the administration of treatment can be discontinued or reduced in dosage and/or frequency.

In other methods, a control value of the level or profile (e.g., a mean and standard deviation) is determined from a control population of individuals who have undergone treatment with a therapeutic agent and whose levels or profiles have plateaued in response to treatment. Measured values of levels or profiles in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment may be indicated.

In other methods, a patient who is not presently receiving treatment but has undergone a previous course of treatment is monitored for antibody levels or profiles to determine whether a resumption of treatment is required. The measured level or profile in the patient can be compared with a value previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucous fluid or cerebrospinal fluid from the patient. The sample is analyzed, for example, for levels or profiles of antibodies to Aβ peptide, e.g., levels or profiles of humanized antibodies. ELISA methods of detecting antibodies specific to Aβ are described in the Examples section. In some methods, the level or profile of an administered antibody is determined using a clearing assay, for example, in an in vitro phagocytosis assay, as described herein. In such methods, a tissue sample from a patient being tested is contacted with amyloid deposits (e.g., from a PDAPP mouse) and phagocytic cells bearing Fc receptors. Subsequent clearing of the amyloid deposit is then monitored. The existence and extent of clearing response provides an indication of the existence and level of antibodies effective to clear Aβ in the tissue sample of the patient under test.

The antibody profile following passive immunization typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to Aβ in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

Additional methods include monitoring, over the course of treatment, any art-recognized physiologic symptom (e.g., physical or mental symptom) routinely relied on by researchers or physicians to diagnose or monitor amyloidogenic diseases (e.g., Alzheimer's disease). For example, one can monitor cognitive impairment. The latter is a symptom of Alzheimer's disease and Down's syndrome but can also occur without other characteristics of either of these diseases. For example, cognitive impairment can be monitored by determining a patient's score on the Mini-Mental State Exam in accordance with convention throughout the course of treatment.

C. Kits

The invention further provides kits for performing the monitoring methods described above. Typically, such kits contain an agent that specifically binds to antibodies to Aβ. The kit can also include a label. For detection of antibodies to Aβ, the label is typically in the form of labeled anti-idiotypic antibodies. For detection of antibodies, the agent can be supplied prebound to a solid phase, such as to the wells of a microtiter dish. Kits also typically contain labeling providing directions for use of the kit. The labeling may also include a chart or other correspondence regime correlating levels of measured label with levels of antibodies to Aβ. The term labeling refers to any written or recorded material that is attached to, or otherwise accompanies a kit at any time during its manufacture, transport, sale or use. For example, the term labeling encompasses advertising leaflets and brochures, packaging materials, instructions, audio or videocassettes, computer discs, as well as writing imprinted directly on kits.

The invention also provides diagnostic kits, for example, research, detection and/or diagnostic kits (e.g., for performing in vivo imaging). Such kits typically contain an antibody for binding to an epitope of Aβ, preferably within residues 1-10. Preferably, the antibody is labeled or a secondary labeling reagent is included in the kit. Preferably, the kit is labeled with instructions for performing the intended application, for example, for performing an in vivo imaging assay. Exemplary antibodies are those described herein.

D. In Vivo Imaging

The invention provides methods of in vivo imaging amyloid deposits in a patient. Such methods are useful to diagnose or confirm diagnosis of Alzheimer's disease, or susceptibility thereto. For example, the methods can be used on a patient presenting with symptoms of dementia. If the patient has abnormal amyloid deposits, then the patient is likely suffering from Alzheimer's disease. The methods can also be used on asymptomatic patients. Presence of abnormal deposits of amyloid indicates susceptibility to future symptomatic disease. The methods are also useful for monitoring disease progression and/or response to treatment in patients who have been previously diagnosed with Alzheimer's disease.

The methods work by administering a reagent, such as antibody that binds to Aβ, to the patient and then detecting the agent after it has bound. Preferred antibodies bind to Aβ deposits in a patient without binding to full length APP polypeptide. Antibodies binding to an epitope of Aβ within amino acids 1-10 are particularly preferred. In some methods, the antibody binds to an epitope within amino acids 7-10 of Aβ. Such antibodies typically bind without inducing a substantial clearing response. In other methods, the antibody binds to an epitope within amino acids 1-7 of Aβ. Such antibodies typically bind and induce a clearing response to Aβ. However, the clearing response can be avoided by using antibody fragments lacking a full-length constant region, such as Fabs. In some methods, the same antibody can serve as both a treatment and diagnostic reagent. In general, antibodies binding to epitopes C-terminal to residue 10 of Aβ do not show as strong a signal as antibodies binding to epitopes within residues 1-10, presumably because the C-terminal epitopes are inaccessible in amyloid deposits. Accordingly, such antibodies are less preferred.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for Aβ is unlabelled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci, to corresponding baseline values. The base line values can represent the mean levels in a population of undiseased individuals. Baseline values can also represent previous levels determined in the same patient. For example, baseline values can be determined in a patient before beginning treatment, and measured values thereafter compared with the baseline values. A decrease in values relative to baseline signals a positive response to treatment.

The present invention will be more fully described by the following non-limiting examples.

EXAMPLES

Example I

Therapeutic Efficacy of Anti-AD Antibodies: mAb 2H3, mAb 10D5, mAb 266, mAb 21F12 and pAb Aβ1-42

This example tests the capacity of various monoclonal and polyclonal antibodies to Aβ to inhibit accumulation of Aβ in the brain of heterozygotic transgenic mice.

A. Study Design

Sixty male and female, heterozygous PDAPP transgenic mice, 8.5 to 10.5 months of age were obtained from Charles River Laboratory. The mice were sorted into six groups to be treated with various antibodies directed to Aβ. Animals were distributed to match the gender, age, parentage and source of the animals within the groups as closely as possible. Table 2 depicts the Experimental design.

TABLE 2

Experimental Design

| Treatment Group | N[a] | Treatment Antibody | Antibody Specificity | Antibody Isotype |
|---|---|---|---|---|
| 1 | 9 | none (PBS alone) | NA[b] | NA |
| 2 | 10 | Polyclonal | Aβ1-42 | mixed |
| 3 | 0 | mAb[d] 2H3 | Aβ1-12 | IgG1 |
| 4 | 8 | mAb 10D5 | Aβ3-7 | IgG1 |
| 5 | 6 | mAb 266 | Aβ13-28 | IgG1 |
| 6 | 8 | mAb 21F12 | Aβ33-42 | IgG2a |

[a]Number of mice in group at termination of the experiment. All groups started with 10 animals per group.
[b]NA: not applicable
[c]mouse polyclonal: anti-aggregated Aβ42
[d]mAb: monoclonal antibody As shown in Table 2, the antibodies included four murine Aβ-specific monoclonal antibodies, 2H3 (directed to Aβ residues 1-12), 10D5 (directed to Aβ residues 3-7), 266 (directed to Aβ residues 13-28 and binds to soluble but not to aggregated AN1792), 21F12 (directed to Aβ residues 33-42). A fifth group was treated with an Aβ-specific polyclonal antibody fraction (raised by immunization with aggregated AN1792). The negative control group received the diluent, PBS, alone without antibody.

B. Monitoring the Course of Treatment

The monoclonal antibodies were injected at a dose of about 10 mg/kg (assuming that the mice weighed 50 g). Antibody titers were monitored over the 28 weeks of treatment. Injections were administered intraperitoneally every seven days on average to maintain anti-Aβ titers above 1000. Although lower titers were measured for mAb 266 since it does not bind well to the aggregated AN1792 used as the capture antigen in the assay, the same dosing schedule was maintained for this group. The group receiving monoclonal antibody 2H3 was discontinued within the first three weeks since the antibody was cleared too rapidly in vivo.

For determination of antibody titers, a subset of three randomly chosen mice from each group were bled just prior to each intraperitoneal inoculation, for a total of 30 bleeds. Antibody titers were measured as Aβ 1-42-binding antibody using a sandwich ELISA with plastic multi-well plates coated with Aβ1-42 as described in detail in the General Materials and Methods. Mean titers for each bleed are set forth in Table 3 for the polyclonal antibody and the monoclonals 10D5 and 21F12.

TABLE 3

| weeks 21F12 | 21F12 | weeks 10D5 | 10D5 | weeks poly | poly |
|---|---|---|---|---|---|
| 0.15 | 500 | 0.15 | 3000 | 0.15 | 1600 |
| 0.5 | 800 | 0.5 | 14000 | 0.5 | 4000 |
| 1 | 2500 | 1 | 5000 | 1 | 4500 |
| 1.5 | 1800 | 1.1 | 5000 | 1.5 | 3000 |
| 2 | 1400 | 1.2 | 1300 | 2 | 1300 |
| 3 | 6000 | 2 | 3000 | 3 | 1600 |
| 3.5 | 550 | 3 | 4000 | 3.5 | 650 |
| 4 | 1600 | 3.5 | 500 | 4 | 1300 |
| 5 | 925 | 4 | 2400 | 5 | 450 |
| 6 | 3300 | 5 | 925 | 6 | 2100 |
| 7 | 4000 | 6 | 1700 | 7 | 1300 |
| 8 | 1400 | 7 | 1600 | 8 | 2300 |
| 9 | 1900 | 8 | 4000 | 9 | 700 |
| 10 | 1700 | 9 | 1800 | 10 | 600 |
| 11 | 1600 | 10 | 1800 | 11 | 600 |
| 12 | 1000 | 11 | 2300 | 12 | 1000 |
| 13 | 1500 | 12 | 2100 | 13 | 900 |
| 14 | 1300 | 13 | 2800 | 14 | 1900 |
| 15 | 1000 | 14 | 1900 | 15 | 1200 |
| 16 | 1700 | 15 | 2700 | 16 | 700 |
| 17 | 1700 | 16 | 1300 | 17 | 2100 |
| 18 | 5000 | 17 | 2200 | 18 | 1800 |
| 19 | 900 | 18 | 2200 | 19 | 1800 |
| 20 | 300 | 19 | 2500 | 20 | 1200 |
| 22 | 1750 | 20 | 980 | 22 | 1000 |
| 23 | 1600 | 22 | 2000 | 23 | 1200 |
| 24 | 1000 | 23 | 1000 | 24 | 675 |
| 25 | 1100 | 24 | 850 | 25 | 850 |
| 26 | 2250 | 25 | 600 | 26 | 1600 |
| 27 | 1400 | 26 | 1100 | 27 | 1900 |
| 28 | | 27 | 1450 | 28 | |
| | | 28 | | | |

Titers averaged about 1000 over this time period for the polyclonal antibody preparation and were slightly above this level for the 10D5- and 21F12-treated animals.

Treatment was continued over a six-month period for a total of 196 days. Animals were euthanized one week after the final dose.

C. Aβ and APP Levels in the Brain:

Following about six months of treatment with the various anti-Aβ antibody preparations, brains were removed from the animals following saline perfusion. One hemisphere was prepared for immunohistochemical analysis and the second was used for the quantitation of Aβ and APP levels. To measure the concentrations of various forms of beta amyloid peptide and amyloid precursor protein (APP), the hemisphere was dissected and homogenates of the hippocampal, cortical, and cerebellar regions were prepared in 5M guanidine. These were serially diluted and the level of amyloid peptide or APP was quantitated by comparison to a series of dilutions of standards of Aβ peptide or APP of known concentrations in an ELISA format.

The levels of total Aβ and of Aβ1-42 measured by ELISA in homogenates of the cortex, and the hippocampus and the level of total Aβ in the cerebellum are shown in Tables 4, 5, and 6, respectively. The median concentration of total Aβ for the control group, inoculated with PBS, was 3.6-fold higher in the hippocampus than in the cortex (median of 63,389 ng/g hippocampal tissue compared to 17,818 ng/g for the cortex). The median level in the cerebellum of the control group (30.6 ng/g tissue) was more than 2.000-fold lower than in the hippocampus. These levels are similar to those previously reported for heterozygous PDAPP transgenic mice of this age (Johnson-Wood et al., supra).

For the cortex, one treatment group had a median Aβ level, measured as Aβ1-42, which differed significantly from that of the control group (p<0.05), those animals receiving the polyclonal anti-Aβ antibody as shown in Table 4. The median level of Aβ1-42 was reduced by 65%, compared to the control for this treatment group. The median levels of Aβ1-42 were also significantly reduced by 55% compared to the control in one additional treatment group, those animals dosed with the mAb 10D5 (p=0.0433).

TABLE 4

CORTEX

| | | Medians | | | | | Means | |
| | | Total Aβ | | | Aβ42 | | | |
| Treatment Group | N[a] | ELISA value[b] | P value[c] | % Change | ELISA value | P value | % Change | Total Aβ ELISA value | Aβ42 ELISA value |
|---|---|---|---|---|---|---|---|---|---|
| PBS | 9 | 17818 | NA[d] | NA | 13802 | NA | NA | 16150 +/− 7456[e] | 12621 +/− 5738 |
| Polyclonal anti-Aβ42 | 10 | 6160 | 0.0055 | −65 | 4892 | 0.0071 | −65 | 5912 +/− 4492 | 4454 +/− 3347 |
| mAb 10D5 | 8 | 7915 | 0.1019 | −56 | 6214 | 0.0433 | −55 | 9695 +/− 6929 | 6943 +/− 3351 |
| mAb 266 | 6 | 9144 | 0.1255 | −49 | 8481 | 0.1255 | −39 | 9204 +/− 9293 | 7489 +/− 6921 |
| mAb 21F12 | 8 | 15158 | 0.2898 | −15 | 13578 | 0.7003 | −2 | 12481 +/− 7082 | 11005 +/− 6324 |

Footnotes:
[a]Number of animals per group at the end of the experiment
[b]ng/g tissue
[c]Mann Whitney analysis
[d]NA: not applicable
[e]Standard Deviation In the hippocampus, the median percent reduction of total Aβ associated with treatment with polyclonal anti-Aβ antibody (50%, p=0.0055) was not as great as that observed in the cortex (65%) (Table 5). However, the absolute magnitude of the reduction was almost 3-fold greater in the hippocampus than in the cortex, a net reduction of 31,683 ng/g tissue in the hippocampus versus 11,658 ng/g tissue in the cortex. When measured as the level of the more amyloidogenic form of Aβ, Aβ1-42, rather than as total Aβ, the reduction achieved with the polyclonal antibody was significant (p=0.0025). The median levels in groups treated with the mAbs 10D5 and 266 were reduced by 33% and 21%, respectively.

indicate that the immunizations with Aβ antibodies deplete Aβ without depleting APP.

In summary, Aβ levels were significantly reduced in the cortex, hippocampus and cerebellum in animals treated with the polyclonal antibody raised against AN1792. To a lesser extent monoclonal antibodies to the amino terminal region of Aβ 1-42, specifically amino acids 1-16 and 13-28 also showed significant treatment effects.

D. Histochemical Analyses:

The morphology of Aβ-immunoreactive plaques in subsets of brains from mice in the PBS, polyclonal Aβ42, 21F12, 266

TABLE 5

HIPPOCAMPUS

| | | Medians | | | | | Means | |
| --- | --- | --- | --- | --- | --- | --- | --- | --- |
| | | Total Aβ | | | Aβ42 | | | |
| Treatment Group | N[a] | ELISA value[b] | P value[c] | % Change | ELISA value | P value | % Change | Total Aβ ELISA value | Aβ42 ELISA value |
| PBS | 9 | 63389 | NA[d] | NA | 54429 | NA | NA | 58351 +/− 13308[e] | 52801 +/− 14701 |
| Polyclonal anti-Aβ42 | 10 | 31706 | 0.0055 | −50 | 27127 | 0.0025 | −50 | 30058 +/− 22454 | 24853 +/− 18262 |
| mAb 10D5 | 8 | 46779 | 0.0675 | −26 | 36290 | 0.0543 | −33 | 44581 +/− 18632 | 36465 +/− 17146 |
| mAb 266 | 6 | 48689 | 0.0990 | −23 | 43034 | 0.0990 | −21 | 36419 +/− 27304 | 32919 +/− 25372 |
| mAb 21F12 | 8 | 51563 | 0.7728 | −19 | 47961 | 0.8099 | −12 | 57327 +/− 28927 | 50305 +/− 23927 |

[a]Number of animals per group at the end of the experiment
[b]ng/g tissue
[c]Mann Whitney analysis
[d]NA: not applicable
[e]Standard Deviation Total Aβ was also measured in the cerebellum (Table 6). Those groups dosed with the polyclonal anti-Aβ and the 266 antibody showed significant reductions of the levels of total Aβ (43% and 46%, p=0.0033 and p=0.0184, respectively) and that group treated with 10D5 had a near significant reduction (29%, p=0.0675).

TABLE 6

CEREBELLUM

| | | Medians Total Aβ | | | Means |
| --- | --- | --- | --- | --- | --- |
| Treatment Group | N[a] | ELISA value[b] | P value[c] | % Change | Total Aβ ELISA value |
| PBS | 9 | 30.64 | NA[d] | NA | 40.00 +/− 31.89[e] |
| Polyclonal anti-Aβ42 | 10 | 17.61 | 0.0033 | −43 | 18.15 +/− 4.36 |
| mAb 10D5 | 8 | 21.68 | 0.0675 | −29 | 27.29 +/− 19.43 |
| mAb 266 | 6 | 16.59 | 0.0184 | −46 | 19.59 +/− 6.59 |
| mAb 21F12 | 8 | 29.80 | >0.9999 | −3 | 32.88 +/− 9.90 |

[a]Number of animals per group at the end of the experiment
[b]ng/g tissue
[c]Mann Whitney analysis
[d]NA: not applicable
[e]Standard Deviation APP concentration was also determined by ELISA in the cortex and cerebellum from antibody-treated and control, PBS-treated mice. Two different APP assays were utilized. The first, designated APP-α/FL, recognizes both APP-alpha (α, the secreted form of APP which has been cleaved within the Aβ sequence), and full-length forms (FL) of APP, while the second recognizes only APP-α. In contrast to the treatment-associated diminution of Aβ in a subset of treatment groups, the levels of APP were virtually unchanged in all of the treated compared to the control animals. These results and 10D5 treatment groups was qualitatively compared to that of previous studies in which standard immunization procedures with Aβ42 were followed.

The largest alteration in both the extent and appearance of amyloid plaques occurred in the animals immunized with the polyclonal Aβ42 antibody. The reduction of amyloid load, eroded plaque morphology and cell-associated Aβ immunoreactivity closely resembled effects produced by the standard immunization procedure. These observations support the ELISA results in which significant reductions in both total Aβ and Aβ42 were achieved by administration of the polyclonal Aβ42 antibody.

In similar qualitative evaluations, amyloid plaques in the 10D5 group were also reduced in number and appearance, with some evidence of cell-associated Aβ immunoreactivity. Relative to control-treated animals, the polyclonal Ig fraction against Aβ and one of the monoclonal antibodies (10D5) reduced plaque burden by 93% and 81%, respectively (p<0.005). 21F12 appeared to have a relatively modest effect on plaque burden. Micrographs of brain after treatment with pAbAβ$_{1-42}$ show diffuse deposits and absence of many of the larger compacted plaques in the pAbAβ$_{1-42}$ treated group relative to control treated animals.

E. Lymphoproliferative Responses

Aβ-dependent lymphoproliferation was measured using spleen cells harvested eight days following the final antibody infusion. Freshly harvested cells, $10^5$ per well, were cultured for 5 days in the presence of Aβ 1-40 at a concentration of 5 μM for stimulation. As a positive control, additional cells were cultured with the T cell mitogen, PHA, and, as a negative control, cells were cultured without added peptide.

Splenocytes from aged PDAPP mice passively immunized with various anti-Aβ antibodies were stimulated in vitro with AN1792 and proliferative and cytokine responses were measured. The purpose of these assays was to determine if passive immunization facilitated antigen presentation, and thus priming of T cell responses specific for AN1792. No AN1792-specific proliferative or cytokine responses were observed in mice passively immunized with the anti-Aβ antibodies.

Example II

Therapeutic Efficacy of Anti-Aβ Antibodies: mAb 2H3, mAb 10D5, mAb 266, mAb 21F12, mAb 3D6, mAb 16C11 and pAb Aβ1-42

In a second study, treatment with 10D5 was repeated and two additional anti-Aβ antibodies were tested, monoclonals 3D6 (Aβ1-5) and 16C11 (Aβ33-42). Control groups received either PBS or an irrelevant isotype-matched antibody (TM2a). The mice were older (11.5-12 month old heterozygotes) than in the previous study, otherwise the experimental design was the same. Once again, after six months of treatment, 10D5 reduced plaque burden by greater than 80% relative to either the PBS or isotype-matched antibody controls (p=0.003). One of the other antibodies against Aβ, 3D6, was equally effective, producing an 86% reduction (p=0.003). In contrast, the third antibody against the peptide, 16C11, failed to have any effect on plaque burden. Similar findings were obtained with Aβ42 ELISA measurements.

These results demonstrate that an antibody response against Aβ peptide, in the absence of T cell immunity, is sufficient to decrease amyloid deposition in PDAPP mice, but that not all anti-Aβ antibodies are equally efficacious. Antibodies directed to epitopes comprising amino acids 1-5 or 3-7 of Aβ are particularly efficacious. In summary, it can be demonstrated that passively administered antibodies against Aβ (i.e., passive immunization) reduces the extent of plaque deposition in a mouse model of Alzheimer's disease.

Example III

Monitoring of Antibody Binding in the CNS

This Example demonstrates that when held at modest serum concentrations (25-70 µg/ml), the antibodies gained access to the CNS at levels sufficient to decorate β-amyloid plaques.

To determine whether antibodies against Aβ could be acting directly within the CNS, brains taken from saline-perfused mice at the end of the Example II, were examined for the presence of the peripherally-administered antibodies. Unfixed cryostat brain sections were exposed to a fluorescent reagent against mouse immunoglobulin (goat anti-mouse IgG-Cy3). Plaques within brains of the 10D5 and 3D6 groups were strongly decorated with antibody, while there was no staining in the 16C11 group. To reveal the full extent of plaque deposition, serial sections of each brain were first immunoreacted with an anti-Aβ antibody, and then with the secondary reagent. 10D5 and 3D6, following peripheral administration, gained access to most plaques within the CNS. The plaque burden was greatly reduced in these treatment groups compared to the 16C11 group. Antibody entry into the CNS was not due to abnormal leakage of the blood-brain barrier since there was no increase in vascular permeability as measured by Evans Blue in PDAPP mice. In addition, the concentration of antibody in the brain parenchyma of aged PDAPP mice was the same as in non-transgenic mice, representing 0.1% of the antibody concentration in serum (regardless of isotype).

These data indicate that peripherally administered antibodies can enter the CNS where they can directly trigger amyloid clearance. It is likely that 16C11 also had access to the plaques but was unable to bind.

Example IV

Ex Vivo Screening Assay for Activity of an Antibody Against Amyloid Deposits

To examine the effect of antibodies on plaque clearance, we established an ex vivo assay in which primary microglial cells were cultured with unfixed cryostat sections of either PDAPP mouse or human AD brains. Microglial cells were obtained from the cerebral cortices of neonate DBA/2N mice (1-3 days). The cortices were mechanically dissociated in HBSS$^{--}$ (Hanks' Balanced Salt Solution, Sigma) with 50 µg/ml DNase I (Sigma). The dissociated cells were filtered with a 100 µm cell strainer (Falcon), and centrifuged at 1000 rpm for 5 minutes. The pellet was resuspended in growth medium (high glucose DMEM, 10% FBS, 25 ng/ml rmGM-CSF), and the cells were plated at a density of 2 brains per T-75 plastic culture flask. After 7-9 days, the flasks were rotated on an orbital shaker at 200 rpm for 2 h at 37° C. The cell suspension was centrifuged at 1000 rpm and resuspended in the assay medium.

10-µm cryostat sections of PDAPP mouse or human AD brains (post-mortem interval <3 hr) were thaw mounted onto poly-lysine coated round glass coverslips and placed in wells of 24-well tissue culture plates. The coverslips were washed twice with assay medium consisting of H—SFM (Hybridoma-serum free medium, Gibco BRL) with 1% FBS, glutamine, penicillin/streptomycin, and 5 ng/ml rmGM-CSF (R&D). Control or anti-Aβ antibodies were added at a 2× concentration (5 µg/ml final) for 1 hour. The microglial cells were then seeded at a density of $0.8 \times 10^6$ cells/ml assay medium. The cultures were maintained in a humidified incubator (37° C., 5% $CO_2$) for 24 hr or more. At the end of the incubation, the cultures were fixed with 4% paraformaldehyde and permeabilized with 0.1% Triton-X100. The sections were stained with biotinylated 3D6 followed by a streptavidin/Cy3 conjugate (Jackson ImmunoResearch). The exogenous microglial cells were visualized by a nuclear stain (DAPI). The cultures were observed with an inverted fluorescent microscope (Nikon, TE300) and photomicrographs were taken with a SPOT digital camera using SPOT software (Diagnostic instruments). For Western blot analysis, the cultures were extracted in 8M urea, diluted 1:1 in reducing tricine sample buffer and loaded onto a 16% tricine gel (Novex). After transfer onto immobilon, blots were exposed to 5 µg/ml of the pabAβ42 followed by an HRP-conjugated anti-mouse antibody, and developed with ECL (Amersham)

When the assay was performed with PDAPP brain sections in the presence of 16C11 (one of the antibodies against Aβ that was not efficacious in vivo), β-amyloid plaques remained intact and no phagocytosis was observed. In contrast, when adjacent sections were cultured in the presence of 10D5, the amyloid deposits were largely gone and the microglial cells showed numerous phagocytic vesicles containing Aβ. Identical results were obtained with AD brain sections; 10D5 induced phagocytosis of AD plaques, while 16C11 was ineffective. In addition, the assay provided comparable results when performed with either mouse or human microglial cells, and with mouse, rabbit, or primate antibodies against Aβ.

Table 7 compares Aβ binding versus phagocytosis for several different antibody binding specificities. It can be seen that antibodies binding to epitopes within aa 1-7 both bind and clear amyloid deposits, whereas antibodies binding to epitopes within amino acids 4-10 bind without clearing amyloid deposits. Antibodies binding to epitopes C-terminal to residue 10 neither bind nor clear amyloid deposits.

TABLE 7

Analysis of Epitope Specificity

| Antibody | epitope | isotype | Staining | Phagocytosis |
|---|---|---|---|---|
| N-Term | | | | |
| mab | | | | |
| 3D6 | 1-5 | IgG2b | + | + |
| 10D5 | 3-7 | IgG1 | + | + |
| 22C8 | 3-7 | IgG2a | + | + |
| 6E10 | 5-10 | IgG1 | + | − |
| 14A8 | 4-10 | rat IgG1 | + | − |
| aa 13-28 | | | | |
| 18G11 | 10-18 | rat IgG1 | − | − |
| 266 | 16-24 | IgG1 | − | − |
| 22D12 | 18-21 | IgG2b | − | − |
| C-Term | | | | |
| 2G3 | −40 | IgG1 | − | − |
| 16C11 | −40/−42 | IgG1 | − | − |
| 21F12 | −42 | IgG2a | − | − |
| Immune serum | | | | |
| rabbit (CFA) | 1-6 | | + | + |
| mouse (CFA) | 3-7 | | + | + |
| mouse (QS-21) | 3-7 | | + | + |
| monkey (QS-21) | 1-5 | | + | + |
| mouse (MAP1-7) | | | + | + |

Table 8 shows results obtained with several antibodies against Aβ, comparing their abilities to induce phagocytosis in the ex vivo assay and to reduce in vivo plaque burden in passive transfer studies. Although 16C11 and 21F12 bound to aggregated synthetic Aβ peptide with high avidity, these antibodies were unable to react with β-amyloid plaques in unfixed brain sections, could not trigger phagocytosis in the ex vivo assay, and were not efficacious in vivo. 10D5, 3D6, and the polyclonal antibody against Aβ were active by all three measures. These results show that efficacy in vivo is due to direct antibody mediated clearance of the plaques within the CNS, and that the ex vivo assay is predictive of in vivo efficacy.

TABLE 8

The ex vivo assay as predictor of in vivo efficacy

| Antibody | Isotype | Avidity for aggregated Aβ (pM) | Binding to β-amyloid plaques | Ex vivo efficacy | In vivo efficacy |
|---|---|---|---|---|---|
| monoclonal | | | | | |
| 3D6 | IgG2b | 470 | + | + | + |
| 10D5 | IgG1 | 43 | + | + | + |
| 16C11 | IgG1 | 90 | − | − | − |
| 21F12 | IgG2a | 500 | − | − | − |
| TM2a | IgG1 | — | − | − | − |
| polyclonal | | | | | |
| 1-42 | mix | 600 | + | + | + |

The same assay has been used to test clearing activity of an antibody against a fragment of synuclein referred to as NAC. Synuclein has been shown to be an amyloid plaque-associated protein. An antibody to NAC was contacted with a brain tissue sample containing amyloid plaques, and microglial cells, as before. Rabbit serum was used as a control. Subsequent monitoring showed a marked reduction in the number and size of plaques indicative of clearing activity of the antibody.

Confocal microscopy was used to confirm that Aβ was internalized during the course of the ex vivo assay. In the presence of control antibodies, the exogenous microglial cells remained in a confocal plane above the tissue, there were no phagocytic vesicles containing Aβ, and the plaques remained intact within the section. In the presence of 10D5, nearly all plaque material was contained in vesicles within the exogenous microglial cells. To determine the fate of the internalized peptide, 10D5 treated cultures were extracted with 8M urea at various time-points, and examined by Western blot analysis. At the one hour time point, when no phagocytosis had yet occurred, reaction with a polyclonal antibody against Aβ revealed a strong 4 kD band (corresponding to the Aβ peptide). Aβ immunoreactivity decreased at day 1 and was absent by day 3. Thus, antibody-mediated phagocytosis of Aβ leads to its degradation.

To determine if phagocytosis in the ex vivo assay was Fc-mediated, F(ab')2 fragments of the anti-Aβ antibody 3D6 were prepared. Although the F(ab')2 fragments retained their full ability to react with plaques, they were unable to trigger phagocytosis by microglial cells. In addition, phagocytosis with the whole antibody could be blocked by a reagent against murine Fc receptors (anti-CD16/32). These data indicate that in vivo clearance of Aβ occurs through Fc-receptor mediated phagocytosis.

Example V

Passage of Antibodies Through the Blood-Brain Barrier

This example determines the concentration of antibody delivered to the brain following intravenous injection into a peripheral tissue of either normal or PDAPP mice. Following treatment, PDAPP or control normal mice were perfused with 0.9% NaCl. Brain regions (hippocampus or cortex) were dissected and rapidly frozen. Brain were homogenized in 0.1% triton+protease inhibitors. Immunoglobulin was detected in the extracts by ELISA. F(ab)'2 goat anti-mouse IgG were coated onto an RIA plate as capture reagent. The serum or the brain extracts were incubated for 1 hr. The isotypes were detected with anti-mouse IgG1-HRP or IgG2a-HRP or IgG2b-HRP (Caltag). Antibodies, regardless of isotype, were present in the CNS at a concentration that is 1:1000 that found in the blood. For example, when the concentration of IgG1 was three times that of IgG2a in the blood, it was three times IgG2a in the brain as well, both being present at 0.1% of their respective levels in the blood. This result was observed in both transgenic and nontransgenic mice indicating that the PDAPP does not have a uniquely leak blood brain barrier.

Example VI

Cloning and Sequencing of the Mouse 3D6 Variable Regions

Cloning and Sequence Analysis of 3D6 VH. The heavy chain variable VH region of 3D6 was cloned by RT-PCR using mRNA prepared from hybridoma cells by two independent methods. The hybridoma producing the 3D6 antibody has been deposited at the American Type Culture Collection, P.O. Box 1549, Manassas, Va. 20108, USA and has been assigned accession number PTA-5130 Apr. 8, 2003. In the first, consensus primers were employed to VH region leader peptide encompassing the translation initiation codon as the 5' primer (DNA #3818-3829), and a g2b (DNA #3832) constant regions specific 3' primer. The sequences from PCR amplified product, as well as from multiple, independently-derived clones, were in complete agreement with one another. As a further check on the sequence of the 3D6 VH region, the result was confirmed by sequencing a VH fragment obtained by 5' RACE RT-PCR methodology and the 3' g2b specific primer (DNA #3832). Again, the sequence was derived from the PCR product, as well as multiple, independently-isolated clones. Both sequences are in complete agreement with one another, (with the exception of V8I substitution in the leader region from the 5' RACE product), indicating that the sequences are derived from the mRNA encoding the VH region of 3D6. The nucleotide (SEQ ID NO:3) and amino acid sequence (SEQ ID NO:4) of the VH region of 3D6 are set forth in Table 9A and in FIG. 2, respectively.

TABLE 9A

Mouse 3D6 VH Nucleotide Sequence

ATGAACTTCGGGCTCAGCTTGATTTTCCTTGTCCTTGTTTTAAAAGGTGTCCAGTGTGAAGT (SEQ ID NO: 3)

GAAGCTGGTGGAGTCTGGGGGAGGCTTAGTGAAGCCTGGAGCGTCTCTGAAACTCTCCTGTG

CAGCCTCTGGATTCACTTTCAGTAACTATGGCATGTCTTGGGTTCGCCAGAATTCAGACAAG

AGGCTGGAGTGGGTTGCATCCATTAGGAGTGGTGGTGGTAGAACCTACTATTCAGACAATGT

AAAGGGCCGATTCACCATCTCCAGAGAGAATGCCAAGAACACCCTGTACCTGCAAATGAGTA

GTCTGAAGTCTGAGGACACGGCCTTGTATTATTGTGTCAGATATGATCACTATAGTGGTAGC

TCCGACTACTGGGGCCAGGGCACCACT

*Leader peptide is underlined.

Cloning and Sequence Analysis of 3D6 VL. The light chain variable VL region of 3D6 was cloned in an analogous manner as the VH region. In the first trial, a consensus primer set was designed for amplification of murine VL regions as follows: 5' primers (DNA #3806-3816) were designed to hybridize to the VL region encompassing the translation initiation codon, and a 3' primer (DNA#3817) was specific for the murine Ck region downstream of the V-J joining region. DNA sequence analysis of the PCR fragment, as well as independently-derived clones isolated using this consensus light chain primer set, revealed that the cDNA obtained was derived from a non-functionally rearranged message as the sequence contained a frameshift mutation between the V-J region junction.

In a second trial, 5'RACE was employed to clone a second VL encoding cDNA. DNA sequence analysis of this product (consensus 11) showed it encoded a functional mRNA. Thus, it can be concluded that the sequence encodes the correct 3D6 light chain mRNA. The nucleotide (SEQ ID NO:1) and amino acid sequence (SEQ ID NO:2) of the VL region of 3D6 are set forth in Table 9B and in FIG. 1, respectively.

TABLE 9B

Mouse 3D6 VL Nucleotide Sequence

ATGATGAGTCCTGCCCAGTTCCTGTTTCTGTTAGTGCTCTGGATTCGGGAAACCAACGGTTA (SEQ ID NO: 1)

TGTTGTGATGACCCAGACTCCACTCACTTTGTCGGTTACCATTGGACAACCAGCCTCCATCT

CTTGCAAGTCAAGTCAGAGCCTCTTAGATAGTGATGGAAAGACATATTTGAATTGGTTGTTA

CAGAGGCCAGGCCAGTCTCCAAAGCGCCTAATCTATCTGGTGTCTAAACTGGACTCTGGAGT

CCCTGACAGGTTCACTGGCAGTGGATCAGGGACAGATTTTACACTGAAAATCAGCAGAATAG

AGGCTGAGGATTTGGGACTTTATTATTGCTGGCAAGGTACACATTTTCCTCGGACGTTCGGT

GGAGGCACCAAGCTGGAAATCAAA

*Leader peptide is underlined

Primers used for the cloning of the 3D6 VL cDNA are set forth in Table 10.

| DNA | Size | Coding Strand? | DNA Sequence | Comments |
|---|---|---|---|---|
| 3806 | 40 | Yes | ACT.AGT.CGA.CAT.GAA.GTT.GCC.TGT.TA G.GCT.GTT.GGT.GCT.G (SEQ ID NO: 39) | mouse kappa variable primer 1 MKV PRIMER 1, MRC set; % A + T = 50.00 [20]; % C + G = 50.00 [20] Davis, Botstein, Roth Melting Temp C. 72.90 |
| 3807 | 39 | Yes | ACT.AGT.CGA.CAT.GGA.GWC.AGA.CAC.AC T.CCT.GYT.ATG.GGT (SEQ ID NO: 40) | mouse kappa variable primer 2 MKV PRIMER 2, MRC set % A + T = 46.15 [18]; % C + G = 48.72 [19] Davis, Botstein, Roth Melting Temp C. 72.05 |
| 3808 | 40 | Yes | ACT.AGT.CGA.CAT.GAG.TGT.GCT.CAC.TC A.GGT.CCT.GGS.GTT.G (SEQ ID NO: 41) | mouse kappa variable primer 3 MKV PRIMER 3, MRC set; % A + T = 45.00 [18]; % C + G = 52.50 [21] Davis, Botstein, Roth Melting Temp C. 73.93 |
| 3809 | 43 | Yes | ACT.AGT.CGA.CAT.GAG.GRC.CCC.TGC.TC A.GWT.TYT.TGG.MWT.CTT.G (SEQ ID NO: 42) | mouse kappa variable primer 4 MKV PRIMER 4, MRC set; % A + T = 41.86 [18]; % C + G = 46.51 [20] Davis, Botstein, Roth Melting Temp C. 72.34 |
| 3810 | 40 | Yes | ACT.AGT.CGA.CAT.GGA.TTT.WCA.GGT.GC A.GAT.TWT.CAG.CTT.C (SEQ ID NO: 43) | mouse kappa variable primer 5 MKV PRIMER 5, MRC set % A + T = 52.50 [21]; % C + G = 42.50 [17] Davis, Botstein, Roth Melting Temp C. 69.83 |
| 3811 | 37 | Yes | ACT.AGT.CGA.CAT.GAG.GTK.CYY.TGY.TS A.GYT.YCT.GRG.G (SEQ ID NO: 44) | mouse kappa variable primer 6 MKV PRIMER 6, MRC set; % A + T = 37.84 [14]; % C + G = 40.54 [15] Davis, Botstein, Roth Melting Temp C. 68.01 |
| 3812 | 41 | Yes | ACT.AGT.CGA.CAT.GGG.CWT.CAA.GAT.GG A.GTC.ACA.KWY.YCW.GG (SEQ ID NO: 45) | mouse kappa variable primer 7 MKV PRIMER 7, MRC set; % A + T = 39.02 [16]; % C + C = 46.34 [19] Davis, Botstein, Roth Melting Temp C. 71.70 |
| 3813 | 41 | Yes | ACT.AGT.CGA.CAT.GTG.GGG.AYC.TKT.TT Y.CMM.TTT.TTC.AAT.TG (SEQ ID NO: 46) | mouse kappa variable primer 8 MKV PRIMER 8, MRC set; % A + T = 53.66 [22]; % C + C = 34.15 [14] Davis, Botstein, Roth Melting Temp C. 66.70 |
| 3814 | 35 | Yes | ACT.AGT.CGA.CAT.GGT.RTC.CWC.ASC.TC A.GTT.CCT.TG (SEQ ID NO: 47) | mouse kappa variable primer 9 MKV PRIMER 9, MRC set. % A + T = 45.71 [16]; % C + G = 45.71 [16] Davis, Botstein, Roth Melting Temp C. 69.36 |

-continued

| DNA | Size | Coding Strand? | DNA Sequence | Comments |
|---|---|---|---|---|
| 3815 | 37 | Yes | ACT.AGT.CGA.CAT.GTA.TAT.ATG.TTT.GT T.GTC.TAT.TTC.T (SEQ ID NO: 48) | mouse kappa variable primer 10 MKV PRIMER 10, MRC set; % A + T = 70.27 [26]; % C + G = 29.73 [11] Davis, Botstein, Roth Melting Temp C. 63.58 |
| 3816 | 38 | Yes | ACT.AGT.CGA.CAT.GGA.AGC.CCC.AGC.TC A.GCT.TCT.CTT.CC (SEQ ID NO: 49) | mouse kappa variable primer 11 MKV PRIMER 11, MRC set; % A + T = 44.74 [17]; % C + G = 55.26 [21] Davis, Botstein, Roth Melting Temp C. 74.40 |
| 3817 | 27 | No | GGA.TCC.CGG.GTG.GAT.GGT.GGG.AAG.AT G (SEQ ID NO: 50) | mouse kappa light chain reverse primer, aa 116-122; Ck constant region primer, MRC set + SmaI site; % A + T = 47.06 [8]; % C + G = 52.94 [9] Davis, Botstein, Roth Melting Temp C. 57.19 |
| 3818 | 37 | Yes | ACT.AGT.CGA.CAT.GAA.ATG.CAG.CTG.GG T.CAT.STT.CTT.C (SEQ ID NO: 51) | mouse heavy variable primer 1 MHV primer 1, MRC set; |
| 3819 | 36 | Yes | ACT.AGT.CGA.CAT.GGG.ATG.GAG.CTR.TA T.CAT.SYT.CTT (SEQ ID NO:52) | mouse heavy variable primer 2 MHV primer 2, MRC set; |
| 3820 | 37 | Yes | ACT.AGT.CGA.CAT.GAA.GWT.GTG.GTT.AA A.CTG.GGT.TTT.T (SEQ ID NO: 53) | mouse heavy variable primer 3 MHV primer 3, MRC set; |
| 3821 | 35 | Yes | ACT.AGT.CGA.CAT.GRA.CTT.TGG.GYT.CA G.CTT.GRT.TT (SEQ ID NO: 54) | mouse heavy variable primer 4 MHV primer 4, MRC set; |
| 3822 | 40 | Yes | ACT.AGT.CGA.CAT.GGA.CTC.CAG.GCT.CA A.TTT.AGT.TTT.CCT.T (SEQ ID NO: 55) | mouse heavy variable primer 5 MHV primer 5, MRC set; |
| 3823 | 37 | Yes | ACT.AGT.CGA.CAT.GGC.TGT.CYT.RGS.GC T.RCT.CTT.CTG.C (SEQ ID NO: 56) | mouse heavy variable primer 6 MHV primer 6, MRC set; |
| 3824 | 36 | Yes | ACT.AGT.CGA.CAT.GGR.ATG.GAG.CKG.GR T.CTT.TMT.CTT (SEQ ID NO: 57) | mouse heavy variable primer 7 MHV primer 7, MRC set; |
| 3825 | 33 | Yes | ACT.AGT.CGA.CAT.GAG.AGT.GCT.GAT.TC T.TTT.GTG (SEQ ID NO: 58) | mouse heavy variable primer 8 MHV primer 8, MRC set; |
| 3826 | 40 | Yes | ACT.AGT.CGA.CAT.GGM.TTG.GGT.GTG.GA M.CTT.GCT.ATT.CCT.G (SEQ ID NO: 59) | mouse heavy variable primer 9 MHV primer 9, MRC set; |
| 3827 | 37 | Yes | ACT.AGT.CGA.CAT.GGG.CAG.ACT.TAC.AT T.CTC.ATT.CCT.G (SEQ ID NO: 60) | mouse heavy variable primer 10 MHV primer 10, MRC set; |
| 3828 | 38 | Yes | ACT.AGT.CGA.CAT.GGA.TTT.TGG.GCT.GA T.TTT.TTT.TAT.TG (SEQ ID NO: 61) | mouse heavy variable primer 11 MHV primer 11, MRC set; |
| 3829 | 37 | Yes | ACT.AGT.CGA.CAT.GAT.GGT.GTT.AAG.TC T.TCT.GTA.CCT.G (SEQ ID NO: 62) | mouse heavy variable primer 12 MHV primer 12, MRC set; |

-continued

| DNA | Size | Coding Strand? | DNA Sequence | Comments |
|---|---|---|---|---|
| 3832 | 27 | No | GGA.TCC.CGG.GAG.TGG.ATA.GAC.tGA.TG G (SEQ ID NO: 63) | mouse IgG2b heavy chain reverse primer aa position 119-124, MRC set; |

From N-terminal to C-terminal, both light and heavy chains comprise the domains FR1, CDR1, FR2, CDR2, FR3, CDR3 and FR4. The assignment of amino acids to each domain is in accordance with the numbering convention of Kabat et al., supra.

Expression of Chimeric 3D6 Antibody: The variable heavy and light chain regions were re-engineered to encode splice donor sequences downstream of the respective VDJ or VJ junctions, and cloned into the mammalian expression vector pCMV-hγ1 for the heavy chain, and pCMV-hκ1 for the light chain. These vectors encode human γ1 and Ck constant regions as exonic fragments downstream of the inserted variable region cassette. Following sequence verification, the heavy chain and light chain expression vectors were co-transfected into COS cells. Two different heavy chain clones (H2.2 & H3.2) were independently co-transfected with 3 different chimeric light chain clones (L3, L4, & L10) to confirm reproducibility of the result. A chimeric 21.6 antibody transfection was carried out as a positive control for the vectors. Conditioned media was collected 48 hrs post transfection and assayed by western blot analysis for antibody production or ELISA for Aβ binding.

The multiple transfectants all expressed heavy chain+light chain combinations which are recognized by a goat anti-human IgG (H+L) antibody on a western blot.

Figure 3A:
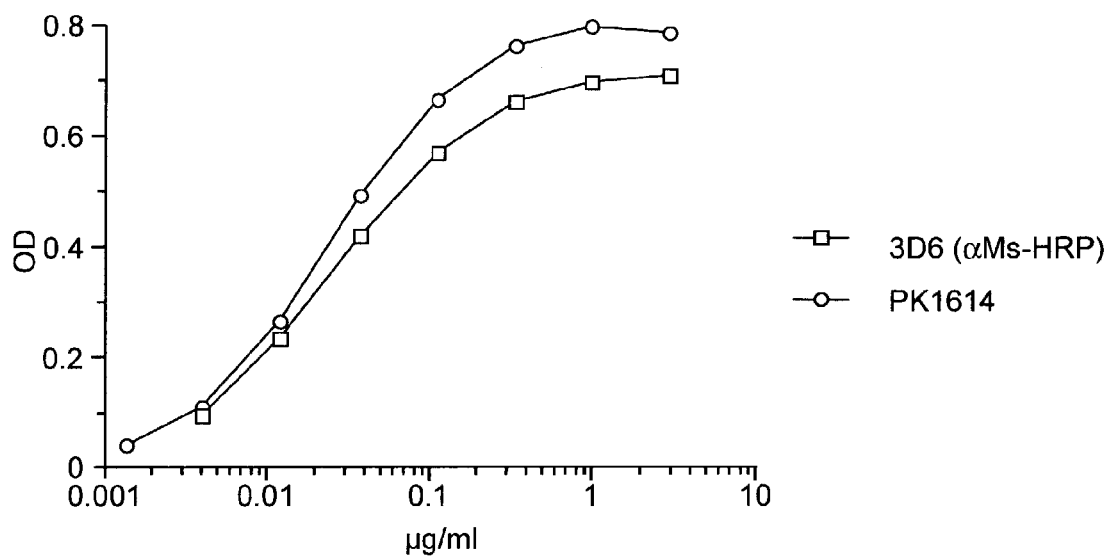
FIG. 3A is a graph depicting binding of Aβ to chimeric 3D6 (PK1614) as compared to murine 3D6.
Figure 3B:
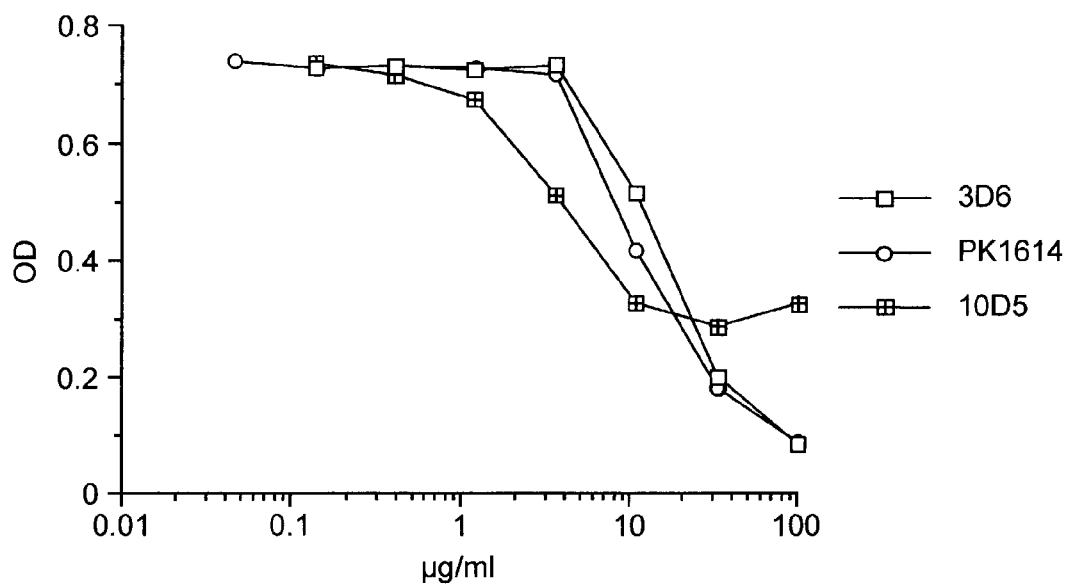
FIG. 3B is a graph depicting competition of biotinylated 3D6 versus unlabeled 3D6, PK1614 and 10D5 for binding to Aβ.

Direct binding of 3D6 and chimeric 3D6 (PK1614) antibodies to Aβ was tested by ELISA analysis. Chimeric 3D6 was found to bind to Aβ with high avidity, similar to that demonstrated by 3D6 (FIG. 3A). Furthermore, an ELISA based competitive inhibition assay revealed that the chimeric 3D6 and the murine 3D6 antibody competed equally with biotinylated-3D6 binding to Aβ (FIG. 3B). The chimeric antibody displayed binding properties indistinguishable from the 3D6 reference sample.

TABLE 11

| Conc (μg/ml) | 3D6 | PK1614 | IgG1 |
|---|---|---|---|
| 0.037 | | 119.3 | |
| 0.11 | 118.6 | 118.9 | |
| 0.33 | 99.7 | 71.25 | |
| 1 | 98.63 | 84.53 | 134.4 |

Moreover, both 3D6 and PK1614 were effective at clearing Aβ plaques. The ex vivo assay demonstrates that as the concentration of antibody increases, the amount of Aβ decreases in a similar manner for both murine and chimeric 3D6 antibodies. Hence, it can be concluded that the sequences encode functional 3D6 heavy and light chains respectively.

Example VII

3D6 Humanization

Homology/Molecular Modeling. In order to identify key structural framework residues in the murine 3D6 antibody, a three-dimensional model was generated based on the closest murine antibodies for the heavy and light chains. For this purpose, an antibody designated 1CR9 was chosen as a template for modeling the 3D6 light chain (PDB ID: 1CR9, Kanyo et al., supra), and an antibody designated 1OPG was chosen as the template for modeling the heavy chain. (PDB ID: 1OPG Kodandapani et al., supra). (See also Table 1.) Amino acid sequence alignment of 3D6 with the light chain and heavy chain of these antibodies revealed that, with the exception of CDR3 of the heavy chain, the 1CR9 and 1OPG antibodies share significant sequence homology with 3D6. In addition, the CDR loops of the selected antibodies fall into the same canonical Chothia structural classes as do the CDR loops of 3D6, again excepting CDR3 of the heavy chain. Therefore, 1 CR9 and 1 OPG were initially selected as antibodies of solved structure for homology modeling of 3D6.

A first pass homology model of 3D6 variable region based on the antibodies noted above was constructed using the Look & SegMod Modules GeneMine (v3.5) software package. This software was purchased under a perpetual license from Molecular Applications Group (Palo Alto, Calif.). This software package, authored by Drs. Michael Levitt and Chris Lee, facilitates the process of molecular modeling by automating the steps involved in structural modeling a primary sequence on a template of known structure based on sequence homology. Working on a Silicon Graphics IRIS workstation under a UNIX environment, the modeled structure is automatically refined by a series of energy minimization steps to relieve unfavorable atomic contacts and optimize electrostatic and van der Walls interactions.

Figure 4:
FIG. 4 depicts a homology model of 3D6 VH and VL, showing α-carbon backbone trace. VH is shown in as a stippled line, and VL is shown as a solid line. CDR regions are indicated in ribbon form.

A further refined model was built using the modeling capability of Quanta®. A query of the PDB database with CDR3 of the heavy chain of 3D6 identified 1 qkz as most homologous and having the identical number of residues as 3D6. Hence, CDR3 of the heavy chain of 3D6 was modeled using the crystal structure of 1 qkz as template. The α-carbon backbone trace of the 3D6 model is shown in FIG. 4. The VH domain is shown as a stippled line, and VL domain is shown as a solid line, and CDR loops are indicated in ribbon form.

Selection of Human Acceptor Antibody Sequences. Suitable human acceptor antibody sequences were identified by computer comparisons of the amino acid sequences of the mouse variable regions with the sequences of known human antibodies. The comparison was performed separately for the 3D6 heavy and light chains. In particular, variable domains from human antibodies whose framework sequences exhibited a high degree of sequence identity with the murine VL and VH framework regions were identified by query of the Kabat Database using NCBI BLAST (publicly accessible through the National Institutes of Health NCBI internet server) with the respective murine framework sequences.

Two candidate sequences were chosen as acceptor sequences based on the following criteria: (1) homology with the subject sequence; (2) sharing canonical CDR structures with the donor sequence; and (3) not containing any rare amino acid residues in the framework regions. The selected acceptor sequence for VL is Kabat ID Number (KABID) 019230 (Genbank Accession No. S40342), and for VH is KABID 045919 (Genbank Accession No. AF115110). First versions of humanized 3D6 antibody utilize these selected acceptor antibody sequences.

Substitution of Amino Acid Residues. As noted supra, the humanized antibodies of the invention comprise variable framework regions substantially from a human immunoglobulin (acceptor immunoglobulin) and complementarity determining regions substantially from a mouse immunoglobulin (donor immunoglobulin) termed 3D6. Having identified the complementarity determining regions of 3D6 and appropriate human acceptor immunoglobulins, the next step was to determine which, if any, residues from these components to substitute to optimize the properties of the resulting humanized antibody. The criteria described supra were used to select residues for substitution.

FIGS. 1 and 2 depict alignments of the original murine 3D6 VL and VH, respectively, with the respective version 1 of the humanized sequence, the corresponding human framework acceptor sequence and, lastly, the human germline V region sequence showing highest homology to the human framework acceptor sequence. The shaded residues indicate the canonical (solid fill), vernier (dotted outline), packing (bold), and rare amino acids (bold italics), and are indicated on the figure. The asterisks indicate residues backmutated to murine residues in the human acceptor framework sequence, and CDR regions are shown overlined. A summary of the changes incorporated into version 1 of humanized 3D6 VH and VL is presented in Table 12.

Tables 13 and 14 set forth Kabat numbering keys for the various light and heavy chains, respectively.

TABLE 13

Key to Kabat Numbering for Light Chain

| KAB # | # | TYPE | mouse 3D6 VL | HUM 3D6VL | KABID 019230 | A19-Germ-line | Comment |
|---|---|---|---|---|---|---|---|
| 1 | 1 | FR1 | Y | Y | D | D | Rare mouse, may contact CDR |
| 2 | 2 | | V | V | I | I | Canonical/CDR contact |
| 3 | 3 | | V | V | V | V | |
| 4 | 4 | | M | M | M | M | |
| 5 | 5 | | T | T | T | T | |
| 6 | 6 | | Q | Q | Q | Q | |
| 7 | 7 | | T | S | S | S | |
| 8 | 8 | | P | P | P | P | |
| 9 | 9 | | L | L | L | L | |
| 10 | 10 | | T | S | S | S | |
| 11 | 11 | | L | L | L | L | |
| 12 | 12 | | S | P | P | P | |
| 13 | 13 | | V | V | V | V | |
| 14 | 14 | | T | T | T | T | |
| 15 | 15 | | I | P | P | P | |

TABLE 12

Summary of changes in humanized 3D6.v1

| Changes | VL (112 residues) | VH (119 residues) |
|---|---|---|
| Hu->Mu: Framework | 4/112 | 3/119 (1 canon, 1 packing) |
| CDR1 | 6/16 | 3/5 |
| CDR2 | 4/7 | 7/14 |
| CDR3 | 5/8 | 4/10 |
| Hu->Mu | 19/112 (17%) | 17/119 (14%) |
| Mu->Hu: Framework | 13/112 | 14/119 |
| Backmutation notes | 1. I2V which is a canonical position. <br> 2. Y36L which is a packing residue and also lies under the CDRs <br> 3. L46R which is a packing residue and lies beneath the CDRs | 4. S49A Vernier/beneath the CDRs. <br> 5. A93V which is a packing and vernier zone residue <br> 6. K94R which is a canonical residue |
| Acceptor notes | 7. KABID 019230/Genbank Acc#S40342 <br> 8. Hu κ LC subgroup II <br> 9. CDRs from same canonical structural group as donor (m3D6) <br> L1 = class 4 <br> L2 = class 1 <br> L3 = class1 <br> 10. Unknown specificity | 11. KABID045919/Genbank Acc#AF115110 <br> 12. Hu HC subgroup III <br> 13. CDRs from same canonical structural group as donor (m3D6) <br> H1 = class 1 <br> H2 = class3 <br> 14. Recognizes capsular polysaccharide of Neisseria meningitidis |
| Acceptor Germline | 15. VH3-23 | 16. A3 & A19 |

TABLE 13-continued

Key to Kabat Numbering for Light Chain

| KAB # | # | TYPE | mouse 3D6 VL | HUM 3D6VL | KABID 019230 | A19-Germ-line | Comment |
|---|---|---|---|---|---|---|---|
| 16 | 16 | | G | G | G | G | |
| 17 | 17 | | Q | E | E | E | |
| 18 | 18 | | P | P | P | P | |
| 19 | 19 | | A | A | A | A | |
| 20 | 20 | | S | S | S | S | |
| 21 | 21 | | I | I | I | I | |
| 22 | 22 | | S | S | S | S | |
| 23 | 23 | | C | C | C | C | |
| 24 | 24 | CDR1 | K | K | R | R | |
| 25 | 25 | | S | S | S | S | |
| 26 | 26 | | S | S | S | S | |
| 27 | 27 | | Q | Q | Q | Q | |
| 27A | 28 | | S | S | S | S | |
| 27B | 29 | | L | L | L | L | |
| 27C | 30 | | L | L | L | L | |
| 27D | 31 | | D | D | H | H | |
| 27E | 32 | | S | S | S | S | |
| 28 | 33 | | D | D | N | N | |
| 29 | 34 | | G | G | G | G | |
| 30 | 35 | | K | K | Y | Y | |
| 31 | 36 | | T | T | N | N | |
| 32 | 37 | | Y | Y | Y | Y | |
| 33 | 38 | | L | L | L | L | |
| 34 | 39 | | N | N | D | D | |
| 35 | 40 | FR2 | W | W | W | W | |
| 36 | 41 | | L | L | Y | Y | Packing residue |
| 37 | 42 | | L | L | L | L | |
| 38 | 43 | | Q | Q | Q | Q | |
| 39 | 44 | | R | K | K | K | |
| 40 | 45 | | P | P | P | P | |
| 41 | 46 | | G | G | G | G | |
| 42 | 47 | | Q | Q | Q | Q | |
| 43 | 48 | | S | S | S | S | |
| 44 | 49 | | P | P | P | P | |
| 45 | 50 | | K | Q | Q | Q | |
| 46 | 51 | | R | R | L | L | Packing residue |
| 47 | 52 | | L | L | L | L | |
| 48 | 53 | | I | I | I | I | |
| 49 | 54 | | Y | Y | Y | Y | |
| 50 | 55 | CDR2 | L | L | L | L | |
| 51 | 56 | | V | V | G | G | |
| 52 | 57 | | S | S | S | S | |
| 53 | 58 | | K | K | N | N | |
| 54 | 59 | | L | L | R | R | |
| 55 | 60 | | D | D | A | A | |
| 56 | 61 | | S | S | S | S | |
| 57 | 62 | FR3 | G | G | G | G | |
| 58 | 63 | | V | V | V | V | |
| 59 | 64 | | P | P | P | P | |
| 60 | 65 | | D | D | D | D | |
| 61 | 66 | | R | R | R | R | |
| 62 | 67 | | F | F | F | F | |
| 63 | 68 | | T | S | S | S | |
| 64 | 69 | | G | G | G | G | |
| 65 | 70 | | S | S | S | S | |
| 66 | 71 | | G | G | G | G | |
| 67 | 72 | | S | S | S | S | |
| 68 | 73 | | G | G | G | G | |
| 69 | 74 | | T | T | T | T | |
| 70 | 75 | | D | D | D | D | |
| 71 | 76 | | F | F | F | F | |
| 72 | 77 | | T | T | T | T | |
| 73 | 78 | | L | L | L | L | |
| 74 | 79 | | K | K | K | K | |
| 75 | 80 | | I | I | I | I | |
| 76 | 81 | | S | S | S | S | |
| 77 | 82 | | R | R | R | R | |
| 78 | 83 | | I | V | V | V | |
| 79 | 84 | | E | E | E | E | |
| 80 | 85 | | A | A | A | A | |
| 81 | 86 | | E | E | E | E | |
| 82 | 87 | | D | D | D | D | |
| 83 | 88 | | L | V | V | V | |

TABLE 13-continued

Key to Kabat Numbering for Light Chain

| KAB # | # | TYPE | mouse 3D6 VL | HUM 3D6VL | KABID 019230 | A19-Germ-line | Comment |
|---|---|---|---|---|---|---|---|
| 84 | 89 | | G | G | G | G | |
| 85 | 90 | | L | V | V | V | |
| 86 | 91 | | Y | Y | Y | Y | |
| 87 | 92 | | Y | Y | Y | Y | |
| 88 | 93 | | C | C | C | C | |
| 89 | 94 | CDR3 | W | W | M | M | |
| 90 | 95 | | Q | Q | Q | Q | |
| 91 | 96 | | G | G | A | A | |
| 92 | 97 | | T | T | L | L | |
| 93 | 98 | | H | H | Q | Q | |
| 94 | 99 | | F | F | T | T | |
| 95 | 100 | | P | P | P | P | |
| 96 | 101 | | R | R | R | | |
| 97 | 102 | | T | T | T | | |
| 98 | 103 | FR4 | F | F | F | | |
| 99 | 104 | | G | G | G | | |
| 100 | 105 | | G | Q | Q | | |
| 101 | 106 | | G | G | G | | |
| 102 | 107 | | T | T | T | | |
| 103 | 108 | | K | K | K | | |
| 104 | 109 | | L | V | V | | |
| 105 | 110 | | E | E | E | | |
| 106 | 111 | | I | I | I | | |
| 106A | 112 | | K | K | K | | |

TABLE 14

Key to Kabat Numbering for Heavy Chain

| KAB # | # | TYPE | Mouse 3D6 VH | HUM 3D6 VH | KABID 045919 | VH3-23 Germ-line | Comment |
|---|---|---|---|---|---|---|---|
| 1 | 1 | FR1 | E | E | E | E | |
| 2 | 2 | | V | V | V | V | |
| 3 | 3 | | K | Q | Q | Q | |
| 4 | 4 | | L | L | L | L | |
| 5 | 5 | | V | L | L | L | |
| 6 | 6 | | E | E | E | E | |
| 7 | 7 | | S | S | S | S | |
| 8 | 8 | | G | G | G | G | |
| 9 | 9 | | G | G | G | G | |
| 10 | 10 | | G | G | G | G | |
| 11 | 11 | | L | L | L | L | |
| 12 | 12 | | V | V | V | V | |
| 13 | 13 | | K | Q | Q | Q | |
| 14 | 14 | | P | P | P | P | |
| 15 | 15 | | G | G | G | G | |
| 16 | 16 | | A | G | G | G | |
| 17 | 17 | | S | S | S | S | |
| 18 | 18 | | L | L | L | L | |
| 19 | 19 | | K | R | R | R | |
| 20 | 20 | | L | L | L | L | |
| 21 | 21 | | S | S | S | S | |
| 22 | 22 | | C | C | C | C | |
| 23 | 23 | | A | A | A | A | |
| 24 | 24 | | A | A | A | A | |
| 25 | 25 | | S | S | S | S | |
| 26 | 26 | | G | G | G | G | |
| 27 | 27 | | F | F | F | F | |
| 28 | 28 | | T | T | T | T | |
| 29 | 29 | | F | F | F | F | |
| 30 | 30 | | S | S | S | S | |
| 31 | 31 | CDR1 | N | N | S | S | |
| 32 | 32 | | Y | Y | Y | Y | |
| 33 | 33 | | G | G | A | A | |
| 34 | 34 | | M | M | V | M | |
| 35 | 35 | | S | S | S | S | |
| 36 | 36 | FR2 | W | W | W | W | |
| 37 | 37 | | V | V | V | V | |
| 38 | 38 | | R | R | R | R | |
| 39 | 39 | | Q | Q | Q | Q | |
| 40 | 40 | | N | A | A | A | Rare mouse, replace w/Hum |
| 41 | 41 | | S | P | P | P | |
| 42 | 42 | | D | G | G | G | Rare mouse, replace w/Hum |
| 43 | 43 | | K | K | K | K | |

TABLE 14-continued

Key to Kabat Numbering for Heavy Chain

| KAB # | # | TYPE | Mouse 3D6 VH | HUM 3D6 VH | KABID 045919 | VH3-23 Germ-line | Comment |
|---|---|---|---|---|---|---|---|
| 44 | 44 | | R | G | G | G | |
| 45 | 45 | | L | L | L | L | |
| 46 | 46 | | E | E | E | E | |
| 47 | 47 | | W | W | W | W | |
| 48 | 48 | | V | V | V | V | |
| 49 | 49 | | A | A | S | S | CDR contact/veneer |
| 50 | 50 | CDR2 | S | S | A | A | |
| 51 | 51 | | I | I | I | I | |
| 52 | 52 | | R | R | S | S | |
| 52A | 53 | | S | S | G | G | |
| 53 | 54 | | G | G | S | S | |
| 54 | 55 | | G | G | G | G | |
| 55 | 56 | | G | G | G | G | |
| 56 | 57 | | R | R | S | S | |
| 57 | 58 | | T | T | T | T | |
| 58 | 59 | | Y | Y | Y | Y | |
| 59 | 60 | | Y | Y | Y | Y | |
| 60 | 61 | | S | S | A | A | |
| 61 | 62 | | D | D | D | D | |
| 62 | 63 | | N | N | S | S | |
| 63 | 64 | | V | V | V | V | |
| 64 | 65 | | K | K | K | K | |
| 65 | 66 | | G | G | G | G | |
| 66 | 67 | FR3 | R | R | R | R | |
| 67 | 68 | | F | F | F | F | |
| 68 | 69 | | T | T | T | T | |
| 69 | 70 | | I | I | I | I | |
| 70 | 71 | | S | S | S | S | |
| 71 | 72 | | R | R | R | R | |
| 72 | 73 | | E | D | D | D | |
| 73 | 74 | | N | N | N | N | |
| 74 | 75 | | A | A | A | S | |
| 75 | 76 | | K | K | K | K | |
| 76 | 77 | | N | N | N | N | |
| 77 | 78 | | T | S | S | T | |
| 78 | 79 | | L | L | L | L | |
| 79 | 80 | | Y | Y | Y | Y | |
| 80 | 81 | | L | L | L | L | |
| 81 | 82 | | Q | Q | Q | Q | |
| 82 | 83 | | M | M | M | M | |
| 82A | 84 | | S | N | N | N | |
| 82B | 85 | | S | S | S | S | |
| 82C | 86 | | L | L | L | L | |
| 83 | 87 | | K | R | R | R | |
| 84 | 88 | | S | A | A | A | |
| 85 | 89 | | E | E | E | E | |
| 86 | 90 | | D | D | D | D | |
| 87 | 91 | | T | T | T | T | |
| 88 | 92 | | A | A | A | A | |
| 89 | 93 | | L | L | L | V | |
| 90 | 94 | | Y | Y | Y | Y | |
| 91 | 95 | | Y | Y | Y | Y | |
| 92 | 96 | | C | C | C | C | |
| 93 | 97 | | V | V | A | A | Packing residue, use mouse |
| 94 | 98 | | R | R | K | K | Canonical, use mouse |
| 95 | 99 | CDR3 | Y | Y | D | | |
| 96 | 100 | | D | D | N | | |
| 97 | 101 | | H | H | Y | | |
| 98 | 102 | | Y | Y | D | | |
| 99 | 103 | | S | S | F | | |
| 100 | 104 | | G | G | W | | |
| 100A | 105 | | S | S | S | | |
| 100B | 106 | | S | S | G | | |
| 100C | 107 | | — | — | T | | |
| 100D | 108 | | — | — | F | | |
| 101 | 109 | | D | D | D | | |
| 102 | 110 | | Y | Y | Y | | |
| 103 | 111 | FR4 | W | W | W | | |
| 104 | 112 | | G | G | G | | |
| 105 | 113 | | Q | Q | Q | | |
| 106 | 114 | | G | G | G | | |
| 107 | 115 | | T | T | T | | |
| 108 | 116 | | T | L | L | | |

TABLE 14-continued

Key to Kabat Numbering for Heavy Chain

| KAB # | # | Mouse 3D6 TYPE VH | HUM 3D6 VH | KABID 045919 | VH3-23 Germ-line | Comment |
|---|---|---|---|---|---|---|
| 109 | 117 | V | V | V | | |
| 110 | 118 | T | T | T | | |
| 111 | 119 | V | V | V | | |
| 112 | 120 | S | S | S | | |
| 113 | 121 | S | S | S | | |

The humanized antibodies preferably exhibit a specific binding affinity for Aβ of at least $10^7$, $10^8$, $10^9$ or $10^{10}$ $M^{-1}$. Usually the upper limit of binding affinity of the humanized antibodies for Aβ is within a factor of three, four or five of that of 3D6 (i.e., $\sim 10^9$ $M^{-1}$). Often the lower limit of binding affinity is also within a factor of three, four or five of that of 3D6.

Assembly and Expression of Humanized 3D6 VH and VL, Version 1 Briefly, for each V region, 4 large single stranded overlapping oligonucleotides were synthesized. In addition, 4 short PCR primers were synthesized for each V region to further facilitate assembly of the particular V region. The DNA sequences of the oligonucleotides employed for this purpose are shown in Table 15.

TABLE 15

DNA oligonucleotides

| DNA# | SIZE | Coding? | Sequence | comments |
|---|---|---|---|---|
| 4060 | 136 | Yes | tccgc aagct tgccg ccacc ATGGA CATGC GCGTG CCCGC CCAGC TGCTG GGCCT GCTGA TGCTG TGGGT GTCCG GCTCC TCCGG CTACG TGGTG ATGAC CCAGT CCCCC CTGTC CCTGC CCGTG ACCCC CGGCG A (SEQ ID NO: 17) | hum 3D6 VL-A |
| 4061 | 131 | No | CTGGG GGAC TGGCC GGGCT TCTGC AGCAG CCAGT TCAGG TAGGT CTTGC CGTCG GAGTC CAGCA GGGAC TGGGA GGACT TGCAG GAGAT GGAGG CGGGC TCGCC GGGGG TCACG GGCAG GGACA GGGGG G (SEQ ID NO: 18) | hum 3D6 VL-B |
| 4062 | 146 | Yes | ACCTG AACTG GCTGC TGCAG AAGCC CGGCC AGTCC CCCCA GCGCC TGATC TACCT GGTGT CCAAG CTGGA CTCCG GCGTG CCCGA CCGCT TCTCC GGCTC CGGCT CCGGC ACCGA CTTCA CCCTG AAGAT CTCCC GCGTG GAGGC C (SEQ ID NO: 19) | hum 3D6 VL-C |
| 4063 | 142 | No | aattc tagga tccac tcacg CTTGA TCTCC ACCTT GGTGC CCTGG CCGAA GGTGC GGGGG AAGTG GGTGC CCTGC AGCA GTAGT ACACG CCCAC GTCCT CGGCC TCCAC GCGGG AGATC TTCAG GGTGA AGTCG GTGCC GG (SEQ ID NO: 20) | hum 3D6 VL-D |
| 4064 | 16 | No | CTGGG GGAC TGGCC G (SEQ ID NO: 21) | hum 3D6 VL A + B back % A + T = 18.75 [3]; % C + G = 81.2 [13] Davis, Botstein, Roth Melting Temp C. 66.96 |
| 4065 | 22 | Yes | ACCTG AACTG GCTGC TGCAG AA (SEQ ID NO: 22) | hum 3D6 VL C + D forward % A + T = 45.45 [10]; % C + G = 54.55 [12] Davis, Botstein, Roth Melting Temp C. 64.54 |

TABLE 15-continued

DNA oligonucleotides

| DNA# | SIZE | Coding? | Sequence | comments |
|---|---|---|---|---|
| 4066 | 138 | Yes | acaga aagct tgccg ccacc ATGGA GTTTG GGCTG AGCTG GCTTT TTCTT GTGGC TATTT TAAAA GGTGT CCAGT GTGAG GTGCA GCTGC TGGAG TCCGG CGGCG GCCTG GTGCA GCCCG GCGGC TCCCT GCGCC TGT (SEQ ID NO: 23) | hum 3D6 VH-A |
| 4067 | 135 | No | GCCGC CGGAG CGGAT GGAGG CCACC CACTC CAGGC CCTTG CCGGG GGCCT GGCGC ACCCA GGACA TGCCG TAGTT GGAGA AGGTG AAGCC GGAGG CGGCG CAGGA CAGGC GCAGG GAGCC GCCGG GCTGC ACCAG (SEQ ID NO: 24) | hum 3D6 VH-B |
| 4068 | 142 | Yes | CTGGA GTGGG TGGCC TCCAT CCGCT CCGGC GGCGG CCGCA CCTAC TACTC CGACA ACGTG AAGGG CCGCT TCACC ATCTC CCGCG ACAAC GCCAA GAACT CCCTG TACCT GCAGA TGAAC TCCCT GCGCG CCGAG GACAC CG (SEQ ID NO: 25) | hum 3D6 VH-C |
| 4069 | 144 | No | ctgca aggat ccact caccG GAGGA CACGG TCACC AGGGT GCCCT GGCCC CAGTA GTCGG AGGAG CCGGA GTAGT GGTCG TAGCG CACGC AGTAG TACAG GGCGG TGTCC TCGGC GCGCA GGGAG TTCAT CTGCA GGTAC AGGG (SEQ ID NO: 26) | hum 3D6 VH-D |
| 4070 | 16 | No | GCCGC CGGAG CGGAT G (SEQ ID NO: 27) | hum 3D6 VH A + B back % A + T = 18.75 [3]; % C + G = 81.25 [13] Davis, Botstein, Roth Melting Temp C. 66.96 |
| 4071 | 20 | Yes | CTGGA GTGGG TGGCC TCCAT (SEQ ID NO: 28) | hum 3D6 VH C + D forward % A + T = 35.00 [7]; % C + G = 65.00 [13] Davis, Botstein, Roth Melting Temp C. 66.55 |
| 4072 | 19 | Yes | tcc gca agc ttg ccg cca c (SEQ ID NO: 29) | Hum 3D6 VL A + B Forward % A + T = 31.58 [6]; % C + G = 68.42[13] Davis, Botstein, Roth Melting Temp C. 66.64 |
| 4073 | 29 | No | aat tct agg atc cac tca cgC TTG ATC TC (SEQ ID NO: 30) | Hum 3D6 VL C + D Back % A + T = 55.17[16]; % C + G = 44.83 [13] Davis, Botstein, Roth Melting Temp C. 66.04 |
| 4074 | 23 | Yes | aca gaa agc ttg ccg cca ccA TG (SEQ ID NO: 31) | Hum 3D6 VH A + B Forward % A + T = 43.48 [10]; % C + G = 56.52 [13] Davis, Botstein, Roth Melting Temp C. 66.33 |

TABLE 15-continued

DNA oligonucleotides

| DNA# | SIZE | Coding? | Sequence | comments |
|---|---|---|---|---|
| 4075 | 22 | No | ctg caa gga tcc act cac cGG A (SEQ ID NO: 32) | Hum 3D6 VH C + D Back % A + T = 40.91 [9]; % C + G = 59.09[13] Davis, Botstein, Roth Melting Temp C. 66.40 |

The humanized light chain was assembled using PCR. DNA sequence analysis of greater than two dozen clones revealed scattered point mutations and deletions throughout the VL region with respect to the expected sequence. Analysis of the sequences indicated that clone 2.3 was amenable to repair of 2 closely spaced single nucleotide deletions in the amino-terminal region. Hence site directed mutagenesis was performed on clone pCRShum3D6v12.3 using oligonucleotides to introduce the 2 deleted nucleotides, and repair of the point mutations was confirmed by DNA sequence analysis, and the VL insert was cloned into the light chain expression vector pCMV-cK.

Assembly of humanized VH using PCR-based methods resulted in clones with gross deletions in the 5' half of the sequence. Further efforts to optimize the PCR conditions met with partial success. The clones assembled via optimized PCR conditions still had 10-20 nt deletions in the region mapping to the overlap of the A+B fragments. Consequently, an alternate strategy was employed for VH assembly utilizing DNA polymerase (T4, Klenow, and Sequenase) mediated overlap extension, followed by T4 DNA ligase to covalently join the overlapping ends. DNA sequence analysis of a subset of the clones resulting from VH assembly using the latter approach revealed scattered point mutations and deletions among the clones. Analysis of over two dozen clones revealed essentially the same pattern as illustrated for the clones. The similar results observed following first pass assembly of VH and VL clones suggests the DNA sequence errors observed resulted from automated synthesizer errors during the synthesis of the long DNAs employed for the assembly.

Humanized VH clone 2.7 was selected for site-directed mutagenesis-mediated repair of the 3 nucleotide deletions it was observed to contain.

Example XIII

Characterization of Humanized 3D6v2 Antibody

A second version of humanized 3D6 was created having each of the substitutions indicated for version 1, except for the D→Y substitution at residue 1. Substitution at this residue was performed in version 1 because the residue was identified as a CDR interacting residue. However, substitution deleted a residue which was rare for human immunoglobulins at that position. Hence, a version was created without the substitution. Moreover, non-germline residues in the heavy chain framework regions were substituted with germline residues, namely, H74=S, H77=T and H89=V. Kabat numbering for the version 2 light and heavy chains, is the same as that depicted in Tables 13 and 14, respectively, except that residue 1 of the version 2 light chain is asp (D), residue 74 of the heavy chain is ser (S), residue 77 of the heavy chain is thr (T) and residue 89 of the heavy chain is val (V). The nucleotide sequence of humanized 3D6 version 1 light and heavy chains are set forth as SEQ ID NOs: 34 and 36, respectively. The nucleotide sequence of humanized 3D6 version 2 light and heavy chains are set forth as SEQ ID NOs: 35 and 37, respectively.

Example IX

Functional Testing of Humanized 3D6 Antibodies

Binding of humanized 3D6v1 to aggregated Aβ. Functional testing of humanized 3D6v1 was conducted using conditioned media from transiently transfected COS cells. The cells were transfected with fully chimeric antibody, a mixture of either chimeric heavy chain+humanized light chain, or chimeric light chain+humanized heavy chain, and lastly, fully humanized antibody. The conditioned media was tested for binding to aggregated Aβ1-42 by ELISA assay. The humanized antibody showed good activity within experimental error, and displayed binding properties indistinguishable from the chimeric 3D6 reference sample. The results are shown in Table 16.

TABLE 16

| ng/ml | Chimeric | hu VH/ ChVL | ChVH/ HuVL | Hu VH/ HuVL |
|---|---|---|---|---|
| 690 | | | 0.867 | |
| 600 | | | | 0.895 |
| 260 | 0.83 | | | |
| 230 | | | 0.774 | |
| 200 | | | | 0.81 |
| 190 | | 0.811 | | |
| 87 | 0.675 | | | |
| 77 | | | 0.594 | |
| 67 | | | | 0.689 |
| 63 | | 0.648 | | |
| 29 | 0.45 | | | |
| 25 | | | 0.381 | |
| 22 | | | | 0.496 |
| 21 | | 0.438 | | |
| 9.6 | 0.251 | | | |
| 8.5 | | | 0.198 | |
| 7.4 | | | | 0.278 |
| 7 | | 0.232 | | |
| 3.2 | 0.129 | | | |
| 2.3 | | 0.124 | | |

To compare the binding affinities of humanized 3D6v1 and 3D6v2 antibodies, ELISA analysis was performed using aggregated Aβ as the antigen. The results show that both 3D6v1 (H1L1) and 3D6v2 (H2L2) have nearly identical Aβ binding properties (FIG. 5).

Replacement NET (rNET) analysis of h3D6v2. The rNET epitope map assay provides information about the contribution of individual residues within the epitope to the overall binding activity of the antibody. rNET analysis uses synthesized systematic single substituted peptide analogs. Binding of an antibody being tested is determined against native peptide (native antigen) and against 19 alternative "single substituted" peptides, each peptide being substituted at a first position with one of 19 non-native amino acids for that position. A profile is generated reflecting the effect of substitution at that position with the various non-native residues. Profiles are likewise generated at successive positions along the antigenic peptide. The combined profile, or epitope map, (reflecting substitution at each position with all 19 non-native residues) can then be compared to a map similarly generated for a second antibody. Substantially similar or identical maps indicate that antibodies being compared have the same or similar epitope specificity.

This analysis was performed for 3D6 and humanized 3D6, version 2. Antibodies were tested for binding against the native Aβ peptide DAEFRHDSGY (SEQ ID NO:33). Residues 1-8 were systematically substituted with each of the 19 non-native residues for that position. Maps were generated accordingly for 3D6 and h3D6v2. The results are presented in tabular form in Table 17.

TABLE 17

Aβ: replacement Net Epitope (rNET) mapping of wt3D6 and humanized 3D6

| Substitution | | Wildtype 3D6 [OD] | Humanized 3D6 [OD] |
|---|---|---|---|
| Residue 1 = | A | 0.464 | 0.643 |
| | C | 0.450 | 0.628 |
| | D | 0.577 | 0.692 |
| | E | 0.576 | 0.700 |
| | F | 0.034 | 0.062 |
| | G | 0.569 | 0.738 |
| | H | 0.054 | 0.117 |
| | I | 0.048 | 0.118 |
| | K | 0.033 | 0.057 |
| | L | 0.073 | 0.148 |
| | M | 0.039 | 0.072 |
| | N | 0.587 | 0.757 |
| | P | 0.069 | 0.144 |
| | Q | 0.441 | 0.689 |
| | R | 0.056 | 0.155 |
| | S | 0.569 | 0.762 |
| | T | 0.450 | 0.702 |
| | V | 0.057 | 0.190 |
| | W | 0.031 | 0.070 |
| | Y | 0.341 | 0.498 |
| Residue 2 = | A | 0.548 | 0.698 |
| | C | 0.553 | 0.694 |
| | D | 0.119 | 0.222 |
| | E | 0.563 | 0.702 |
| | F | 0.577 | 0.717 |
| | G | 0.527 | 0.720 |
| | H | 0.534 | 0.741 |
| | I | 0.522 | 0.722 |
| | K | 0.548 | 0.722 |
| | L | 0.482 | 0.705 |
| | M | 0.535 | 0.705 |
| | N | 0.525 | 0.735 |
| | P | 0.445 | 0.707 |
| | Q | 0.567 | 0.756 |
| | R | 0.562 | 0.719 |
| | S | 0.587 | 0.705 |
| | T | 0.552 | 0.712 |
| | V | 0.550 | 0.702 |
| | W | 0.553 | 0.701 |
| | Y | 0.547 | 0.704 |
| Residue 3 = | A | 0.038 | 0.061 |
| | C | 0.222 | 0.410 |
| | D | 0.019 | 0.027 |
| | E | 0.542 | 0.689 |
| | F | 0.034 | 0.060 |
| | G | 0.016 | 0.019 |
| | H | 0.016 | 0.020 |
| | I | 0.019 | 0.024 |

TABLE 17-continued

Aβ: replacement Net Epitope (rNET) mapping of wt3D6 and humanized 3D6

| Substitution | | Wildtype 3D6 [OD] | Humanized 3D6 [OD] |
|---|---|---|---|
| | K | 0.053 | 0.090 |
| | L | 0.019 | 0.026 |
| | M | 0.019 | 0.027 |
| | N | 0.024 | 0.032 |
| | P | 0.017 | 0.020 |
| | Q | 0.153 | 0.406 |
| | R | 0.015 | 0.023 |
| | S | 0.016 | 0.021 |
| | T | 0.015 | 0.019 |
| | V | 0.016 | 0.021 |
| | W | 0.149 | 0.304 |
| | Y | 0.016 | 0.020 |
| Residue 4 = | A | 0.016 | 0.020 |
| | C | 0.020 | 0.023 |
| | D | 0.017 | 0.020 |
| | E | 0.016 | 0.021 |
| | F | 0.557 | 0.703 |
| | G | 0.016 | 0.020 |
| | H | 0.470 | 0.723 |
| | I | 0.119 | 0.360 |
| | K | 0.015 | 0.018 |
| | L | 0.559 | 0.716 |
| | M | 0.549 | 0.725 |
| | N | 0.085 | 0.089 |
| | P | 0.030 | 0.056 |
| | Q | 0.065 | 0.110 |
| | R | 0.016 | 0.019 |
| | S | 0.026 | 0.031 |
| | T | 0.016 | 0.021 |
| | V | 0.213 | 0.494 |
| | W | 0.291 | 0.568 |
| | Y | 0.529 | 0.730 |
| Residue 5 = | A | 0.275 | 0.435 |
| | C | 0.359 | 0.635 |
| | D | 0.080 | 0.163 |
| | E | 0.115 | 0.187 |
| | F | 0.439 | 0.569 |
| | G | 0.485 | 0.679 |
| | H | 0.577 | 0.680 |
| | I | 0.510 | 0.671 |
| | K | 0.573 | 0.693 |
| | L | 0.517 | 0.691 |
| | M | 0.418 | 0.611 |
| | N | 0.476 | 0.655 |
| | P | 0.093 | 0.198 |
| | Q | 0.388 | 0.565 |
| | R | 0.613 | 0.702 |
| | S | 0.487 | 0.633 |
| | T | 0.530 | 0.639 |
| | V | 0.493 | 0.562 |
| | W | 0.393 | 0.461 |
| | Y | 0.278 | 0.230 |
| Residue 6 = | A | 0.587 | 0.707 |
| | C | 0.585 | 0.703 |
| | D | 0.584 | 0.701 |
| | E | 0.579 | 0.702 |
| | F | 0.586 | 0.704 |
| | G | 0.592 | 0.709 |
| | H | 0.596 | 0.688 |
| | I | 0.602 | 0.708 |
| | K | 0.585 | 0.691 |
| | L | 0.584 | 0.688 |
| | M | 0.583 | 0.687 |
| | N | 0.580 | 0.686 |
| | P | 0.587 | 0.705 |
| | Q | 0.570 | 0.695 |
| | R | 0.576 | 0.686 |
| | S | 0.573 | 0.689 |
| | T | 0.573 | 0.700 |
| | V | 0.588 | 0.715 |
| | W | 0.576 | 0.696 |
| | Y | 0.595 | 0.708 |

TABLE 17-continued

Aβ: replacement Net Epitope (rNET) mapping of wt3D6 and humanized 3D6

| Substitution | | Wildtype 3D6 [OD] | Humanized 3D6 [OD] |
|---|---|---|---|
| Residue 7 = | A | 0.580 | 0.688 |
| | C | 0.559 | 0.676 |
| | D | 0.573 | 0.681 |
| | E | 0.565 | 0.677 |
| | F | 0.546 | 0.668 |
| | G | 0.562 | 0.679 |
| | H | 0.557 | 0.675 |
| | I | 0.552 | 0.681 |
| | K | 0.565 | 0.685 |
| | L | 0.566 | 0.701 |
| | M | 0.562 | 0.697 |
| | N | 0.573 | 0.688 |
| | P | 0.582 | 0.678 |
| | Q | 0.563 | 0.679 |
| | R | 0.551 | 0.677 |
| | S | 0.563 | 0.674 |
| | T | 0.560 | 0.685 |
| | V | 0.563 | 0.687 |
| | W | 0.547 | 0.685 |
| | Y | 0.560 | 0.682 |
| Residue 8 = | A | 0.573 | 0.687 |
| | C | 0.583 | 0.700 |
| | D | 0.586 | 0.697 |
| | E | 0.601 | 0.701 |
| | F | 0.586 | 0.687 |
| | G | 0.569 | 0.681 |
| | H | 0.559 | 0.683 |
| | I | 0.568 | 0.686 |
| | K | 0.557 | 0.698 |
| | L | 0.570 | 0.686 |
| | M | 0.571 | 0.693 |
| | N | 0.573 | 0.700 |
| | P | 0.574 | 0.694 |
| | Q | 0.590 | 0.703 |
| | R | 0.589 | 0.699 |
| | S | 0.599 | 0.719 |
| | T | 0.586 | 0.689 |
| | V | 0.578 | 0.688 |
| | W | 0.567 | 0.687 |
| | Y | 0.574 | 0.680 |

Notably, the profiles are virtually identical for 3D6 and h3D6v2 when one looks at the substitutions at each position (i.e., the values fluctuate in an identical manner when comparing the data in column 1 (3D6) versus column 2 (h3D6v2). These data demonstrate that the specificity of h3D6v2 is preserved, as the h3D6v2 rNET epitope map is virtually identical to m3D6 using both Aβ residues 1-4 and 5-8.

Immunohistochemistry on PDAPP brain sections demonstrates specificity of h3D6v1 antibody. Humanized 3D6v1 antibody recognized Aβ in cryostat prepared brain sections from PDAPP mice. Humanized 3D6v1 and PK1614 both bound to PDAPP plaques in the same dose response fashion, as measured by the amount of fluorescence (quantitated in pixels) per slide versus the amount of antibody used to stain the tissue (FIG. 6). Identical anti-human secondary antibodies were used in this experiment. Sectioning, staining, and image procedures were previously described. In identical experiments, image analysis of h3D6v2 staining on PDAPP and AD brain sections revealed that h3D6v2 recognizes Aβ plaques in a similar manner to 3D6v1 (e.g., highly decorated plaques).

Competitive binding analysis of h3D6. The ability of h3D6 antibodies v1 and v2 to compete with murine 3D6 was measured by ELISA using a biotinylated 3D6 antibody. Competitive binding analysis revealed that h3D6v1, h3D6v2, and chimeric PK1614 can all compete with m3D6 to bind Aβ (FIG. 7). h3D6v1 and h3D6v2 were identical in their ability to compete with 3D6 to Aβ. The 10D5 antibody was used as a negative control, as it has a different binding epitope than 3D6. BIAcore analysis also revealed a high affinity of h3D6v1 and h3D6v2 for Aβ (Table 18).

TABLE 18

Affinity Measurements of Aβ Antibodies Using BIAcore Technology

| Antibody | ka1 (1/Ms) | kd1 (1/s) | Kd (nM) |
|---|---|---|---|
| Mu 3D6 | 4.06E+05 | 3.57E−04 | 0.88 |
| Chimeric 3D6 | 4.58E+05 | 3.86E−04 | 0.84 |
| Hu 3D6v1 | 1.85E+05 | 3.82E−04 | 2.06 |
| Hu 3D6v2 | 1.70E+05 | 3.78E−04 | 2.24 |

In comparison to 3D6, which has a Kd of 0.88 nM, both h3D6v1 and h3D6v2 had about a 2 to 3 fold less binding affinity, measured at 2.06 nM and 2.24 nM for h3D6v1 and h3D6v2, respectively. The ELISA competitive binding assay revealed an approximate 6-fold less binding affinity for h3D6v1 and h3D6v2. Typically humanized antibodies lose about 3-4 fold in binding affinity in comparison to their murine counterparts. Therefore, a loss of about 3 fold (average of ELISA and BIAcore results) for h3D6v1 and h3D6v2 is within the accepted range.

Ex vivo assay using h3D6v2 antibody. The ability of h3D6v2 to stimulate microglial cells was tested through an ex vivo phagocytosis assay (FIG. 8). h3D6v2 was as effective as chimeric 3D6 at inducing phagocytosis of Aβ aggregates from PDAPP mouse brain tissue. IgG was used as a negative control in this experiment because it is incapable of binding Aβ and therefore cannot induce phagocytosis.

In vivo brain localization of h3D6. $^{125}$I labeled h3D6v2, m3D6, and antibody DAE13 were each IV-injected into 14 individual PDAPP mice in separate experiments. Mice were sacrificed after Day 7 and perfused for further analysis. Their brain regions were dissected and measured for $^{125}$I activity in specific brain regions. Radiolabel activity in the brain was compared with activity in serum samples. Results are set forth in Tables 19 and 20, for serum and brain regions, respectively.

TABLE 19

| m3D6 | DAE13 | Hu3D6 |
|---|---|---|
| 30389.1 | 17463.9 | 40963.8 |
| 12171 | 13200.6 | 24202.2 |
| 3418.2 | 36284.7 | 12472.4 |
| 18678.9 | 421.3 | 33851.8 |
| 27241 | 19702 | 27187.3 |
| 26398.8 | 24855.8 | 29016.9 |
| 27924.8 | 29287.4 | 33830.7 |
| 12008.4 | 12733.1 | 26734.9 |
| 29487.8 | 27722.5 | 30144.5 |
| 25498.6 | 30460.7 | 35126.9 |
| 9652 | 23320.1 | 28414.8 |
| 24599.3 | 7119.1 | 16956.1 |
| 29240 | 28093.5 | 18190.7 |
| 11922.7 | 24659.7 | 25671.4 |
| 17443.1 | 26748.9 | |

TABLE 20

| m3D6 | | | DAE13 | | | Hu3D6 (H2L2) | | |
|---|---|---|---|---|---|---|---|---|
| cere | cort | hipp | cere | cort | hipp | cere | cort | hipp |
| 1991.9 | 1201.1 | 4024 | 1277.5 | 2522.9 | 5711.9 | 2424.6 | 3759.4 | 11622 |
| 238.9 | 746.1 | 2523 | 502.5 | 2123.5 | 6965.8 | 1509.8 | 2274.9 | 7018.2 |
| 645.9 | 603 | 1241.1 | 2325 | 3528.2 | 7801.6 | 500 | 2265.9 | 5316.3 |
| 1000 | 2508.2 | 4644.2 | 232.7 | 849.8 | 1891.9 | 2736.2 | 5703.7 | 10395.5 |
| 1266.9 | 3737.9 | 7975.8 | 891.6 | 2621 | 8245.2 | 1192.2 | 3188 | 10170 |
| 1422 | 2398.7 | 7731.1 | 1102.6 | 2087.5 | 7292.3 | 2269.4 | 3481.4 | 9621.6 |
| 1700.4 | 2154.4 | 7124.1 | 1650.6 | 3488.4 | 10284.8 | 1526.7 | 3028 | 8331.3 |
| 542.5 | 812.4 | 2456.8 | 712.9 | 2318.5 | 6643.3 | 1538.1 | 4194.1 | 11244.8 |
| 1309 | 3010.5 | 8693.5 | 1172.9 | 1953.6 | 7363 | 1245.7 | 1699.4 | 6831.2 |
| 1372.2 | 997.5 | 2425.4 | 1067.9 | 3697.2 | 12280.7 | 2708.8 | 2789 | 7887.4 |
| 778.6 | 1291.9 | 5654.4 | 1952.2 | 2120.7 | 6412.7 | 2251.3 | 3897.5 | 11121.5 |
| 1199.3 | 1683.4 | 4887.3 | 1005.2 | 1852.5 | 5121.4 | 1529.6 | 1772.2 | 7986.9 |
| 1021.8 | 3234.5 | 8036.2 | 961.5 | 3382.9 | 8473.1 | 644.1 | 1663.4 | 5056.5 |
| 742.1 | 1056.7 | 3405.2 | 852.3 | 1943.2 | 6717.4 | 1516.4 | 1620.6 | 9888 |
| 1273.7 | 1320.8 | 4262.6 | 997.5 | 3065.7 | 10213.1 | | | |

The data show that h3D6v2 localized to the brain, and was particularly concentrated in the hippocampal region where Aβ is known to aggregate. Brain counts for m3D6 and DAE13 were comparable to h3D6v2. All three antibodies were able to cross the blood barrier as demonstrated by Aβ plaque binding in vivo.

Example X

Cloning and Sequencing of the Mouse 10D5 Variable Regions

Cloning and Sequence Analysis of 10D5 VH. The VH and VL regions of 10D5 from hybridoma cells were cloned by RT-PCR using 5' RACE procedures. The nucleotide sequence (SEQ ID NO:13) and deduced amino acid sequence (SEQ ID NO:14) derived from two independent cDNA clones encoding the presumed 10D5 VL domain, are set forth in Table 21 and FIG. 9. The nucleotide sequence (SEQ ID NO:15) and deduced amino acid sequence (SEQ ID NO:16) derived from two independent cDNA clones encoding the presumed 10D5 VH domain, are set forth in Table 22 and FIG. 10. The 10D5 VL and VH sequences meet the criteria for functional V regions in so far as they contain a contiguous ORF from the initiator methionine to the C-region, and share conserved residues characteristic of immunoglobulin V region genes.

TABLE 21

Mouse 10D5 VL DNA sequence

```
ATGAAGTTGCCTGTTAGGCTGTTGGTACTGATGTTCTGGATTCCTGCTTCCAGCAGTGATGT    (SEQ ID NO: 13)

TTTGATGACCCAAACTCCACTCTCCCTGCCTGTCAGTCTTGGAGATCAAGCCTCCATCTCTT

GCAGATCTAGTCAGAACATTATACATAGTAATGGAAACACCTATTTAGAATGGTACCTGCAG

AAACCAGGCCAGTCTCCAAAGCTCCTGATCTACAAAGTTTCCAACCGATTTTCTGGGGTCCC

AGACAGGTTCAGTGGCAGTGGATCAGGGACAGATTTCACACTCAAGATCAAGAAAGTGGAGG

CTGAGGATCTGGGAATTTATTACTGCTTTCAAGGTTCACATGTTCCGCTCACGTTCGGTGCT

GGGACCAAGCTGGAGCTGGAA
```

*Leader peptide underlined

TABLE 22

Mouse 10D5 VH DNA sequence.

```
ATGGACAGGCTTACTTCCTCATTCCTGCTGCTGATTGTCCCTGCATATGTCCTGTCCCAGGC    (SEQ ID NO: 15)

TACTCTGAAAGAGTCTGGCCCTGGAATATTGCAGTCCTCCCAGACCCTCAGTCTGACTTGTT

CTTTCTCTGGGTTTTCACTGAGCACTTCTGGTATGGGAGTGAGCTGGATTCGTCAGCCTTCA

GGAAAGGGTCTGGAGTGGCTGGCACACATTTACTGGGATGATGACAAGCGCTATAACCCATC

CCTGAAGAGCCGGCTCACAATCTCCAAGGATACCTCCAGAAAGCAGGTATTCCTCAAGATCA

CCAGTGTGGACCCTGCAGATACTGCCACATACTACTGTGTTCGAAGGCCCATTACTCCGGTA

CTAGTCGATGCTATGGACTACTGGGGTCAAGGAACCTCAGTCACCGTCTCCTCA
```

*Leader peptide underlined.

Example XI

Efficacy of mAb 3D6 on Various Neuropathological Endpoints in PDAPP Mice

This Example describes the efficacy of murine mAb 3D6 on various neuropathological endpoints. A comparison is made between passive immunization with 3D6 (at varying doses) and active immunization with an Aβ peptide.

Immunizations

PDAPP mice were passively immunized with mAb 3D6 at three different doses, 10 mg/kg, 1 mg/kg and 10 mg/kg once a month (1×4). An unrelated IgGγ2a antibody (TY 11/15) and PBS injections served as controls. Active immunization with Aβ peptide served as a comparison. Between 20 and 35 animals were analyzed in each group.

The neuropathological endpoints assayed include amyloid burden and neuritic burden.

Amyloid Burden

The extent of the frontal cortex occupied by amyloid deposits was determined by immunostaining with 3D6 followed by quantitative image analysis. The results of this analysis are shown in Table 6. Each of the immunotherapies led to a significant reduction of amyloid burden.

Neuritic Burden

Neuritic burden following passive immunization with 3D6 was determined in PDAPP mice by immunostaining of brain sections with anti-APP antibody 8E5 followed by quantitative image analysis. Neuritic dystrophy is indicated by the appearance of dystrophic neurites (e.g., neurites with a globular appearance) located in the immediate vicinity of amyloid plaques. The results of this analysis are shown in Table 7. 3D6 (IgGγ2a isotype, recognizing Aβ 1-5) did not significantly reduce neuritic burden as compared to active immunization with Aβ peptide. Previously, it had been observed that 10D5 (IgGγ1 isotype recognizing Aβ 3-7) was unable to significantly reduce neuritic burden.

dosages to different patients starting from about 0.01 the level of presumed efficacy, and increasing by a factor of three until a level of about 10 times the effective mouse dosage is reached.

A phase II trial is performed to determine therapeutic efficacy. Patients with early to mid Alzheimer's Disease defined using Alzheimer's disease and Related Disorders Association (ADRDA) criteria for probable AD are selected. Suitable patients score in the 12-26 range on the Mini-Mental State Exam (MMSE). Other selection criteria are that patients are likely to survive the duration of the study and lack complicating issues such as use of concomitant medications that may interfere. Baseline evaluations of patient function are made using classic psychometric measures, such as the MMSE, and the ADAS, which is a comprehensive scale for evaluating patients with Alzheimer's Disease status and function. These psychometric scales provide a measure of progression of the Alzheimer's condition. Suitable qualitative life scales can also be used to monitor treatment. Disease progression can also be monitored by MRI. Blood profiles of patients can also be monitored including assays of immunogen-specific antibodies and T-cells responses.

Following baseline measures, patients begin receiving treatment. They are randomized and treated with either therapeutic agent or placebo in a blinded fashion. Patients are monitored at least every six months. Efficacy is determined by a significant reduction in progression of a treatment group relative to a placebo group.

A second phase II trial is performed to evaluate conversion of patients from non-Alzheimer's Disease early memory loss, sometimes referred to as age-associated memory impairment (AAMI) or mild cognitive impairment (MCI), to probable Alzheimer's disease as defined as by ADRDA criteria. Patients with high risk for conversion to Alzheimer's Disease are selected from a non-clinical population by screening reference populations for early signs of memory loss or other difficulties associated with pre-Alzheimer's symptomatol-

TABLE 23

Frontal Cortex Amyloid Burden

|  | PBS | TY 11/15 | 3D6, 10 mg/kg | 3D6, 1 mg/kg | 3D6, 10 mg/kg/4 wks. | Active |
|---|---|---|---|---|---|---|
| N | 31 | 30 | 29 | 31 | 32 | 24 |
| Median (% AB) | 15.182297 | 13.303288 | 0.865671 | 2.286513 | 1.470956 | 2.162772 |
| Range | 0.160-31.961 | 0-61.706 | 0-7.064 | 0.077-63.362 | 0-10.688 | 0-30.715 |
| p Value (*M-W) |  | .9425 ns | ***.0001 | ***<.0001 | ***<.0001 | ***.0004 |
| % Change | N/A | 12% | 94% | 85% | 90% | 86% |

TABLE 24

Frontal Cortex Neuritic Burden

|  | PBS | TY 11/15 | 3D6, 10 mg/kg | 3D6, 1 mg/kg | 3D6, 10 mg/kg/4 wks. | Active |
|---|---|---|---|---|---|---|
| N | 31 | 30 | 29 | 31 | 32 | 24 |
| Median (% NB) | 0.3946 | 0.3958 | 0.4681 | 0.3649 | 0.4228 | 0.2344 |
| Range | 0-1.3828 | 0-2.6800 | 0-1.3098 | 0-1.5760 | 0-1.8215 | 0-1.1942 |
| p Value (*M-W) |  | .8967 ns | .9587 ns | .6986 ns | >.9999 | ***.0381 |
| % Change |  | 0% | 0% | 7% | 0% | 41% |

The characterization of various neuropathological endpoints in the PDAPP mouse model of Alzheimer's disease may assist the skilled artisan in designing appropriate human therapeutic immunization protocols.

Example XII

Prevention and Treatment of Human Subjects

A single-dose phase I trial is performed to determine safety in humans. A therapeutic agent is administered in increasing ogy, a family history of Alzheimer's Disease, genetic risk factors, age, sex, and other features found to predict high-risk for Alzheimer's Disease. Baseline scores on suitable metrics including the MMSE and the ADAS together with other metrics designed to evaluate a more normal population are collected. These patient populations are divided into suitable groups with placebo comparison against dosing alternatives with the agent. These patient populations are followed at intervals of about six months, and the endpoint for each patient is whether or not he or she converts to probable Alzheimer's Disease as defined by ADRDA criteria at the end of the observation.

General Materials and Methods

A. Preparation of Polyclonal and Monoclonal Aβ Antibodies

The anti-Aβ polyclonal antibody was prepared from blood collected from two groups of animals. The first group consisted of 100 female Swiss Webster mice, 6 to 8 weeks of age. They were immunized on days 0, 15, and 29 with 100 μg of AN1792 combined with CFA/IFA. A fourth injection was given on day 36 with one-half the dose of AN1792. Animals were exsanguinated upon sacrifice at day 42, serum was prepared and the sera were pooled to create a total of 64 ml. The second group consisted of 24 female mice isogenic with the PDAPP mice but nontransgenic for the human APP gene, 6 to 9 weeks of age. They were immunized on days 0, 14, 28 and 56 with 100 μg of AN1792 combined with CFA/IFA. These animals were also exsanguinated upon sacrifice at day 63, serum was prepared and pooled for a total of 14 ml. The two lots of sera were pooled. The antibody fraction was purified using two sequential rounds of precipitation with 50% saturated ammonium sulfate. The final precipitate was dialyzed against PBS and tested for endotoxin. The level of endotoxin was less than 1 EU/mg.

The anti-Aβ monoclonal antibodies were prepared from ascites fluid. The fluid was first delipidated by the addition of concentrated sodium dextran sulfate to ice-cold ascites fluid by stirring on ice to a reach a final concentration of 0.238%. Concentrated $CaCl_2$ was then added with stirring to reach a final concentration of 64 mM. This solution was centrifuged at 10,000×g and the pellet was discarded. The supernatant was stirred on ice with an equal volume of saturated ammonium sulfate added dropwise. The solution was centrifuged again at 10,000×g and the supernatant was discarded. The pellet was resuspended and dialyzed against 20 mM Tris-HCl, 0.4 M NaCl, pH 7.5. This fraction was applied to a Pharmacia FPLC Sepharose Q Column and eluted with a reverse gradient from 0.4 M to 0.275 M NaCl in 20 mM Tris-HCl, pH 7.5.

The antibody peak was identified by absorbance at 280 nm and appropriate fractions were pooled. The purified antibody preparation was characterized by measuring the protein concentration using the BCA method and the purity using SDS-PAGE. The pool was also tested for endotoxin. The level of endotoxin was less than 1 EU/mg. titers, titers less than 100 were arbitrarily assigned a titer value of 25.

B. Measurement of Antibody Titers

Mice were bled by making a small nick in the tail vein and collecting about 200 μl of blood into a microfuge tube. Guinea pigs were bled by first shaving the back hock area and then using an 18 gauge needle to nick the metatarsal vein and collecting the blood into microfuge tubes. Blood was allowed to clot for one hr at room temperature (RT), vortexed, then centrifuged at 14,000×g for 10 min to separate the clot from the serum. Serum was then transferred to a clean microfuge tube and stored at 4° C. until titered.

Antibody titers were measured by ELISA. 96-well microtiter plates (Costar EIA plates) were coated with 100 μl of a solution containing either 10 μg/ml either Aβ42 or SAPP or other antigens as noted in each of the individual reports in Well Coating Buffer (0.1 M sodium phosphate, pH 8.5, 0.1% sodium azide) and held overnight at RT. The wells were aspirated and sera were added to the wells starting at a 1/100 dilution in Specimen Diluent (0.014 M sodium phosphate, pH 7.4, 0.15 M NaCl, 0.6% bovine serum albumin, 0.05% thimerosal). Seven serial dilutions of the samples were made directly in the plates in three-fold steps to reach a final dilution of 1/218,700. The dilutions were incubated in the coated-plate wells for one hr at RT. The plates were then washed four times with PBS containing 0.05% Tween 20. The second antibody, a goat anti-mouse Ig conjugated to horseradish peroxidase (obtained from Boehringer Mannheim), was added to the wells as 100 μl of a 1/3000 dilution in Specimen Diluent and incubated for one hr at RT. Plates were again washed four times in PBS, Tween 20. To develop the chromogen, 100 μl of Slow TMB (3,3',5,5'-tetramethyl benzidine obtained from Pierce Chemicals) was added to each well and incubated for 15 min at RT. The reaction was stopped by the addition of 25 μl of 2 M $H_2SO_4$. The color intensity was then read on a Molecular Devices Vmax at (450 nm-650 nm).

Titers were defined as the reciprocal of the dilution of serum giving one half the maximum OD. Maximal OD was generally taken from an initial 1/100 dilution, except in cases with very high titers, in which case a higher initial dilution was necessary to establish the maximal OD. If the 50% point fell between two dilutions, a linear extrapolation was made to calculate the final titer. To calculate geometric mean antibody titers, titers less than 100 were arbitrarily assigned a titer value of 25.

C. Brain Tissue Preparation

After euthanasia, the brains were removed and one hemisphere was prepared for immunohistochemical analysis, while three brain regions (hippocampus, cortex and cerebellum) were dissected from the other hemisphere and used to measure the concentration of various Aβ proteins and APP forms using specific ELISAs (Johnson-Wood et al., supra).

Tissues destined for ELISAs were homogenized in 10 volumes of ice-cold guanidine buffer (5.0 M guanidine-HCl, 50 mM Tris-HCl, pH 8.0). The homogenates were mixed by gentle agitation using an Adams Nutator (Fisher) for three to four hr at RT, then stored at −20° C. prior to quantitation of Aβ and APP. Previous experiments had shown that the analytes were stable under this storage condition, and that synthetic Aβ protein (Bachem) could be quantitatively recovered when spiked into homogenates of control brain tissue from mouse littermates (Johnson-Wood et al., supra).

D. Measurement of Aβ Levels

The brain homogenates were diluted 1:10 with ice cold Casein Diluent (0.25% casein, PBS, 0.05% sodium azide, 20 μg/ml aprotinin, 5 mM EDTA pH 8.0, 10 μg/ml leupeptin) and then centrifuged at 16,000×g for 20 min at 4° C. The synthetic Aβ protein standards (1-42 amino acids) and the APP standards were prepared to include 0.5 M guanidine and 0.1% bovine serum albumin (BSA) in the final composition. The "total" Aβ sandwich ELISA utilizes monoclonal antibody monoclonal antibody 266, specific for amino acids 13-28 of Aβ (Seubert et al., supra), as the capture antibody, and biotinylated monoclonal antibody 3D6, specific for amino acids 1-5 of Aβ (Johnson-Wood et al., supra), as the reporter antibody. The 3D6 monoclonal antibody does not recognize secreted APP or full-length APP, but detects only Aβ species with an amino-terminal aspartic acid. This assay has a lower limit of sensitivity of 50 ng/ml (11 nM) and shows no cross-reactivity to the endogenous murine Aβ protein at concentrations up to 1 ng/ml (Johnson-Wood et al., supra).

The Aβ1-42 specific sandwich ELISA employs mAβ 21F12, specific for amino acids 33-42 of Aβ (Johnson-Wood, et al. supra), as the capture antibody. Biotinylated mAβ 3D6 is also the reporter antibody in this assay which has a lower limit of sensitivity of about 125 μg/ml (28 μM, Johnson-Wood et al., supra). For the Aβ ELISAs, 100 μl of either mAβ 266 (at 10 μg/ml) or mAβ 21F12 at (5 μg/ml) was coated into the wells of 96-well immunoassay plates (Costar) by overnight incubation at RT. The solution was removed by aspiration and the wells were blocked by the addition of 200 µl of 0.25% human serum albumin in PBS buffer for at least 1 hr at RT. Blocking solution was removed and the plates were stored desiccated at 4° C. until used. The plates were rehydrated with Wash Buffer [Tris-buffered saline (0.15 M NaCl, 0.01 M Tris-HCl, pH 7.5), plus 0.05% Tween 20] prior to use. The samples and standards were added in triplicate aliquots of 100 µl per well and then incubated overnight at 4° C. The plates were washed at least three times with Wash Buffer between each step of the assay. The biotinylated mAβ 3D6, diluted to 0.5 µg/ml in Casein Assay Buffer (0.25% casein, PBS, 0.05% Tween 20, pH 7.4), was added and incubated in the wells for 1 hr at RT. An avidin-horseradish peroxidase conjugate, (Avidin-HRP obtained from Vector, Burlingame, Calif.), diluted 1:4000 in Casein Assay Buffer, was added to the wells for 1 hr at RT. The colorimetric substrate, Slow TMB-ELISA (Pierce), was added and allowed to react for 15 minutes at RT, after which the enzymatic reaction was stopped by the addition of 25 µl 2 NH2SO4. The reaction product was quantified using a Molecular Devices Vmax measuring the difference in absorbance at 450 nm and 650 nm.

E. Measurement of APP Levels

Two different APP assays were utilized. The first, designated APP-α/FL, recognizes both APP-alpha (α) and full-length (FL) forms of APP. The second assay is specific for APP-α. The APP-α/FL assay recognizes secreted APP including the first 12 amino acids of Aβ. Since the reporter antibody (2H3) is not specific to the α-clip-site, occurring between amino acids 612-613 of $APP^{695}$ (Esch et al., Science 248:1122-1124 (1990)); this assay also recognizes full length APP (APP-FL). Preliminary experiments using immobilized APP antibodies to the cytoplasmic tail of APP-FL to deplete brain homogenates of APP-FL suggest that approximately 30-40% of the APP-α/FL APP is FL (data not shown). The capture antibody for both the APP-α/FL and APP-α assays is mAb 8E5, raised against amino acids 444 to 592 of the $APP^{695}$ form (Games et al., supra). The reporter mAb for the APP-α/FL assay is mAb 2H3, specific for amino acids 597-608 of $APP^{695}$ (Johnson-Wood et al., supra) and the reporter antibody for the APP-α assay is a biotinylated derivative of mAb 16H9, raised to amino acids 605 to 611 of APP. The lower limit of sensitivity of the APP-αFL assay is about 1 ng/ml (150 µM) (Johnson-Wood et al.) and that of the APP-α specific assay is 22 ng/ml (0.3 nM). For both APP assays, mAb 8E5 was coated onto the wells of 96-well EIA plates as described above for mAb 266. Purified, recombinant secreted APP-α was used as the reference standard for the APP-α assay and the APP-α/FL assay (Esch et al., supra). The brain homogenate samples in 5 M guanidine were diluted 1:10 in ELISA Specimen Diluent (0.014 M phosphate buffer, pH 7.4, 0.6% bovine serum albumin, 0.05% thimerosal, 0.5 M NaCl, 0.1% NP40). They were then diluted 1:4 in Specimen Diluent containing 0.5 M guanidine. Diluted homogenates were then centrifuged at 16,000×g for 15 seconds at RT. The APP standards and samples were added to the plate in duplicate aliquots and incubated for 1.5 hr at RT. The biotinylated reporter antibody 2H3 or 16H9 was incubated with samples for 1 hr at RT. Streptavidin-alkaline phosphatase (Boehringer Mannheim), diluted 1:1000 in specimen diluent, was incubated in the wells for 1 hr at RT. The fluorescent substrate 4-methylumbellipheryl-phosphate was added for a 30-min RT incubation and the plates were read on a Cytofluor™ 2350 fluorimeter (Millipore) at 365 nm excitation and 450 nm emission.

F. Immunohistochemistry

Brains were fixed for three days at 40 C in 4% paraformaldehyde in PBS and then stored from one to seven days at 4° C. in 1% paraformaldehyde, PBS until sectioned. Forty-micron-thick coronal sections were cut on a vibratome at RT and stored in cryoprotectant (30% glycerol, 30% ethylene glycol in phosphate buffer) at −20° C. prior to immunohistochemical processing. For each brain, six sections at the level of the dorsal hippocampus, each separated by consecutive 240 µm intervals, were incubated overnight with one of the following antibodies: (1) a biotinylated anti-Aβ (mAb, 3D6, specific for human Aβ) diluted to a concentration of 2 µg/ml in PBS and 1% horse serum; or (2) a biotinylated mAb specific for human APP, 8E5, diluted to a concentration of 3 µg/ml in PBS and 1.0% horse serum; or (3) a mAb specific for glial fibrillary acidic protein (GFAP; Sigma Chemical Co.) diluted 1:500 with 0.25% Triton X-100 and 1% horse serum, in Tris-buffered saline, pH 7.4 (TBS); or (4) a mAb specific for CD11b, MAC-1 antigen, (Chemicon International) diluted 1:100 with 0.25% Triton X-100 and 1% rabbit serum in TBS; or (5) a mAb specific for MHC II antigen, (Pharmingen) diluted 1:100 with 0.25% Triton X-100 and 1% rabbit serum in TBS; or (6) a rat mAb specific for CD 43 (Pharmingen) diluted 1:100 with 1% rabbit serum in PBS or (7) a rat mAb specific for CD 45RA (Pharmingen) diluted 1:100 with 1% rabbit serum in PBS; or (8) a rat monoclonal Aβ specific for CD 45RB (Pharmingen) diluted 1:100 with 1% rabbit serum in PBS; or (9) a rat monoclonal Aβ specific for CD 45 (Pharmingen) diluted 1:100 with 1% rabbit serum in PBS; or (10) a biotinylated polyclonal hamster Aβ specific for CD3e (Pharmingen) diluted 1:100 with 1% rabbit serum in PBS or (11) a rat mAb specific for CD3 (Serotec) diluted 1:200 with 1% rabbit serum in PBS; or with (12) a solution of PBS lacking a primary antibody containing 1% normal horse serum.

Sections reacted with antibody solutions listed in 1,2 and 6-12 above were pretreated with 1.0% Triton X-100, 0.4% hydrogen peroxide in PBS for 20 min at RT to block endogenous peroxidase. They were next incubated overnight at 4° C. with primary antibody. Sections reacted with 3D6 or 8E5 or CD3e mAbs were then reacted for one hr at RT with a horseradish peroxidase-avidin-biotin-complex with kit components "A" and "B" diluted 1:75 in PBS (Vector Elite Standard Kit, Vector Labs, Burlingame, Calif.). Sections reacted with antibodies specific for CD 45RA, CD 45RB, CD 45, CD3 and the PBS solution devoid of primary antibody were incubated for 1 hour at RT with biotinylated anti-rat IgG (Vector) diluted 1:75 in PBS or biotinylated anti-mouse IgG (Vector) diluted 1:75 in PBS, respectively. Sections were then reacted for one hr at RT with a horseradish peroxidase-avidin-biotin-complex with kit components "A" and "B" diluted 1:75 in PBS (Vector Elite Standard Kit, Vector Labs, Burlingame, Calif.).

Sections were developed in 0.01% hydrogen peroxide, 0.05% 3,3'-diaminobenzidine (DAB) at RT. Sections destined for incubation with the GFAP-, MAC-1- AND MHC II-specific antibodies were pretreated with 0.6% hydrogen peroxide at RT to block endogenous peroxidase then incubated overnight with the primary antibody at 4° C. Sections reacted with the GFAP antibody were incubated for 1 hr at RT with biotinylated anti-mouse IgG made in horse (Vector Laboratories; Vectastain Elite ABC Kit) diluted 1:200 with TBS. The sections were next reacted for one hr with an avidin-biotin-peroxidase complex (Vector Laboratories; Vectastain Elite ABC Kit) diluted 1:1000 with TBS. Sections incubated with the MAC-1- or MHC II-specific monoclonal antibody as the primary antibody were subsequently reacted for 1 hr at RT with biotinylated anti-rat IgG made in rabbit diluted 1:200 with TBS, followed by incubation for one hr with avidin-biotin-peroxidase complex diluted 1:1000 with TBS. Sections incubated with GFAP-, MAC-1- and MHC II-specific antibodies were then visualized by treatment at RT with 0.05% DAB, 0.01% hydrogen peroxide, 0.04% nickel chloride, TBS for 4 and II min, respectively.

Immunolabeled sections were mounted on glass slides (VWR, Superfrost slides), air dried overnight, dipped in Propar (Anatech) and overlaid with coverslips using Permount (Fisher) as the mounting medium.

To counterstain Aβ plaques, a subset of the GFAP-positive sections were mounted on Superfrost slides and incubated in aqueous 1% Thioflavin S (Sigma) for 7 min following immunohistochemical processing. Sections were then dehydrated and cleared in Propar, then overlaid with coverslips mounted with Permount.

G. Image Analysis

A Videometric 150 Image Analysis System (Oncor, Inc., Gaithersburg, Md.) linked to a Nikon Microphot-FX microscope through a CCD video camera and a Sony Trinitron monitor was used for quantification of the immunoreactive slides. The image of the section was stored in a video buffer and a color- and saturation-based threshold was determined to select and calculate the total pixel area occupied by the immunolabeled structures. For each section, the hippocampus was manually outlined and the total pixel area occupied by the hippocampus was calculated. The percent amyloid burden was measured as: (the fraction of the hippocampal area containing Aβ deposits immunoreactive with mAb 3D6)×100. Similarly, the percent neuritic burden was measured as: (the fraction of the hippocampal area containing dystrophic neurites reactive with monoclonal antibody 8E5)×100. The C-Imaging System (Compix, Inc., Cranberry Township, Pa.) operating the Simple 32 Software Application program was linked to a Nikon Microphot-FX microscope through an Optronics camera and used to quantitate the percentage of the retrospenial cortex occupied by GFAP-positive astrocytes and MAC-1- and MHC II-positive microglia. The image of the imdwmunoreacted section was stored in a video buffer and a monochrome-based threshold was determined to select and calculate the total pixel area occupied by immunolabeled cells. For each section, the retrosplenial cortex (RSC) was manually outlined and the total pixel area occupied by the RSC was calculated. The percent astrocytosis was defined as: (the fraction of RSC occupied by GFAP-reactive astrocytes)×100. Similarly, percent microgliosis was defined as: (the fraction of the RSC occupied by MAC-1- or MHC II-reactive microglia)×100. For all image analyses, six sections at the level of the dorsal hippocampus, each separated by consecutive 240 μm intervals, were quantitated for each animal. In all cases, the treatment status of the animals was unknown to the observer.

Although the foregoing invention has been described in detail for purposes of clarity of understanding, it will be obvious that certain modifications may be practiced within the scope of the appended claims. All publications and patent documents cited herein, as well as text appearing in the figures and sequence listing, are hereby incorporated by reference in their entirety for all purposes to the same extent as if each were so individually denoted.

From the foregoing it will be apparent that the invention provides for a number of uses. For example, the invention provides for the use of any of the antibodies to Aβ described above in the treatment, prophylaxis or diagnosis of amyloidogenic disease, or in the manufacture of a medicament or diagnostic composition for use in the same.

We claim:

1. A method of lessening the severity of Alzheimer's disease in the brain of a patient comprising administering a humanized immunoglobulin that binds to Aβ to a patient having or at risk of the disease thereby lessening the severity of the disease, wherein the humanized antibody comprises:
   a humanized immunoglobulin light chain comprising (i) three variable region complementarity determining regions (CDRs) from the 3D6 immunoglobulin light chain,
   a humanized immunoglobulin heavy chain comprising (i) three variable region complementarity determining regions (CDRs) from the 3D6 immunoglobulin heavy chain,
   wherein 3D6 is an antibody of American Type Culture Collection deposit PTA-5130.

2. The method of claim 1, wherein at least one light or heavy chain variable region framework residue is substituted with the corresponding amino acid residue from the mouse 3D6 light or heavy chain variable region, wherein the framework residue is selected from the group consisting of:
   (a) a residue that non-covalently binds antigen directly;
   (b) a residue adjacent to a CDR;
   (c) a CDR-interacting residue; and
   (d) a residue participating in the VL-VH interface.

3. The method of claim 1, wherein the patient has the disease.

4. The method of claim 1, wherein the humanized immunoglobulin is administered intravenously or subcutaneously.

5. A method of reducing plaque burden in the brain of a patient having Alzheimer's disease comprising administering a humanized immunoglobulin that binds to Aβ to the patient thereby reducing plaque burden, wherein the humanized antibody comprises:
   a humanized immunoglobulin light chain comprising (i) three variable region complementarity determining regions (CDRs) from the 3D6 immunoglobulin light chain variable region sequence set forth as SEQ ID NO:2, and (ii) a variable framework region from a human acceptor immunoglobulin light chain sequence, provided that at least one framework residue is substituted with the corresponding amino acid residue from the mouse 3D6 light chain variable region sequence, wherein the framework residue is selected from the group consisting of:
   (a) a residue that non-covalently binds antigen directly;
   (b) a residue adjacent to a CDR;
   (c) a CDR-interacting residue; and
   (d) a residue participating in the VL-VH interface; and
   a humanized immunoglobulin heavy chain comprising (i) three variable region complementarity determining regions (CDRs) from the 3D6 immunoglobulin heavy chain variable region sequence set forth as SEQ ID NO:4, and (ii) a variable framework region from a human acceptor immunoglobulin heavy chain, provided that at least one framework residue is substituted with the corresponding amino acid residue from the mouse 3D6 heavy chain variable region sequence, wherein the framework residue is selected from the group consisting of:
(a) a residue that non-covalently binds antigen directly;
(b) a residue adjacent to a CDR;
(c) a CDR-interacting residue; and
(d) a residue participating in the VL-VH interface.

6. The method of claim 5, wherein the humanized immunoglobulin is administered intravenously or subcutaneously.

* * * * *

UNITED STATES PATENT AND TRADEMARK OFFICE
CERTIFICATE OF CORRECTION

PATENT NO. : 9,051,363 B2  
APPLICATION NO. : 11/842042  
DATED : June 9, 2015  
INVENTOR(S) : Dale B. Schenk Page 1 of 1

It is certified that error appears in the above-identified patent and that said Letters Patent is hereby corrected as shown below:

Title page,
"(73) Assignees: Janssen Sciences Ireland UC, (IE)
                Wyeth LLC, Madison, NJ (US)"

should read

-- (73) Assignee: Janssen Sciences Ireland UC, (IE) --

Signed and Sealed this
Twenty-sixth Day of July, 2016

Michelle K. Lee
*Director of the United States Patent and Trademark Office*

SEQUENCE LISTING

```
<160> NUMBER OF SEQ ID NOS: 63

<210> SEQ ID NO 1
<211> LENGTH: 396
<212> TYPE: DNA
<213> ORGANISM: Mus musculus
<220> FEATURE:
<221> NAME/KEY: CDS
<222> LOCATION: (1)...(396)
<220> FEATURE:
<221> NAME/KEY: sig_peptide
<222> LOCATION: (1)...(60)

<400> SEQUENCE: 1 atg atg agt cct gcc cag ttc ctg ttt ctg tta gtg ctc tgg att cgg      48
Met Met Ser Pro Ala Gln Phe Leu Phe Leu Leu Val Leu Trp Ile Arg
-20              -15                 -10                  -5 gaa acc aac ggt tat gtt gtg atg acc cag act cca ctc act ttg tcg      96
Glu Thr Asn Gly Tyr Val Val Met Thr Gln Thr Pro Leu Thr Leu Ser
              1               5                  10 gtt acc att gga caa cca gcc tcc atc tct tgc aag tca agt cag agc     144
Val Thr Ile Gly Gln Pro Ala Ser Ile Ser Cys Lys Ser Ser Gln Ser
         15                  20                  25 ctc tta gat agt gat gga aag aca tat ttg aat tgg ttg tta cag agg     192
Leu Leu Asp Ser Asp Gly Lys Thr Tyr Leu Asn Trp Leu Leu Gln Arg
     30                  35                  40 cca ggc cag tct cca aag cgc cta atc tat ctg gtg tct aaa ctg gac     240
Pro Gly Gln Ser Pro Lys Arg Leu Ile Tyr Leu Val Ser Lys Leu Asp
 45                  50                  55                  60 tct gga gtc cct gac agg ttc act ggc agt gga tca ggg aca gat ttt     288
Ser Gly Val Pro Asp Arg Phe Thr Gly Ser Gly Ser Gly Thr Asp Phe
```

```
                    65                  70                  75
aca ctg aaa atc agc aga ata gag gct gag gat ttg gga ctt tat tat        336
Thr Leu Lys Ile Ser Arg Ile Glu Ala Glu Asp Leu Gly Leu Tyr Tyr
                80                  85                  90 tgc tgg caa ggt aca cat ttt cct cgg acg ttc ggt gga ggc acc aag        384
Cys Trp Gln Gly Thr His Phe Pro Arg Thr Phe Gly Gly Gly Thr Lys
        95                  100                 105 ctg gaa atc aaa                                                        396
Leu Glu Ile Lys
    110

<210> SEQ ID NO 2
<211> LENGTH: 132
<212> TYPE: PRT
<213> ORGANISM: Mus musculus
<220> FEATURE:
<221> NAME/KEY: SIGNAL
<222> LOCATION: (1)...(20)

<400> SEQUENCE: 2

Met Met Ser Pro Ala Gln Phe Leu Phe Leu Leu Val Leu Trp Ile Arg
-20                 -15                 -10                 -5

Glu Thr Asn Gly Tyr Val Val Met Thr Gln Thr Pro Leu Thr Leu Ser
                 1                  5                  10

Val Thr Ile Gly Gln Pro Ala Ser Ile Ser Cys Lys Ser Ser Gln Ser
         15                  20                  25

Leu Leu Asp Ser Asp Gly Lys Thr Tyr Leu Asn Trp Leu Leu Gln Arg
     30                  35                  40

Pro Gly Gln Ser Pro Lys Arg Leu Ile Tyr Leu Val Ser Lys Leu Asp
 45                  50                  55                  60

Ser Gly Val Pro Asp Arg Phe Thr Gly Ser Gly Ser Gly Thr Asp Phe
                 65                  70                  75

Thr Leu Lys Ile Ser Arg Ile Glu Ala Glu Asp Leu Gly Leu Tyr Tyr
                 80                  85                  90

Cys Trp Gln Gly Thr His Phe Pro Arg Thr Phe Gly Gly Gly Thr Lys
         95                  100                 105

Leu Glu Ile Lys
    110

<210> SEQ ID NO 3
<211> LENGTH: 414
<212> TYPE: DNA
<213> ORGANISM: Mus musculus
<220> FEATURE:
<221> NAME/KEY: CDS
<222> LOCATION: (1)...(414)
<220> FEATURE:
<221> NAME/KEY: sig_peptide
<222> LOCATION: (1)...(57)

<400> SEQUENCE: 3 atg aac ttc ggg ctc agc ttg att ttc ctt gtc ctt gtt tta aaa ggt        48
Met Asn Phe Gly Leu Ser Leu Ile Phe Leu Val Leu Val Leu Lys Gly
                 -15                 -10                 -5 gtc cag tgt gaa gtg aag ctg gtg gag tct ggg gga ggc tta gtg aag        96
Val Gln Cys Glu Val Lys Leu Val Glu Ser Gly Gly Gly Leu Val Lys
                 1                   5                   10 cct gga gcg tct ctg aaa ctc tcc tgt gca gcc tct gga ttc act ttc       144
Pro Gly Ala Ser Leu Lys Leu Ser Cys Ala Ala Ser Gly Phe Thr Phe
         15                  20                  25 agt aac tat ggc atg tct tgg gtt cgc cag aat tca gac aag agg ctg       192
```

```
Ser Asn Tyr Gly Met Ser Trp Val Arg Gln Asn Ser Asp Lys Arg Leu
 30              35                  40                  45 gag tgg gtt gca tcc att agg agt ggt ggt aga acc tac tat tca      240
Glu Trp Val Ala Ser Ile Arg Ser Gly Gly Arg Thr Tyr Tyr Ser
             50                  55                  60 gac aat gta aag ggc cga ttc acc atc tcc aga gag aat gcc aag aac  288
Asp Asn Val Lys Gly Arg Phe Thr Ile Ser Arg Glu Asn Ala Lys Asn
                 65                  70                  75 acc ctg tac ctg caa atg agt agt ctg aag tct gag gac acg gcc ttg  336
Thr Leu Tyr Leu Gln Met Ser Ser Leu Lys Ser Glu Asp Thr Ala Leu
                 80                  85                  90 tat tat tgt gtc aga tat gat cac tat agt ggt agc tcc gac tac tgg  384
Tyr Tyr Cys Val Arg Tyr Asp His Tyr Ser Gly Ser Ser Asp Tyr Trp
         95                 100                 105 ggc cag ggc acc act gtc aca gtc tcc tca                          414
Gly Gln Gly Thr Thr Val Thr Val Ser Ser
110                 115
```

<210> SEQ ID NO 4
<211> LENGTH: 138
<212> TYPE: PRT
<213> ORGANISM: Mus musculus
<220> FEATURE:
<221> NAME/KEY: SIGNAL
<222> LOCATION: (1)...(19)

<400> SEQUENCE: 4

```
Met Asn Phe Gly Leu Ser Leu Ile Phe Leu Val Leu Val Leu Lys Gly
                -15                 -10                 -5

Val Gln Cys Glu Val Lys Leu Val Glu Ser Gly Gly Gly Leu Val Lys
             1               5                  10

Pro Gly Ala Ser Leu Lys Leu Ser Cys Ala Ala Ser Gly Phe Thr Phe
         15                  20                  25

Ser Asn Tyr Gly Met Ser Trp Val Arg Gln Asn Ser Asp Lys Arg Leu
 30              35                  40                  45

Glu Trp Val Ala Ser Ile Arg Ser Gly Gly Gly Arg Thr Tyr Tyr Ser
             50                  55                  60

Asp Asn Val Lys Gly Arg Phe Thr Ile Ser Arg Glu Asn Ala Lys Asn
                 65                  70                  75

Thr Leu Tyr Leu Gln Met Ser Ser Leu Lys Ser Glu Asp Thr Ala Leu
                 80                  85                  90

Tyr Tyr Cys Val Arg Tyr Asp His Tyr Ser Gly Ser Ser Asp Tyr Trp
         95                 100                 105

Gly Gln Gly Thr Thr Val Thr Val Ser Ser
110                 115
```

<210> SEQ ID NO 5
<211> LENGTH: 132
<212> TYPE: PRT
<213> ORGANISM: Artificial Sequence
<220> FEATURE:
<221> NAME/KEY: SIGNAL
<222> LOCATION: (1)...(20)
<223> OTHER INFORMATION: humanized 3D6 light chain variable region

<400> SEQUENCE: 5

```
Met Met Ser Pro Ala Gln Phe Leu Phe Leu Leu Val Leu Trp Ile Arg
-20                 -15                 -10                 -5

Glu Thr Asn Gly Tyr Val Val Met Thr Gln Ser Pro Leu Ser Leu Pro
             1               5                  10
```

```
Val Thr Pro Gly Glu Pro Ala Ser Ile Ser Cys Lys Ser Gln Ser
        15              20              25

Leu Leu Asp Ser Asp Gly Lys Thr Tyr Leu Asn Trp Leu Leu Gln Lys
    30              35              40

Pro Gly Gln Ser Pro Gln Arg Leu Ile Tyr Leu Val Ser Lys Leu Asp
45              50              55              60

Ser Gly Val Pro Asp Arg Phe Ser Gly Ser Gly Ser Gly Thr Asp Phe
                65              70              75

Thr Leu Lys Ile Ser Arg Val Glu Ala Glu Asp Val Gly Val Tyr Tyr
            80              85              90

Cys Trp Gln Gly Thr His Phe Pro Arg Thr Phe Gly Gln Gly Thr Lys
        95              100             105

Val Glu Ile Lys
    110

<210> SEQ ID NO 6
<211> LENGTH: 125
<212> TYPE: PRT
<213> ORGANISM: Homo sapiens
<220> FEATURE:
<221> NAME/KEY: SIGNAL
<222> LOCATION: (1)...(13)

<400> SEQUENCE: 6

Met Gly Leu Leu Met Leu Trp Val Ser Gly Ser Ser Gly Asp Ile Val
            -10                  -5                   1

Met Thr Gln Ser Pro Leu Ser Leu Pro Val Thr Pro Gly Glu Pro Ala
     5              10                  15

Ser Ile Ser Cys Arg Ser Ser Gln Ser Leu Leu His Ser Asn Gly Tyr
20              25                  30                  35

Asn Tyr Leu Asp Trp Tyr Leu Gln Lys Pro Gly Gln Ser Pro Gln Leu
            40                  45                  50

Leu Ile Tyr Leu Gly Ser Asn Arg Ala Ser Gly Val Pro Asp Arg Phe
        55                  60                  65

Ser Gly Ser Gly Ser Gly Thr Asp Phe Thr Leu Lys Ile Ser Arg Val
        70                  75                  80

Glu Ala Glu Asp Val Gly Val Tyr Tyr Cys Met Gln Ala Leu Gln Thr
    85                  90                  95

Pro Arg Thr Phe Gly Gln Gly Thr Lys Val Glu Ile Lys
100                 105                 110

<210> SEQ ID NO 7
<211> LENGTH: 100
<212> TYPE: PRT
<213> ORGANISM: Homo sapiens

<400> SEQUENCE: 7

Asp Ile Val Met Thr Gln Ser Pro Leu Ser Leu Pro Val Thr Pro Gly
1                5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
                85                  90                  95

Leu Gln Thr Pro
            100

<210> SEQ ID NO 8
<211> LENGTH: 138
<212> TYPE: PRT
<213> ORGANISM: Artificial Sequence
<220> FEATURE:
<223> OTHER INFORMATION: Humanized 3D6 heavy chain variable region
<220> FEATURE:
<221> NAME/KEY: SIGNAL
<222> LOCATION: (1)...(19)

<400> SEQUENCE: 8

Met Asn Phe Gly Leu Ser Leu Ile Phe Leu Val Leu Val Leu Lys Gly
                -15                 -10                  -5

Val Gln Cys Glu Val Gln Leu Leu Glu Ser Gly Gly Gly Leu Val Gln
             1               5                  10

Pro Gly Gly Ser Leu Arg Leu Ser Cys Ala Ala Ser Gly Phe Thr Phe
        15                  20                  25

Ser Asn Tyr Gly Met Ser Trp Val Arg Gln Ala Pro Gly Lys Gly Leu
 30                  35                  40                  45

Glu Trp Val Ala Ser Ile Arg Ser Gly Gly Gly Arg Thr Tyr Tyr Ser
                 50                  55                  60

Asp Asn Val Lys Gly Arg Phe Thr Ile Ser Arg Asp Asn Ala Lys Asn
                 65                  70                  75

Ser Leu Tyr Leu Gln Met Asn Ser Leu Arg Ala Glu Asp Thr Ala Leu
                 80                  85                  90

Tyr Tyr Cys Val Arg Tyr Asp His Tyr Ser Gly Ser Ser Asp Tyr Trp
             95                 100                 105

Gly Gln Gly Thr Leu Val Thr Val Ser Ser
110                 115

<210> SEQ ID NO 9
<211> LENGTH: 121
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Val Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Asn Tyr Asp Phe Trp Ser Gly Thr Phe Asp Tyr Trp Gly
                100                 105                 110

Gln Gly Thr Leu Val Thr Val Ser Ser
        115                 120
```

```
<210> SEQ ID NO 10
<211> LENGTH: 98
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 11
<211> LENGTH: 132
<212> TYPE: PRT
<213> ORGANISM: Artificial Sequence
<220> FEATURE:
<221> NAME/KEY: SIGNAL
<222> LOCATION: (1)...(20)
<223> OTHER INFORMATION: humanized 3D6 light chain variable region

<400> SEQUENCE: 11

Met Met Ser Pro Ala Gln Phe Leu Phe Leu Leu Val Leu Trp Ile Arg
-20                 -15                 -10                  -5

Glu Thr Asn Gly Asp Val Val Met Thr Gln Ser Pro Leu Ser Leu Pro
                  1               5                  10

Val Thr Pro Gly Glu Pro Ala Ser Ile Ser Cys Lys Ser Ser Gln Ser
             15                  20                  25

Leu Leu Asp Ser Asp Gly Lys Thr Tyr Leu Asn Trp Leu Leu Gln Lys
         30                  35                  40

Pro Gly Gln Ser Pro Gln Arg Leu Ile Tyr Leu Val Ser Lys Leu Asp
 45                  50                  55                  60

Ser Gly Val Pro Asp Arg Phe Ser Gly Ser Gly Ser Gly Thr Asp Phe
                 65                  70                  75

Thr Leu Lys Ile Ser Arg Val Glu Ala Glu Asp Val Gly Val Tyr Tyr
             80                  85                  90

Cys Trp Gln Gly Thr His Phe Pro Arg Thr Phe Gly Gln Gly Thr Lys
         95                  100                 105

Val Glu Ile Lys
    110

<210> SEQ ID NO 12
<211> LENGTH: 138
<212> TYPE: PRT
<213> ORGANISM: Artificial Sequence
<220> FEATURE:
<223> OTHER INFORMATION: Humanized 3D6 light chain variable region
<220> FEATURE:
<221> NAME/KEY: SIGNAL
<222> LOCATION: (1)...(19)

<400> SEQUENCE: 12
```

```
Met Asn Phe Gly Leu Ser Leu Ile Phe Leu Val Val Leu Lys Gly
            -15                 -10                 -5

Val Gln Cys Glu Val Gln Leu Leu Glu Ser Gly Gly Gly Leu Val Gln
            1               5                   10

Pro Gly Gly Ser Leu Arg Leu Ser Cys Ala Ala Ser Gly Phe Thr Phe
        15                  20                  25

Ser Asn Tyr Gly Met Ser Trp Val Arg Gln Ala Pro Gly Lys Gly Leu
30                  35                  40                  45

Glu Trp Val Ala Ser Ile Arg Ser Gly Gly Arg Thr Tyr Tyr Ser
                50                  55                  60

Asp Asn Val Lys Gly Arg Phe Thr Ile Ser Arg Asp Asn Ser Lys Asn
            65                  70                  75

Thr Leu Tyr Leu Gln Met Asn Ser Leu Arg Ala Glu Asp Thr Ala Val
        80                  85                  90

Tyr Tyr Cys Val Arg Tyr Asp His Tyr Ser Gly Ser Ser Asp Tyr Trp
    95                  100                 105

Gly Gln Gly Thr Leu Val Thr Val Ser Ser
110             115

<210> SEQ ID NO 13
<211> LENGTH: 393
<212> TYPE: DNA
<213> ORGANISM: Mus musculus
<220> FEATURE:
<221> NAME/KEY: CDS
<222> LOCATION: (1)...(393)
<220> FEATURE:
<221> NAME/KEY: sig_peptide
<222> LOCATION: (1)...(57)

<400> SEQUENCE: 13 atg aag ttg cct gtt agg ctg ttg gta ctg atg ttc tgg att cct gct      48
Met Lys Leu Pro Val Arg Leu Leu Val Leu Met Phe Trp Ile Pro Ala
            -15                 -10                 -5 tcc agc agt gat gtt ttg atg acc caa act cca ctc tcc ctg cct gtc      96
Ser Ser Ser Asp Val Leu Met Thr Gln Thr Pro Leu Ser Leu Pro Val
            1               5                   10 agt ctt gga gat caa gcc tcc atc tct tgc aga tct agt cag aac att     144
Ser Leu Gly Asp Gln Ala Ser Ile Ser Cys Arg Ser Ser Gln Asn Ile
        15                  20                  25 ata cat agt aat gga aac acc tat tta gaa tgg tac ctg cag aaa cca     192
Ile His Ser Asn Gly Asn Thr Tyr Leu Glu Trp Tyr Leu Gln Lys Pro
30                  35                  40                  45 ggc cag tct cca aag ctc ctg atc tac aaa gtt tcc aac cga ttt tct     240
Gly Gln Ser Pro Lys Leu Leu Ile Tyr Lys Val Ser Asn Arg Phe Ser
                50                  55                  60 ggg gtc cca gac agg ttc agt ggc agt gga tca ggg aca gat ttc aca     288
Gly Val Pro Asp Arg Phe Ser Gly Ser Gly Ser Gly Thr Asp Phe Thr
            65                  70                  75 ctc aag atc aag aaa gtg gag gct gag gat ctg gga att tat tac tgc     336
Leu Lys Ile Lys Lys Val Glu Ala Glu Asp Leu Gly Ile Tyr Tyr Cys
        80                  85                  90 ttt caa ggt tca cat gtt ccg ctc acg ttc ggt gct ggg acc aag ctg     384
Phe Gln Gly Ser His Val Pro Leu Thr Phe Gly Ala Gly Thr Lys Leu
    95                  100                 105 gag ctg gaa                                                          393
Glu Leu Glu
110

<210> SEQ ID NO 14
```

```
<211> LENGTH: 131
<212> TYPE: PRT
<213> ORGANISM: Mus musculus
<220> FEATURE:
<221> NAME/KEY: SIGNAL
<222> LOCATION: (1)...(19)

<400> SEQUENCE: 14

Met Lys Leu Pro Val Arg Leu Val Leu Met Phe Trp Ile Pro Ala
                -15             -10                 -5
Ser Ser Ser Asp Val Leu Met Thr Gln Thr Pro Leu Ser Leu Pro Val
            1               5                   10
Ser Leu Gly Asp Gln Ala Ser Ile Ser Cys Arg Ser Ser Gln Asn Ile
        15                  20                  25
Ile His Ser Asn Gly Asn Thr Tyr Leu Glu Trp Tyr Leu Gln Lys Pro
30                  35                  40                  45
Gly Gln Ser Pro Lys Leu Leu Ile Tyr Lys Val Ser Asn Arg Phe Ser
                50                  55                  60
Gly Val Pro Asp Arg Phe Ser Gly Ser Gly Ser Gly Thr Asp Phe Thr
            65                  70                  75
Leu Lys Ile Lys Lys Val Glu Ala Glu Asp Leu Gly Ile Tyr Tyr Cys
        80                  85                  90
Phe Gln Gly Ser His Val Pro Leu Thr Phe Gly Ala Gly Thr Lys Leu
    95                  100                 105
Glu Leu Glu
110

<210> SEQ ID NO 15
<211> LENGTH: 426
<212> TYPE: DNA
<213> ORGANISM: Mus musculus
<220> FEATURE:
<221> NAME/KEY: CDS
<222> LOCATION: (1)...(426)
<220> FEATURE:
<221> NAME/KEY: sig_peptide
<222> LOCATION: (1)...(57)

<400> SEQUENCE: 15 atg gac agg ctt act tcc tca ttc ctg ctg ctg att gtc cct gca tat      48
Met Asp Arg Leu Thr Ser Ser Phe Leu Leu Leu Ile Val Pro Ala Tyr
                -15             -10                 -5 gtc ctg tcc cag gct act ctg aaa gag tct ggc cct gga ata ttg cag      96
Val Leu Ser Gln Ala Thr Leu Lys Glu Ser Gly Pro Gly Ile Leu Gln
            1               5                   10 tcc tcc cag acc ctc agt ctg act tgt tct ttc tct ggg ttt tca ctg     144
Ser Ser Gln Thr Leu Ser Leu Thr Cys Ser Phe Ser Gly Phe Ser Leu
        15                  20                  25 agc act tct ggt atg gga gtg agc tgg att cgt cag cct tca gga aag     192
Ser Thr Ser Gly Met Gly Val Ser Trp Ile Arg Gln Pro Ser Gly Lys
30                  35                  40                  45 ggt ctg gag tgg ctg gca cac att tac tgg gat gat gac aag cgc tat     240
Gly Leu Glu Trp Leu Ala His Ile Tyr Trp Asp Asp Asp Lys Arg Tyr
                50                  55                  60 aac cca tcc ctg aag agc cgg ctc aca atc tcc aag gat acc tcc aga     288
Asn Pro Ser Leu Lys Ser Arg Leu Thr Ile Ser Lys Asp Thr Ser Arg
            65                  70                  75 aag cag gta ttc ctc aag atc acc agt gtg gac cct gca gat act gcc     336
Lys Gln Val Phe Leu Lys Ile Thr Ser Val Asp Pro Ala Asp Thr Ala
        80                  85                  90 aca tac tac tgt gtt cga agg ccc att act ccg gta cta gtc gat gct     384
Thr Tyr Tyr Cys Val Arg Arg Pro Ile Thr Pro Val Leu Val Asp Ala
```

```
Thr Tyr Tyr Cys Val Arg Arg Pro Ile Thr Pro Val Leu Val Asp Ala
         95                 100                 105 atg gac tac tgg ggt caa gga acc tca gtc acc gtc tcc tca              426
Met Asp Tyr Trp Gly Gln Gly Thr Ser Val Thr Val Ser Ser
110                 115                 120

<210> SEQ ID NO 16
<211> LENGTH: 142
<212> TYPE: PRT
<213> ORGANISM: Mus musculus
<220> FEATURE:
<221> NAME/KEY: SIGNAL
<222> LOCATION: (1)...(19)

<400> SEQUENCE: 16

Met Asp Arg Leu Thr Ser Ser Phe Leu Leu Leu Ile Val Pro Ala Tyr
                -15                 -10                 -5

Val Leu Ser Gln Ala Thr Leu Lys Glu Ser Gly Pro Gly Ile Leu Gln
                 1               5                  10

Ser Ser Gln Thr Leu Ser Leu Thr Cys Ser Phe Ser Gly Phe Ser Leu
         15                  20                  25

Ser Thr Ser Gly Met Gly Val Ser Trp Ile Arg Gln Pro Ser Gly Lys
30                  35                  40                  45

Gly Leu Glu Trp Leu Ala His Ile Tyr Trp Asp Asp Lys Arg Tyr
                 50                  55                  60

Asn Pro Ser Leu Lys Ser Arg Leu Thr Ile Ser Lys Asp Thr Ser Arg
                 65                  70                  75

Lys Gln Val Phe Leu Lys Ile Thr Ser Val Asp Pro Ala Asp Thr Ala
                 80                  85                  90

Thr Tyr Tyr Cys Val Arg Arg Pro Ile Thr Pro Val Leu Val Asp Ala
         95                 100                 105

Met Asp Tyr Trp Gly Gln Gly Thr Ser Val Thr Val Ser Ser
110                 115                 120

<210> SEQ ID NO 17
<211> LENGTH: 136
<212> TYPE: DNA
<213> ORGANISM: Artificial Sequence
<220> FEATURE:
<223> OTHER INFORMATION: primer

<400> SEQUENCE: 17
tccgcaagct tgccgccacc atggacatgc gcgtgcccgc ccagctgctg ggcctgctga         60
tgctgtgggt gtccggctcc tccggctacg tggtgatgac ccagtccccc ctgtccctgc        120
ccgtgacccc cggcga                                                        136

<210> SEQ ID NO 18
<211> LENGTH: 131
<212> TYPE: DNA
<213> ORGANISM: Artificial Sequence
<220> FEATURE:
<223> OTHER INFORMATION: primer

<400> SEQUENCE: 18 ctgggggac tggccgggct tctgcagcag ccagttcagg taggtcttgc cgtcggagtc          60
cagcagggac tggaggact tgcaggagat ggaggcgggc tcgccggggg tcacgggcag         120
ggacaggggg g                                                             131

<210> SEQ ID NO 19
```

```
<211> LENGTH: 146
<212> TYPE: DNA
<213> ORGANISM: Artificial Sequence
<220> FEATURE:
<223> OTHER INFORMATION: primer

<400> SEQUENCE: 19
acctgaactg gctgctgcag aagcccggcc agtcccccca gcgcctgatc tacctggtgt    60
ccaagctgga ctccggcgtg cccgaccgct tctccggctc cggctccggc accgacttca   120
ccctgaagat ctcccgcgtg gaggcc                                        146

<210> SEQ ID NO 20
<211> LENGTH: 142
<212> TYPE: DNA
<213> ORGANISM: Artificial Sequence
<220> FEATURE:
<223> OTHER INFORMATION: primer

<400> SEQUENCE: 20
aattctagga tccactcacg cttgatctcc accttggtgc cctggccgaa ggtgcggggg    60
aagtgggtgc cctgccagca gtagtacacg cccacgtcct cggcctccac gcgggagatc   120
ttcagggtga agtcggtgcc gg                                            142

<210> SEQ ID NO 21
<211> LENGTH: 16
<212> TYPE: DNA
<213> ORGANISM: Artificial Sequence
<220> FEATURE:
<223> OTHER INFORMATION: primer

<400> SEQUENCE: 21 ctgggggac tggccg                                                    16

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
acctgaactg gctgctgcag aa                                            22

<210> SEQ ID NO 23
<211> LENGTH: 138
<212> TYPE: DNA
<213> ORGANISM: Artificial Sequence
<220> FEATURE:
<223> OTHER INFORMATION: primer

<400> SEQUENCE: 23
acagaaagct tgccgccacc atggagtttg gctgagctg cttttttctt gtggctattt    60
taaaaggtgt ccagtgtgag gtgcagctgc tggagtccgg cggcggcctg gtgcagcccg   120
gcggctccct gcgcctgt                                                 138

<210> SEQ ID NO 24
<211> LENGTH: 135
<212> TYPE: DNA
<213> ORGANISM: Artificial Sequence
<220> FEATURE:
<223> OTHER INFORMATION: primer

<400> SEQUENCE: 24
```

```
gccgccggag cggatggagg ccacccactc caggcccttg ccgggggcct ggcgcaccca    60
ggacatgccg tagttggaga aggtgaagcc ggaggcggcg caggacaggc cagggagcc    120 gccgggctgc accag                                                    135

<210> SEQ ID NO 25
<211> LENGTH: 142
<212> TYPE: DNA
<213> ORGANISM: Artificial Sequence
<220> FEATURE:
<223> OTHER INFORMATION: primer

<400> SEQUENCE: 25
ctggagtggg tggcctccat ccgctccggc ggcggccgca cctactactc cgacaacgtg    60
aagggccgct tcaccatctc ccgcgacaac gccaagaact ccctgtacct gcagatgaac   120
tccctgcgcg ccgaggacac cg                                           142

<210> SEQ ID NO 26
<211> LENGTH: 144
<212> TYPE: DNA
<213> ORGANISM: Artificial Sequence
<220> FEATURE:
<223> OTHER INFORMATION: primer

<400> SEQUENCE: 26
ctgcaaggat ccactcaccg gaggacacgg tcaccagggt gccctggccc cagtagtcgg    60
aggagccgga gtagtggtcg tagcgcacgc agtagtacag ggcggtgtcc tcggcgcgca   120
gggagttcat ctgcaggtac aggg                                         144

<210> SEQ ID NO 27
<211> LENGTH: 16
<212> TYPE: DNA
<213> ORGANISM: Artificial Sequence
<220> FEATURE:
<223> OTHER INFORMATION: primer

<400> SEQUENCE: 27
gccgccggag cggatg                                                    16

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
ctggagtggg tggcctccat                                                20

<210> SEQ ID NO 29
<211> LENGTH: 19
<212> TYPE: DNA
<213> ORGANISM: Artificial Sequence
<220> FEATURE:
<223> OTHER INFORMATION: primer

<400> SEQUENCE: 29
tccgcaagct tgccgccac                                                 19

<210> SEQ ID NO 30
<211> LENGTH: 29
<212> TYPE: DNA
```

<210> SEQ ID NO 30
<211> LENGTH: 29
<212> TYPE: DNA
<213> ORGANISM: Artificial Sequence
<220> FEATURE:
<223> OTHER INFORMATION: primer

<400> SEQUENCE: 30
aattctagga tccactcacg cttgatctc                                    29

<210> SEQ ID NO 31
<211> LENGTH: 23
<212> TYPE: DNA
<213> ORGANISM: Artificial Sequence
<220> FEATURE:
<223> OTHER INFORMATION: primer

<400> SEQUENCE: 31
acagaaagct tgccgccacc atg                                          23

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
ctgcaaggat ccactcaccg ga                                           22

<210> SEQ ID NO 33
<211> LENGTH: 10
<212> TYPE: PRT
<213> ORGANISM: Artificial Sequence
<220> FEATURE:
<223> OTHER INFORMATION: native ABeta peptide

<400> SEQUENCE: 33

Asp Ala Glu Phe Arg His Asp Ser Gly Tyr
 1               5                  10

<210> SEQ ID NO 34
<211> LENGTH: 402
<212> TYPE: DNA
<213> ORGANISM: Artificial Sequence
<220> FEATURE:
<223> OTHER INFORMATION: h3D6 version 1 VL

<400> SEQUENCE: 34
atggacatgc gcgtgcccgc ccagctgctg ggcctgctga tgctgtgggt gtccggctcc     60
tccggctacg tggtgatgac ccagtccccc ctgtccctgc ccgtgacccc cggcgagccc    120
gcctccatct cctgcaagtc ctcccagtcc ctgctggact ccgacggcaa gacctacctg    180
aactggctgc tgcagaagcc cggccagtcc ccccagcgcc tgatctacct ggtgtccaag    240
ctggactccg gcgtgcccga ccgcttctcc ggctccggct ccggcaccga cttcaccctg    300
aagatctccc gcgtggaggc cgaggacgtg gccgtgtact actgctggca gggcacccac    360
ttcccccgca ccttcggcca gggcaccaag gtggagatca ag                      402

<210> SEQ ID NO 35
<211> LENGTH: 402
<212> TYPE: DNA
<213> ORGANISM: Artificial Sequence
<220> FEATURE:
<223> OTHER INFORMATION: h3D6 version 2 VL

<400> SEQUENCE: 35

```
atggacatgc gcgtgcccgc ccagctgctg ggcctgctga tgctgtgggt gtccggctcc    60
tccggcgacg tggtgatgac ccagtccccc ctgtccctgc ccgtgacccc cggcgagccc   120
gcctccatct cctgcaagtc ctcccagtcc ctgctggact ccgacggcaa gacctacctg   180
aactggctgc tgcagaagcc cggccagtcc ccccagcgcc tgatctacct ggtgtccaag   240
ctggactccg gcgtgcccga ccgcttctcc ggctccggct ccggcaccga cttcacccig   300 aagatctccc gcgtggaggc cgaggacgtg gccgtgtact actgctggca gggcacccac   360 ttccccccgca ccttcggcca gggcaccaag gtggagatca ag                     402
```

```
<210> SEQ ID NO 36
<211> LENGTH: 414
<212> TYPE: DNA
<213> ORGANISM: Artificial Sequence
<220> FEATURE:
<223> OTHER INFORMATION: h3D6 version 1 VH

<400> SEQUENCE: 36
```

```
atggagtttg gctgagctg  gcttttctt  gtggctattt  taaaaggtgt ccagtgtgag    60
gtgcagctgc tggagtccgg cggcggcctg gtgcagcccg gcggctccct cgcctgtcc    120 tgcgccgcct ccggcttcac cttctccaac tacggcatgt cctgggtgcg ccaggccccc   180
ggcaagggcc tggagtgggt ggcctccatc cgctccggcg gcggccgcac ctactactcc   240
gacaacgtga agggccgctt caccatctcc cgcgacaacg ccaagaactc cctgtacctg   300
cagatgaact ccctgcgcgc cgaggacacc gccctgtact actgcgtgcg ctacgaccac   360
tactccggct cctccgacta ctggggccag ggcaccctgg tgaccgtgtc ctcc         414
```

```
<210> SEQ ID NO 37
<211> LENGTH: 414
<212> TYPE: DNA
<213> ORGANISM: Artificial Sequence
<220> FEATURE:
<223> OTHER INFORMATION: h3D6 version 2 VH

<400> SEQUENCE: 37
```

```
atggagtttg gctgagctg  gcttttctt  gtggctattt  taaaaggtgt ccagtgtgag    60
gtgcagctgc tggagtccgg cggcggcctg gtgcagcccg gcggctccct cgcctgtcc    120 tgcgccgcct ccggcttcac cttctccaac tacggcatgt cctgggtgcg ccaggccccc   180
ggcaagggcc tggagtgggt ggcctccatc cgctccggcg gcggccgcac ctactactcc   240
gacaacgtga agggccgctt caccatctcc cgcgacaact ccaagaacac cctgtacctg   300
cagatgaact ccctgcgcgc cgaggacacc gccgtgtact actgcgtgcg ctacgaccac   360
tactccggct cctccgacta ctggggccag ggcaccctgg tgaccgtgtc ctcc         414
```

```
<210> SEQ ID NO 38
<211> LENGTH: 770
<212> TYPE: PRT
<213> ORGANISM: Homo sapiens

<400> SEQUENCE: 38
```

```
Met Leu Pro Gly Leu Ala Leu Leu Leu Leu Ala Ala Trp Thr Ala Arg
 1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45
```

```
Asn Gly Lys Trp Asp Ser Asp Pro Ser Gly Thr Lys Thr Cys Ile Asp
 50                  55                  60
Thr Lys Glu Gly Ile Leu Gln Tyr Cys Gln Glu Val Tyr Pro Glu Leu
 65                  70                  75                  80
Gln Ile Thr Asn Val Val Glu Ala Asn Gln Pro Val Thr Ile Gln Asn
                 85                  90                  95
Trp Cys Lys Arg Gly Arg Lys Gln Cys Lys Thr His Pro His Phe Val
                100                 105                 110
Ile Pro Tyr Arg Cys Leu Val Gly Glu Phe Val Ser Asp Ala Leu Leu
                115                 120                 125
Val Pro Asp Lys Cys Lys Phe Leu His Gln Glu Arg Met Asp Val Cys
130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
                180                 185                 190
Ser Asp Asn Val Asp Ser Ala Asp Ala Glu Glu Asp Asp Ser Asp Val
                195                 200                 205
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
                260                 265                 270
Ala Thr Thr Thr Thr Thr Thr Glu Ser Val Glu Glu Val Val Arg
                275                 280                 285
Glu Val Cys Ser Glu Gln Ala Glu Thr Gly Pro Cys Arg Ala Met Ile
                290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
                340                 345                 350
Thr Gln Glu Pro Leu Ala Arg Asp Pro Val Lys Leu Pro Thr Thr Ala
                355                 360                 365
Ala Ser Thr Pro Asp Ala Val Asp Lys Tyr Leu Glu Thr Pro Gly Asp
                370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
                420                 425                 430
Gln His Phe Gln Glu Lys Val Glu Ser Leu Glu Gln Glu Ala Ala Asn
                435                 440                 445
Glu Arg Gln Gln Leu Val Glu Thr His Met Ala Arg Val Glu Ala Met
450                 455                 460
Leu Asn Asp Arg Arg Arg Leu Ala Leu Glu Asn Tyr Ile Thr Ala Leu
```

```
               465                 470                 475                 480
        Gln Ala Val Pro Pro Arg Pro Arg His Val Phe Asn Met Leu Lys Lys
                        485                 490                 495
        Tyr Val Arg Ala Glu Gln Lys Asp Arg Gln His Thr Leu Lys His Phe
                    500                 505                 510
        Glu His Val Arg Met Val Asp Pro Lys Lys Ala Ala Gln Ile Arg Ser
                515                 520                 525
        Gln Val Met Thr His Leu Arg Val Ile Tyr Glu Arg Met Asn Gln Ser
            530                 535                 540
        Leu Ser Leu Leu Tyr Asn Val Pro Ala Val Ala Glu Glu Ile Gln Asp
        545                 550                 555                 560
        Glu Val Asp Glu Leu Leu Gln Lys Glu Gln Asn Tyr Ser Asp Asp Val
                        565                 570                 575
        Leu Ala Asn Met Ile Ser Glu Pro Arg Ile Ser Tyr Gly Asn Asp Ala
                    580                 585                 590
        Leu Met Pro Ser Leu Thr Glu Thr Lys Thr Thr Val Glu Leu Leu Pro
                595                 600                 605
        Val Asn Gly Glu Phe Ser Leu Asp Asp Leu Gln Pro Trp His Ser Phe
            610                 615                 620
        Gly Ala Asp Ser Val Pro Ala Asn Thr Glu Asn Glu Val Glu Pro Val
        625                 630                 635                 640
        Asp Ala Arg Pro Ala Ala Asp Arg Gly Leu Thr Thr Arg Pro Gly Ser
                        645                 650                 655
        Gly Leu Thr Asn Ile Lys Thr Glu Glu Ile Ser Glu Val Lys Met Asp
                    660                 665                 670
        Ala Glu Phe Arg His Asp Ser Gly Tyr Glu Val His His Gln Lys Leu
                675                 680                 685
        Val Phe Phe Ala Glu Asp Val Gly Ser Asn Lys Gly Ala Ile Ile Gly
            690                 695                 700
        Leu Met Val Gly Gly Val Val Ile Ala Thr Val Ile Val Ile Thr Leu
        705                 710                 715                 720
        Val Met Leu Lys Lys Lys Gln Tyr Thr Ser Ile His His Gly Val Val
                        725                 730                 735
        Glu Val Asp Ala Ala Val Thr Pro Glu Glu Arg His Leu Ser Lys Met
                    740                 745                 750
        Gln Gln Asn Gly Tyr Glu Asn Pro Thr Tyr Lys Phe Phe Glu Gln Met
                755                 760                 765
        Gln Asn
            770

<210> SEQ ID NO 39
<211> LENGTH: 40
<212> TYPE: DNA
<213> ORGANISM: Artificial Sequence
<220> FEATURE:
<223> OTHER INFORMATION: primer

<400> SEQUENCE: 39
actagtcgac atgaagttgc ctgttaggct gttggtgctg                           40

<210> SEQ ID NO 40
<211> LENGTH: 39
<212> TYPE: DNA
<213> ORGANISM: Artificial Sequence
<220> FEATURE:
<223> OTHER INFORMATION: primer
```

```
<400> SEQUENCE: 40
actagtcgac atggagwcag acacactcct gytatgggt                               39

<210> SEQ ID NO 41
<211> LENGTH: 40
<212> TYPE: DNA
<213> ORGANISM: Artificial Sequence
<220> FEATURE:
<223> OTHER INFORMATION: primer

<400> SEQUENCE: 41
actagtcgac atgagtgtgc tcactcaggt cctggsgttg                              40

<210> SEQ ID NO 42
<211> LENGTH: 43
<212> TYPE: DNA
<213> ORGANISM: Artificial Sequence
<220> FEATURE:
<223> OTHER INFORMATION: primer

<400> SEQUENCE: 42
actagtcgac atgaggrccc ctgctcagwt tyttggmwtc ttg                          43

<210> SEQ ID NO 43
<211> LENGTH: 40
<212> TYPE: DNA
<213> ORGANISM: Artificial Sequence
<220> FEATURE:
<223> OTHER INFORMATION: primer

<400> SEQUENCE: 43
actagtcgac atggatttwc aggtgcagat twtcagcttc                              40

<210> SEQ ID NO 44
<211> LENGTH: 37
<212> TYPE: DNA
<213> ORGANISM: Artificial Sequence
<220> FEATURE:
<223> OTHER INFORMATION: primer

<400> SEQUENCE: 44
actagtcgac atgaggtkcy ytgytsagyt yctgrgg                                 37

<210> SEQ ID NO 45
<211> LENGTH: 41
<212> TYPE: DNA
<213> ORGANISM: Artificial Sequence
<220> FEATURE:
<223> OTHER INFORMATION: primer

<400> SEQUENCE: 45
actagtcgac atgggcwtca agatggagtc acakwyycwg g                            41

<210> SEQ ID NO 46
<211> LENGTH: 41
<212> TYPE: DNA
<213> ORGANISM: Artificial Sequence
<220> FEATURE:
<223> OTHER INFORMATION: primer

<400> SEQUENCE: 46
actagtcgac atgtggggay ctktttycmm ttttcaatt g                             41

<210> SEQ ID NO 47
<211> LENGTH: 35
```

<210> SEQ ID NO 47
<211> LENGTH: 35
<212> TYPE: DNA
<213> ORGANISM: Artificial Sequence
<220> FEATURE:
<223> OTHER INFORMATION: primer

<400> SEQUENCE: 47
actagtcgac atggtrtccw casctcagtt ccttg          35

<210> SEQ ID NO 48
<211> LENGTH: 37
<212> TYPE: DNA
<213> ORGANISM: Artificial Sequence
<220> FEATURE:
<223> OTHER INFORMATION: primer

<400> SEQUENCE: 48
actagtcgac atgtatatat gtttgttgtc tatttct          37

<210> SEQ ID NO 49
<211> LENGTH: 38
<212> TYPE: DNA
<213> ORGANISM: Artificial Sequence
<220> FEATURE:
<223> OTHER INFORMATION: primer

<400> SEQUENCE: 49
actagtcgac atggaagccc cagctcagct tctcttcc          38

<210> SEQ ID NO 50
<211> LENGTH: 27
<212> TYPE: DNA
<213> ORGANISM: Artificial Sequence
<220> FEATURE:
<223> OTHER INFORMATION: primer

<400> SEQUENCE: 50
ggatcccggg tggatggtgg gaagatg          27

<210> SEQ ID NO 51
<211> LENGTH: 37
<212> TYPE: DNA
<213> ORGANISM: Artificial Sequence
<220> FEATURE:
<223> OTHER INFORMATION: primer

<400> SEQUENCE: 51
actagtcgac atgaaatgca gctgggtcat sttcttc          37

<210> SEQ ID NO 52
<211> LENGTH: 36
<212> TYPE: DNA
<213> ORGANISM: Artificial Sequence
<220> FEATURE:
<223> OTHER INFORMATION: primer

<400> SEQUENCE: 52
actagtcgac atgggatgga gctrtatcat sytctt          36

<210> SEQ ID NO 53
<211> LENGTH: 37
<212> TYPE: DNA
<213> ORGANISM: Artificial Sequence
<220> FEATURE:
<223> OTHER INFORMATION: primer

<400> SEQUENCE: 53
actagtcgac atgaagwtgt ggttaaactg ggttttt                                37

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
actagtcgac atgractttg ggytcagctt grttt                                  35

<210> SEQ ID NO 55
<211> LENGTH: 40
<212> TYPE: DNA
<213> ORGANISM: Artificial Sequence
<220> FEATURE:
<223> OTHER INFORMATION: primer

<400> SEQUENCE: 55
actagtcgac atggactcca ggctcaattt agttttcctt                             40

<210> SEQ ID NO 56
<211> LENGTH: 37
<212> TYPE: DNA
<213> ORGANISM: Artificial Sequence
<220> FEATURE:
<223> OTHER INFORMATION: primer

<400> SEQUENCE: 56
actagtcgac atggctgtcy trgsgctrct cttctgc                                37

<210> SEQ ID NO 57
<211> LENGTH: 36
<212> TYPE: DNA
<213> ORGANISM: Artificial Sequence
<220> FEATURE:
<223> OTHER INFORMATION: primer

<400> SEQUENCE: 57
actagtcgac atggratgga gckggrtctt tmtctt                                 36

<210> SEQ ID NO 58
<211> LENGTH: 33
<212> TYPE: DNA
<213> ORGANISM: Artificial Sequence
<220> FEATURE:
<223> OTHER INFORMATION: primer

<400> SEQUENCE: 58
actagtcgac atgagagtgc tgattctttt gtg                                    33

<210> SEQ ID NO 59
<211> LENGTH: 40
<212> TYPE: DNA
<213> ORGANISM: Artificial Sequence
<220> FEATURE:
<223> OTHER INFORMATION: primer

<400> SEQUENCE: 59
actagtcgac atggmttggg tgtggamctt gctattcctg                             40

<210> SEQ ID NO 60
<211> LENGTH: 37
<212> TYPE: DNA
<213> ORGANISM: Artificial Sequence

```
<220> FEATURE:
<223> OTHER INFORMATION: primer

<400> SEQUENCE: 60
actagtcgac atgggcagac ttacattctc attcctg                            37

<210> SEQ ID NO 61
<211> LENGTH: 38
<212> TYPE: DNA
<213> ORGANISM: Artificial Sequence
<220> FEATURE:
<223> OTHER INFORMATION: primer

<400> SEQUENCE: 61
actagtcgac atggattttg ggctgatttt ttttattg                           38

<210> SEQ ID NO 62
<211> LENGTH: 37
<212> TYPE: DNA
<213> ORGANISM: Artificial Sequence
<220> FEATURE:
<223> OTHER INFORMATION: primer

<400> SEQUENCE: 62
actagtcgac atgatggtgt taagtcttct gtacctg                            37

<210> SEQ ID NO 63
<211> LENGTH: 27
<212> TYPE: DNA
<213> ORGANISM: Artificial Sequence
<220> FEATURE:
<223> OTHER INFORMATION: primer

<400> SEQUENCE: 63
ggatcccggg agtggataga ctgatgg                                       27
```